(12) United States Patent
Lorens et al.

(10) Patent No.: US 8,574,827 B2
(45) Date of Patent: Nov. 5, 2013

(54) MODULATORS OF ANGIOGENESIS AND TUMORIGENESIS

(75) Inventors: James B. Lorens, Bones (NO); Robert E. Atchison, San Francisco, CA (US); Annabelle Friera, South San Francisco, CA (US); Sacha Holland, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 1991 days.

(21) Appl. No.: 10/696,909

(22) Filed: Oct. 29, 2003

(65) Prior Publication Data

US 2005/0118604 A1   Jun. 2, 2005

Related U.S. Application Data

(60) Provisional application No. 60/421,989, filed on Oct. 29, 2002, provisional application No. 60/512,251, filed on Oct. 17, 2003.

(51) Int. Cl.
*C12Q 1/00* (2006.01)
*G01N 33/53* (2006.01)

(52) U.S. Cl.
USPC ................ 435/4; 435/7.1; 435/7.2; 435/7.21

(58) Field of Classification Search
USPC ........................................................... 435/4
See application file for complete search history.

(56) References Cited

U.S. PATENT DOCUMENTS

| 6,180,084 B1 | 1/2001 | Ruoslahti et al. | |
| 2003/0157573 A1* | 8/2003 | Mor | 435/7.2 |
| 2004/0048253 A1* | 3/2004 | Panzer et al. | 435/6 |
| 2004/0077574 A1* | 4/2004 | Klinghoffer et al. | 514/44 |

FOREIGN PATENT DOCUMENTS

| WO | WO 00/76309 A2 | 12/2000 |
| WO | WO 01/32926 A2 | 5/2001 |
| WO | WO 01/63281 A1 | 8/2001 |
| WO | WO 02/081627 A2 | 10/2002 |
| WO | WO 2004/008147 A2 | 1/2004 |

OTHER PUBLICATIONS

Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Jain (Sci. Am., 1994, 271:58-65).*
O'Bryan et al. (Molecular and Cellular Biology, 1991, 11: 5016-5031).*
Varnum, et al. (Nature, Feb. 16, 1994, 373:623-626).*
ATCC No. CRL-1620, cell line A-172 (www.atcc.org).*
Sigma-Aldrich Catalog No. V3501, Vitamin K1 (www.sigma-aldrich.com).*
Lee, et al. (Molecular and Cellular Biology, Dec. 1999, 19: 8075-8082).*
Healy et al. (Am. J. of Physiology, Lung Cell Molecular Physiology, Jun. 2001 280: L1273-L1281).*
Varner and Cheresh (Current Opinion in Cell Biology, Oct. 1996, 8:724-730).*
Gura (Science, 1997, 278:1041-1042).*
Kaiser (Science, 2006, 313, 1370).*
Clamp and Jayson (British Journal of Cancer, 2005 93:967-972).*
Galliccio et al. (Blood, Mar. 1, 2005, vol. 105, No. 5, pp. 1970-1976).*
Zips et al (In vivo, 2005, 19:1-7).*
Hanahan and Folkman (Cell, 1996, 86: 353-364, 1996).*
Fràter-Schröder et al. (Proc. Natl. Acad. Sci. USA, 1987, 84:5277).*
Holland, S.J., et al, "Probing Angiogenic Pathways Using Functional Genomics," *Molecular Biology of the Cell*, Nov. 2002, vol. 13, Supplement, pp. 70a-71a, Abstract No. 394.
O'Donnell, K., et al., "Expression of Receptor Tyrosine Kinase Axl and its Ligand Gas6 in Rheumatoid Arthritis: Evidence for a Novel Endothelial Cell Survival Pathway," *American Journal of Pathology*, Apr. 1999, vol. 154, No. 4, pp. 1171-1180.
Zantek, N., et al., "MCF-10A-NeoST: A New Cell System for Studying Cell-ECM and Cell-Cell Interactions in Breast Cancer," Clinical Cancer Research, Nov. 2001, vol. 7, pp. 3640-3648.

* cited by examiner

*Primary Examiner* — Peter J Reddig
(74) *Attorney, Agent, or Firm* — Klarquist Sparkman, LLP

(57) ABSTRACT

The present invention relates to regulation of angiogenesis and tumorigenesis. The invention further relates to methods for identifying and using agents, including small organic molecules, antibodies, peptides, cyclic peptides, nucleic acids, antisense nucleic acids, RNAi, and ribozymes, that modulate angiogenesis via modulation of endothelial cell haptotaxis; as well as to the use of expression profiles and compositions in diagnosis and therapy of angiogenesis and cancer.

13 Claims, 20 Drawing Sheets

FIG. 4
GFP-Transglutaminase II Screening Hit Inhibits Haptotaxis
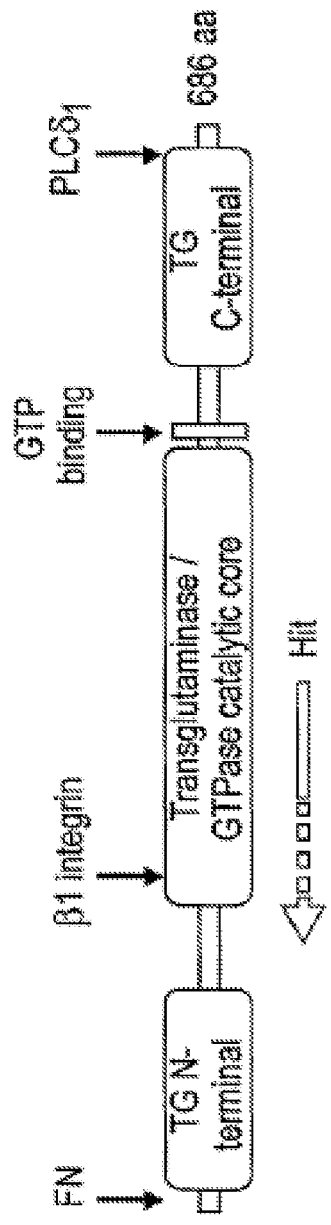
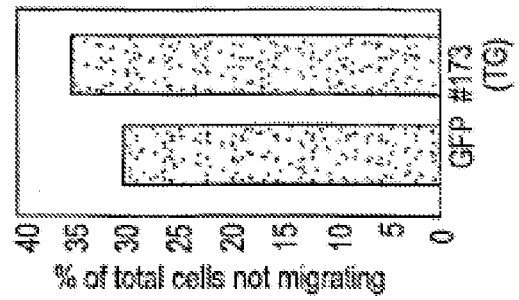

GFP-Zip Kinase Screening Hit Inhibits Haptotaxis

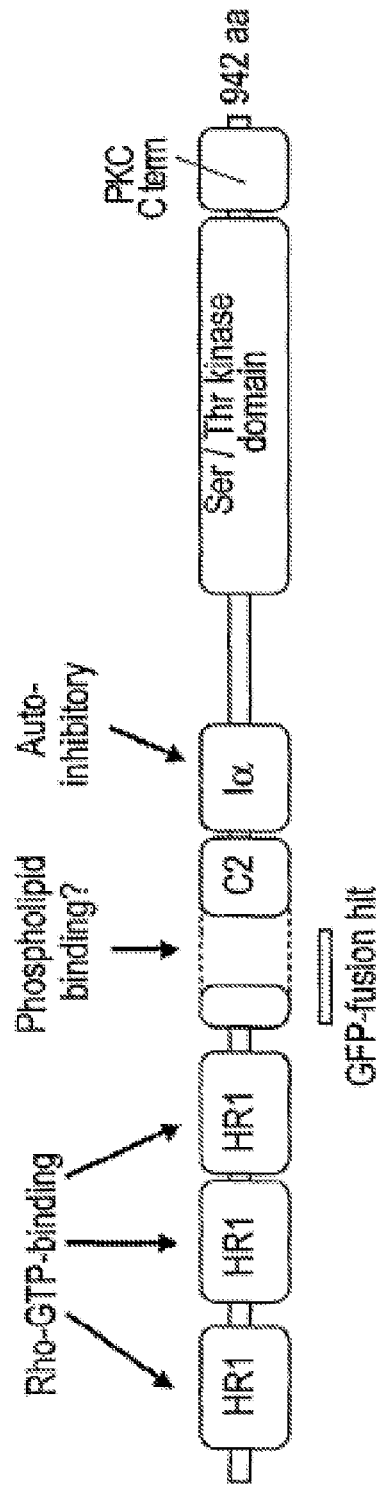
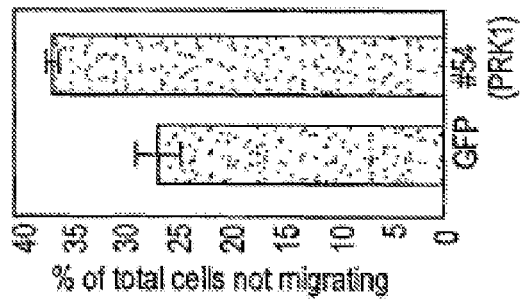
FIG. 6

FIG. 7  PRK1 mRNA Expression is Restricted to Endothelial Cells and PBMCs

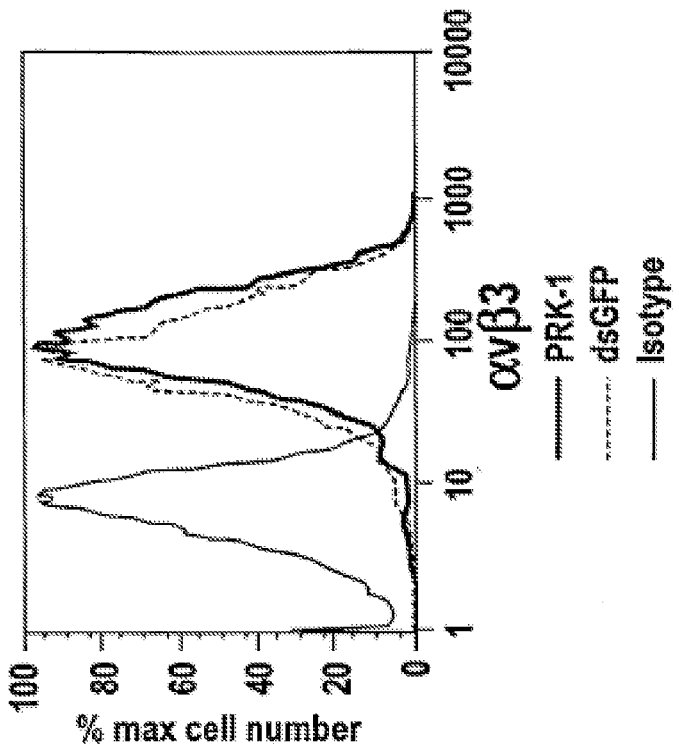
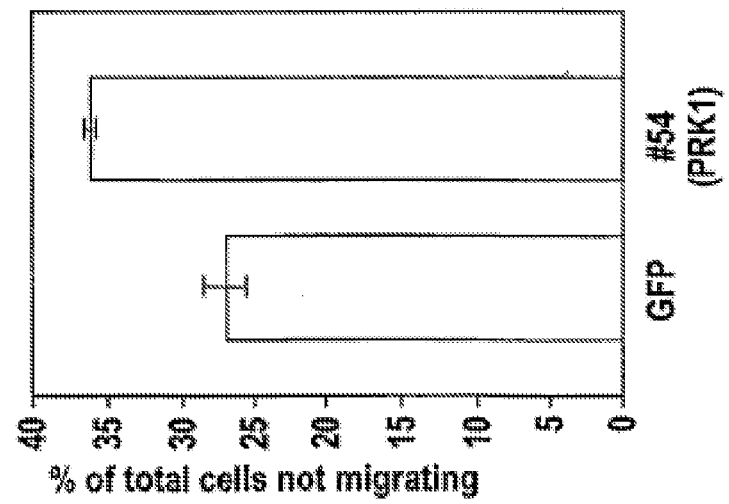
FIG. 8
GFP-PRK-1 Screening Hit Inhibits Haptotaxis and Reduces αvβ3 Levels FIG. 9 PRK-1 RNAi Reduces PRK-1 Message, Haptotaxis and αvβ3 Expression FIG. 11  Axl and Gas6 were Isolated in the Haptotaxis Screen

FIG. 16
Axl Extracelluar Domain was Isolated in VEGFR2 Screen
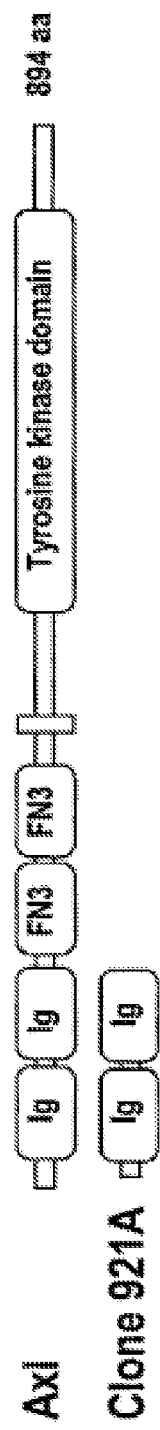
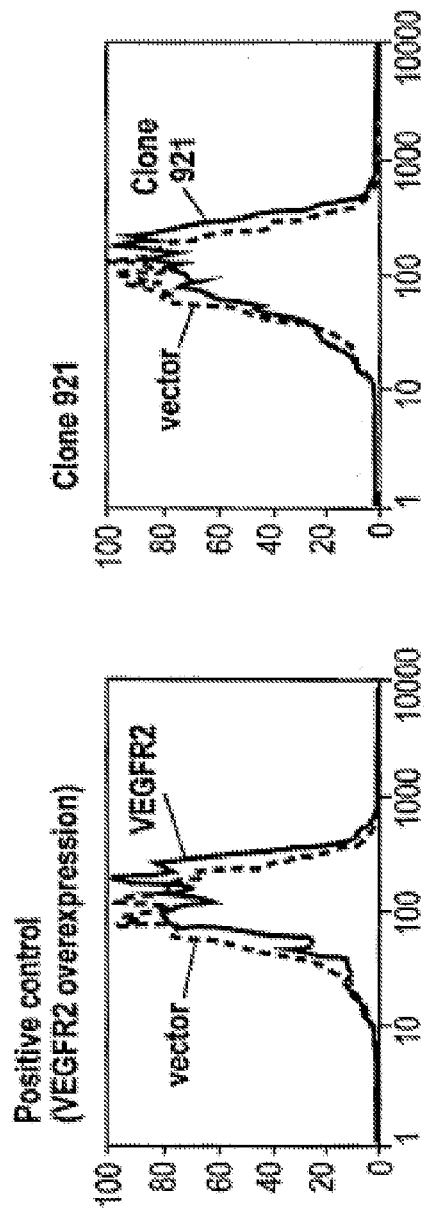

FIG. 17  Axl RNAis Inhibit Tube Formation in the Co-Culture Assay

MODULATORS OF ANGIOGENESIS AND TUMORIGENESIS

CROSS-REFERENCES TO RELATED APPLICATIONS

The present application claims priority to U.S. Ser. No. 60/421,989, filed Oct. 29, 2002, and U.S. Ser. No. 60/512,251, filed Oct. 17, 2003, each herein incorporated by reference in their entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of angiogenesis and tumorigenesis. The invention further relates to methods for identifying and using agents, including small organic molecules, antibodies, peptides, cyclic peptides, nucleic acids, antisense nucleic acids, RNAi, and ribozymes, that modulate angiogenesis and tumorigenesis via modulation of endothelial cell haptotaxis; as well as to the use of expression profiles and compositions in diagnosis and therapy of angiogenesis and cancer.

BACKGROUND OF THE INVENTION

The migration of activated endothelial cells through a vitronectin-rich provisional matrix is critical to the formation of new blood vessels during angiogenesis and is dependent on adhesion receptors containing alphav integrins (such as alphavbeta3 which binds to vitronectin). Peptide and antibody inhibitors of alphavbeta3 integrin inhibit tumor growth in vivo.

Angiogenesis is typically limited in a normal adult to the placenta, ovary, endometrium and sites of wound healing. However, angiogenesis, or its absence, plays an important role in the maintenance of a variety of pathological states. Some of these states are characterized by neovascularization, e.g., cancer and tumorigenesis, e.g., endometriosis, diabetic retinopathy, glaucoma, glomerulonephritis, and age related macular degeneration. Others, e.g., stroke, infertility, heart disease, e.g., restenosis, ulcers, and scleroderma, are diseases of angiogenic insufficiency. Therefore, there is a need to identify nucleic acids encoding proteins involved in the regulation of angiogenesis and tumorigenesis, to identify, e.g., modulators of angiogenesis, as well as new therapeutic and diagnostic applications.

SUMMARY OF THE INVENTION

Novel targets for anti-angiogenic and anti-tumorigenic therapy have been identified using a functional genetic screen based on endothelial cell haptotaxis. Inhibition or activation of these targets (by small molecule inhibitors; protein, antibody and peptide therapeutics; RNAi; antisense; gene therapy etc.) have therapeutic value in modulating angiogenesis and tumorigenesis, e.g., breast, lung, colon, ovarian, liver, thyroid, stomach, bladder, and prostate cancer, basal cell carcinoma, melanoma, lymphomas, leukemias, e.g., myeloid leukemia (CML and AML), endometriosis, diabetic retinopathy, glaucoma, glomerulonephritis, age related macular degeneration, as well as, e.g., stroke, infertility, heart disease, e.g., restenosis, ulcers, and scleroderma.

The present invention therefore provides nucleic acids encoding proteins involved in modulation of vitronectin induced endothelial cell haptotaxis and modulation of angiogenesis and tumorigenesis. The invention therefore provides methods of screening for compounds, e.g., small organic molecules, antibodies, nucleic acids, peptides, cyclic peptides, nucleic acids, antisense molecules, RNAi, and ribozymes, that are capable of modulating angiogenesis or tumorigenesis, e.g., either activating or inhibiting angiogenesis or tumorigenesis. Therapeutic and diagnostic methods and reagents are also provided.

In one aspect, the present invention provides a method for identifying a compound that modulates angiogenesis and tumorigenesis, the method comprising the steps of: (i) contacting the compound with an angiogenesis or tumorigenesis modulating polypeptide or fragment thereof, the polypeptide encoded by a nucleic acid that hybridizes under stringent conditions to a reference nucleic acid encoding the polypeptide, the polypeptide selected from the group consisting of Axl, tubulin cofactor D, transglutaminase 2, cytosine deaminase, peptidase M41 (paraplegin), CD13 aminopeptidase, PRK-1, zip kinase, Gas6, SRm160, non-muscle myosin heavy chain, calmodulin 2, novel symporter, novel semaphorin, novel zinc finger helicase (FLJ22611), plexin-A2, deoxycytidylate deaminase, and a novel sugar transporter; and (ii) determining the functional effect of the compound upon the polypeptide.

In one embodiment, the functional effect is determined in vitro. In another embodiment, the functional effect is a physical effect. In another embodiment, the functional effect is determined by measuring ligand binding to the polypeptide. In another embodiment, the functional effect is a chemical effect.

In one embodiment, the polypeptide is expressed in a eukaryotic host cell. In another embodiment, the functional effect is a physical effect. In another embodiment, the functional effect is determined by measuring ligand binding to the polypeptide. In another embodiment, the functional effect is a chemical or phenotypic effect. In another embodiment, the polypeptide is expressed in a eukaryotic host cell, e.g., an endothelial cell. In another embodiment, the functional effect is determined by measuring $\alpha v \beta 3$ expression, haptotaxis, tumor cell proliferation, or tumor growth in vivo.

In one embodiment, modulation is inhibition of angiogenesis or tumorigenesis.

In one embodiment, the polypeptide is recombinant.

In one embodiment, the compound is an antibody, a peptide, an antisense molecule, a RNAi molecule, or a small organic molecule.

In another aspect, the present invention provides a method for identifying a compound that modulates tumorigenesis or angiogenesis, the method comprising the steps of (i) contacting the compound with an angiogenesis or tumorigenesis modulating polypeptide or fragment or inactive variant thereof, the polypeptide selected from the group consisting of Axl, tubulin cofactor D, transglutaminase 2, cytosine deaminase, peptidase M41 (paraplegin), CD13 aminopeptidase, PRK-1, zip kinase, Gas6, SRm160, non-muscle myosin heavy chain, calmodulin 2, novel symporter, novel semaphorin, novel zinc finger helicase (FLJ22611), plexin-A2, deoxycytidylate deaminase, and a novel sugar transporter (ii) determining the physical effect of the compound upon the polypeptide or fragment thereof or inactive variant thereof; and (iii) determining the chemical or phenotypic effect of the compound upon a cell comprising the polypeptide or fragment thereof or inactive variant thereof, thereby identifying a compound that modulates tumorigenesis or angiogenesis.

In another aspect, the present invention provides a method of modulating angiogenesis or tumorigenesis in a subject, the method comprising the step of administering to the subject a therapeutically effective amount of a compound identified using the methods described herein.

In one embodiment, the subject is a human.

In one embodiment, the compound is an antibody, an antisense molecule, a peptide, or an RNAi molecule, or a small organic molecule.

In one embodiment, the compound inhibits angiogenesis or tumorigenesis.

BRIEF DESCRIPTION OF THE DRAWINGS

FIG. 4 shows that a transgluaminase II protein is involved in haptotaxis.

FIG. 6 shows that a PRK-1 protein is involved in haptotaxis.

FIG. 8 shows that a PRK-1 protein is involved in haptotaxis and $\alpha v \beta 3$ expression.

FIG. 16 shows that an Axl extracellular domain was isolated in a VEGF-R2 screen.

DETAILED DESCRIPTION OF THE INVENTION

Introduction

Figure 1:
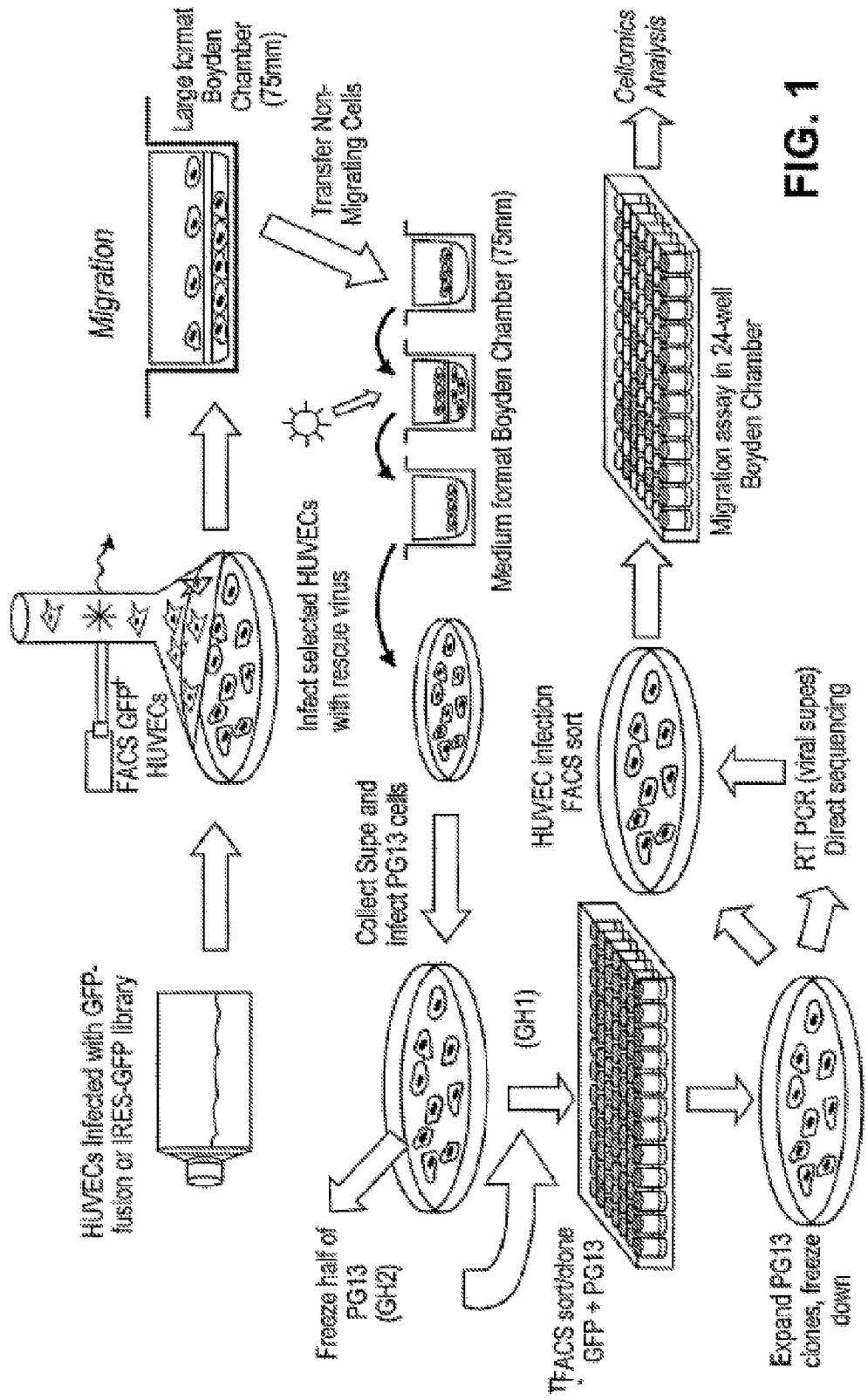
FIG. 1 shows a screening protocol for haptotactic migration inhibitors.
Figure 2:
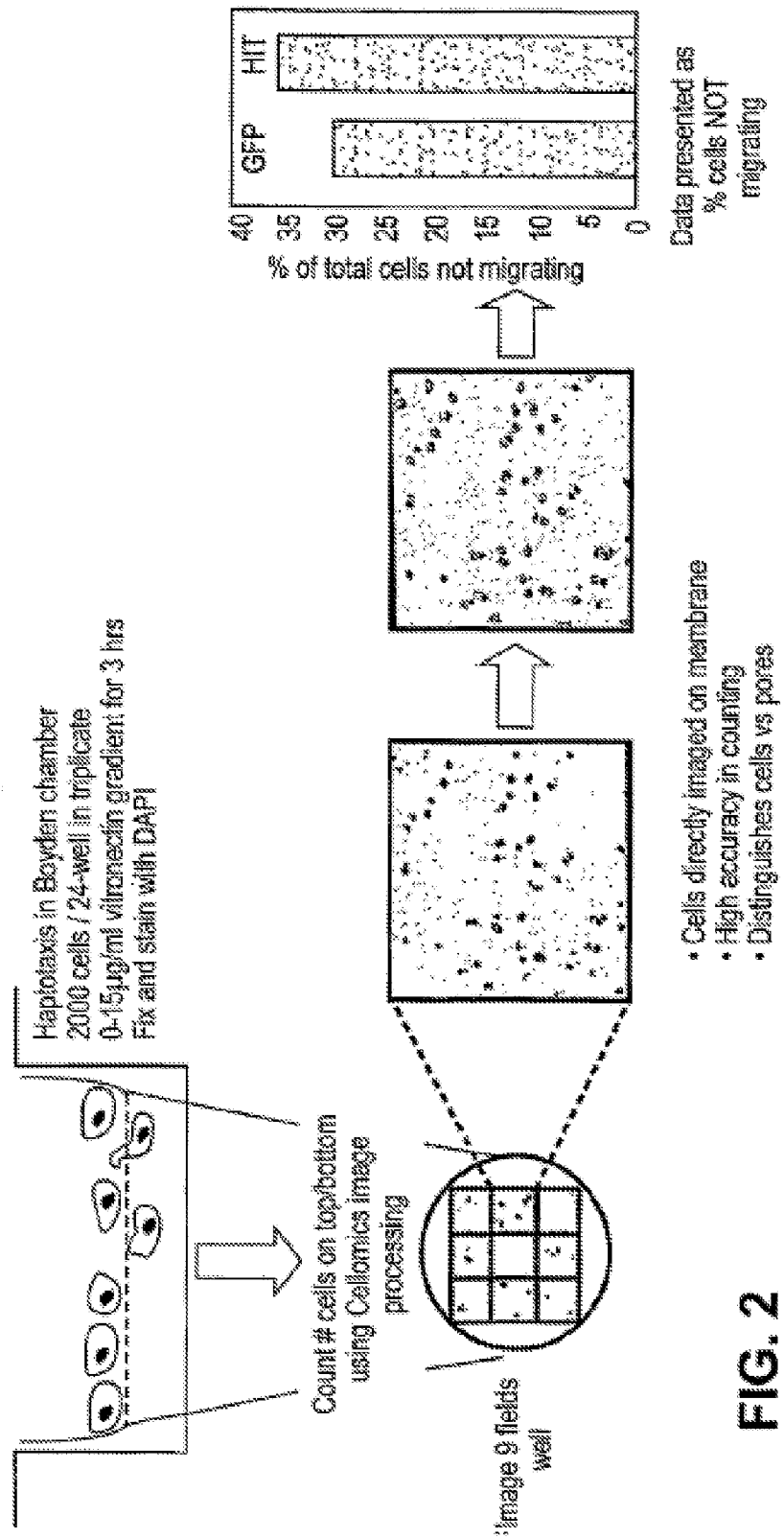
FIG. 2 shows a cellomics haptotaxis assay.
Figure 3:
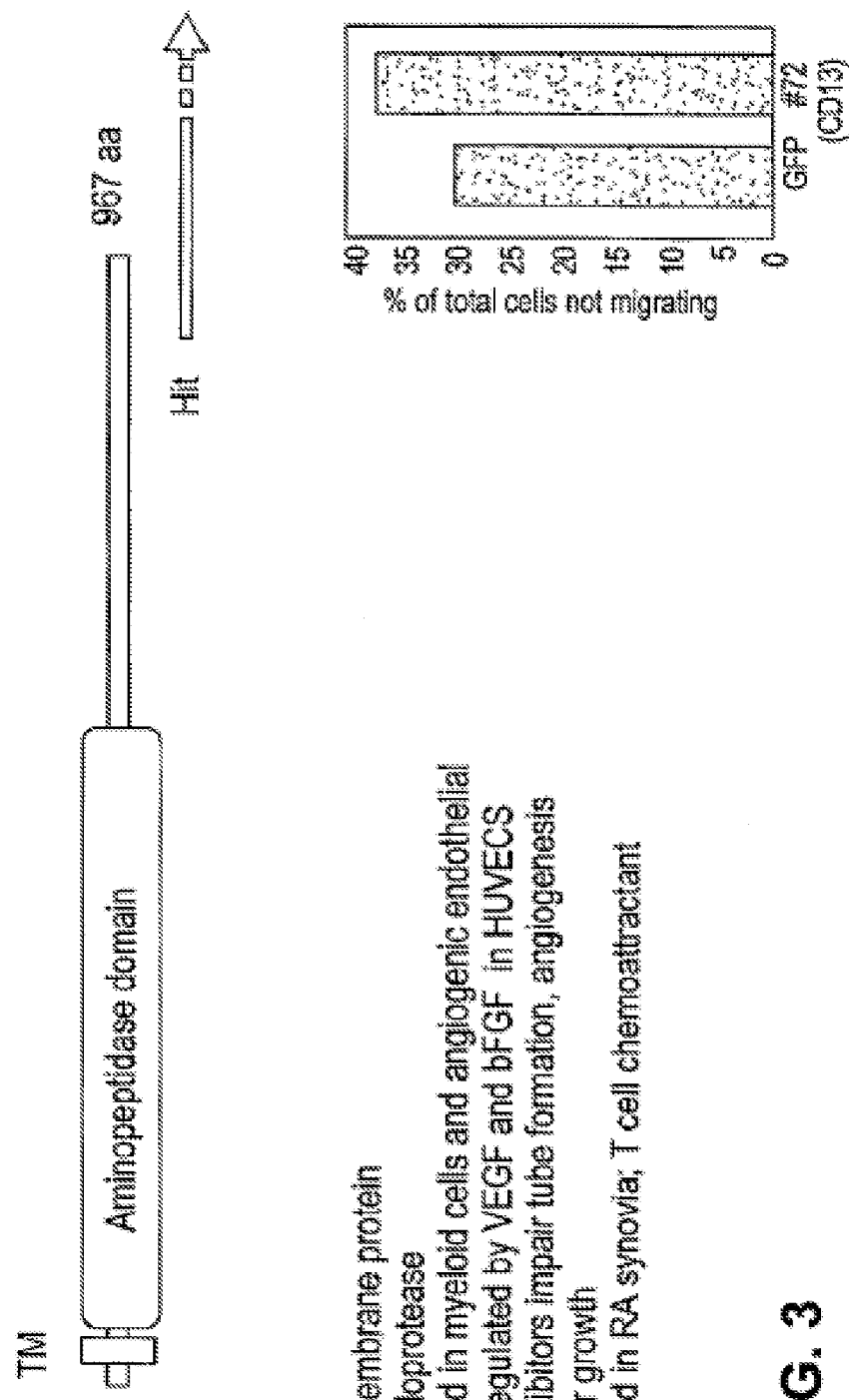
FIG. 3 shows that a CD13/N-aminiopeptidase is involved in haptotaxis.
Figure 5:
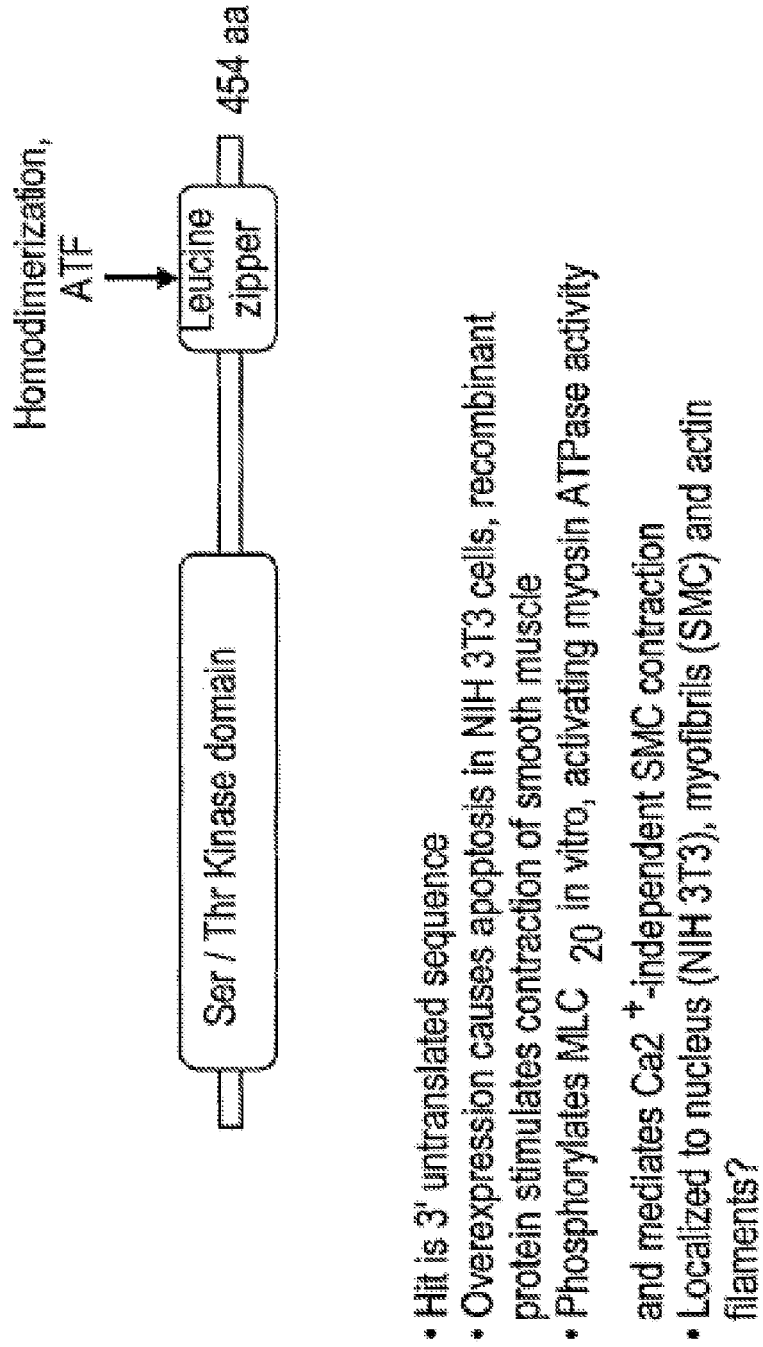
FIG. 5 shows that a zip kinase protein is involved in haptotaxis.
Figure 7:
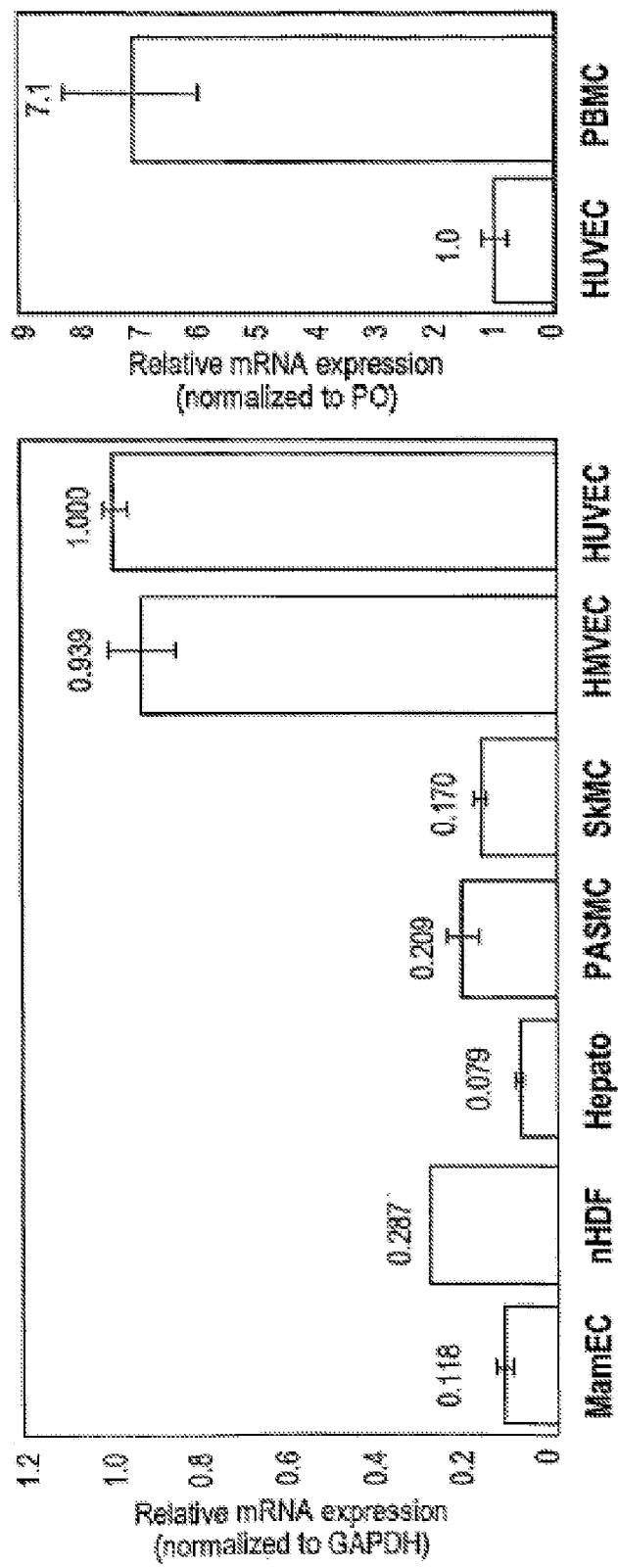
FIG. 7 shows that PRK1 mRNA is expressed in endothelial cells and PBMCs.
Figure 9:
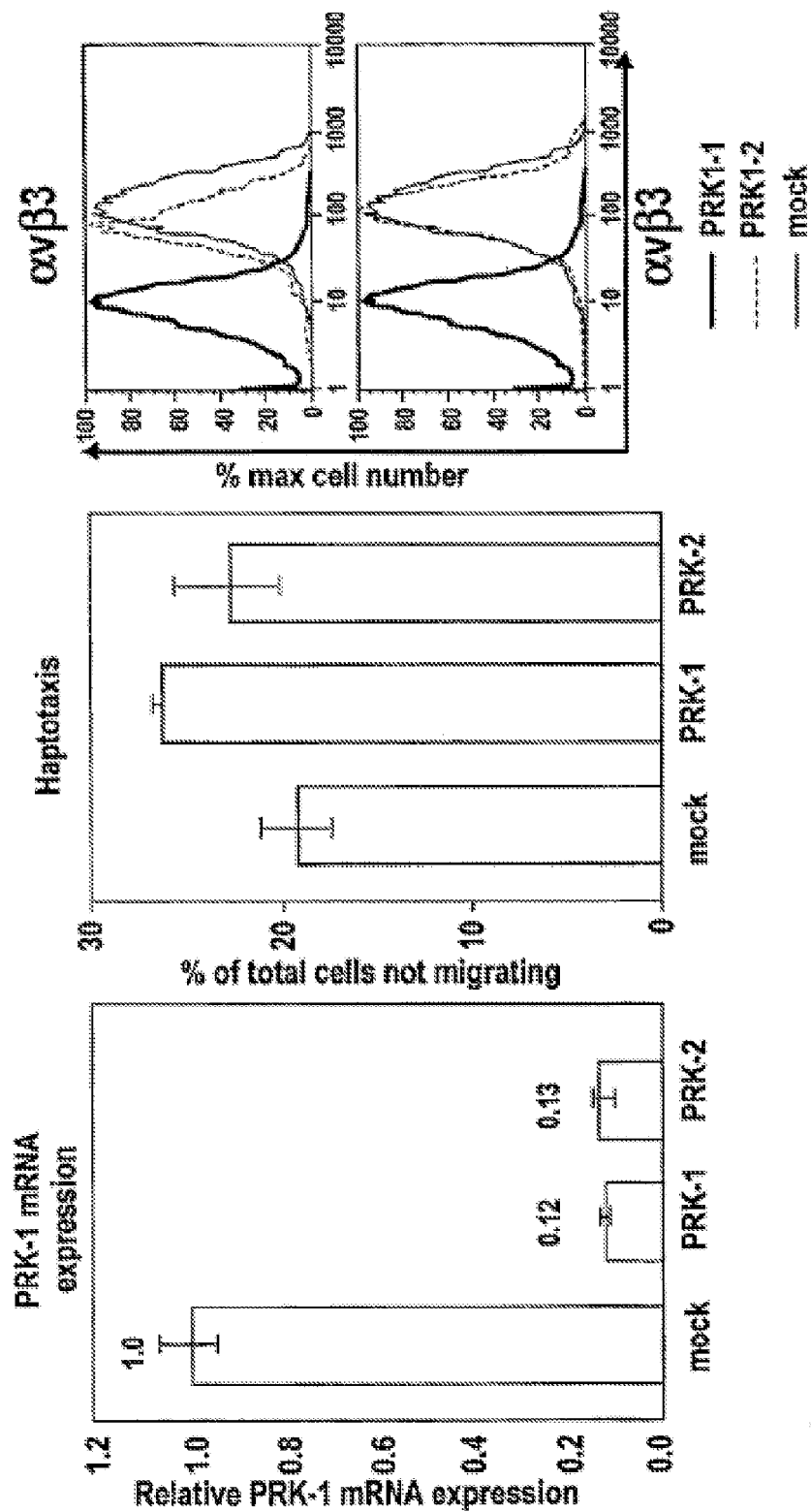
FIG. 9 shows that PRK-1 RNAi reduces PRK-1 message, haptotaxis and $\alpha v \beta 3$ expression.
Figure 10:
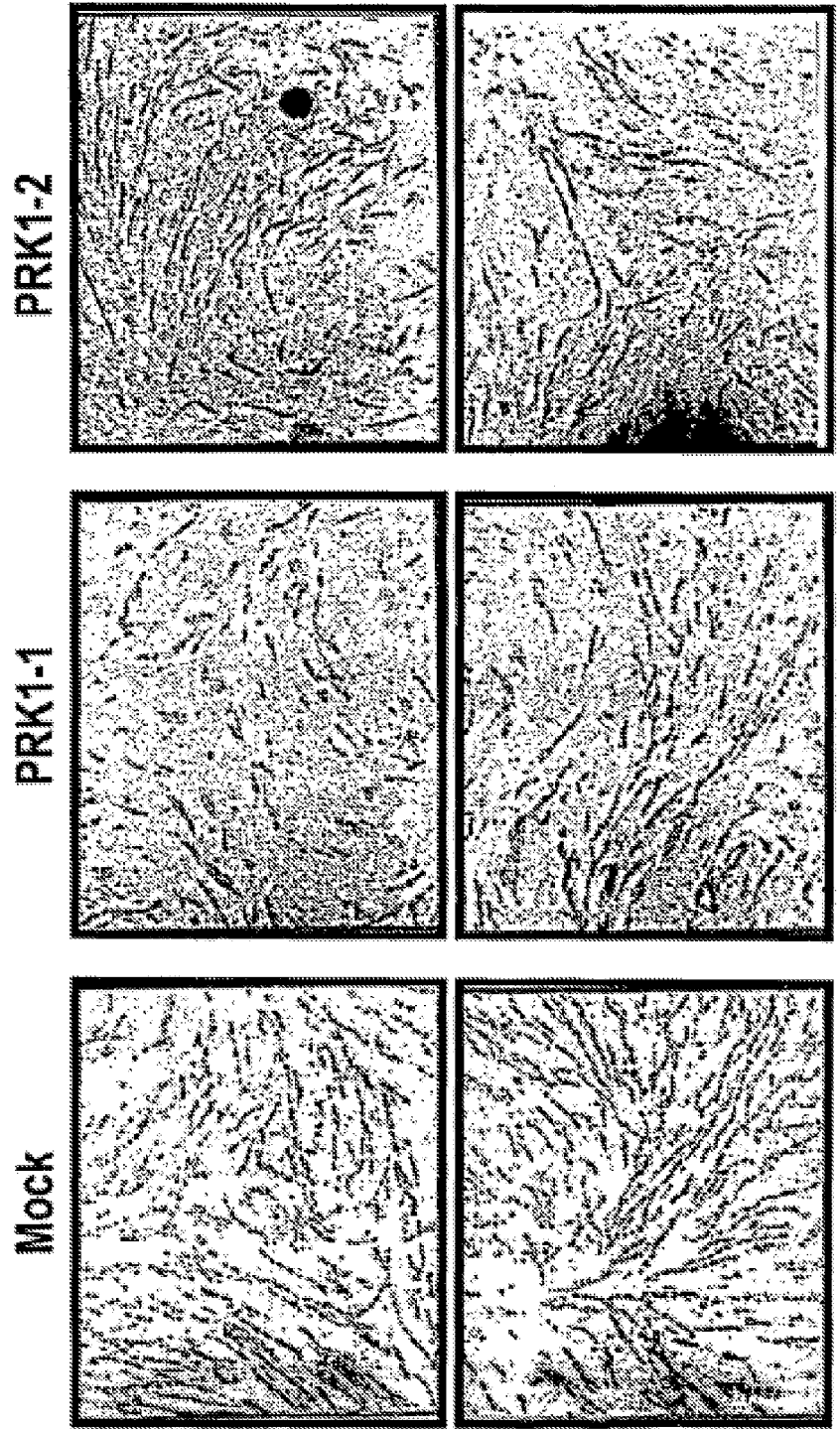
FIG. 10 shows that PRK-1 RNAi reduces tube formation in a co-culture assay.
Figure 11:
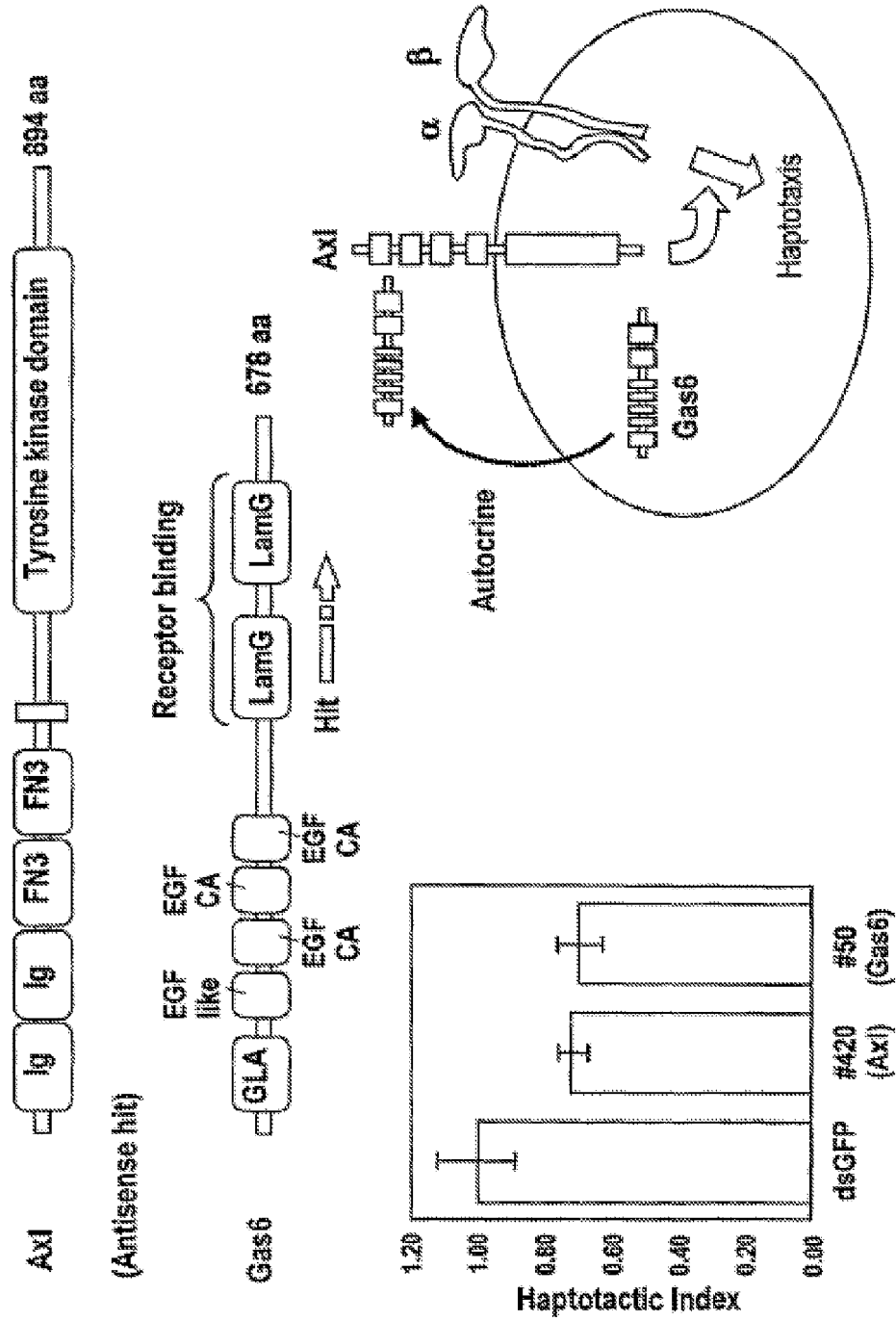
FIG. 11 shows that Axl and Gas6 are involved in haptotaxis.
Figure 12:
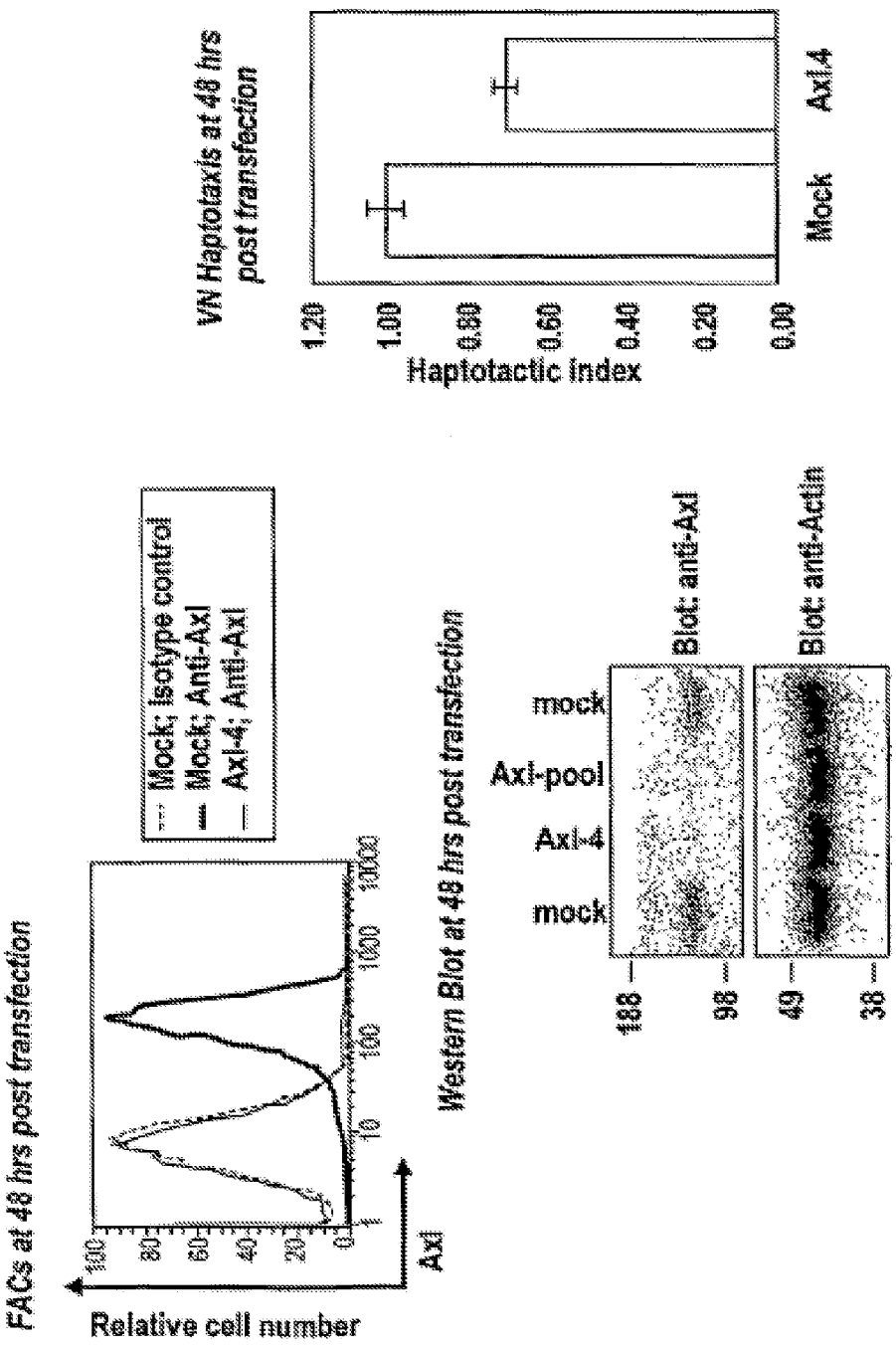
FIG. 12 shows that Axl RNAi reduces Axl mRNA expression.
Figure 13:
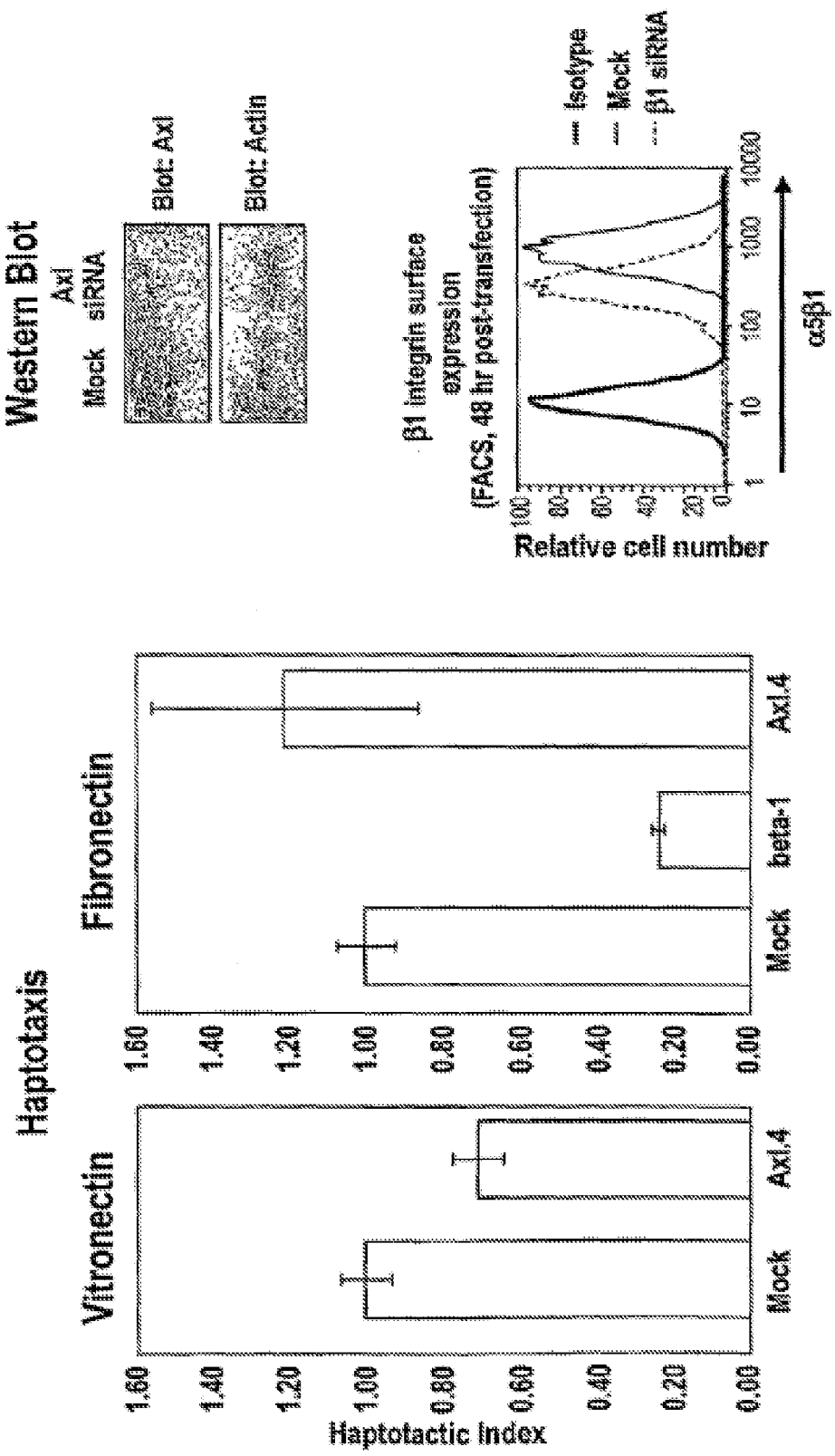
FIG. 13 shows that Axl RNAi inhibit haptotaxis to vitronectin.
Figure 14:
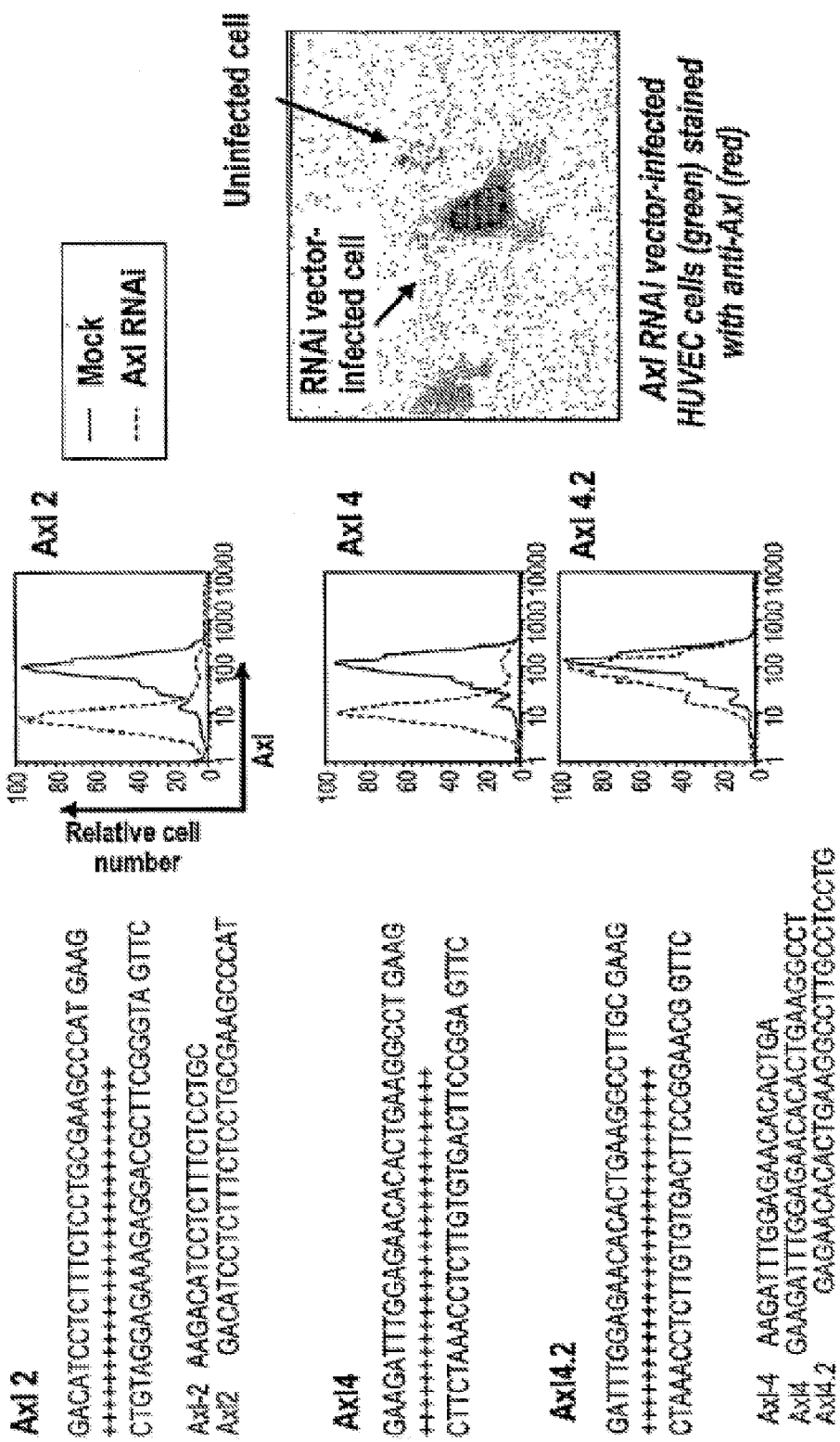
FIG. 14 shows that Axl RNAi reduces Axl protein expression. Sequences are as follows: Ax12 line 1, SEQ ID NO: 61 and line 2, reverse of SEQ ID NO: 62; Ax1-2, SEQ ID NO: 63; Ax12, SEQ ID NO: 64; Ax14 line 1, SEQ ID NO: 65 and line 2, reverse of SEQ ID NO: 66; Axl 4.2 line 1, SEQ ID NO: 67 and line 2, reverse of SEQ ID NO: 68; Axl-4, SEQ ID NO: 69; Ax14, SEQ ID NO: 70; Ax14.2, SEQ ID NO: 71.
Figure 15:
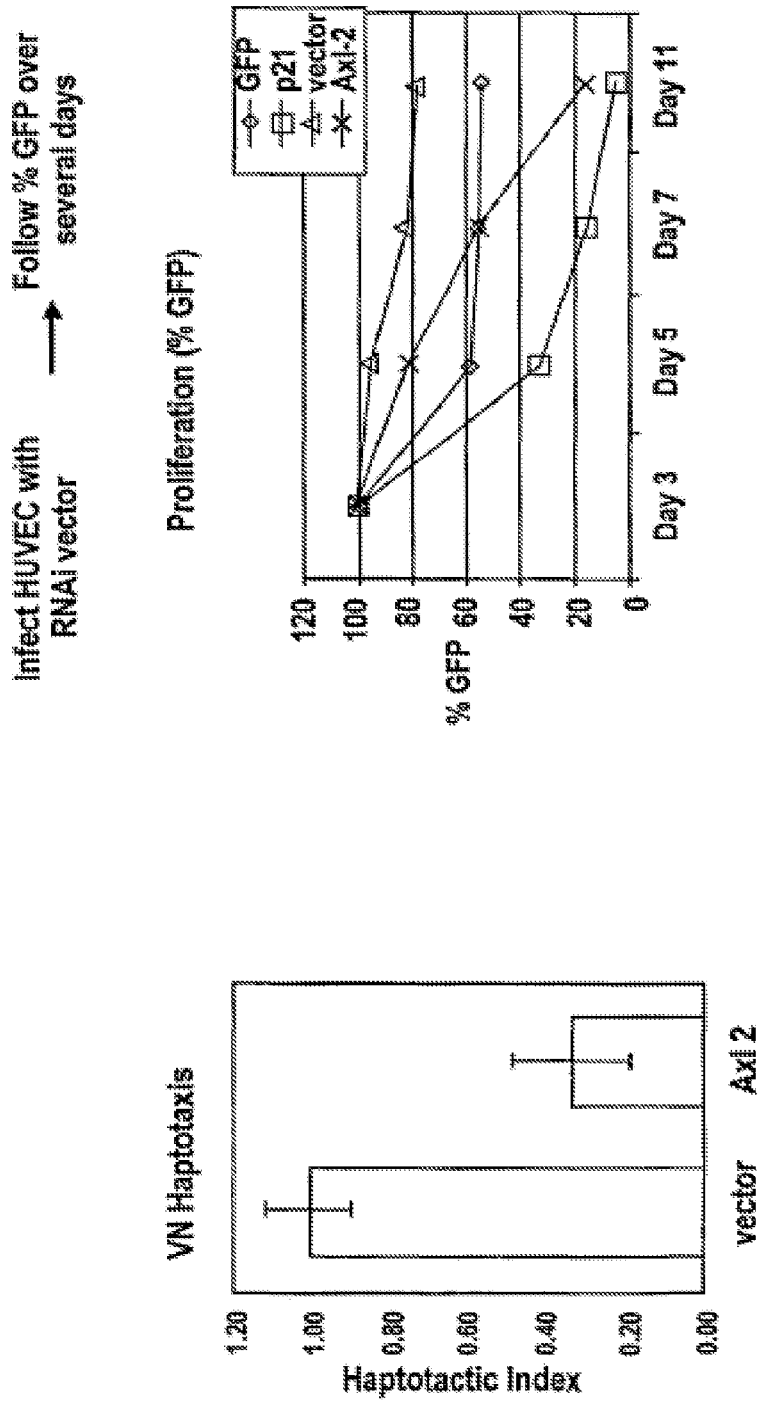
FIG. 15 shows that Axl RNAi inhibits vitronectin haptotaxis and HUVEC proliferation.
Figure 17:
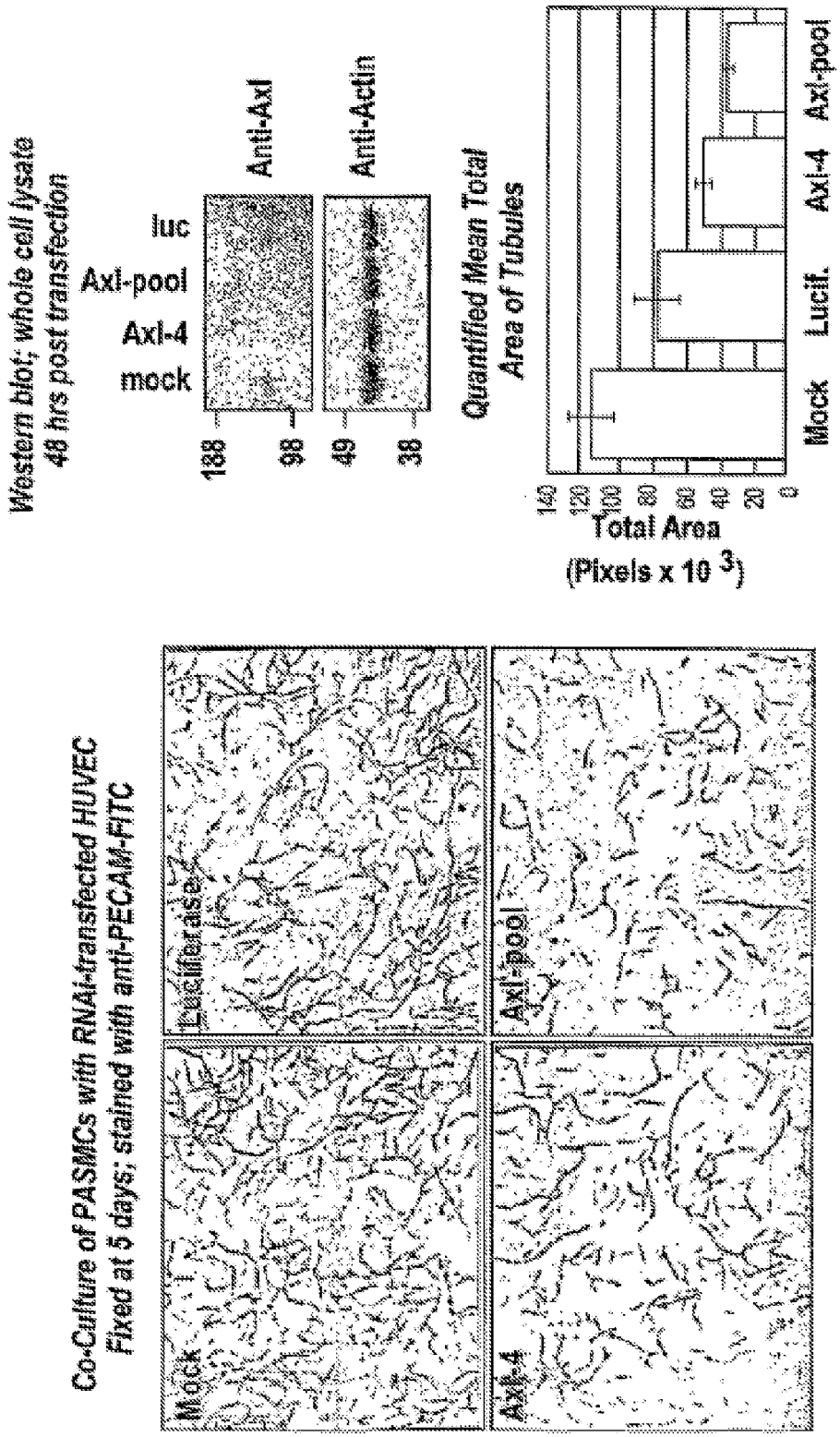
FIG. 17 shows that Axl RNAi inhibits tube formation in a co-culture assay.
Figure 18:
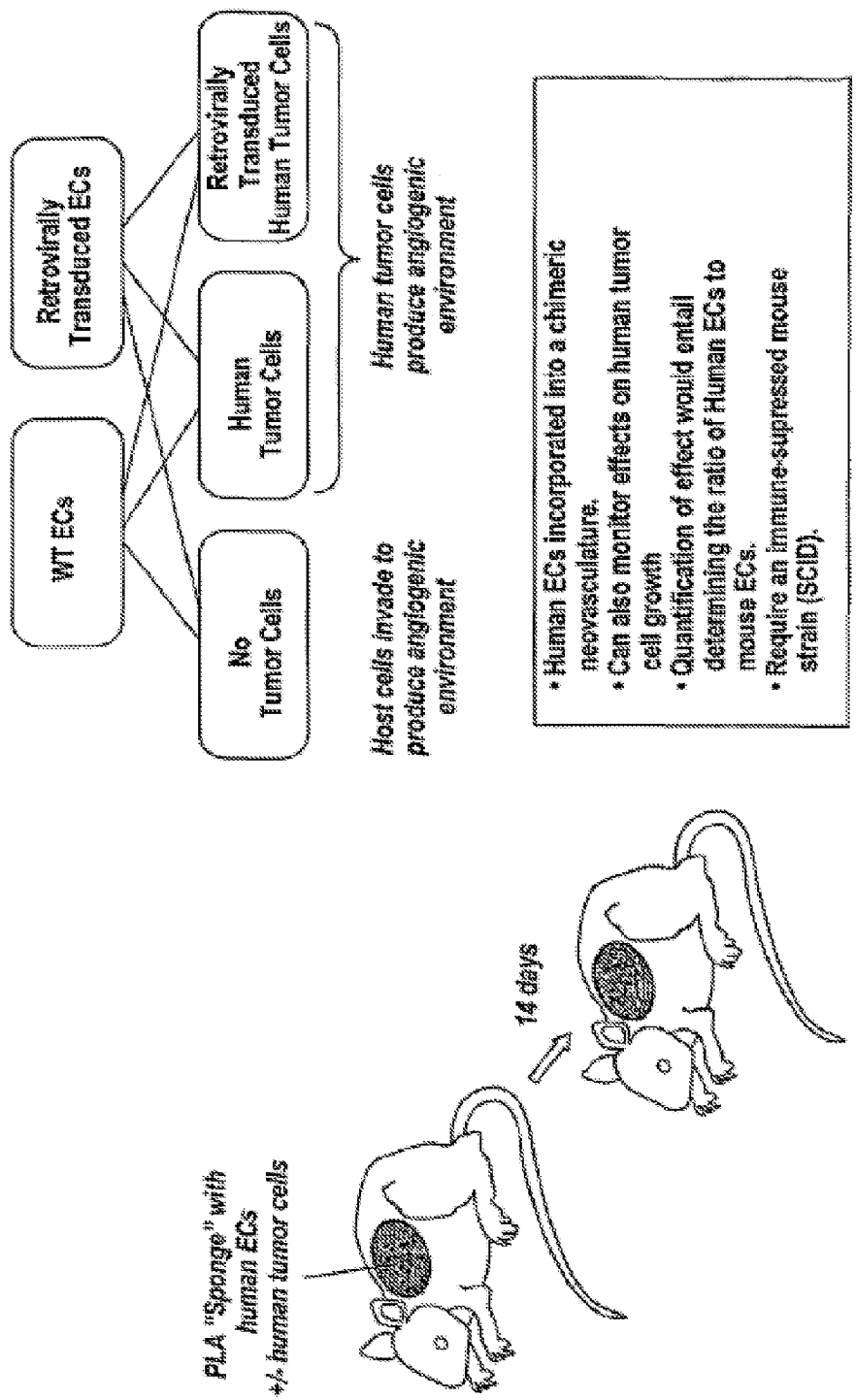
FIG. 18 shows a sponge angiogenesis/xenograft model.
Figure 19:
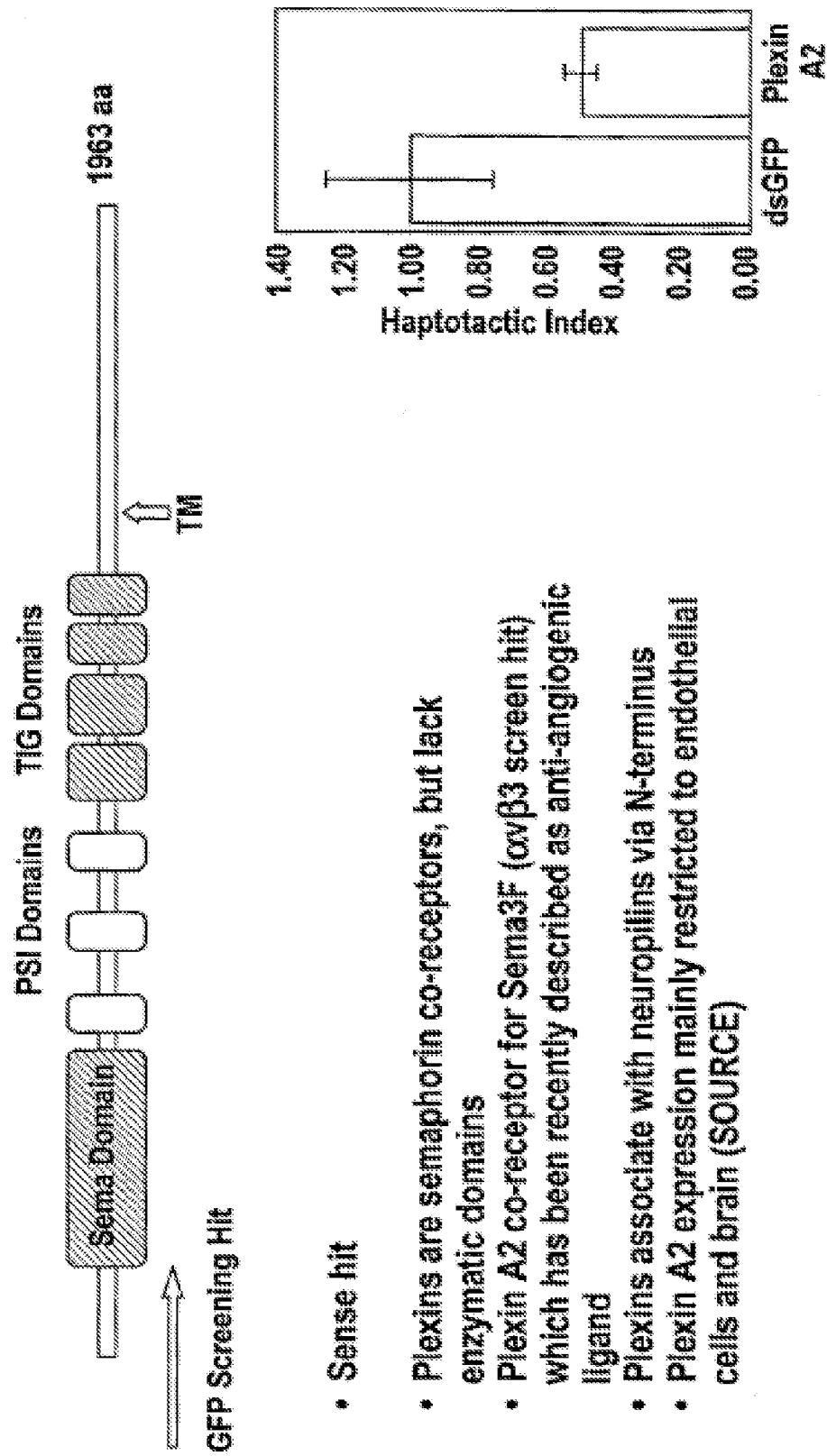
FIG. 19 shows that a deoxycytidylate deaminase is involved in angiogenesis.
Figure 20:
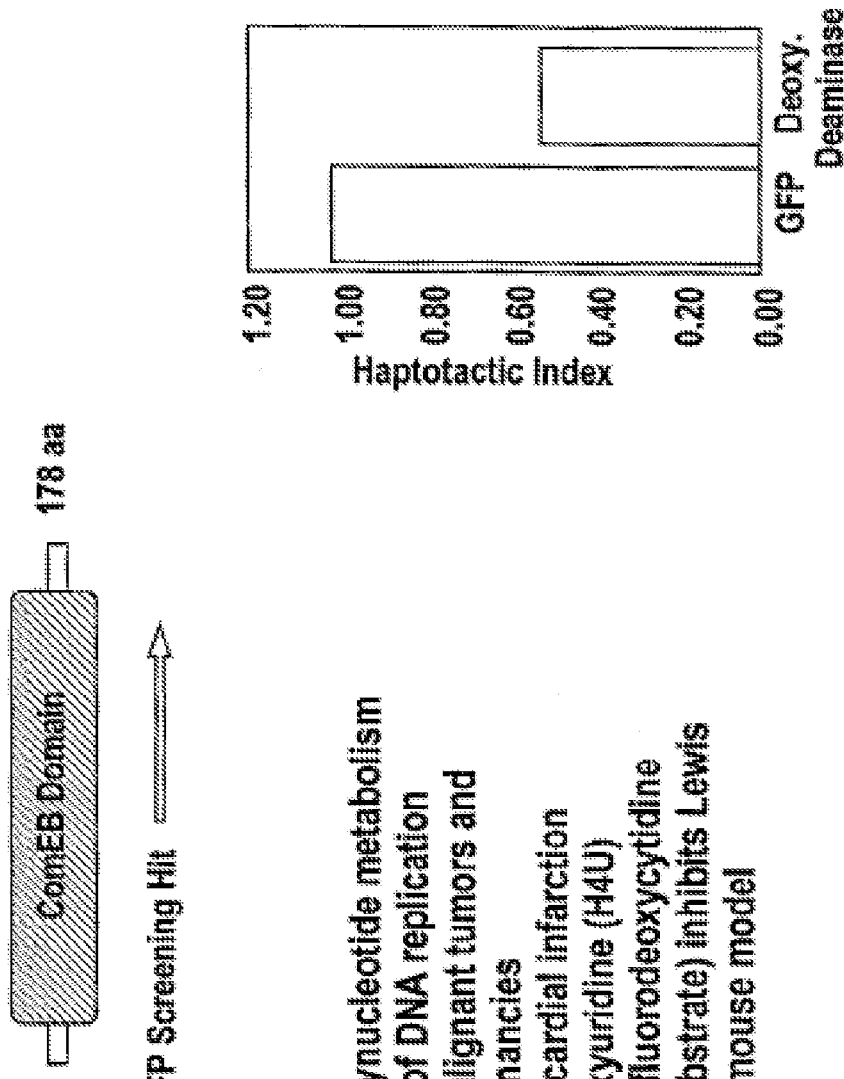
FIG. 20 shows that a plexin-A2 is involved in angiogenesis.

We have used a functional genetic screening strategy to identify proteins involved in regulating endothelial cell migration on specific matrix components, e.g. vitronectin. Using a retroviral-based system, we have stably expressed complex libraries of various types of genetic elements (e.g. cDNAs and GFP-fusions) in human primary endothelial cells (e.g. HUVECs). Starting with early passage primary endothelial cells representing an "angiogenic state" (i.e., proliferative, highly motile), single cells that have switched to a more differentiated "angiostatic state" (i.e., quiescent, reduced motility) can be identified. In order to focus on the migration step of the angiogenic cycle, conditions were established which allowed highly efficient migration of HUVEC cells along a haptotactic gradient of specific matrix proteins (e.g. vitronectin/fibronectin) in a Boyden chamber assay. Large populations of HUVEC cells were then infected with a GFP-fused cDNA library and selected for impaired haptotaxis. Additional assays for proteins involved in angiogenesis and tumorigenesis include a VEGFR2 assay, a HUVEC/smooth muscle cell co-culture assay for endothelial tube formation, chemo-invasion assays, and tumor cell proliferation assays. Finally, human/mouse tumor xenograft assays, mouse sponge angiogenesis and tumorigenesis assays (sponge with human ECs +/− human tumor cells in SCID mice), a collagen-antibody induced arthritis model for RA, and retinal neovascularization assays can be used to identify angiogenesis and tumorigenesis proteins in vivo and to assay for modulators of such proteins.

The angiogenesis and tumorigenesis proteins identified using the haptotaxis assay described herein, e.g., Axl, its ligand, Gas6, tubulin cofactor D, transglutaminase 2, cytosine deaminase, plexin-A2, peptidase M41 (paraplegin), CD 13 aminopeptidase, PRK-1, zip kinase, SRm160, non-muscle myosin heavy chain, calmodulin 2, novel symporter, novel semaphorin, novel zinc finger helicase (FLJ22611), and a novel sugar transporter, therefore represent targets for the development of angiogenic drugs, preferably anti-angiogenic drugs, e.g., anti-angiogenic drugs for treatment of neovascularization, e.g., cancer, diabetic retinopathy, endometriosis, glomerulonephritis, restenosis, glaucoma, rheumatoid arthritis, and age related macular degeneration, or angiogenic drugs for treatment of angiogenic insufficiency, e.g., stroke, infertility, heart disease, ulcers, and scleroderma. Modulators include small organic molecules, nucleic acids, peptides, cyclic peptides, antibodies, antisense molecules, RNAi molecules, and ribozymes. The nucleic acids and proteins of the invention are also useful for diagnostic applications, using, e.g., nucleic acid probes, oligonucleotides, and antibodies. These polypeptides are also involved in tumorigenesis and cellular proliferation, and are useful for the development of therapeutic molecules to treat diseases associated with angiogenesis, tumorigenesis, and cellular proliferation. Furthermore, the polypeptides described herein and the nucleic acids encoding them are useful for diagnostic assays for diseases associated with angiogenesis, tumorigenesis, and cellular proliferation.

In one embodiment, the protein Axl is involved in angiogenesis, tumorigenesis, and cellular proliferation. Axl is a receptor tyrosine kinase that posses transforming activity in vitro. Axl is activated by its ligand, Gas6. Axl, Sky, and Mer form a family of receptor tyrosine kinases that are activated by Gas6. Axl is expressed in myeloid cell types and vasculature, e.g., endothelial cells (HUVEC), VSMC, monocytes, macrophages, CD34+ cells, bronchial epithelium, breast epithelium, neurons, and chondrocytes. Axl is upregulated in VSMC after vascular injury. Gas6-Axl interactions stimulate cell survival and chemotaxis. Knockout and transgenic mice for Axl show no overt phenotypes. Axl is associated with several diseases, including rheumatoid arthritis (O'Donnell et al., *Am. J. Pathol.* 154:1171-1180 (1999)), endometriosis (Sun et al., *Mol. Human Reproduction* 8:552-559 (2002)), cancer, e.g. myeloid leukemias such as AML and CML, thyroid carcinomas, and breast cancer. Axl can be activated using antibody crosslinking, pervanadate, or Gas6.

In another embodiment, the protein PRK-1 is involved in angiogenesis and tumorigenesis. PRK-1 is a cytoplasmic serine/threonine kinase related to PKC. PRK-1 binds Rho GTPase through the N-terminus and is regulated by activation loop phosphorylation by PD-1. PRK activation by PDK1 is Rho-dependent and membrane localized. PRK-1 I exhibits elevated expression in endothelial cells and PBMC. PRK-1 is upregulated in breast and prostate epithelial carcinoma cells as compared to normal cells and activates androgen receptor signaling (see, e.g., Metzger et al., *EMBO J.* 22:270-280 (2003)). PRK-1 RNAi inhibits PRK-1 protein and VN and FN haptotaxis, (including a PRK-1 3' UTR RNAi and a PRK-1 RNAi vector). PRK-1 RNAi reduces tube formation in the co-culture assays, as well as SDF-1 and VEGF chemotaxis in HUVECs. PRK-1 RNAi inhibits vitronectin-induced haptotaxis in PASMCs. Expression of kinase inactive PRK-1 in HUVECs increases vitronectin haptotaxis. The PRK-1 screening hit GH1-54 co-immunoprecipitates with full-length PRK-1. In vitro kinase assays with PRK-1 can be used to assay for PRK-1 modulators and thus for modulators of angiogenesis.

In another embodiment, the protein PRK-2 is involved in angiogenesis and tumorigenesis. PRK-2 is widely expressed in adherent cell types. PRK-2 siRNA inhibits vitronectin-induced haptotaxis in HUVECS and PASMCs and also inhibits PRK-2 protein expression. In another embodiment, the proteins deoxycytidylate deaminase (sense hit) (, transglutaminase II (antisense hit), plexin-A2 (sense hit), and ZIP-kinase/DAP kinase 3 (sense 3' UTR hit), are involved in angiogenesis and tumorigenesis. ZIP kinase exhibits a restricted tissue expression pattern and is highly expressed in hepatocytes. ZIP kinase RNAi inhibits VN haptotaxis.

DEFINITIONS

By "disorder associated with angiogenesis or tumorigenesis" or "disease associated with angiogenesis or tumorigenesis" herein is meant a disease state which is marked by either an excess or a deficit of vessel development. Angiogenesis and tumorigenesis disorders associated with increased angiogenesis include, but are not limited to, breast, lung, colon, ovarian, liver, stomach, bladder, thyroid, and prostate cancer, basal cell carcinoma, melanoma, lymphomas, leukemias, e.g., myeloid leukemia (AML, CML), endometriosis, diabetic retinopathy, glaucoma, glomerulonephritis, rheumatoid arthritis, and age related macular degeneration. Pathological states for which it may be desirable to increase angiogenesis include stroke, infertility, heart disease, e.g., restenosis, ulcers, and scleroderma. An increase in angiogenesis may also be desirable in transplantation or for artificial or in vitro growth of organs.

By "disorder associated with cellular proliferation or tumorigenesis" or "disease associated with cellular proliferation or tumorigenesis" herein is meant a disease state which is marked by either an excess or a deficit of cellular proliferation or apoptosis. Such disorders associated with increased cellular proliferation include, but are not limited to, cancer and non-cancerous pathological proliferation.

The terms "angiogenesis and/or tumorigenesis polypeptide" or a nucleic acid encoding an "angiogenesis and/or tumorigenesis polypeptide" refer to nucleic acid and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules.

The phrase "functional effects" in the context of assays for testing compounds that modulate activity of an angiogenesis and tumorigenesis protein includes the determination of a parameter that is indirectly or directly under the influence of an angiogenesis polypeptide, e.g., a chemical or phenotypic effect such as loss-of angiogenesis or tumorigenesis phenotype represented by a change in expression of a cell surface marker $\alpha v \beta 3$ integrin, changes in cellular migration, changes in endothelial tube formation, and changes in tumor growth, or changes in cellular proliferation, especially endothelial cell proliferation; or enzymatic activity; or, e.g., a physical effect such as ligand binding or inhibition of ligand binding. A functional effect therefore includes ligand binding activity, the ability of cells to proliferate, expression in cells undergoing angiogenesis or tumorigenesis, and other characteristics of angiogenic and tumorigenic cells. "Functional effects" include in vitro, in vivo, and ex vivo activities.

By "determining the functional effect" is meant assaying for a compound that increases or decreases a parameter that is indirectly or directly under the influence of an angiogenesis protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; ligand binding assays, e.g., binding to antibodies; measuring inducible markers or transcriptional activation of the angiogenesis protein; measuring changes in enzymatic activity; the ability to increase or decrease cellular proliferation, apoptosis, cell cycle arrest, measuring changes in cell surface markers, e.g., $\alpha v \beta 3$ integrin; and measuring cellular proliferation, particularly endothelial cell proliferation. Determination of the functional effect of a compound on angiogenesis or tumorigenesis can also be performed using assays known to those of skill in the art such as endothelial cell tube formation assays; haptotaxis assays; the chick CAM assay; the mouse corneal assay; VEGF receptor assays, co-culture tube formation assays, and assays that assess vascularization of an implanted tumor. Tumorigenesis can be measured using in vivo mouse models such as a xenograft model. The functional effects can be evaluated by many means known to those skilled in the art, e.g., microscopy for quantitative or qualitative measures of alterations in morphological features, e.g., tube or blood vessel formation, measurement of changes in RNA or protein levels for angiogenesis-associated sequences, measurement of RNA stability, identification of downstream or reporter gene expression (CAT, luciferase, gal, GFP and the like), e.g., via chemiluminescence, fluorescence, calorimetric reactions, antibody binding, inducible markers, etc.

"Inhibitors," "activators," and "modulators" of angiogenesis and tumorigenesis polynucleotide and polypeptide sequences are used to refer to activating, inhibitory, or modulating molecules identified using in vitro and in vivo assays of angiogenesis and tumorigenesis polynucleotide and polypeptide sequences. Inhibitors are compounds that, e.g., bind to, partially or totally block activity, decrease, prevent, delay activation, inactivate, desensitize, or down regulate the activity or expression of angiogenesis and tumorigenesis proteins, e.g., antagonists. "Activators" are compounds that increase, open, activate, facilitate, enhance activation, sensitize, agonize, or up regulate angiogenesis and tumorigenesis protein activity, agonists. Inhibitors, activators, or modulators also include genetically modified versions of angiogenesis and tumorigenesis proteins, e.g., versions with altered activity, as well as naturally occurring and synthetic ligands, antagonists, agonists, antibodies, peptides, cyclic peptides, nucleic acids, antisense molecules, ribozymes, RNAi molecules, small organic molecules and the like. Such assays for inhibitors and activators include, e.g., expressing angiogenesis or tumorigenesis protein in vitro, in cells, or cell extracts, applying putative modulator compounds, and then determining the functional effects on activity, as described above.

Samples or assays comprising angiogenesis or tumorigenesis proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of an angiogenesis or tumorigenesis protein is achieved when the activity value relative to the control is about 80%, preferably 50%, more preferably 25-0%. Activation of an angiogenesis or tumorigenesis protein is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate angiogenesis and tumorigenesis. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"RNAi molecule" or an "siRNA" refers to a nucleic acid that forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is 15-50 nucleotides in length, and the double stranded siRNA is about 15-50 base pairs in length, preferable about preferably about 20-30 base nucleotides, preferably about 20-25 nucleotides in length, e.g. 20, 21, 22, 23, 24, 25, 26, 27, 28, 29, or 30 nucleotides in length.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., SEQ ID NO:1 or 2 SEQ ID NO:3 or 4), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=4 and a comparison of both strands. For amino acid sequences, the BLASTP program uses as defaults a wordlength of 3, and expectation (E) of 10, and the BLOSUM62 scoring matrix (see Henikoff& Henikoff, *Proc. Natl. Acad. Sci. USA* 89:10915 (1989)) alignments (B) of 50, expectation (E) of 10, M=5, N=−4, and a comparison of both strands.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., ligand binding domains, etc. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al. (1990) PCR *Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* (3$^{rd}$ ed. 1997)). Techniques for the production of single chain antibodies or recombinant antibodies (U.S. Pat. No. 4,946,778, U.S. Pat. No. 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., *Bio/Technology* 10:779-783 (1992); Lonberg et al., *Nature* 368:856-859 (1994); Morrison, *Nature* 368:812-13 (1994); Fishwild et al., *Nature Biotechnology* 14:845-51 (1996); Neuberger, *Nature Biotechnology* 14:826 (1996); and Lonberg & Huszar, *Intern. Rev. Immunol.* 13:65-93 (1995)). Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)). Antibodies can also be made bispecific, i.e., able to recognize two different antigens (see, e.g., WO 93/08829, Traunecker et al., *EMBO J.* 10:3655-3659 (1991); and Suresh et al., *Methods in Enzymology* 121: 210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522-525 (1986); Riechmann et al., *Nature* 332: 323-327 (1988); Verhoeyen et al., *Science* 239:1534-1536 (1988) and Presta, *Curr. Op. Struct. Biol.* 2:593-596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies, polymorphic variants, alleles, orthologs, and conservatively modified variants, or splice variants, or portions thereof, can be selected to obtain only those polyclonal antibodies that are specifically immunoreactive with angiogenesis proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

Assays for Proteins that Modulate Angiogenesis, Tumorigenesis, and Cellular Proliferation High throughput functional genomics assays can be used to identify modulators of angiogenesis and tumorigenesis. Such assays can monitor changes in cell surface marker expression, $\alpha v\beta 3$ integrin production, proliferation, and differentiation using either cell lines or primary cells. Typically, early passage or primary endothelial cells are contacted with a cDNA or a random peptide library (encoded by nucleic acids). The cDNA library can comprise sense, antisense, full length, and truncated cDNAs. The peptide library is encoded by nucleic acids. The effect of the cDNA or peptide library on the endothelial cells is then monitored, using an assay such as cell surface marker expression (e.g., $\alpha v\beta 3$ integrin) or a phenotypic assay for angiogenesis such as migration towards an ECM (extracellular matrix) component (see, e.g., Klemke et al., *J. Cell Biol.* 4:961-972 (1998)) or endothelial cell tube formation assays, as well as other bioassays such as the chick CAM assay, the mouse corneal assay, haptotaxis assays, VEGF-R assays, co-culture tube formation assays, and assays measuring the effect of administering potential modulators on implanted tumors. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tags. In vivo assays for tumor growth, such as mouse xenograft models, can also be used.

Proteins interacting with the peptide or with the protein encoded by the cDNA can be isolated using a yeast two-hybrid system, mammalian two hybrid system, or phage display screen, etc. Targets so identified can be further used as bait in these assays to identify additional members of the angiogenesis pathway, which members are also targets for drug development (see, e.g., Fields et al., *Nature* 340:245 (1989); Vasavada et al., *Proc. Nat'l Acad. Sci. USA* 88:10686 (1991); Fearon et al., *Proc. Nat'l Acad. Sci. USA* 89:7958 (1992); Dang et al., *Mol. Cell. Biol.* 11:954 (1991); Chien et al., *Proc. Nat'l Acad. Sci. USA* 9578 (1991); and U.S. Pat. Nos. 5,283,173, 5,667,973, 5,468,614, 5,525,490, and 5,637,463).

Suitable endothelial cell lines include human umbilical vein cells (see, e.g., Jaffe et al., *J. Clin. Invest.* 52:2745-2754 (1973)); human adult dermal capillary-derived cells (see, e.g., Davison et al., *In Vitro* 19:937-945 (1983)); human adipose capillary derived cells (see, e.g., Kern et al., *J. Clin Invest.* 71:1822-1829 (1983); bovine aorta (see, e.g., Booyse et al., *Thromb. Diathes. Ahemorrh.* 34:825-839 (1975); and rat brain capillary derived cells (see, e.g., Bowman et al., *In Vitro* 17:353-362 (1981)). For culture of endothelial cell lines, explants, and primary cells, see Freshney et al., *Culture of Animal Cells* (3$^{rd}$ ed. 1994). Suitable angiogenesis cell surface markers include alphavbeta3 integrin (see, e.g., Elicerir & Cheresh, *Cancer J. Sci. Am.* 6 Supp. 3:S245-249 (2000), Maeshima et al., *J. Biol. Chem.* (Jun. 8, 2001)).

Cell surface markers such as $\alpha v\beta 3$ can be assayed using fluorescently labeled antibodies and FACS. Cell proliferation can be measured using $^3$H-thymidine or dye inclusion. Angiogenesis or tumorigenesis phenotype is measured by loss of phenotype observation.

cDNA libraries are made from any suitable source, preferably from endothelial cells. Libraries encoding random peptides are made according to techniques well known to those of skill in the art (see, e.g., U.S. Pat. No. 6,153,380, 6,114,111, and 6,180,343). Any suitable vector can be used for the cDNA and peptide libraries, including, e.g., retroviral vectors.

In a preferred embodiment, target proteins that modulate angiogenesis or tumorigenesis are identified using a high throughput cell based assay (using a microtiter plate format) and FACS screening for $\alpha v\beta 3$ cell surface expression. cDNA libraries are made which include, e.g., sense, antisense, full length, and truncated cDNAs. The cDNAs are cloned into a retroviral vector. Endothelial cells are infected with the library, cultured for a short effector phase and then the cells with reduced $\alpha v\beta 3$ surface levels are enriched by antibody staining and magnetic cell sorting. The enriched cell population is then sorted into microtiter plates using fluorescent antibodies and FACS. Resultant cell colonies are analyzed by immunofluorescence for reduced $\alpha v\beta 3$ surface levels. Selected colonies are infected with wild type MMLV virus to rescue the proviral vector. The infectious supernatant is used to infect endothelial cells, which are subsequently analyzed for $\alpha v\beta 3$ levels by FACS. The cDNA is isolated and sequenced to determined if it represents a wild type or mutated cDNA, e.g., whether the cDNA represents a negative transdominant mutant. Optionally, a marker such as GFP can be used to select for retrovirally infected cells.

Isolation of Nucleic Acids

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Nucleic acids, polymorphic variants, orthologs, and alleles can be isolated using nucleic acid probes and oligonucleotides under stringent hybridization conditions, by screening libraries. Alternatively, expression libraries can be used to clone angiogenesis proteins, polymorphic variants, orthologs, and allels by detecting expressed homologs immunologically with antisera or purified antibodies made against human angiogenesis proteins or portions thereof.

To make a cDNA library, one should choose a source that is rich in the desired RNA, e.g., endothelial cells. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating nucleic acids and orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences directly from mRNA, from cDNA, from genomic libraries or cDNA libraries. Degenerate oligonucleotides can be designed to amplify homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of angiogenesis protein encoding mRNA in physiological samples, for nucleic acid sequencing, or for other purposes. Genes amplified by the PCR reaction can be purified from agarose gels and cloned into an appropriate vector.

Gene expression can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g. and the like.

Nucleic acids can be used with high density oligonucleotide array technology (e.g., GeneChip™) to identify angiogenesis protein, orthologs, alleles, conservatively modified variants, and polymorphic variants in this invention. In the case where the homologs being identified are linked to a known disease state, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

The gene is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding an angiogenesis protein, one typically subclones the desired nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the nucleic acid in host cells. A typical expression cassette thus contains a promoter operably linked to the nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/ $A^+$, pMTO10/$A^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal. Inducible expression vectors are often chosen if expression of the protein of interest is detrimental to eukaryotic cells.

In one embodiment, the vectors of the invention have a regulatablei promoter, e.g., tet-regulated systems and the RU-486 system (see, e.g., Gossen & Bujard, *Proc. Nat'l.*

Acad. Sci. USA 89:5547 (1992); Oligino et al., Gene Ther. 5:491-496 (1998); Wang et al., Gene Ther. 4:432-441 (1997); Neering et al., Blood 88:1147-1155 (1996); and Rendahl et al., Nat. Biotechnol. 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a protein encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of eukaryotic and prokaryotic cells are performed according to standard techniques (see, e.g., Morrison, J. Bact. 132:349-351 (1977); Clark-Curtiss & Curtiss, Methods in Enzymology 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of the protein of choice, which is recovered from the culture using standard techniques identified below.

Purification of Polypeptides

Either naturally occurring or recombinant protein can be purified for use in functional assays. Naturally occurring protein can be purified, e.g., from human tissue. Recombinant protein can be purified from any suitable expression system.

The protein may be purified to substantial purity by standard techniques, including selective precipitation with such substances as ammonium sulfate; column chromatography, immunopurification methods, and others (see, e.g., Scopes, Protein Purification: Principles and Practice (1982); U.S. Pat. No. 4,673,641; Ausubel et al., supra; and Sambrook et al., supra).

A number of procedures can be employed when recombinant protein is being purified. For example, proteins having established molecular adhesion properties can be reversible fused to the protein. With the appropriate ligand, angiogenesis protein can be selectively adsorbed to a purification column and then freed from the column in a relatively pure form. The fused protein is then removed by enzymatic activity. Finally, protein could be purified using immunoaffinity columns.

A. Purification of Protein from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human proteins are separated from other bacterial proteins by standard separation techniques, e.g., with Ni-NTA agarose resin.

Alternatively, it is possible to purify protein from bacteria periplasm. After lysis of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of Angiogenesis or Tumorigenesis Proteins

A. Assays

Modulation of an angiogenesis protein, and corresponding modulation of angiogenesis or tumorigenesis, can be assessed using a variety of in vitro and in vivo assays, including high throughput ligand binding and cell based assays, as described herein. Such assays can be used to test for inhibitors and activators of the angiogenesis protein, and, consequently, inhibitors and activators of angiogenesis. Such modulators of the angiogenesis protein are useful for treating angiogenesis and tumorigenesis disorders. Modulators of the angiogenesis protein are tested using either recombinant or naturally occurring protein, preferably human protein.

Measurement of an angiogenic or tumorigenic or loss-of-angiogenesis or tumorigenesis phenotype on the protein or cell expressing the protein, either recombinant or naturally occurring, can be performed using a variety of assays, in vitro, in vivo, and ex vivo. For example, recombinant or naturally occurring protein can be used in vitro, in a ligand binding or enzymatic function assay. Protein present in a cellular extract can also be used in in vitro assays. Cell- and animal-based in vivo assays can also be used to assay for angiogenesis modulators. Any suitable physical, chemical, or phenotypic change that affects activity or binding can be used to assess the influence of a test compound on the polypeptide of this invention. When the functional effects are determined using intact cells or animals, one can also measure a variety of effects such as, in the case of angiogenesis associated with tumors, tumor growth, neovascularization, endothelial tube formation, cell surface markers such as $\alpha v\beta 3$, hormone release, transcriptional changes to both known and uncharacterized genetic markers (e.g., northern blots), changes in cell metabolism such as cell growth or pH changes, and changes in intracellular second messengers such as cGMP. In one embodiment, measurement of $\alpha v\beta 3$ integrin cell surface expression and FACS sorting is used to identify modulators of angiogenesis.

In Vitro Assays

Assays to identify compounds with angiogenesis or tumorigenesis modulating activity, e.g., anti-angiogenic or anti-tumorigenic activity, can be performed in vitro, e.g., binding assays. Purified recombinant or naturally occurring protein can be used in the in vitro methods of the invention. In addition to purified protein, the recombinant or naturally occurring protein can be part of a cellular lysate. As described below, the assay can be either solid state or soluble. Preferably, the protein is bound to a solid support, either covalently or non-covalently. Often, the in vitro assays of the invention are ligand binding or ligand affinity assays, either non-competitive or competitive. Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the protein or chimera comprising a fragment thereof is contacted with a potential modulator and incubated for a suitable amount of time. In one embodiment, the potential modulator is bound to a solid support, and the protein is added. In another embodiment, the protein is bound to a solid support. A wide variety of modulators can be used, as described below, including small organic molecules, peptides, and antibodies. A wide variety of assays can be used to identify angiogenesis-modulator binding, including labeled protein-protein binding assays, electrophoretic mobility shifts, immunoassays, and the like. In some cases, the binding of the candidate modulator is determined through the use of competitive binding assays, where interference with binding of a known ligand is measured in the presence of a potential modulator. Often, either the potential modulator or the known ligand is labeled.

Cell-Based In Vivo Assays

In another embodiment, the protein is expressed in a cell, and ftmctional, e.g., physical and chemical or phenotypic, changes are assayed to identify angiogenesis or tumorigenesis modulators, preferably anti-angiogenesis or anti-tumorigenesis compounds. Cells expressing angiogenesis proteins can also be used in binding assays or enzymatic assays. Any suitable functional effect can be measured, as described herein. For example, ligand binding, cell surface marker expression, cellular proliferation, VEGF-R assays, co-culture assays for tube formation, and cell migration assays are all suitable assays to identify potential modulators using a cell based system. Suitable cells for such cell based assays include both primary endothelial cells and cell lines, as described herein. The protein can be naturally occurring or recombinant.

As described above, in one embodiment, loss-of angiogenesis or tumorigenesis phenotype is measured by contacting endothelial cells comprising an angiogenesis target with a potential modulator. Modulation of angiogenesis or tumorigenesis is identified by screening for cell surface marker expression, e.g., $\alpha v\beta 3$ integrin expression levels, using fluorescent antibodies and FACS sorting.

In another embodiment, cellular proliferation can be measured using $^3$H-thymidine incorporation or dye inclusion.

In another embodiment, cellular polypeptide levels are determined by measuring the level of protein or mRNA. The level of protein or proteins are measured using immunoassays such as western blotting, ELISA and the like with an antibody that selectively binds to the polypeptide or a fragment thereof. For measurement of mRNA, amplification, e.g., using PCR, LCR, or hybridization assays, e.g., northern hybridization, RNAse protection, dot blotting, are preferred. The level of protein or niRNA is detected using directly or indirectly labeled detection agents, e.g., fluorescently or radioactively labeled nucleic acids, radioactively or enzymatically labeled antibodies, and the like, as described herein.

Alternatively, protein expression can be measured using a reporter gene system. Such a system can be devised using an angiogenesis protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

A variety of phenotypic angiogenesis or tumorigenesis assays are known to those of skill in the art. Various models have been employed to evaluate angiogenesis (e.g., Croix et al., *Science* 289:1197-1202 (2000) and Kahn et al., *Amer. J. Pathol.* 156:1887-1900). Assessment of angiogenesis or tumorigenesis in the presence of a potential modulator can be performed using cell-culture-based assays, e.g., endothelial cell tube formation assays and haptotaxis assays, as well as other animal based bioassays such as the chick CAM assay, the mouse corneal assay, and assays measuring the effect of administering potential modulators on implanted tumors.

For determination of cellular proliferation, any suitable functional effect can be measured, as described herein. For example, cellular morphology (e.g., cell volume, nuclear volume, cell perimeter, and nuclear perimeter), ligand binding, kinase activity, apoptosis, cell surface marker expression, cellular proliferation, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoescht dye with FACS analysis), $G_0/G_1$ cell cycle arrest, are all suitable assays to identify potential modulators using a cell based system. Suitable cells for such cell based assays include both primary cancer or tumor cells and cell lines, as described herein, e.g., A549 (lung), MCF7 (breast; p53 wild-type), H1299 (lung, p53 null), Hela (cervical), PC3 (prostate, p53 mutant), MDA-MB-231 (breast, p53 wild-type). Cancer cell lines can be p53 mutant, p53 null, or express wild type p53.

Animal Models

A number of animal based assays for angiogenesis or tumorigenesis phenotypes are known to those of skill in the art and can be used to assay for modulators of angiogenesis. For example, the chick CAM assay is described by O'Reilly, et al. Cell 79: 315-328 (1994). Briefly, 3 day old chicken embryos with intact yolks are separated from the egg and placed in a petri dish. After 3 days of incubation, a methylcellulose disc containing the protein to be tested is applied to the CAM of individual embryos. After about 48 hours of incubation, the embryos and CAMs are observed to determine whether endothelial growth has been inhibited.

The mouse corneal assay involves implanting a growth factor-containing pellet, along with another pellet containing the suspected endothelial growth inhibitor, in the cornea of a mouse and observing the pattern of capillaries that are elaborated in the cornea.

Angiogenesis can also be measured by determining the extent of neovascularization of a tumor. For example, carcinoma cells can be subcutaneously inoculated into athymic or nude mice or SCID mice and tumor growth then monitored. Immunoassays using endothelial cell-specific antibodies are typically used to stain for vascularization of tumor and the number of vessels in the tumor.

As described above, animal models of angiogenesis find use in screening for modulators of angiogenesis and tumorigenesis. Similarly, transgenic animal technology including gene knockout technology, for example as a result of homologous recombination with an appropriate gene targeting vector, or gene overexpression, will result in the absence or increased expression of the protein. The same technology can also be applied to make knock-out cells. When desired, tissue-specific expression or knockout of the protein may be necessary. Transgenic animals generated by such methods find use as animal models of angiogenesis and are additionally useful in screening for modulators of angiogenesis and tumorigenesis.

Knock-out cells and transgenic mice can be made by insertion of a marker gene or other heterologous gene into the endogenous gene site in the mouse genome via homologous recombination. Such mice can also be made by substituting the endogenous gene with a mutated version of the gene, or by mutating the endogenous gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

B. Modulators

The compounds tested as modulators of the angiogenesis protein can be any small organic molecule, or a biological entity, such as a protein, e.g., an antibody or peptide, a sugar, a nucleic acid, e.g., an antisense oligonucleotide, RNAi molecule, or a ribozyme, or a lipid. Alternatively, modulators can be genetically altered versions of an angiogenesis protein. Typically, test compounds will be small organic molecules, peptides, lipids, and lipid analogs.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St.

Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974, pyrrolidines, U.S. Pat. Nos. 5,525, 735 and 5,519,134; morpholino compounds, U.S. Pat. Nos. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using an angiogenesis protein, or a cell or tissue expressing an angiogenesis protein, either naturally occurring or recombinant. In another embodiment, the invention provides solid phase based in vitro assays in a high throughput format, where the angiogenesis protein is attached to a solid phase substrate. Any one of the assays described herein can be adapted for high throughput screening, e.g., ligand binding, cellular proliferation, cell surface marker flux, e.g., $\alpha v \beta 3$ integrin, etc. In one preferred embodiment, the cell-based system using $\alpha v \beta 3$ integrin modulation and FACS assays is used in a high throughput format for identifying modulators of angiogenesis proteins, and therefore modulators of T cell angiogenesis.

In the high throughput assays of the invention, either soluble or solid state, it is possible to screen up to several thousand different modulators or ligands in a single day. This methodology can be used for angiogenesis proteins in vitro, or for cell-based assays comprising an angiogenesis protein. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The*

*Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as polyGly sequences of between about 5 and 200 amino acids (SEQ ID NO:72). Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Antibodies to Angiogenesis and Tumorigenesis Polypeptides

In addition to the detection of gene and gene expression using nucleic acid hybridization technology, one can also use immunoassays to detect proteins of the invention. Such assays are useful for screening for modulators of angiogenesis, as well as for therapeutic and diagnostic applications. Immunoassays can be used to qualitatively or quantitatively analyze angiogenesis protein. A general overview of the applicable technology can be found in Harlow & Lane, *Antibodies: A Laboratory Manual* (1988).

A. Production of Antibodies

Methods of producing polyclonal and monoclonal antibodies that react specifically with the angiogenesis proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of immunogens comprising portions of an angiogenesis protein may be used to produce antibodies specifically reactive with protein. For example, recombinant protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of 104 or greater are selected and tested for their cross reactivity against non-angiogenesis proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular ortholog, such as a human ortholog, can also be made, by subtracting out other cross-reacting orthologs from a species such as a non-human mammal. In this manner, antibodies that bind only to a desired protein may be obtained.

Once the specific antibodies against the protein are available, the protein can be detected by a variety of immunoassay methods. In addition, the antibody can be used therapeutically as modulators. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

Protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); Basic and Clinical Immunology (Stites & Terr, eds., 7th ed. 1991). Immunological binding assays (or immunoassays) typically use an antibody that specifically binds to a protein or antigen of choice (in this case the protein or antigenic subsequence thereof). The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled protein or a labeled antibody. Alternatively, the labeling agent may be a third moiety, such a secondary antibody, that specifically binds to the antibody/ protein complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111: 1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting protein in samples may be either competitive or noncompetitive. Noncompetitive immunoassays are assays in which the amount of antigen is directly measured. In one preferred "sandwich" assay, for example, the antibodies can be bound directly to a solid substrate on which they are immobilized. These immobilized antibodies then capture protein present in the test sample. Proteins thus immobilized are then bound by a labeling agent, such as a second antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of protein present in the sample is measured indirectly by measuring the amount of a known, added (exogenous) protein displaced (competed away) from an antibody by the unknown protein present in a sample. In one competitive assay, a known amount of protein is added to a sample and the sample is then contacted with an antibody that specifically binds to protein. The amount of exogenous protein bound to the antibody is inversely proportional to the concentration of protein present in the sample. In a particularly preferred embodiment, the antibody is immobilized on a solid substrate. The amount of protein bound to the antibody may be determined either by measuring the amount of protein present in protein/antibody complex, or alternatively by measuring the amount of remaining uncomplexed protein. The amount of protein may be detected by providing a labeled molecule.

A hapten inhibition assay is another preferred competitive assay. In this assay the known protein is immobilized on a solid substrate. A known amount of antibody is added to the sample, and the sample is then contacted with the immobilized protein. The amount of antibody bound to the known immobilized protein is inversely proportional to the amount of protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein can be immobilized to a solid support. Proteins are added to the assay that compete for binding of the antisera to the immobilized antigen. The ability of the added proteins to compete for binding of the antisera to the immobilized protein is compared to the ability of the protein to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein that is required to inhibit 50% of binding, then the second protein is said to specifically bind to the polyclonal antibodies generated to the immunogen.

Other Assay Formats

Western blot (immunoblot) analysis is used to detect and quantify the presence of protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the protein. The antibodies specifically bind to the protein on the solid support. These antibodies may be directly labeled or alternatively may be subsequently detected using labeled antibodies (e.g., labeled sheep anti-mouse antibodies) that specifically bind to the antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize the protein, or secondary antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Gene Therapy

The present invention provides the nucleic acids of angiogenesis or tumorigenesis associated protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a protein of the present invention, thereby mitigating the effects of absent, partial inactivation, or abnormal expression of the angiogenesis or tumorigenesis' gene, particularly as it relates to angiogenesis. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10):1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Böhm eds., 1995); and Yu et al., *Gene Therapy* 1: 13-26 (1994)).

The nucleic acids of the invention can also be used to make transgenic animals, such as transgenic mice, either by knockout or overexpression. Such animals are useful, e.g., for testing modulators of angiogenesis and tumorigenesis.

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17th ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the angiogenesis protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Identification of Genes Involved in Modulation of Angiogenesis and Tumorigenesis In Vitro Using a retroviral base system, complex libraries of cDNAs and GFP-fusions have been expressed in human primary endothelial cells (e.g., HUVECS). Cells that switch to a differentiated angiostatic state can be identified. The cells are then assayed for migration along a haptotactic gradient of specific matrix proteins such as vitronectin and fibronectin in a Boyden chamber assay. Cells were selected for impaired haptotaxis (see, e.g., Klemke et al., *J. Cell Biol.* 4:961-972 (1998)).

Example 2

Identification of Genes Involved in Modulation of Angiogenesis and Tumorigenesis In Vivo This study in mice was designed to provide information on the growth and angiogenic characteristics of MDA-MB-231 infected with either EFS-U6TO-Axl4 vector or EFS-U6TO-FF1 (isogenic negative control) and implanted subcutaneously in mice (Strain:CB-17 scid). MDA-MB-231 (wt) cells will also be implanted and measured. Tumor Cell Injection Density: $1 \times 10^7$ per injection site (shaved right hind flank).

When tumors reach a diameter of approximately 1 cm, animals are randomly divided into subgroups according to tumor size using a stratified randomization method (Day 0). Tumors in selected subgroups are resected by survival surgery and fixed in formalin and the animals will be observed for signs of metastasis via changes in body weight and/or clinical signs. Animals showing any of these signs in severity are terminated and the lungs, liver, sternum, femur, and lymph nodes (axial and mesenteric) are harvested and fixed in 10% buffered formalin for histological examination. Tumors in remaining subgroups will continue to be measured until they reach 2,000 mm3.

The mean tumor volume for each group was calculated for each time point. Comparisons between groups at specific times are made using an unpaired, two-tailed t-test, and the results analyzed using analysis of variance (ANOVA) or the student's t-test. Differentials in tumor growth between groups are determined by calculating volume-doubling time (VDT), or by determining the survival time.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying a compound that inhibits angiogenesis, the method comprising:

assaying in vitro kinase activity of an Axl polypeptide comprising an amino acid sequence with greater than about 95% identity to full length SEQ ID NO: 4 in the presence of the compound, wherein the Axl polypeptide has kinase activity in the absence of said compound;

performing a cell-based assay in an endothelial cell comprising said Axl polypeptide in the presence of the compound, which assay produces an angiogenesis phenotype selected from the group consisting of αvβ3 expression, tube formation, and haptotaxis in said endothelial cell in the absence of the compound; and identifying a compound that inhibits the in vitro kinase activity of the Axl polypeptide and that inhibits the angiogenesis phenotype in the cell-based assay, wherein inhibition of the in vitro kinase activity of the Axl polypeptide in the presence of the compound and inhibition of the angiogenesis phenotype in the cell-based assay in the presence of the compound identifies the compound as a compound that inhibits angiogenesis.

2. The method of claim 1, wherein the polypeptide is recombinant.

3. The method of claim 1, wherein the compound is an antibody.

4. The method of claim 1, wherein the compound is an antisense molecule.

5. The method of claim 1, wherein the compound is an RNAi molecule.

6. The method of claim 1, wherein the compound is a small organic molecule.

7. An in vitro method for identifying a compound that inhibits angiogenesis, the method comprising:

contacting the compound with an endothelial cell that expresses a recombinant Axl polypeptide comprising an amino acid sequence with greater than about 95% identity to full length SEQ ID NO: 4, wherein the Axl polypeptide has kinase activity in the absence of said compound;

performing a cell-based assay, which assay produces an angiogenesis phenotype selected from the group consisting of αvβ3 expression, tube formation, and haptotaxis in said endothelial cell in the absence of the compound; and identifying a compound that inhibits the angiogenesis phenotype in the cell-based assay, wherein inhibition of the angiogenesis phenotype in the cell-based assay in the presence of the compound identifies the compound as a compound that inhibits angiogenesis.

8. The method of claim 7, wherein the compound is an antibody.

9. The method of claim 7, wherein the compound is an antisense molecule.

10. The method of claim 7, wherein the compound is an RNAi molecule.

11. The method of claim 7, wherein the compound is a small organic molecule.

12. The method of claim 1 or 7, wherein the Axl polypeptide comprises SEQ ID NO: 4.

13. The method of claim 1, wherein inhibition of the angiogenesis phenotype in the cell-based assay is caused by down regulation of expression of the Axl polypeptide.

* * * * *

SEQUENCE LISTING

<160> NUMBER OF SEQ ID NOS: 72

<210> SEQ ID NO 1
<211> LENGTH: 80
<212> TYPE: DNA
<213> ORGANISM: Artificial Sequence
<220> FEATURE:
<223> OTHER INFORMATION: Description of Artificial Sequence:synthetic
      Axl GH2_420_G3F1

<400> SEQUENCE: 1 ctccagggt tcaggataac ctccaccctc atccatgttg acatagagga tttcgtcagg      60
ctcctgggca ggaggcaagg                                                 80

<210> SEQ ID NO 2
<211> LENGTH: 113
<212> TYPE: DNA
<213> ORGANISM: Artificial Sequence
<220> FEATURE:
<223> OTHER INFORMATION: Description of Artificial Sequence:synthetic
      Axl GH2_420_G3R1

<400> SEQUENCE: 2
atctatctaa ccactgtgct tgggttctgc ggccttgcct cctgcccagg agcctgacga     60
aatcctctat gtcaacatgg atgagggtgg aggttatcct gaaccccctg gag           113

<210> SEQ ID NO 3
<211> LENGTH: 5014
<212> TYPE: DNA
<213> ORGANISM: Homo sapiens
<220> FEATURE:
<223> OTHER INFORMATION: AXL receptor tyrosine kinase (AXL), transcript
      variant 1 cDNA

<400> SEQUENCE: 3
gagtggagtt ctggaggaat gtttaccaga cacagagccc agagggacag cgcccagagc     60
ccagatagag agacacggcc tcactggctc agcaccaggg tccccttccc cctcctcagc    120
tccctccctg gccccttaa gaaagagctg atcctctcct ctcttgagtt aaccccctgat    180 tgtccaggtg gcccctggct ctggcctggt gggcggaggc aaaggggggag ccaggggcgg    240 agaaagggtt gcccaagtct gggagtgagg gaaggaggca ggggtgctga gaaggcggct    300
gctgggcaga gccggtggca agggcctccc ctgccgctgt gccaggcagg cagtgccaaa    360
tccggggagc ctggagctgg gggagggcc ggggacagcc cggccctgcc ccctcccccg    420
ctgggagccc agcaacttct gaggaaagtt tggcacccat ggcgtggcgg tgccccagga    480
tgggcagggt cccgctggcc tggtgcttgg cgctgtgcgg ctgggcgtgc atggccccca    540
ggggcacgca ggctgaagaa agtcccttcg tgggcaaccc agggaatatc acaggtgccc    600
ggggactcac gggcacccctt cggtgtcagc tccaggttca gggagagccc ccgaggtac    660 attggcttcg ggatggacag atcctggagc tcgcggacag cacccagacc caggtgcccc    720
tgggtgagga tgaacaggat gactggatag tggtcagcca gctcagaatc acctccctgc    780
agctttccga cacgggacag taccagtgtt tggtgtttct gggacatcag accttcgtgt    840
cccagcctgg ctatgttggg ctggaggct tgccttactt cctggaggag cccgaagaca    900
ggactgtggc cgccaacacc cccttcaacc tgagctgcca agctcaggga ccccagagc    960 ccgtggacct actctggctc caggatgctg tcccctgcc cacggctcca ggtcacggcc   1020
cccagcgcag cctgcatgtt ccagggctga acaagacatc ctctttctcc tgcgaagccc   1080

```
ataacgccaa gggggtcacc acatcccgca cagccaccat cacagtgctc ccccagcagc   1140
cccgtaacct ccacctggtc tcccgccaac ccacggagct ggaggtggct tggactccag   1200
gcctgagcgg catctacccc ctgacccact gcaccctgca ggctgtgctg tcagacgatg   1260
ggatgggcat ccaggcggga gaaccagacc ccccagagga gcccctcacc tcgcaagcat   1320
ccgtgccccc ccatcagctt cggctaggca gcctccatcc tcacacccct tatcacatcc   1380
gcgtggcatg caccagcagc cagggcccct catcctggac ccactggctt cctgtggaga   1440
cgccggaggg agtgccctg ggccccctg agaacattag tgctacgcgg aatgggagcc   1500
aggccttcgt gcattggcaa gagccccggg cgccctgca gggtaccctg ttagggtacc   1560
ggctggcgta tcaaggccag gacaccccag aggtgctaat ggacataggg ctaaggcaag   1620
aggtgaccct ggagctgcag ggggacgggt ctgtgtccaa tctgacagtg tgtgtggcag   1680
cctacactgc tgctggggat ggaccctgga gcctcccagt accctggag gcctggcgcc   1740
cagggcaagc acagccagtc caccagctgg tgaaggaacc ttcaactcct gccttctcgt   1800
ggccctggtg gtatgtactg ctaggagcag tcgtggccgc tgcctgtgtc ctcatcttgg   1860
ctctcttcct tgtccaccgg cgaaagaagg agacccgtta tggagaagtg tttgaaccaa   1920
cagtggaaag aggtgaactg gtagtcaggt accgcgtgcg caagtcctac agtcgtcgga   1980
ccactgaagc taccttgaac agcctgggca tcagtgaaga gctgaaggag aagctgcggg   2040
atgtgatggt ggaccggcac aaggtggccc tggggaagac tctgggagag ggagagtttg   2100
gagctgtgat ggaaggccag ctcaaccagg acgactccat cctcaaggtg gctgtgaaga   2160
cgatgaagat tgccatctgc acgaggtcag agctggagga tttcctgagt gaagcggtct   2220
gcatgaagga atttgaccat cccaacgtca tgaggctcat cggtgtctgt ttccagggtt   2280
ctgaacgaga gagcttccca gcacctgtgg tcatcttacc tttcatgaaa catggagacc   2340
tacacagctt cctcctctat tcccggctcg ggaccagcc agtgtacctg cccactcaga   2400
tgctagtgaa gttcatggca gacatcgcca gtggcatgga gtatctgagt accaagagat   2460
tcatacaccg ggacctggcg gccaggaact gcatgctgaa tgagaacatg tccgtgtgtg   2520
tggcggactt cgggctctcc aagaagatct acaatgggga ctactaccgc cagggacgta   2580
tcgccaagat gccagtcaag tggattgcca ttgagagtct agctgaccgt gtctacacca   2640
gcaagagcga tgtgtggtcc ttcggggtga caatgtggga gattgccaca agaggccaaa   2700
ccccatatcc gggcgtggag aacagcgaga tttatgacta tctgcgccag ggaaatcgcc   2760
tgaagcagcc tgcggactgt ctggatggac tgtatgcctt gatgtcgcgg tgctgggagc   2820
taaatcccca ggaccggcca agttttacag agctgcggga agatttggag aacacactga   2880
aggccttgcc tcctgcccag gagcctgacg aaatcctcta tgtcaacatg gatgagggtg   2940
gaggttatcc tgaaccccct ggagctgcag gaggagctga cccccaacc cagccagacc   3000
ctaaggattc ctgtagctgc tcactgcggc tgaggtcca tcctgctgga cgctatgtcc   3060
tctgcccttc cacaaccct agcccgctc agcctgctga tagggctcc ccagcagccc   3120
cagggcagga ggatggtgcc tgagacaacc ctccacctgg tactccctct caggatccaa   3180
gctaagcact gccactgggg aaaactccac cttcccactt tcccacccca cgccttatcc   3240
ccacttgcag ccctgtcttc ctaccttatcc cacctccatc ccagacaggt ccctcccctt   3300
ctctgtgcag tagcatcacc ttgaaagcag tagcatcacc atctgtaaaa ggaaggggtt   3360
ggattgcaat atctgaagcc ctcccaggtg ttaacattcc aagactctag agtccaaggt   3420
ttaaagagtc tagattcaaa ggttctaggt ttcaaagatg ctgtgagtct tggttctaa   3480
```

```
ggacctgaaa ttccaaagtc tctaattcta ttaaagtgct aaggttctaa ggcctacttt    3540
tttttttttt tttttttttt tttttttttt tgcgatagag tctcactgtg tcacccaggc    3600
tggagtgcag tggtgcaatc tcgcctcact gcaaccttca cctaccgagt tcaagtgatt    3660
ttcctgcctt ggcctcccaa gtagctggga ttacaggtgt gtgccaccac acccggctaa    3720
tttttatatt tttagtagag acagggtttc accatgttgg ccaggctggt ctaaaactcc    3780
tgacctcaag tgatctgccc acctcagcct cccaaagtgc tgagattaca ggcatgagcc    3840
actgcactca accttaagac ctactgttct aaagctctga cattatgtgg ttttagattt    3900
tctggttcta acattttga taaagcctca aggttttagg ttctaaagtt ctaagattct    3960
gattttagga gctaaggctc tatgagtcta atgtttatt cttctagagt tcagagtcct    4020
taaaatgtaa gattatagat tctaaagatt ctatagttct agacatggag gttctaaggc    4080
ctaggattct aaaatgtgat gttctaaggc tctgagagtc tagattctct ggctgtaagg    4140
ctctagatca taaggcttca aaatgttatc ttctcaagtt ctaagattct aatgatgatc    4200
aattatagtt tctgaggctt tatgataata gattctcttg tataagatcc tagatcctaa    4260
gggtcgaaag ctctagaatc tgcaattcaa aagttccaag agtctaaaga tggagttct    4320 aaggtccggt gttctaagat gtgatattct aagacttact ctaagatctt agattctctg    4380
tgtctaagat tctagatcag atgctccaag attctagatg attaaataag attctaacgg    4440
tctgttctgt ttcaaggcac tctagattcc attggtccaa gattccggat cctaagcatc    4500
taagttataa gactctcaca ctcagttgtg actaactaga caccaaagtt ctaataattt    4560
ctaatgttgg acacctttag gttctttgct gcattctgcc tctctaggac catggttaag    4620
agtccaagaa tccacatttc taaaatctta tagttctagg cactgtagtt ctaagactca    4680
aatgttctaa gtttctaaga ttctaaaggt ccacaggtct agactattag gtgcaatttc    4740
aaggttctaa ccctatactg tagtattctt tggggtgccc ctctccttct tagctatcat    4800
tgcttcctcc tccccaactg tgggggtgtg ccccttcaa gcctgtgcaa tgcattaggg    4860
atgcctcctt tcccgcaggg gatggacgat ctcccacctt tcgggccatg ttgccccgt     4920 gagccaatcc ctcaccttct gagtacagag tgtggactct ggtgcctcca gaggggctca    4980
ggtcacataa aactttgtat atcaacgaaa aaaa                                5014
```

<210> SEQ ID NO 4
<211> LENGTH: 894
<212> TYPE: PRT
<213> ORGANISM: Homo sapiens
<220> FEATURE:
<223> OTHER INFORMATION: AXL receptor tyrosine kinase (AXL), isoform 1;
      AXL transforming sequence/gene; oncogene AXL

<400> SEQUENCE: 4

```
Met Ala Trp Arg Cys Pro Arg Met Gly Arg Val Pro Leu Ala Trp Cys
 1               5                  10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
```

-continued

```
                85                  90                  95
Ile Val Val Ser Gln Leu Arg Ile Thr Ser Leu Gln Leu Ser Asp Thr
            100                 105                 110
Gly Gln Tyr Gln Cys Leu Val Phe Leu Gly His Gln Thr Phe Val Ser
            115                 120                 125
Gln Pro Gly Tyr Val Gly Leu Glu Gly Leu Pro Tyr Phe Leu Glu Glu
            130                 135                 140
Pro Glu Asp Arg Thr Val Ala Ala Asn Thr Pro Phe Asn Leu Ser Cys
145                 150                 155                 160
Gln Ala Gln Gly Pro Pro Glu Pro Val Asp Leu Leu Trp Leu Gln Asp
                165                 170                 175
Ala Val Pro Leu Ala Thr Ala Pro Gly His Gly Pro Gln Arg Ser Leu
            180                 185                 190
His Val Pro Gly Leu Asn Lys Thr Ser Ser Phe Ser Cys Glu Ala His
            195                 200                 205
Asn Ala Lys Gly Val Thr Thr Ser Arg Thr Ala Thr Ile Thr Val Leu
            210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
                245                 250                 255
His Cys Thr Leu Gln Ala Val Leu Ser Asp Asp Gly Met Gly Ile Gln
            260                 265                 270
Ala Gly Glu Pro Asp Pro Pro Glu Glu Pro Leu Thr Ser Gln Ala Ser
            275                 280                 285
Val Pro Pro His Gln Leu Arg Leu Gly Ser Leu His Pro His Thr Pro
            290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                325                 330                 335
Pro Glu Asn Ile Ser Ala Thr Arg Asn Gly Ser Gln Ala Phe Val His
            340                 345                 350
Trp Gln Glu Pro Arg Ala Pro Leu Gln Gly Thr Leu Leu Gly Tyr Arg
            355                 360                 365
Leu Ala Tyr Gln Gly Gln Asp Thr Pro Glu Val Leu Met Asp Ile Gly
            370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                405                 410                 415
Trp Ser Leu Pro Val Pro Leu Glu Ala Trp Arg Pro Gly Gln Ala Gln
            420                 425                 430
Pro Val His Gln Leu Val Lys Glu Pro Ser Thr Pro Ala Phe Ser Trp
            435                 440                 445
Pro Trp Trp Tyr Val Leu Leu Gly Ala Val Val Ala Ala Ala Cys Val
            450                 455                 460
Leu Ile Leu Ala Leu Phe Leu Val His Arg Arg Lys Lys Glu Thr Arg
465                 470                 475                 480
Tyr Gly Glu Val Phe Glu Pro Thr Val Glu Arg Gly Glu Leu Val Val
                485                 490                 495
Arg Tyr Arg Val Arg Lys Ser Tyr Ser Arg Arg Thr Thr Glu Ala Thr
            500                 505                 510
```

```
Leu Asn Ser Leu Gly Ile Ser Glu Glu Leu Lys Glu Lys Leu Arg Asp
        515                 520                 525

Val Met Val Asp Arg His Lys Val Ala Leu Gly Lys Thr Leu Gly Glu
        530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
    610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 5
<211> LENGTH: 4987
<212> TYPE: DNA
<213> ORGANISM: Homo sapiens
<220> FEATURE:
<223> OTHER INFORMATION: AXL receptor tyrosine kinase (AXL), transcript
      variant 2 cDNA
```

<400> SEQUENCE: 5

```
gagtggagtt ctggaggaat gtttaccaga cacagagccc agagggacag cgcccagagc    60
ccagatagag agacacggcc tcactggctc agcaccaggg tccccttccc cctcctcagc   120
tccctccctg gcccctttaa gaaagagctg atcctctcct ctcttgagtt aaccctgat    180
tgtccaggtg gcccctggct ctggcctggt gggcggaggc aaagggggag ccaggggcgg   240
agaaagggtt gcccaagtct gggagtgagg gaaggaggca ggggtgctga gaaggcggct   300
gctgggcaga gccggtggca agggcctccc ctgccgctgt gccaggcagg cagtgccaaa   360
tccggggagc ctggagctgg ggggagggcc gggacagccc cggccctgcc ccctccccg    420
ctggagccc agcaacttct gaggaaagtt tggcacccat ggcgtggcgg tgccccagga   480
tgggcagggt cccgctggcc tggtgcttgg cgctgtgcgg ctgggcgtgc atggccccca   540
ggggcacgca ggctgaagaa agtcccttcg tgggcaaccc agggaatatc acaggtgccc   600
ggggactcac gggcacccct tcggtgtcag ctccaggttc agggagagcccc ccgaggtac   660
attggcttcg ggatggacag atcctggagc tcgcggacag cacccagacc caggtgcccc   720
tgggtgagga tgaacaggat gactggatag tggtcagcca gctcagaatc acctccctgc   780
agctttccga cacgggacag taccagtgtt tggtgtttct gggacatcag accttcgtgt   840
cccagcctgg ctatgttggg ctggagggct tgccttactt cctggaggag cccgaagaca   900
ggactgtggc cgccaacacc cccttcaacc tgagctgcca agctcaggga ccccagagc    960
ccgtggacct actctggctc caggatgctg tcccctggc cacggctcca ggtcacggcc  1020
cccagcgcag cctgcatgtt ccagggctga caagacatc ctctttctcc tgcgaagccc  1080
ataacgccaa gggggtcacc acatcccgca cagccaccat cacagtgctc ccccagcagc  1140
cccgtaacct ccacctggtc tcccgccaac ccacggagct ggaggtggct tggactccag  1200
gcctgagcgg catctacccc ctgacccact gcacccctgca ggctgtgctg tcagacgatg  1260
ggatgggcat ccaggcggga gaaccagacc ccccagagga gccctcacc tcgcaagcat   1320
ccgtgccccc ccatcagctt cggctaggca gcctccatcc tcacacccct tatcacatcc  1380
gcgtggcatg caccagcagc cagggcccct catcctggac ccactggctt cctgtggaga  1440
cgccggaggt agtgccctg gcccccctg agaacattag tgctacgcgg aatgggagcc    1500
aggccttcgt gcattggcaa gagcccccggg cgccctgca gggtaccctg ttagggtacc   1560
ggctggcgta tcaaggccag gacacccaag aggtgctaat ggacataggg ctaaggcaag   1620
aggtgaccct ggagctgcag ggggacgggt ctgtgtccaa tctgacagtg tgtgtggcag   1680
cctacactgc tgctggggat ggaccctgga gcctccagt accccctgag gcctggcgcc   1740
cagtgaagga accttcaact cctgccttct cgtggccctg gtggtatgta ctgctaggag   1800
cagtcgtggc cgctgcctgt gtcctcatct tggctctctt ccttgtccac cggcgaaaga   1860
aggagacccg ttatggagaa gtgtttgaac caacagtgga aagaggtgaa ctggtagtca   1920
ggtaccgcgt gcgcaagtcc tacagtcgtc ggaccactga agctaccttg aacagcctgg  1980
gcatcagtga agagctgaag gagaagctgc gggatgtgat ggtggaccgg cacaaggtgg   2040
ccctggggaa gactctggga gagggagagt ttggagctgt gatgaaggc cagctcaacc    2100
aggacgactc catcctcaag gtggctgtga agacgatgaa gattgccatc tgcacgaggt   2160
cagagctgga ggatttcctg agtgaagcgg tctgcatgaa ggaatttgac catcccaacg   2220
tcatgaggct catcggtgtc tgtttccagg gttctgaacg agagagcttc ccagcacctg   2280
tggtcatctt acctttcatg aaacatggag acctacacag cttcctcctc tattcccggc   2340
```

```
tcggggacca gccagtgtac ctgcccactc agatgctagt gaagttcatg gcagacatcg    2400
ccagtggcat ggagtatctg agtaccaaga gattcataca ccgggacctg gcggccagga    2460
actgcatgct gaatgagaac atgtccgtgt gtgtggcgga cttcgggctc tccaagaaga    2520
tctacaatgg ggactactac cgccagggac gtatcgccaa gatgccagtc aagtggattg    2580
ccattgagag tctagctgac cgtgtctaca ccagcaagag cgatgtgtgg tccttcgggg    2640
tgacaatgtg ggagattgcc acaagaggcc aaacccata tccgggcgtg gagaacagcg     2700
agatttatga ctatctgcgc cagggaaatc gcctgaagca gcctgcggac tgtctggatg    2760
gactgtatgc cttgatgtcg cggtgctggg agctaaatcc ccaggaccgg ccaagttta    2820 cagagctgcg ggaagatttg gagaacacac tgaaggcctt gcctcctgcc caggagcctg    2880
acgaaatcct ctatgtcaac atggatgagg gtggaggtta tcctgaaccc cctggagctg    2940
caggaggagc tgacccccca acccagccag accctaagga ttcctgtagc tgcctcactg    3000
cggctgaggt ccatcctgct ggacgctatg tcctctgccc ttccacaacc cctagccccg    3060
ctcagcctgc tgatagggc tccccagcag ccccagggca ggaggatggt gcctgagaca     3120
accctccacc tggtactccc tctcaggatc caagctaagc actgccactg gggaaaactc    3180
caccttccca ctttcccacc ccacgcctta tccccacttg cagccctgtc ttcctaccta    3240
tcccacctcc atcccagaca ggtccctccc cttctctgtg cagtagcatc accttgaaag    3300
cagtagcatc accatctgta aaaggaaggg gttggattgc aatatctgaa gccctcccag    3360
gtgttaacat tccaagactc tagagtccaa ggtttaaaga gtctagattc aaaggttcta    3420
ggtttcaaag atgctgtgag tctttggttc taaggacctg aaattccaaa gtctctaatt    3480
ctattaaagt gctaaggttc taaggcctac tttttttttt tttttttttt tttttttttt    3540
ttttgcgata gagtctcact gtgtcaccca ggctggagtg cagtggtgca atctcgcctc    3600
actgcaacct tcacctaccg agttcaagtg attttcctgc cttggcctcc caagtagctg    3660
ggattacagg tgtgtgccac cacacccggc taattttta atttttagta gagacagggt     3720
ttcaccatgt tggccaggct ggtctaaaac tcctgacctc aagtgatctg cccacctcag    3780
cctcccaaag tgctgagatt acaggcatga gccactgcac tcaaccttaa gacctactgt    3840
tctaaagctc tgacattatg tggttttaga ttttctggtt ctaacatttt tgataaagcc    3900
tcaaggtttt aggttctaaa gttctaagat tctgatttta ggagctaagg ctctatgagt    3960
ctagatgttt attcttctag agttcagagt ccttaaaatg taagattata gattctaaag    4020
attctatagt tctagacatg gaggttctaa ggcctaggat tctaaaatgt gatgttctaa    4080
ggctctgaga gtctagattc tctggctgta aggctctaga tcataaggct tcaaaatgtt    4140
atcttctcaa gttctaagat tctaatgatg atcaattata gtttctgagg ctttatgata    4200
atagattctc ttgtataaga tcctagatcc taagggtcga aagctctaga atctgcaatt    4260
caaaagttcc aagagtctaa agatggagtt tctaaggtcc ggtgttctaa gatgtgatat    4320
tctaagactt actctaagat cttagattct ctgtgtctaa gattctagat cagatgctcc    4380
aagattctag atgattaaat aagattctaa cggtctgttc tgtttcaagg cactctagat    4440
tccattggtc caagattccg gatcctaagc atctaagtta taagactctc acactcagtt    4500
gtgactaact agacaccaaa gttctaataa tttctaatgt tggacacctt taggttcttt    4560
gctgcattct gcctctctag gaccatggtt aagagtccaa gaatccacat ttctaaaatc    4620
ttatagttcc aggcactgta gttctaagac tcaaatgttc taagtttcta agattctaaa    4680
ggtccacagg tctagactat taggtgcaat ttcaaggttc taaccctata ctgtagtatt    4740
```

```
ctttggggtg ccctctcct tcttagctat cattgcttcc tcctcccaa ctgtgggggt    4800 gtgccccctt caagcctgtg caatgcatta gggatgcctc ctttcccgca ggggatggac    4860
gatctcccac ctttcgggcc atgttgcccc cgtgagccaa tccctcacct tctgagtaca    4920
gagtgtggac tctggtgcct ccagagggc tcaggtcaca taaaactttg tatatcaacg    4980
aaaaaaa                                                              4987
```

```
<210> SEQ ID NO 6
<211> LENGTH: 885
<212> TYPE: PRT
<213> ORGANISM: Homo sapiens
<220> FEATURE:
<223> OTHER INFORMATION: AXL receptor tyrosine kinase (AXL), isoform 2;
      AXL transforming sequence/gene; oncogene AXL

<400> SEQUENCE: 6
```

```
Met Ala Trp Arg Cys Pro Arg Met Gly Arg Val Pro Leu Ala Trp Cys
  1               5                  10                  15

Leu Ala Leu Cys Gly Trp Ala Cys Met Ala Pro Arg Gly Thr Gln Ala
             20                  25                  30

Glu Glu Ser Pro Phe Val Gly Asn Pro Gly Asn Ile Thr Gly Ala Arg
         35                  40                  45

Gly Leu Thr Gly Thr Leu Arg Cys Gln Leu Gln Val Gln Gly Glu Pro
     50                  55                  60

Pro Glu Val His Trp Leu Arg Asp Gly Gln Ile Leu Glu Leu Ala Asp
 65                  70                  75                  80

Ser Thr Gln Thr Gln Val Pro Leu Gly Glu Asp Gln Asp Asp Trp
                 85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asp Asp Gly Met Gly Ile Gln
            260                 265                 270

Ala Gly Glu Pro Asp Pro Pro Glu Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
```

```
            305                 310                 315                 320
Thr His Trp Leu Pro Val Glu Thr Pro Glu Gly Val Pro Leu Gly Pro
                    325                 330                 335

Pro Glu Asn Ile Ser Ala Thr Arg Asn Gly Ser Gln Ala Phe Val His
                340                 345                 350

Trp Gln Glu Pro Arg Ala Pro Leu Gln Gly Thr Leu Leu Gly Tyr Arg
            355                 360                 365

Leu Ala Tyr Gln Gly Gln Asp Thr Pro Glu Val Leu Met Asp Ile Gly
        370                 375                 380

Leu Arg Gln Glu Val Thr Leu Glu Leu Gln Gly Asp Gly Ser Val Ser
385                 390                 395                 400

Asn Leu Thr Val Cys Val Ala Ala Tyr Thr Ala Gly Asp Gly Pro
                405                 410                 415

Trp Ser Leu Pro Val Pro Leu Glu Ala Trp Arg Pro Val Lys Glu Pro
                420                 425                 430

Ser Thr Pro Ala Phe Ser Trp Pro Trp Trp Tyr Val Leu Leu Gly Ala
                435                 440                 445

Val Val Ala Ala Ala Cys Val Leu Ile Leu Ala Leu Phe Leu Val His
        450                 455                 460

Arg Arg Lys Lys Glu Thr Arg Tyr Gly Glu Val Phe Glu Pro Thr Val
465                 470                 475                 480

Glu Arg Gly Glu Leu Val Val Arg Tyr Arg Val Arg Lys Ser Tyr Ser
                    485                 490                 495

Arg Arg Thr Thr Glu Ala Thr Leu Asn Ser Leu Gly Ile Ser Glu Glu
                500                 505                 510

Leu Lys Glu Lys Leu Arg Asp Val Met Val Asp Arg His Lys Val Ala
            515                 520                 525

Leu Gly Lys Thr Leu Gly Glu Gly Glu Phe Gly Ala Val Met Glu Gly
        530                 535                 540

Gln Leu Asn Gln Asp Asp Ser Ile Leu Lys Val Ala Val Lys Thr Met
545                 550                 555                 560

Lys Ile Ala Ile Cys Thr Arg Ser Glu Leu Glu Asp Phe Leu Ser Glu
                565                 570                 575

Ala Val Cys Met Lys Glu Phe Asp His Pro Asn Val Met Arg Leu Ile
                580                 585                 590

Gly Val Cys Phe Gln Gly Ser Glu Arg Glu Ser Phe Pro Ala Pro Val
            595                 600                 605

Val Ile Leu Pro Phe Met Lys His Gly Asp Leu His Ser Phe Leu Leu
        610                 615                 620

Tyr Ser Arg Leu Gly Asp Gln Pro Val Tyr Leu Pro Thr Gln Met Leu
625                 630                 635                 640

Val Lys Phe Met Ala Asp Ile Ala Ser Gly Met Glu Tyr Leu Ser Thr
                645                 650                 655

Lys Arg Phe Ile His Arg Asp Leu Ala Ala Arg Asn Cys Met Leu Asn
                660                 665                 670

Glu Asn Met Ser Val Cys Val Ala Asp Phe Gly Leu Ser Lys Lys Ile
            675                 680                 685

Tyr Asn Gly Asp Tyr Tyr Arg Gln Gly Arg Ile Ala Lys Met Pro Val
        690                 695                 700

Lys Trp Ile Ala Ile Glu Ser Leu Ala Asp Arg Val Tyr Thr Ser Lys
705                 710                 715                 720

Ser Asp Val Trp Ser Phe Gly Val Thr Met Trp Glu Ile Ala Thr Arg
                725                 730                 735
```

-continued

```
Gly Gln Thr Pro Tyr Pro Gly Val Glu Asn Ser Glu Ile Tyr Asp Tyr
                740                 745                 750

Leu Arg Gln Gly Asn Arg Leu Lys Gln Pro Ala Asp Cys Leu Asp Gly
            755                 760                 765

Leu Tyr Ala Leu Met Ser Arg Cys Trp Glu Leu Asn Pro Gln Asp Arg
    770                 775                 780

Pro Ser Phe Thr Glu Leu Arg Glu Asp Leu Glu Asn Thr Leu Lys Ala
785                 790                 795                 800

Leu Pro Pro Ala Gln Glu Pro Asp Glu Ile Leu Tyr Val Asn Met Asp
                805                 810                 815

Glu Gly Gly Gly Tyr Pro Glu Pro Pro Gly Ala Ala Gly Gly Ala Asp
            820                 825                 830

Pro Pro Thr Gln Pro Asp Pro Lys Asp Ser Cys Ser Cys Leu Thr Ala
        835                 840                 845

Ala Glu Val His Pro Ala Gly Arg Tyr Val Leu Cys Pro Ser Thr Thr
850                 855                 860

Pro Ser Pro Ala Gln Pro Ala Asp Arg Gly Ser Pro Ala Ala Pro Gly
865                 870                 875                 880

Gln Glu Asp Gly Ala
                885

<210> SEQ ID NO 7
<211> LENGTH: 266
<212> TYPE: DNA
<213> ORGANISM: Artificial Sequence
<220> FEATURE:
<223> OTHER INFORMATION: Description of Artificial Sequence:synthetic
      tubulin cofactor D GH1-13-PCR-G3F1

<400> SEQUENCE: 7
cttccgcagc agggtctggt tgctctcagg gagtctgcag ccatcgaggc acctgaggac      60
agtggcagca tagggcaaac agtcttcacg ttttccatgt ttaaatattt gtgccagggc     120
ctgcagcgtc ccatccatgg tgatgacccc ctgcatggtc tggaaggagg aacgggccag     180
attgcacagg ctccagtcca ggaactcagc catcttgctt tgcttgacat caggacgtgt     240
gataaatctg gacacaagga cagcag                                          266

<210> SEQ ID NO 8
<211> LENGTH: 3927
<212> TYPE: DNA
<213> ORGANISM: Homo sapiens
<220> FEATURE:
<223> OTHER INFORMATION: tubulin-specific chaperone d (TBCD), tubulin
      cofactor D cDNA

<400> SEQUENCE: 8
tagcgggcgc ctccttttca tccctcatcc ttcatccctg gctttcgcgc tctagcggag      60
tgggatctgc gaacacgtga ggcgggggcg cggtccccag gctgccgaga tggccctgag     120
cgacgaaccg gccgcgggtg gccccgagga ggaggcggag gacgagacac tggcctttgg     180
cgcggcgctg gaagcgttcg gcgagagcgc ggagacccgg cgctgctggg ccgcctgcg     240 ggaggtgcac ggcggcggcg cggagcgcga ggtggccctg agcggttcc gcgtaataat     300 ggacaaatac caggagcagc ctcatctgtt ggacccgcac cttgaatgga tgatgaactt     360
gttgttggac atagtgcaag atcagacatc tccagcttcc cttgtacatc tggcttttaa     420
atttctttac atcatcacca aggttcgagg ctataaaaca tttcttcgtt tatttcctca     480
tgaagttgcc gatgtagagc ctgttttaga tttggtcaca attcagaatc ccaaggacca     540
```

-continued

```
tgaagcttgg gaaacccgct acatgctttt gctctggctc tccgtgacct gcctgatccc      600
ttttgatttt tctcgccttg acgggaacct cctcacccag cctgggcaag cacgaatgtc      660
cataatggac cgtattctcc aaatagcaga gtcctacttg attgtcagtg acaaggcccg      720
agatgcagct gctgtccttg tgtccagatt tatcacacgt cctgatgtca agcaaagcaa      780
gatggctgag ttcctggact ggagcctgtg caatctggcc cgttcctcct tccagaccat      840
gcaggggtc atcaccatgg atgggacgct gcaggcctg gcacaaatat ttaaacatgg       900
aaaacgtgaa gactgtttgc cctatgctgc cactgtcctc aggtgcctcg atggctgcag      960
actccctgag agcaaccaga ccctgctgcg gaagctgggg gtgaagcttg tgcagcgact     1020
ggggctgaca ttcctgaagc cgaaggtggc agcatggagg taccagcgtg gctgccgatc     1080
tttggctgca aatctgcagc tcctcactca gggtcagagt gagcagaagc cactcatcct     1140
gaccgaagat gacgacgaag atgacgacgt cccagagggg gtggagcgtg tgatagagca     1200
gctgctggtc gggctgaagg acaaggacac ggtcgtgcgg tggtctgcag ccaagggcat     1260
cggtaggatg gctggcaggc ttcccagagc cctggcggat gatgtggtcg ggtctgtgct     1320
ggactgcttc agtttccagg agactgacaa ggcgtggcat gggggatgtc tggcgctggc     1380
agagctgggc aggagaggcc tgttgctgcc gtctcgactc gtggatgttg tcgccgtgat     1440
cctgaaggcg ctgacctacg acgagaagcg gggtgcctgc agcgtgggca ccaacgtcag     1500
ggacgccgcc tgctacgtgt gctgtgcctt cgcgcgtgcc tatgagcctc aggagctgaa     1560
gcccttgtg actgcaatct cgagtgcact ggtgattgct gcggtgtttg accgagacat     1620
aaactgcaga agagcagcct ctgccgcctt ccaggagaat gtggggagac agggcacttt     1680
ccctcatggt attgatattt tgaccacagc tgactatttt gccgtcggta acagatccaa     1740
ctgtttcctg gttataagtg tgtttattgc cggctttcct gagtacacgc agccaatgat     1800
agaccacctg gttaccatga agatcagcca ctgggatggg gtcatccgag agttggctgc     1860
gagggcgctg cacaacctgg cccagcaggc acccgagttc agcgccacgc aagtcttccc     1920
gaggctgctg tccatgacac tgagtccaga tcttcacatg aggcatgggt cgattctcgc     1980
ctgcgcagaa gttgcttacg ccttgtacaa acttgcagcc caagagaaca ggcccgtcac     2040
ggaccatctg gacgagcagg cagtgcaggg cctgaagcag attcaccagc agctctatga     2100
tcgtcagtta tacaggggtc tgggaggaca gctcatgaga caagcagtgt gtgtttttaat    2160
agaaaagttg tcactttcca aaatgccctt tagaggtgac accgtaattg atggttggca     2220
atggctgata aatgacactt tgagacatct ccatctcatc tcaagtcact cccgccagca     2280
gatgaaggat gcagcagtct cggccctggc tgctctatgc agtgaatatt acatgaagga     2340
gccggggag gcagatcccg caattcagga ggagctgatc acgcagtacc tggctgagct      2400
tcggaacccc gaggagatga ctcgctgtgg cttctcgttg gccttgggcg cccttccagg     2460
cttccttctg aaaggccggc tccagcaggt tctcacaggt ttaagagcag ttacccacac     2520
ttccccccgag gacgtaagtt ttgctgagtc caggagagac ggcttgaagg ccattgcgag    2580
gatttgccag actgttggtg tgaaagcagg agccccagac gaagctgtgt gcggagagaa     2640
tgtttcccag atttactgtg cgctgctggg ctgcatggac gactacacca cggacagcag     2700
aggggacgtg ggcacctggg tccgcaaggc cgccatgacc agtctgatgg atctgacact     2760
tctgctggct cggagccagc ctgagctgat cgaggcccat acctgtgagc gcatcatgtg     2820
ctgtgtggcc cagcaggcca gtgagaagat tgaccgtttc cgtgctcacg ccgccagcgt     2880
gttcctgacg ctcctgcact ttgacagccc tcccatcccc cacgtgcccc accgaggaga     2940
```

-continued

```
actggaaaag ctgtttccca ggtccgatgt ggcctccgtg aactggagtg caccttccca    3000
ggccttccca cgcatcaccc agctccttgg gctgcccacc taccgctacc acgtcctgct    3060
ggggctagtc gtgtccctgg gcggcttgac ggagtcgacg atccggcact ccacccagag    3120
cctctttgag tacatgaagg gcattcgaga cgacccgcag gccctgggca gcttcagcgg    3180 gaccccttctg cagatctttg aggacaacct tctgaatgag agggtgtccg tgccgctgct    3240
gaagacgctg gaccacgtgc tcacccacgg ctgcttcgac atcttcacca cggaggagga    3300 ccacccctt gctgtgaagt tgcttgcgct ctgtaagaaa gaaatcaaga attcaaaaga    3360
tatccagaag ctcctgtcag gcatcgcagt gttctgcggg atggtgcagt ccccggcga    3420 cgtgaggagg caggccctcc tgcagctgtg tctgctcctc tgccaccgtt cccgctgat    3480 ccggaagacc acggccagcc aggtgtacga gacattgctc acctacagtg acgtcgtggg    3540
cgcggatgtg ctggacgagg tggtgactgt gctcagtgac actgcgtggg acgcggagct    3600
tgcagtggtg agagagcagc gcaaccgtct gtgtgacctt ctgggcgtac ccaggcccca    3660
gctggtgccc cagcctggtg cctgctgaag ccagtcctgg agcccatacc tcacccctgc    3720
ctggtgagga tgtcttgttc ctgagggagg ccggtgtgga aagccttgca cagtggtgcc    3780
tccagctgtt gaagggtagc gctggccctt ggaggctggc actagctgac agcttttcct    3840
ctctgcacct cgctctggt gacttgggg ggacgcctct gccttcactt gaacacaaat    3900
gtgcttccta taaaatcatg taccaag                                         3927
```

<210> SEQ ID NO 9
<211> LENGTH: 1192
<212> TYPE: PRT
<213> ORGANISM: Homo sapiens
<220> FEATURE:
<223> OTHER INFORMATION: beta-tubulin cofactor D

<400> SEQUENCE: 9

```
Met Ala Leu Ser Asp Glu Pro Ala Ala Gly Gly Pro Glu Glu Glu Ala
  1               5                  10                  15

Glu Asp Glu Thr Leu Ala Phe Gly Ala Ala Leu Glu Ala Phe Gly Glu
             20                  25                  30

Ser Ala Glu Thr Arg Ala Leu Leu Gly Arg Leu Arg Glu Val His Gly
         35                  40                  45

Gly Gly Ala Glu Arg Glu Val Ala Leu Glu Arg Phe Arg Val Ile Met
     50                  55                  60

Asp Lys Tyr Gln Glu Gln Pro His Leu Asp Pro His Leu Glu Trp
 65                  70                  75                  80

Met Met Asn Leu Leu Leu Asp Ile Val Gln Asp Gln Thr Ser Pro Ala
                 85                  90                  95

Ser Leu Val His Leu Ala Phe Lys Phe Leu Tyr Ile Ile Thr Lys Val
            100                 105                 110

Arg Gly Tyr Lys Thr Phe Leu Arg Leu Phe Pro His Glu Val Ala Asp
        115                 120                 125

Val Glu Pro Val Leu Asp Leu Val Thr Ile Gln Asn Pro Lys Asp His
    130                 135                 140

Glu Ala Trp Glu Thr Arg Tyr Met Leu Leu Trp Leu Ser Val Thr
145                 150                 155                 160

Cys Leu Ile Pro Phe Asp Phe Ser Arg Leu Asp Gly Asn Leu Leu Thr
                165                 170                 175

Gln Pro Gly Gln Ala Arg Met Ser Ile Met Asp Arg Ile Leu Gln Ile
            180                 185                 190
```

```
Ala Glu Ser Tyr Leu Ile Val Ser Asp Lys Ala Arg Asp Ala Ala Ala
            195                 200                 205

Val Leu Val Ser Arg Phe Ile Thr Arg Pro Asp Val Lys Gln Ser Lys
        210                 215                 220

Met Ala Glu Phe Leu Asp Trp Ser Leu Cys Asn Leu Ala Arg Ser Ser
225                 230                 235                 240

Phe Gln Thr Met Gln Gly Val Ile Thr Met Asp Gly Thr Leu Gln Ala
                245                 250                 255

Leu Ala Gln Ile Phe Lys His Gly Lys Arg Glu Asp Cys Leu Pro Tyr
            260                 265                 270

Ala Ala Thr Val Leu Arg Cys Leu Asp Gly Cys Arg Leu Pro Glu Ser
        275                 280                 285

Asn Gln Thr Leu Leu Arg Lys Leu Gly Val Lys Leu Val Gln Arg Leu
    290                 295                 300

Gly Leu Thr Phe Leu Lys Pro Lys Val Ala Ala Trp Arg Tyr Gln Arg
305                 310                 315                 320

Gly Cys Arg Ser Leu Ala Ala Asn Leu Gln Leu Leu Thr Gln Gly Gln
                325                 330                 335

Ser Glu Gln Lys Pro Leu Ile Leu Thr Glu Asp Asp Glu Asp Asp
            340                 345                 350

Asp Val Pro Glu Gly Val Glu Arg Val Ile Glu Gln Leu Leu Val Gly
        355                 360                 365

Leu Lys Asp Lys Asp Thr Val Val Arg Trp Ser Ala Ala Lys Gly Ile
    370                 375                 380

Gly Arg Met Ala Gly Arg Leu Pro Arg Ala Leu Ala Asp Asp Val Val
385                 390                 395                 400

Gly Ser Val Leu Asp Cys Phe Ser Phe Gln Glu Thr Asp Lys Ala Trp
                405                 410                 415

His Gly Gly Cys Leu Ala Leu Ala Glu Leu Gly Arg Arg Gly Leu Leu
            420                 425                 430

Leu Pro Ser Arg Leu Val Asp Val Ala Val Ile Leu Lys Ala Leu
        435                 440                 445

Thr Tyr Asp Glu Lys Arg Gly Ala Cys Ser Val Gly Thr Asn Val Arg
    450                 455                 460

Asp Ala Ala Cys Tyr Val Cys Cys Ala Phe Ala Arg Ala Tyr Glu Pro
465                 470                 475                 480

Gln Glu Leu Lys Pro Phe Val Thr Ala Ile Ser Ser Ala Leu Val Ile
                485                 490                 495

Ala Ala Val Phe Asp Arg Asp Ile Asn Cys Arg Arg Ala Ala Ser Ala
            500                 505                 510

Ala Phe Gln Glu Asn Val Gly Arg Gln Gly Thr Phe Pro His Gly Ile
        515                 520                 525

Asp Ile Leu Thr Thr Ala Asp Tyr Phe Ala Val Gly Asn Arg Ser Asn
    530                 535                 540

Cys Phe Leu Val Ile Ser Val Phe Ile Ala Gly Phe Pro Glu Tyr Thr
545                 550                 555                 560

Gln Pro Met Ile Asp His Leu Val Thr Met Lys Ile Ser His Trp Asp
                565                 570                 575

Gly Val Ile Arg Glu Leu Ala Ala Arg Ala Leu His Asn Leu Ala Gln
            580                 585                 590

Gln Ala Pro Glu Phe Ser Ala Thr Gln Val Phe Pro Arg Leu Leu Ser
        595                 600                 605

Met Thr Leu Ser Pro Asp Leu His Met Arg His Gly Ser Ile Leu Ala
    610                 615                 620
```

```
Cys Ala Glu Val Ala Tyr Ala Leu Tyr Lys Leu Ala Ala Gln Glu Asn
625                 630                 635                 640

Arg Pro Val Thr Asp His Leu Asp Glu Gln Ala Val Gln Gly Leu Lys
            645                 650                 655

Gln Ile His Gln Gln Leu Tyr Asp Arg Gln Leu Tyr Arg Gly Leu Gly
        660                 665                 670

Gly Gln Leu Met Arg Gln Ala Val Cys Val Leu Ile Glu Lys Leu Ser
    675                 680                 685

Leu Ser Lys Met Pro Phe Arg Gly Asp Thr Val Ile Asp Gly Trp Gln
690                 695                 700

Trp Leu Ile Asn Asp Thr Leu Arg His Leu His Leu Ile Ser Ser His
705                 710                 715                 720

Ser Arg Gln Gln Met Lys Asp Ala Ala Val Ser Ala Leu Ala Ala Leu
                725                 730                 735

Cys Ser Glu Tyr Tyr Met Lys Glu Pro Gly Glu Ala Asp Pro Ala Ile
            740                 745                 750

Gln Glu Glu Leu Ile Thr Gln Tyr Leu Ala Glu Leu Arg Asn Pro Glu
        755                 760                 765

Glu Met Thr Arg Cys Gly Phe Ser Leu Ala Leu Gly Ala Leu Pro Gly
    770                 775                 780

Phe Leu Leu Lys Gly Arg Leu Gln Gln Val Leu Thr Gly Leu Arg Ala
785                 790                 795                 800

Val Thr His Thr Ser Pro Glu Asp Val Ser Phe Ala Glu Ser Arg Arg
                805                 810                 815

Asp Gly Leu Lys Ala Ile Ala Arg Ile Cys Gln Thr Val Gly Val Lys
            820                 825                 830

Ala Gly Ala Pro Asp Glu Ala Val Cys Gly Glu Asn Val Ser Gln Ile
        835                 840                 845

Tyr Cys Ala Leu Leu Gly Cys Met Asp Asp Tyr Thr Thr Asp Ser Arg
    850                 855                 860

Gly Asp Val Gly Thr Trp Val Arg Lys Ala Ala Met Thr Ser Leu Met
865                 870                 875                 880

Asp Leu Thr Leu Leu Leu Ala Arg Ser Gln Pro Glu Leu Ile Glu Ala
                885                 890                 895

His Thr Cys Glu Arg Ile Met Cys Cys Val Ala Gln Gln Ala Ser Glu
            900                 905                 910

Lys Ile Asp Arg Phe Arg Ala His Ala Ala Ser Val Phe Leu Thr Leu
        915                 920                 925

Leu His Phe Asp Ser Pro Pro Ile Pro His Val Pro His Arg Gly Glu
    930                 935                 940

Leu Glu Lys Leu Phe Pro Arg Ser Asp Val Ala Ser Val Asn Trp Ser
945                 950                 955                 960

Ala Pro Ser Gln Ala Phe Pro Arg Ile Thr Gln Leu Leu Gly Leu Pro
                965                 970                 975

Thr Tyr Arg Tyr His Val Leu Leu Gly Leu Val Val Ser Leu Gly Gly
            980                 985                 990

Leu Thr Glu Ser Thr Ile Arg His Ser Thr Gln Ser Leu Phe Glu Tyr
        995                 1000                1005

Met Lys Gly Ile Gln Ser Asp Pro Gln Ala Leu Gly Ser Phe Ser Gly
    1010                1015                1020

Thr Leu Leu Gln Ile Phe Glu Asp Asn Leu Leu Asn Glu Arg Val Ser
1025                1030                1035                1040

Val Pro Leu Leu Lys Thr Leu Asp His Val Leu Thr His Gly Cys Phe
```

Asp Ile Phe Thr Thr Glu Glu Asp His Pro Phe Ala Val Lys Leu Leu
            1045               1050               1055
                1060               1065               1070

Ala Leu Cys Lys Lys Glu Ile Lys Asn Ser Lys Asp Ile Gln Lys Leu
    1075               1080               1085

Leu Ser Gly Ile Ala Val Phe Cys Gly Met Val Gln Phe Pro Gly Asp
 1090               1095               1100

Val Arg Arg Gln Ala Leu Leu Gln Leu Cys Leu Leu Cys His Arg
1105               1110               1115               1120

Phe Pro Leu Ile Arg Lys Thr Thr Ala Ser Gln Val Tyr Glu Thr Leu
        1125               1130               1135

Leu Thr Tyr Ser Asp Val Val Gly Ala Asp Val Leu Asp Glu Val Val
            1140               1145               1150

Thr Val Leu Ser Asp Thr Ala Trp Asp Ala Glu Leu Ala Val Val Arg
        1155               1160               1165

Glu Gln Arg Asn Arg Leu Cys Asp Leu Leu Gly Val Pro Arg Pro Gln
    1170               1175               1180

Leu Val Pro Gln Pro Gly Ala Cys
1185               1190

<210> SEQ ID NO 10
<211> LENGTH: 331
<212> TYPE: DNA
<213> ORGANISM: Artificial Sequence
<220> FEATURE:
<223> OTHER INFORMATION: Description of Artificial Sequence:synthetic
      transglutaminase 2 GH1-173-PCR-G3F1

<400> SEQUENCE: 10
ccagtgtgct tgggttctgc ggcaccctgg atctccccaa actcattgcg gaagtactcg    60
atgagaaggt tgctgttctg gtcatgggcc gagttgtagt tggtcacgac gcgggtaggg   120
atgcccaggc acctcagcac tgtgcaggcc acggcggcaa gacccagcac tggccatact   180
tgacgcgctg gcagccgtgg ttcttccagc gccgcaggat gtccacgctg ccgatccagg   240
acatggggct gacccgcaga cccagcacag tggttagatg ataaagcggc cgctcgacta   300
gtctgaggtc tgatactcac tgactgtcgt a                                  331

<210> SEQ ID NO 11
<211> LENGTH: 687
<212> TYPE: PRT
<213> ORGANISM: Homo sapiens
<220> FEATURE:
<223> OTHER INFORMATION: transglutaminase 2, protein-glutamine
      gamma-glutamyltransferase, tissue transglutaminase
      (TGase C, TGC, TGase-H)

<400> SEQUENCE: 11

Met Ala Glu Glu Leu Val Leu Glu Arg Cys Asp Leu Glu Leu Glu Thr
 1               5                  10                  15

Asn Gly Arg Asp His His Thr Ala Asp Leu Cys Arg Glu Lys Leu Val
            20                  25                  30

Val Arg Arg Gly Gln Pro Phe Trp Leu Thr Leu His Phe Glu Gly Arg
        35                  40                  45

Asn Tyr Glu Ala Ser Val Asp Ser Leu Thr Phe Ser Val Val Thr Gly
    50                  55                  60

Pro Ala Pro Ser Gln Glu Ala Gly Thr Lys Ala Arg Phe Pro Leu Arg
65                  70                  75                  80

Asp Ala Val Glu Glu Gly Asp Trp Thr Ala Thr Val Val Asp Gln Gln

```
                     85                  90                  95
Asp Cys Thr Leu Ser Leu Gln Leu Thr Thr Pro Ala Asn Ala Pro Ile
                100                 105                 110
Gly Leu Tyr Arg Leu Ser Leu Glu Ala Ser Thr Gly Tyr Gln Gly Ser
                115                 120                 125
Ser Phe Val Leu Gly His Phe Ile Leu Leu Phe Asn Ala Trp Cys Pro
                130                 135                 140
Ala Asp Ala Val Tyr Leu Asp Ser Glu Glu Arg Gln Glu Tyr Val
145                 150                 155                 160
Leu Thr Gln Gln Gly Phe Ile Tyr Gln Gly Ser Ala Lys Phe Ile Lys
                165                 170                 175
Asn Ile Pro Trp Asn Phe Gly Gln Phe Glu Asp Gly Ile Leu Asp Ile
                180                 185                 190
Cys Leu Ile Leu Leu Asp Val Asn Pro Lys Phe Leu Lys Asn Ala Gly
                195                 200                 205
Arg Asp Cys Ser Arg Arg Ser Pro Val Tyr Val Gly Arg Val Val
                210                 215                 220
Ser Gly Met Val Asn Cys Asn Asp Asp Gln Gly Val Leu Leu Gly Arg
225                 230                 235                 240
Trp Asp Asn Asn Tyr Gly Asp Gly Val Ser Pro Met Ser Trp Ile Gly
                245                 250                 255
Ser Val Asp Ile Leu Arg Arg Trp Lys Asn His Gly Cys Gln Arg Val
                260                 265                 270
Lys Tyr Gly Gln Cys Trp Val Phe Ala Ala Val Ala Cys Thr Val Leu
                275                 280                 285
Arg Cys Leu Gly Ile Pro Thr Arg Val Val Thr Asn Tyr Asn Ser Ala
                290                 295                 300
His Asp Gln Asn Ser Asn Leu Leu Ile Glu Tyr Phe Arg Asn Glu Phe
305                 310                 315                 320
Gly Glu Ile Gln Gly Asp Lys Ser Glu Met Ile Trp Asn Phe His Cys
                325                 330                 335
Trp Val Glu Ser Trp Met Thr Arg Pro Asp Leu Gln Pro Gly Tyr Glu
                340                 345                 350
Gly Trp Gln Ala Leu Asp Pro Thr Pro Gln Glu Lys Ser Glu Gly Thr
                355                 360                 365
Tyr Cys Cys Gly Pro Val Pro Val Arg Ala Ile Lys Glu Gly Asp Leu
                370                 375                 380
Ser Thr Lys Tyr Asp Ala Pro Phe Val Phe Ala Glu Val Asn Ala Asp
385                 390                 395                 400
Val Val Asp Trp Ile Gln Gln Asp Asp Gly Ser Val His Lys Ser Ile
                405                 410                 415
Asn Arg Ser Leu Ile Val Gly Leu Lys Ile Ser Thr Lys Ser Val Gly
                420                 425                 430
Arg Asp Glu Arg Glu Asp Ile Thr His Thr Tyr Lys Tyr Pro Glu Gly
                435                 440                 445
Ser Ser Glu Glu Arg Glu Ala Phe Thr Arg Ala Asn His Leu Asn Lys
                450                 455                 460
Leu Ala Glu Lys Glu Glu Thr Gly Met Ala Met Arg Ile Arg Val Gly
465                 470                 475                 480
Gln Ser Met Asn Met Gly Ser Asp Phe Asp Val Phe Ala His Ile Thr
                485                 490                 495
Asn Asn Thr Ala Glu Glu Tyr Val Cys Arg Leu Leu Leu Cys Ala Arg
                500                 505                 510
```

-continued

```
Thr Val Ser Tyr Asn Gly Ile Leu Gly Pro Glu Cys Gly Thr Lys Tyr
    515                 520                 525

Leu Leu Asn Leu Asn Leu Glu Pro Phe Ser Glu Lys Ser Val Pro Leu
    530                 535                 540

Cys Ile Leu Tyr Glu Lys Tyr Arg Asp Cys Leu Thr Glu Ser Asn Leu
545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
            580                 585                 590

Ile Leu Gly Glu Pro Lys Gln Lys Arg Lys Leu Val Ala Glu Val Ser
        595                 600                 605

Leu Gln Asn Pro Leu Pro Val Ala Leu Glu Gly Cys Thr Phe Thr Val
    610                 615                 620

Glu Gly Ala Gly Leu Thr Glu Glu Gln Lys Thr Val Glu Ile Pro Asp
625                 630                 635                 640

Pro Val Glu Ala Gly Glu Val Lys Val Arg Met Asp Leu Leu Pro
                645                 650                 655

Leu His Met Gly Leu His Lys Leu Val Val Asn Phe Glu Ser Asp Lys
            660                 665                 670

Leu Lys Ala Val Lys Gly Phe Arg Asn Val Ile Ile Gly Pro Ala
        675                 680                 685

<210> SEQ ID NO 12
<211> LENGTH: 3257
<212> TYPE: DNA
<213> ORGANISM: Homo sapiens
<220> FEATURE:
<223> OTHER INFORMATION: transglutaminase 2, C polypeptide,
      protein-glutamine gamma-glutamyltransferase (TGM2)
      cDNA

<400> SEQUENCE: 12
aacaggcgtg acgccagttc taaacttgaa acaaaacaaa acttcaaagt acaccaaaat     60
agaacctcct taaagcataa atctcacgga gggtctcggc cgccagtgga aggagccacc    120
gcccccgccc cgaccatggc cgaggagctg gtcttagaga ggtgtgatct ggagctggag    180
accaatggcc gagaccacca cacggccgac ctgtgccggg agaagctggt ggtgcgacgg    240
ggccagccct tctggctgac cctgcacttt gagggccgca actaccaggc cagtgtagac    300
agtctcacct tcagtgtcgt gaccggccca gcccctagcc aggaggccgg gaccaaggcc    360
cgttttccac taagagatgc tgtggaggag ggtgactgga cagccaccgt ggtggaccag    420
caagactgca ccctctcgct gcagctcacc accccggcca acgcccccat cggcctgtat    480
cgcctcagcc tggaggcctc cactggctac cagggatcca gctttgtgct gggccacttc    540
attttgctct tcaacgcctg gtgcccagcg gatgctgtgt acctggactc ggaagaggag    600
cggcaggagt atgtcctcac ccagcagggc tttatctacc agggctcggc caagttcatc    660
aagaacatac cttggaattt tgggcagttt caagatggga tcctagacat ctgcctgatc    720
cttctagatg tcaaccccaa gttcctgaag aacgccggcc gtgactgctc ccggcgcagc    780
agccccgtct acgtgggccg ggtgggtagt ggcatggtca actgcaacga tgaccagggt    840
gtgctgctgg gacgctggga caacaactac ggggacggcg tcagcccat gtcctggatc    900 ggcagcgtgg acatcctgcg gcgctggaag aaccacggct ccagcgcgt caagtatggc    960 cagtgctggg tcttcgccgc cgtggcctgc acagtgctga ggtgcctagg catccctacc   1020
cgcgtcgtga ccaactacaa ctcggcccat gaccagaaca gcaaccttct catcgagtac   1080
```

```
ttccgcaatg agtttgggga gatccagggt gacaagagcg agatgatctg gaacttccac    1140
tgctgggtgg agtcgtggat gaccaggccg gacctgcagc cggggtacga gggctggcag    1200
gccctggacc caacgcccca ggagaagagc gaaggaacgt actgctgtgg cccagttcca    1260
gttcgtgcca tcaaggaggg cgacctgagc accaagtacg atgcgccctt tgtctttgcg    1320
gaggtcaatg ccgacgtggt agactggatc cagcaggacg atgggtctgt gcacaaatcc    1380
atcaaccgtt ccctgatcgt tgggctgaag atcagcacta agagcgtggg ccgagacgag    1440
cgggaggata tcacccacac ctacaaatac ccagaggggt cctcagagga gagggaggcc    1500
ttcacaaggg cgaaccacct gaacaaactg gccgagaagg aggagacagg gatggccatg    1560
cggatccgtg tgggccagag catgaacatg ggcagtgact tgacgtctt tgcccacatc    1620 accaacaaca ccgctgagga gtacgtctgc cgcctcctgc tctgtgcccg caccgtcagc    1680
tacaatggga tcttggggcc cgagtgtggc accaagtacc tgctcaacct aaccctggag    1740
cctttctctg agaagagcgt tcctctttgc atcctctatg agaaataccg tgactgcctt    1800
acggagtcca acctcatcaa ggtgcgggcc ctcctcgtgg agccagttat caacagctac    1860
ctgctggctg agagggacct ctacctggag aatccagaaa tcaagatccg gatccttggg    1920
gagcccaagc agaaacgcaa gctggtggct gaggtgtccc tgcagaaccc gctccctgtg    1980
gccctggaag gctgcacctt cactgtggag ggggccggcc tgactgagga gcagaagacg    2040
gtggagatcc cagaccccgt ggaggcaggg gaggaagtta aggtgagaat ggacctcgtg    2100
ccgctccaca tgggcctcca caagctggtg gtgaacttcg agagcgacaa gctgaaggct    2160
gtgaagggct tccggaatgt catcattggc cccgcctaag gaccctgc tcccagcctg    2220 ctgagagccc ccaccttgat cccaatcctt atcccaagct agtgagcaaa atatgccct    2280 tattgggccc cagaccccag ggcagggtgg gcagcctatg ggggctctcg gaaatggaat    2340
gtgcccctgg cccatctcag cctcctgagc ctgtgggtcc ccactcaccc cctttgctgt    2400
gaggaatgct ctgtgccaga aacagtggga gccctgacct gtgctgactg gggctggggt    2460
gagagaggaa agacctacat tccctctcct gcccagatgc cctttggaaa gccattgacc    2520
acccaccata ttgtttgatc tacttcatag ctccttggag caggcaaaaa agggacagca    2580
tgcccttggc tggatcagga atccagctcc ctagactgca tcccgtacct cttcccatga    2640
ctgcacccag ctccaggggc ccttgggaca cccagagctg ggtggggaca gtgataggcc    2700
caaggtcccc tccacatccc agcagcccaa gcttaatagc cctcccctc aacctcacca    2760 ttgtgaagca cctactatgt gctgggtgcc tcccacactt gctgggctc acggggcctc    2820 caacccattt aatcaccatg ggaaactgtt gtgggcgctg cttccaggat aaggagactg    2880
aggcttagag agaggaggca gcccctcca ccagtggc ctcgtggtta taagcaaggc    2940
tgggtaatgt gaaggcccaa gagcagagtc tgggcctctg actctgagtc cactgctcca    3000
tttataaccc cagcctgacc tgagactgtc gcagaggctg tctggggcct ttatcaaaaa    3060
aagactcagc caagacaagg aggtagagag gggactgggg gactgggagt cagagccctg    3120
gctgggttca ggtccacgt ctggccagcg actgccttct cctctctggg cctttgtttc    3180
cttgttggtc agaggagtga ttgaacctgc tcatctccaa ggatcctctc cactccatgt    3240
ttgcaataca caattcc                                                   3257
```

<210> SEQ ID NO 13
<211> LENGTH: 687
<212> TYPE: PRT
<213> ORGANISM: Homo sapiens
<220> FEATURE:
<223> OTHER INFORMATION: transglutaminase 2, C polypeptide,
      protein-glutamine-gamma-glutamyltransferase

<400> SEQUENCE: 13

```
Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
            20                  25                  30

Val Arg Arg Gly Gln Pro Phe Trp Leu Thr Leu His Phe Glu Gly Arg
        35                  40                  45

Asn Tyr Gln Ala Ser Val Asp Ser Leu Thr Phe Ser Val Val Thr Gly
    50                  55                  60

Pro Ala Pro Ser Gln Glu Ala Gly Thr Lys Ala Arg Phe Pro Leu Arg
65                  70                  75                  80

Asp Ala Val Glu Glu Gly Asp Trp Thr Ala Thr Val Val Asp Gln Gln
                85                  90                  95

Asp Cys Thr Leu Ser Leu Gln Leu Thr Thr Pro Ala Asn Ala Pro Ile
            100                 105                 110

Gly Leu Tyr Arg Leu Ser Leu Glu Ala Ser Thr Gly Tyr Gln Gly Ser
        115                 120                 125

Ser Phe Val Leu Gly His Phe Ile Leu Leu Phe Asn Ala Trp Cys Pro
    130                 135                 140

Ala Asp Ala Val Tyr Leu Asp Ser Glu Glu Glu Arg Gln Glu Tyr Val
145                 150                 155                 160

Leu Thr Gln Gln Gly Phe Ile Tyr Gln Gly Ser Ala Lys Phe Ile Lys
                165                 170                 175

Asn Ile Pro Trp Asn Phe Gly Gln Phe Gln Asp Gly Ile Leu Asp Ile
            180                 185                 190

Cys Leu Ile Leu Leu Asp Val Asn Pro Lys Phe Leu Lys Asn Ala Gly
        195                 200                 205

Arg Asp Cys Ser Arg Arg Ser Ser Pro Val Tyr Val Gly Arg Val Gly
    210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Val Ser Pro Met Ser Trp Ile Gly
                245                 250                 255

Ser Val Asp Ile Leu Arg Arg Trp Lys Asn His Gly Cys Gln Arg Val
            260                 265                 270

Lys Tyr Gly Gln Cys Trp Val Phe Ala Ala Val Ala Cys Thr Val Leu
        275                 280                 285

Arg Cys Leu Gly Ile Pro Thr Arg Val Val Thr Asn Tyr Asn Ser Ala
    290                 295                 300

His Asp Gln Asn Ser Asn Leu Leu Ile Glu Tyr Phe Arg Asn Glu Phe
305                 310                 315                 320

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
            340                 345                 350

Gly Trp Gln Ala Leu Asp Pro Thr Pro Gln Glu Lys Ser Glu Gly Thr
        355                 360                 365

Tyr Cys Cys Gly Pro Val Pro Val Arg Ala Ile Lys Glu Gly Asp Leu
    370                 375                 380

Ser Thr Lys Tyr Asp Ala Pro Phe Val Phe Ala Glu Val Asn Ala Asp
385                 390                 395                 400
```

Val Val Asp Trp Ile Gln Gln Asp Asp Gly Ser Val His Lys Ser Ile
            405                 410                 415

Asn Arg Ser Leu Ile Val Gly Leu Lys Ile Ser Thr Lys Ser Val Gly
        420                 425                 430

Arg Asp Glu Arg Glu Asp Ile Thr His Thr Tyr Lys Tyr Pro Glu Gly
    435                 440                 445

Ser Ser Glu Glu Arg Glu Ala Phe Thr Arg Ala Asn His Leu Asn Lys
450                 455                 460

Leu Ala Glu Lys Glu Thr Gly Met Ala Met Arg Ile Arg Val Gly
465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Leu Cys Ala Arg
            500                 505                 510

Thr Val Ser Tyr Asn Gly Ile Leu Gly Pro Glu Cys Gly Thr Lys Tyr
        515                 520                 525

Leu Leu Asn Leu Thr Leu Glu Pro Phe Ser Glu Lys Ser Val Pro Leu
    530                 535                 540

Cys Ile Leu Tyr Glu Lys Tyr Arg Asp Cys Leu Thr Glu Ser Asn Leu
545                 550                 555                 560

Ile Lys Val Arg Ala Leu Leu Val Glu Pro Val Ile Asn Ser Tyr Leu
                565                 570                 575

Leu Ala Glu Arg Asp Leu Tyr Leu Glu Asn Pro Glu Ile Lys Ile Arg
            580                 585                 590

Ile Leu Gly Glu Pro Lys Gln Lys Arg Lys Leu Val Ala Glu Val Ser
        595                 600                 605

Leu Gln Asn Pro Leu Pro Val Ala Leu Glu Gly Cys Thr Phe Thr Val
    610                 615                 620

Glu Gly Ala Gly Leu Thr Glu Glu Gln Lys Thr Val Glu Ile Pro Asp
625                 630                 635                 640

Pro Val Glu Ala Gly Glu Glu Val Lys Val Arg Met Asp Leu Val Pro
                645                 650                 655

Leu His Met Gly Leu His Lys Leu Val Val Asn Phe Glu Ser Asp Lys
            660                 665                 670

Leu Lys Ala Val Lys Gly Phe Arg Asn Val Ile Ile Gly Pro Ala
        675                 680                 685

<210> SEQ ID NO 14
<211> LENGTH: 1781
<212> TYPE: DNA
<213> ORGANISM: Homo sapiens
<220> FEATURE:
<223> OTHER INFORMATION: similar to transglutaminase 2, C polypeptide,
      protein-glutamine-gamma-glutamyltransferase, clone
      MGC:1193 cDNA

<400> SEQUENCE: 14
ctccgcctcg gcagtgccag ccgccagtgg tcgcacttgg agggtctcgc cgccagtgga      60
aggagccacc gccccgccc gaccatggcc gaggagctgg tcttagagag gtgtgatctg     120
gagctggaga ccaatggccg agaccaccac acggccgacc tgtgccggga agctggtg      180 gtgcgacggg gccagccctt ctggctgacc ctgcactttg agggccgcaa ctacgaggcc     240
agtgtagaca gtctcacctt cagtgtcgtg accggcccag ccctagcca ggaggccggg     300 accaaggccc gttttccact aagagatgct gtggaggagg gtgactggac agccaccgtg     360
gtggaccagc aagactgcac cctctcgctg cagctcacca cccggccaa cgcccccatc     420

```
ggcctgtatc gcctcagcct ggaggcctcc actggctacc agggatccag ctttgtgctg      480
ggccacttca ttttgctctt caacgcctgg tgcccagcgg atgctgtgta cctggactcg      540
gaagaggagc ggcaggagta tgtcctcacc cagcagggct ttatctacca gggctcggcc      600
aagttcatca agaacatacc ttggaatttt gggcagtttg aagatgggat cctagacatc      660
tgcctgatcc ttctagatgt caaccccaag ttcctgaaga cgccggccg tgactgctcc      720 cgccgcagca gccccgtcta cgtgggccgg tggtgagtg gcatggtcaa ctgcaacgat      780
gaccagggtg tgctgctggg acgctgggac aacaactacg ggacggcgt cagccccatg      840 tcctggatcg gcagcgtgga catcctgcgg cgctggaaga ccacggctg ccagcgcgtc      900 aagtatggcc agtgctgggt cttcgccgcc gtggcctgca cagtgctgag gtgcctgggc      960
atccctaccc gcgtcgtgac caactacaac tcggcccatg accagaacag caaccttctc     1020
atcgagtact ccgcaatga gtttggggag atccaggtg acaagagcga gatgatctgg      1080
aacttccact gctgggtgga gtcgtggatg accaggccgg acctgcagcc ggggtacgag      1140
ggctggcagg ccctggaccc aacgccccag gagaagagcg aagggacgta ctgctgtggc      1200
ccagttccag ttcgtgccat caaggagggc gacctgagca ccaagtacga tgcgcccttt      1260
gtctttgcgg aggtcaatgc cgacgtggta gactggatcc agcaggacga tgggtctgtg      1320
cacaaatcca tcaaccgttc cctgatcgtt gggctgaaga tcagcactaa gagcgtgggc      1380
cgagacgagc gggaggatat cacccacacc tacaaatacc agaggggtc ctcagaggag      1440 agggaggcct tcacaagggc gaaccacctg aacaaactgg ccgagaagga ggagacaggg      1500
atggccatgc ggatccgtgt gggccagagc atgaacatgg gcagtgactt tgacgtcttt      1560
gcccacatca ccaacaacac cgctgaggag tacgtctgcc gcctcctgct ctgtgcccgc      1620
accgtcagct acaatgggat cttggggccc gagtgtggca ccaagtacct gctcaacctc     1680
aacctggagc ctttctctgg taaagccctg tgttcctgga gcatttgttg accgccaact     1740
gacaacatgc taggtagtga cctaaaaaaa aaaaaaaaaa a                          1781
```

<210> SEQ ID NO 15
<211> LENGTH: 548
<212> TYPE: PRT
<213> ORGANISM: Homo sapiens
<220> FEATURE:
<223> OTHER INFORMATION: similar to transglutaminase 2, C polypeptide,
      protein-glutamine gamma-glutamyltransferase

<400> SEQUENCE: 15

```
Met Ala Glu Glu Leu Val Leu Glu Arg Cys Asp Leu Glu Leu Glu Thr
  1               5                  10                  15

Asn Gly Arg Asp His His Thr Ala Asp Leu Cys Arg Glu Lys Leu Val
             20                  25                  30

Val Arg Arg Gly Gln Pro Phe Trp Leu Thr Leu His Phe Glu Gly Arg
         35                  40                  45

Asn Tyr Glu Ala Ser Val Asp Ser Leu Thr Phe Ser Val Val Thr Gly
     50                  55                  60

Pro Ala Pro Ser Gln Glu Ala Gly Thr Lys Ala Arg Phe Pro Leu Arg
 65                  70                  75                  80

Asp Ala Val Glu Glu Gly Asp Trp Thr Ala Thr Val Val Asp Gln Gln
                 85                  90                  95

Asp Cys Thr Leu Ser Leu Gln Leu Thr Thr Pro Ala Asn Ala Pro Ile
            100                 105                 110

Gly Leu Tyr Arg Leu Ser Leu Glu Ala Ser Thr Gly Tyr Gln Gly Ser
```

```
               115                 120                 125
Ser Phe Val Leu Gly His Phe Ile Leu Leu Phe Asn Ala Trp Cys Pro
130                 135                 140

Ala Asp Ala Val Tyr Leu Asp Ser Glu Glu Arg Gln Glu Tyr Val
145                 150                 155                 160

Leu Thr Gln Gln Gly Phe Ile Tyr Gln Gly Ser Ala Lys Phe Ile Lys
                    165                 170                 175

Asn Ile Pro Trp Asn Phe Gly Gln Phe Glu Asp Gly Ile Leu Asp Ile
                180                 185                 190

Cys Leu Ile Leu Leu Asp Val Asn Pro Lys Phe Leu Lys Asn Ala Gly
            195                 200                 205

Arg Asp Cys Ser Arg Arg Ser Ser Pro Val Tyr Val Gly Arg Val Val
210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Val Ser Pro Met Ser Trp Ile Gly
                245                 250                 255

Ser Val Asp Ile Leu Arg Arg Trp Lys Asn His Gly Cys Gln Arg Val
                260                 265                 270

Lys Tyr Gly Gln Cys Trp Val Phe Ala Ala Val Ala Cys Thr Val Leu
            275                 280                 285

Arg Cys Leu Gly Ile Pro Thr Arg Val Val Thr Asn Tyr Asn Ser Ala
290                 295                 300

His Asp Gln Asn Ser Asn Leu Leu Ile Glu Tyr Phe Arg Asn Glu Phe
305                 310                 315                 320

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
                340                 345                 350

Gly Trp Gln Ala Leu Asp Pro Thr Pro Gln Glu Lys Ser Glu Gly Thr
            355                 360                 365

Tyr Cys Cys Gly Pro Val Pro Val Arg Ala Ile Lys Glu Gly Asp Leu
370                 375                 380

Ser Thr Lys Tyr Asp Ala Pro Phe Val Phe Ala Glu Val Asn Ala Asp
385                 390                 395                 400

Val Val Asp Trp Ile Gln Gln Asp Asp Gly Ser Val His Lys Ser Ile
                405                 410                 415

Asn Arg Ser Leu Ile Val Gly Leu Lys Ile Ser Thr Lys Ser Val Gly
            420                 425                 430

Arg Asp Glu Arg Glu Asp Ile Thr His Thr Tyr Lys Tyr Pro Glu Gly
            435                 440                 445

Ser Ser Glu Glu Arg Glu Ala Phe Thr Arg Ala Asn His Leu Asn Lys
450                 455                 460

Leu Ala Glu Lys Glu Glu Thr Gly Met Ala Met Arg Ile Arg Val Gly
465                 470                 475                 480

Gln Ser Met Asn Met Gly Ser Asp Phe Asp Val Phe Ala His Ile Thr
            485                 490                 495

Asn Asn Thr Ala Glu Glu Tyr Val Cys Arg Leu Leu Leu Cys Ala Arg
                500                 505                 510

Thr Val Ser Tyr Asn Gly Ile Leu Gly Pro Glu Cys Gly Thr Lys Tyr
            515                 520                 525

Leu Leu Asn Leu Asn Leu Glu Pro Phe Ser Gly Lys Ala Leu Cys Ser
530                 535                 540
```

Trp Ser Ile Cys
545

<210> SEQ ID NO 16
<211> LENGTH: 1910
<212> TYPE: DNA
<213> ORGANISM: Homo sapiens
<220> FEATURE:
<223> OTHER INFORMATION: transglutaminase cDNA

<400> SEQUENCE: 16

| | | | | |
|---|---|---|---|---|
| caggcgtgac | gccagttcta | aatcttgaaa | cagaacaaaa | cttcaaagta caccaaaata | 60 |
| gaacctcctt | aaagcataaa | tctcacggag | ggtctcgccg | ccagtggaag gagccaccgc | 120 |
| ccccgcccga | ccatggccga | ggagctggtc | ttagagaggt | gtgatctgga gctggagacc | 180 |
| aatggccgag | accaccacac | ggccgacctg | tgccgggaga | gctggtggt gcgacgggc | 240 |
| cagcccttct | ggctgaccct | gcactttgag | ggccgcaact | acgaggccag tgtagacagt | 300 |
| ctcaccttca | gtgtcgtgac | cggcccagcc | cctagccagg | aggccgggac caaggcccgt | 360 |
| tttccactaa | gagatgctgt | ggaggagggt | gactggacag | ccaccgtggt ggaccagcaa | 420 |
| gactgcaccc | tctcgctgca | gctcaccacc | ccggccaacg | cccccatcgg cctgtatcgc | 480 |
| ctcagcctgg | aggcctccac | tggctaccag | ggatccagct | ttgtgctggg ccacttcatt | 540 |
| ttgctcttca | cgcctggtg | cccagcggat | gctgtgtacc | tggactcgga agaggagcgg | 600 |
| caggagtatg | tcctcaccca | gcagggcttt | atctaccagg | gctcggccaa gttcatcaag | 660 |
| aacatacctt | ggaattttgg | gcagtttgaa | gatgggatcc | tagacatctg cctgatcctt | 720 |
| ctagatgtca | accccaagtt | cctgaagaac | gccggccgtg | actgctcccg ccgcagcagc | 780 |
| cccgtctacg | tgggccgggt | gtggagtggc | atggtcaact | gcaacgatga ccagggtgtg | 840 |
| ctgctgggac | gctgggacaa | caactacggg | gacggcgtca | gccccatgtc ctggatcggc | 900 |
| agcgtggaca | tcctgcggcg | ctggaagaac | cacggctgcc | agcgcgtcaa gtatggccag | 960 |
| tgctgggtct | tcgccgccgt | ggcctgcaca | gtgctgaggt | gcctgggcat ccctacccgc | 1020 |
| gtcgtgacca | actacaactc | ggcccatgac | cagaacagca | accttctcat cgagtacttc | 1080 |
| cgcaatgagt | ttgggagat | ccagggtgac | aagagcgaga | tgatctggaa cttccactgc | 1140 |
| tgggtggagt | cgtggatgac | caggccggac | ctgcagccgg | ggtacgaggg ctggcaggcc | 1200 |
| ctggacccaa | cgccccagga | gaagagcgaa | gggacgtact | gctgtggccc agttccagtt | 1260 |
| cgtgccatca | ggagggcga | cctgagcacc | aagtacgatg | cgccctttgt ctttgcggag | 1320 |
| gtcaatgccg | acgtggtaga | ctggatccag | caggacgatg | ggtctgtgca caaatccatc | 1380 |
| aaccgttccc | tgatcgttgg | gctgaagatc | agcactaaga | gcgtgggccg agacgagcgg | 1440 |
| gaggatatca | cccacaccta | caaatacca | gaggggtcct | cagaggagag ggaggccttc | 1500 |
| acaagggcga | accacctgaa | caaactggcc | gagaaggagg | agacagggat ggccatgcgg | 1560 |
| atccgtgtgg | gccagagcat | gaacatgggc | agtgactttg | acgtctttgc ccacatcacc | 1620 |
| aacaacaccg | ctgaggagta | cgtctgccgc | ctcctgctct | gtgccgcac cgtcagctac | 1680 |
| aatgggatct | tggggcccga | gtgtggcacc | aagtacctgc | tcaacctcaa cctggagcct | 1740 |
| ttctctggta | aagccctgtg | ttcctggagc | atttgttgac | cgccaactga caacatgcta | 1800 |
| ggtagtgacc | taaccactta | gcatgtgtga | tttcaccca | cagacactta catggcgctg | 1860 |
| actctggggc | aggccctgtc | ctaagcactt | tataaatatc | aacccactta | 1910 |

<210> SEQ ID NO 17
<211> LENGTH: 548

```
<212> TYPE: PRT
<213> ORGANISM: Homo sapiens
<220> FEATURE:
<223> OTHER INFORMATION: transglutaminase

<400> SEQUENCE: 17

Met Ala Glu Glu Leu Val Leu Glu Arg Cys Asp Leu Glu Leu Glu Thr
1               5                   10                  15

Asn Gly Arg Asp His His Thr Ala Asp Leu Cys Arg Glu Lys Leu Val
            20                  25                  30

Val Arg Arg Gly Gln Pro Phe Trp Leu Thr Leu His Phe Glu Gly Arg
        35                  40                  45

Asn Tyr Glu Ala Ser Val Asp Ser Leu Thr Phe Ser Val Val Thr Gly
    50                  55                  60

Pro Ala Pro Ser Gln Glu Ala Gly Thr Lys Ala Arg Phe Pro Leu Arg
65                  70                  75                  80

Asp Ala Val Glu Glu Gly Asp Trp Thr Ala Thr Val Val Asp Gln Gln
                85                  90                  95

Asp Cys Thr Leu Ser Leu Gln Leu Thr Thr Pro Ala Asn Ala Pro Ile
            100                 105                 110

Gly Leu Tyr Arg Leu Ser Leu Glu Ala Ser Thr Gly Tyr Gln Gly Ser
        115                 120                 125

Ser Phe Val Leu Gly His Phe Ile Leu Leu Phe Asn Ala Trp Cys Pro
130                 135                 140

Ala Asp Ala Val Tyr Leu Asp Ser Glu Glu Glu Arg Gln Glu Tyr Val
145                 150                 155                 160

Leu Thr Gln Gln Gly Phe Ile Tyr Gln Gly Ser Ala Lys Phe Ile Lys
                165                 170                 175

Asn Ile Pro Trp Asn Phe Gly Gln Phe Glu Asp Gly Ile Leu Asp Ile
            180                 185                 190

Cys Leu Ile Leu Leu Asp Val Asn Pro Lys Phe Leu Lys Asn Ala Gly
        195                 200                 205

Arg Asp Cys Ser Arg Arg Ser Ser Pro Val Tyr Val Gly Arg Val Trp
    210                 215                 220

Ser Gly Met Val Asn Cys Asn Asp Asp Gln Gly Val Leu Leu Gly Arg
225                 230                 235                 240

Trp Asp Asn Asn Tyr Gly Asp Gly Val Ser Pro Met Ser Trp Ile Gly
                245                 250                 255

Ser Val Asp Ile Leu Arg Arg Trp Lys Asn His Gly Cys Gln Arg Val
            260                 265                 270

Lys Tyr Gly Gln Cys Trp Val Phe Ala Ala Val Ala Cys Thr Val Leu
        275                 280                 285

Arg Cys Leu Gly Ile Pro Thr Arg Val Val Thr Asn Tyr Asn Ser Ala
    290                 295                 300

His Asp Gln Asn Ser Asn Leu Leu Ile Glu Tyr Phe Arg Asn Glu Phe
305                 310                 315                 320

Gly Glu Ile Gln Gly Asp Lys Ser Glu Met Ile Trp Asn Phe His Cys
                325                 330                 335

Trp Val Glu Ser Trp Met Thr Arg Pro Asp Leu Gln Pro Gly Tyr Glu
            340                 345                 350

Gly Trp Gln Ala Leu Asp Pro Thr Pro Gln Glu Lys Ser Glu Gly Thr
        355                 360                 365

Tyr Cys Cys Gly Pro Val Pro Val Arg Ala Ile Lys Glu Gly Asp Leu
    370                 375                 380

Ser Thr Lys Tyr Asp Ala Pro Phe Val Phe Ala Glu Val Asn Ala Asp
```

```
                385                 390                 395                 400
Val Val Asp Trp Ile Gln Gln Asp Asp Gly Ser Val His Lys Ser Ile
                    405                 410                 415

Asn Arg Ser Leu Ile Val Gly Leu Lys Ile Ser Thr Lys Ser Val Gly
                420                 425                 430

Arg Asp Glu Arg Glu Asp Ile Thr His Thr Tyr Lys Tyr Pro Glu Gly
            435                 440                 445

Ser Ser Glu Glu Arg Glu Ala Phe Thr Arg Ala Asn His Leu Asn Lys
        450                 455                 460

Leu Ala Glu Lys Glu Glu Thr Gly Met Ala Met Arg Ile Arg Val Gly
465                 470                 475                 480

Gln Ser Met Asn Met Gly Ser Asp Phe Asp Val Phe Ala His Ile Thr
                485                 490                 495

Asn Asn Thr Ala Glu Glu Tyr Val Cys Arg Leu Leu Cys Ala Arg
                500                 505                 510

Thr Val Ser Tyr Asn Gly Ile Leu Gly Pro Glu Cys Gly Thr Lys Tyr
            515                 520                 525

Leu Leu Asn Leu Asn Leu Glu Pro Phe Ser Gly Lys Ala Leu Cys Ser
        530                 535                 540

Trp Ser Ile Cys
545

<210> SEQ ID NO 18
<211> LENGTH: 671
<212> TYPE: DNA
<213> ORGANISM: Artificial Sequence
<220> FEATURE:
<223> OTHER INFORMATION: Description of Artificial Sequence:cytosine
      deaminase GH1-27-PCR-G3F1

<400> SEQUENCE: 18
ccagcggtgg ctccagtgtg ctggtctgcg gacgtgtgcc atgcggagct gaatgccatc      60
atgaacaaaa attcgaccga tgtgaaaggc tgtagtatgt atgttgcctt gttcccttgt     120
aatgaatgcg ctaagctcat catccaggca ggtataaaag aagtgatttt cttgttttga     180
taaataccat gatagtgacg aggcaactgc tgcgaggctc ctgtttaata tggccggggt     240
gacattccgg aaattcatac cgaagtgcag caagattgtc attgactttg attcaattaa     300
cagcagaccg agtcaaaagc ttcagtgagt tacatctcat tcaatctcca gaagattggg     360
attatcgtct tctaagaggt tgctaatgcc tttcatcttg aagttacaca taacttctta     420
ctagccagta tggcaaaagt aggcatctta gaatataaa gcctccaatc ttccttactg      480
tctctcttgt cacatggaat ctacatgtgt ttgaactatt gctttaggga tttaaaatag     540
gggagcctgt ggtggcctgg tgcacagggg ctagaacgag agtgcctccc cttcttgtgt     600
cctggctggc tgggatgctg tggctcttca gaggagcatc agcctgtctg tcatctgctg     660
cgatccggca g                                                         671

<210> SEQ ID NO 19
<211> LENGTH: 178
<212> TYPE: PRT
<213> ORGANISM: Homo sapiens
<220> FEATURE:
<223> OTHER INFORMATION: deoxycytidylate deaminase, dCMP deaminase
      (DCTD)

<400> SEQUENCE: 19

Met Ser Glu Val Ser Cys Lys Lys Arg Asp Asp Tyr Leu Glu Trp Pro
1               5                   10                  15
```

```
Glu Tyr Phe Met Ala Val Ala Phe Leu Ser Ala Gln Arg Ser Lys Asp
             20                  25                  30

Pro Asn Ser Gln Val Gly Ala Cys Ile Val Asn Ser Glu Asn Lys Ile
         35                  40                  45

Val Gly Ile Gly Tyr Asn Gly Met Pro Asn Gly Cys Ser Asp Asp Val
     50                  55                  60

Leu Pro Trp Arg Arg Thr Ala Glu Asn Lys Leu Asp Thr Lys Tyr Pro
 65                  70                  75                  80

Tyr Val Cys His Ala Glu Leu Asn Ala Ile Met Asn Lys Asn Ser Thr
                 85                  90                  95

Asp Val Lys Gly Cys Ser Met Tyr Val Ala Leu Phe Pro Cys Asn Glu
            100                 105                 110

Cys Ala Lys Leu Ile Ile Gln Ala Gly Ile Lys Glu Val Ile Phe Met
        115                 120                 125

Ser Asp Lys Tyr His Asp Ser Asp Glu Ala Thr Ala Ala Arg Leu Leu
    130                 135                 140

Phe Asn Met Ala Gly Val Thr Phe Arg Lys Phe Ile Pro Lys Cys Ser
145                 150                 155                 160

Lys Ile Val Ile Asp Phe Asp Ser Ile Asn Ser Arg Pro Ser Gln Lys
                165                 170                 175

Leu Gln

<210> SEQ ID NO 20
<211> LENGTH: 1831
<212> TYPE: DNA
<213> ORGANISM: Homo sapiens
<220> FEATURE:
<223> OTHER INFORMATION: dCMP deaminase (DCTD) cDNA

<400> SEQUENCE: 20
atgagtgaag tttcctgcaa gaaacgggac gactatttgg aatggccaga gtattttatg      60
gctgtggcct tcttatcagc acagagaagc aaagatccaa attcccaggt cggcgcctgc     120
atcgtgaatt cagaaaacaa gattgtcggg attgggtaca atgggatgcc aaatgggtgc     180
agtgatgacg tgttgccttg gagaaggaca gcagagaata agctggacac caaataccog     240 tacgtgtgcc atgcggagct gaatgccatc atgaacaaaa attcgaccga tgtgaaaggc     300
tgtagtatgt atgtcgcctt gttcccttgt aatgaatgcg ctaagctcat catccaggca     360
ggtataaaag aagtgatttt cacgtctgat aaataccatg atagtgacga ggcaactgct     420
gcgaggctcc tgtttaatat ggccggggtg acattccgga aattcatacc gaagtgcagc     480
aagattgtca ttgactttga ttcaattaac agcagaccga gtcaaaagct tcagtgagtt     540
acatctcatt caatctccag aagattggga ttatcgtctt ctaagaggtt gctaatgcct     600
ttcatcttga agttacacat aacttcttac tagccagtat ggcaaaagta ggcatctaaa     660
gaatataaag cctcaaatct tccttactgt ctctcttgtc acatggaatc tacatgtgtt     720
tgaactattg ctttaggatt taaaataggg gagcctgtgg tggcctggtg cacagggcta     780
gaacgagagt gcctcccctt cttgtgtcct ggctggctgg gatgctggtg gctcttcaga     840
ggagcatcag ctgtctgtca tctgctgcga tccggcagcc tctcttcact gctacatgtg     900
ctggaaggac aaataaataa ttgtggttgt gttcttaatg gggacgagca gacacactga     960
tctgaacatc tggcccaagt gaagcatggc atatagtgcc cttggaagaa aattaggcct    1020
caaatgacga tagcattgaa gtgtttgctg cagagttgag ggaaaccccc agccaccctc    1080
ccggaatccg agatagggtg gcacatctgt cctgacagac gaggagtgta actgaaccag    1140
```

```
gaatatttcc tccattcctg ctctcccact gcacacaggg tggtggcaca ttatccctct    1200 gggggggtggg gacgcctgtt gttttggctc aatttgggtt tgttggtcac atggagctct    1260
tccatttcgt ttagctgaat aatgagttgt tcctagagga gacagcctgt ctctccttgt    1320
tgcccccaaa gcccatgccc tgccgtggtg gcagctgggg ctgtggatgg gaggggtccc    1380
caacatggat gtgttgcccc tcctccgcat gccaacgcag ttcatgtaca aggcccctct    1440
gcaactggag agaaaattaa ttcctatccc gtgagtggat tgtgagaaat ccacccacg    1500 tggagacagc ttactgcagc actgttggtg ttcggagctc ttctgtgccc tggctccatg    1560
ctttcaccta cacaagcatc accttcctaa tcaccgcggg gcggggagcg tgtggctgtg    1620
ccccttctct ttaatctcat ttaattttta ttaaacatgc tcagtacctg tgttgagaaa    1680
aggctttctt tatcctaaag attattaccat ttttaaagtg ctcttatatt ttcatgagtt    1740
tttattttgt ctctgagatt ttgtattcca cattctaggg tattctgtaa tttggctcct    1800
taccaatatt attaaaatct tattaaaatc t                                    1831
```

<210> SEQ ID NO 21
<211> LENGTH: 178
<212> TYPE: PRT
<213> ORGANISM: Homo sapiens
<220> FEATURE:
<223> OTHER INFORMATION: dCMP deaminase (DCTD)

<400> SEQUENCE: 21

```
Met Ser Glu Val Ser Cys Lys Lys Arg Asp Asp Tyr Leu Glu Trp Pro
 1               5                  10                  15

Glu Tyr Phe Met Ala Val Ala Phe Leu Ser Ala Gln Arg Ser Lys Asp
            20                  25                  30

Pro Asn Ser Gln Val Gly Ala Cys Ile Val Asn Ser Glu Asn Lys Ile
        35                  40                  45

Val Gly Ile Gly Tyr Asn Gly Met Pro Asn Gly Cys Ser Asp Asp Val
    50                  55                  60

Leu Pro Trp Arg Arg Thr Ala Glu Asn Lys Leu Asp Thr Lys Tyr Pro
65                  70                  75                  80

Tyr Val Cys His Ala Glu Leu Asn Ala Ile Met Asn Lys Asn Ser Thr
                85                  90                  95

Asp Val Lys Gly Cys Ser Met Tyr Val Ala Leu Phe Pro Cys Asn Glu
           100                 105                 110

Cys Ala Lys Leu Ile Ile Gln Ala Gly Ile Lys Glu Val Ile Phe Thr
       115                 120                 125

Ser Asp Lys Tyr His Asp Ser Asp Glu Ala Thr Ala Ala Arg Leu Leu
   130                 135                 140

Phe Asn Met Ala Gly Val Thr Phe Arg Lys Phe Ile Pro Lys Cys Ser
145                 150                 155                 160

Lys Ile Val Ile Asp Phe Asp Ser Ile Asn Ser Arg Pro Ser Gln Lys
               165                 170                 175

Leu Gln
```

<210> SEQ ID NO 22
<211> LENGTH: 688
<212> TYPE: DNA
<213> ORGANISM: Artificial Sequence
<220> FEATURE:
<223> OTHER INFORMATION: Description of Artificial Sequence:synthetic peptidase M41 (paraplegin) GH1-40-PCR-G3F1
<220> FEATURE:
<221> NAME/KEY: modified_base

```
<222> LOCATION: (1)..(688)
<223> OTHER INFORMATION: n = g, a, c or t

<400> SEQUENCE: 22
gtggaaatgc cctgttactc tgtggggatg acggcagtgg gcctggccat cctgtggtat     60
gttttccgtc tggccgggat gactggaagg gaaggtggat tcagtgcttt taatcagctt    120
aaaatggctc gtttcaccat tgtggattgg aagatgggga aagggagtca gcttcaaaga    180
cgtggcagga atgcacgaag ccaaactgga agtccgcgag tttgtggatt atctgaagag    240
cccagaacgc ttcctccagc ttggcgccag gtcccaaagg gcgcactgct gctcggcccc    300
cccggctgtg ggaagacgct tctggccaag gcggtgccca cggaggctca ggtgcccttc    360
ctggcgatgc cggcccagag ttcgtggagg tcattggagg cctcggcgct cccgtgtgcg    420
gagcctcttt aaggaagccc gagcccgggc cccctgcatc gtctacatcg atagatcgac    480
gcggtgggca agaagcgctc caccaccatg tccggcttct ccaacacnga ggaggagcag    540
acgctcaacc agcttctggt nagaaatgga tggaaatggg taccacagac catgtcatcg    600
tcctggcgtc cacgaaaccg agctgacatt ttggacggtg ctcttatagg ccaggccgaa    660
ctgggaccgg gacgtcttct ttgatctc                                        688

<210> SEQ ID NO 23
<211> LENGTH: 3087
<212> TYPE: DNA
<213> ORGANISM: Homo sapiens
<220> FEATURE:
<223> OTHER INFORMATION: spastic paraplegia 7, paraplegin (pure and
      complicated autosomal recessive) (SPG7) cDNA

<400> SEQUENCE: 23
tttcaggcca acatggccgt gctgctgctg ctgctccgtg ccctccgccg gggtccaggc     60
ccgggtcctc ggccgctgtg ggcccaggcc ccggcctgga gtccagggtt ccccgccagg    120
cccgggaggg ggcggccgta catggccagc aggcctccgg gggacctcgc cgaggctgga    180
ggccgagctc tgcagagctt acaattgaga ctgctaaccc ctacctttga agggatcaac    240
ggattgttgt tgaaacaaca tttagttcag aatccagtca gactctggca acttttaggt    300
ggtactttct attttaacac ctcaaggttg aagcagaaga ataaggagaa ggataagtcg    360
aaggggaagg cgcctgaaga ggacgaagag gagaggagac gccgtgagcg ggacgaccag    420
atgtaccgag agcggctgcg caccttgctg gtcatcgcgg ttgtcatgag cctcctgaat    480
gctctcagca ccagcggagg cagcatttcc tggaacgact tgtccacga gatgctggcc    540 aagggcgagg tgcagcgcgt ccaggtggtg cctgagagcg acgtggtgga agtctacctg    600
caccctggag ccgtggtgtt tggcggcct cggctagcct tgatgtaccg aatgcaggtt    660
gcaaatattg acaagtttga agagaagctt cgagcagctg aagatgagct gaatatcgag    720
gccaaggaca ggatcccagt ttcctacaag cgaacaggat tctttggaaa tgccctgtac    780
tctgtgggga tgacggcagt gggcctggcc atcctgtggt atgttttccg tctggccggg    840
atgactggaa gggaaggtgg attcagtgct tttaatcagc ttaaaatggc tcgtttcacc    900
attgtggatg ggaagatggg gaaaggagtc agcttcaaag acgtggcagg aatgcacgaa    960
gccaaactgg aagtccgcga gtttgtggat tatctgaaga gccagaacgc ttcctccag   1020 cttggcgcca agtcccaaa gggcgcactg ctgctcggcc ccccggctg tgggaagacg   1080 ctgctggcca aggcggtggc cacggaggct caggtgccct tcctggcgat ggccggccca   1140
gagttcgtgg aggtcattgg aggcctcggc gctgcccgtg tgcggagcct ctttaaggaa   1200
```

-continued

```
gcccgagccc gggcccsctg catcgtctac atcgatgaga tcgacgcggt gggcaagaag    1260
cgctccacca ccatgtccgg cttctccaac acggaggagg agcagacgct caaccagctt    1320
ctggtagaaa tggatggaat gggtaccaca gaccatgtca tcgtcctggc gtccacgaac    1380
cgagctgaca ttttggacgg tgctctgatg aggccaggcc gactgaccg  gcacgtcttc    1440 attgatctcc ccacgctgca ggagaggcgg gagattttg  agcagcacct gaagagcctg    1500
aagctgaccc agtccagcac cttttactcc cagcgtctgg cagagctgac accaggattc    1560
agtggggctg acatcgccaa catctgcaat gaggctgcgc tgcacgcggc gcgggaggga    1620
cacacttccg tgcacactct caacttcgag tacgccgtgg agcgcgtcct cgcagggact    1680
gccaaaaaga gcaagatcct gtccaaggaa gaacagaaag tggttgcgtt tcatgagtcg    1740
ggccacgcct tggtgggctg gatgctggag cacacggagg ccgtgatgaa ggtctccata    1800 accccctcgga caaacgccgc cctgggcttt gctcagatgc tccccagaga ccagcacctc    1860
ttcaccaagg agcagctgtt tgagcggatg tgcatggcct tgggaggacg ggcctcggaa    1920
gcactgtcct tcaacgaggt cacttctggg gcacaggacg acctgaggaa ggtcacccgc    1980
atcgcctact ccatggtgaa gcagtttggg atggcacctg gcatcgggcc catctccttc    2040
cctgaggcgc aggagggcct catgggcatc gggcggcgcc ccttcagcca aggcctgcag    2100
cagatgatgg accatgaagc aagactgctg gtggccaagg cctacagaca caccgagaag    2160
gtgctgcagg acaacctgga caagttgcag gcgctggcaa acgcccttct ggaaaaggaa    2220
gtgataaact atgaggacat tgaggctctc attggcccgc cgccccatgg gccgaagaaa    2280
atgatcgcac cgcagaggtg gatcgacgcc cagagggaga acaggactt ggcgaggag    2340 gagaccgaag agacccagca gcctccactt ggaggcgaag agccgacttg gcccaagtag    2400
ttgggaggtg ttggctgcac gtgcgggtgg tccgggaagt gagggctcac tcagccaccc    2460
tgagttgctt ttcagctgag gtttgcactt cctctcgcgg ccctcagtag tccctgcaca    2520
gtgacttctg agatctgttg attgatgacc cttttcatga ttttaagttt ctctgcagaa    2580
actactgacg gagtcctgtg tttgtgagtc gtttccccta tggggaaggt tatcagtgct    2640
tcccgagtga gcatggaaca cttcgagttc ccagggttat agacagtcgt tcccagtgtg    2700
gctgaggcca cccagaggca gcagagcatt cagactccaa acagacccct gttcatgccg    2760
acgcttgcac gaccgcccca gttcctgtgg ctccctcgga atgctaaggg gatcggacat    2820
gaaaggaccc tgtgagccga ttgtcctatc tccagcggcc ctgtcatcca gctcactcat    2880 caatgggggcc agtcaggccc aggcactggg ctccggagga ctcaccactg cccccctgctg    2940 ccatgtggac tggtgcaagt tgaggacttc ttgctggtct agtcacgcat gcagtgttgg    3000
ggatgccttg gttttactg ctctgagaat tgttgagata ctttactaat aaactgtgta    3060
gttggaaaaa aaaaaaaaa aaaaaaa                                           3087
```

<210> SEQ ID NO 24
<211> LENGTH: 795
<212> TYPE: PRT
<213> ORGANISM: Homo sapiens
<220> FEATURE:
<223> OTHER INFORMATION: paraplegin

<400> SEQUENCE: 24

```
Met Ala Val Leu Leu Leu Leu Leu Arg Ala Leu Arg Arg Gly Pro Gly
 1               5                  10                  15

Pro Gly Pro Arg Pro Leu Trp Gly Pro Gly Pro Ala Trp Ser Pro Gly
            20                  25                  30
```

-continued

```
Phe Pro Ala Arg Pro Gly Arg Gly Arg Pro Tyr Met Ala Ser Arg Pro
         35                  40                  45

Pro Gly Asp Leu Ala Glu Ala Gly Gly Arg Ala Leu Gln Ser Leu Gln
 50                  55                  60

Leu Arg Leu Leu Thr Pro Thr Phe Glu Gly Ile Asn Gly Leu Leu Leu
 65                  70                  75                  80

Lys Gln His Leu Val Gln Asn Pro Val Arg Leu Trp Gln Leu Leu Gly
                 85                  90                  95

Gly Thr Phe Tyr Phe Asn Thr Ser Arg Leu Lys Gln Lys Asn Lys Glu
                100                 105                 110

Lys Asp Lys Ser Lys Gly Lys Ala Pro Glu Glu Asp Glu Glu Glu Arg
                115                 120                 125

Arg Arg Arg Glu Arg Asp Asp Gln Met Tyr Arg Glu Arg Leu Arg Thr
130                 135                 140

Leu Leu Val Ile Ala Val Val Met Ser Leu Leu Asn Ala Leu Ser Thr
145                 150                 155                 160

Ser Gly Gly Ser Ile Ser Trp Asn Asp Phe Val His Glu Met Leu Ala
                165                 170                 175

Lys Gly Glu Val Gln Arg Val Gln Val Val Pro Glu Ser Asp Val Val
                180                 185                 190

Glu Val Tyr Leu His Pro Gly Ala Val Phe Gly Arg Pro Arg Leu
                195                 200                 205

Ala Leu Met Tyr Arg Met Gln Val Ala Asn Ile Asp Lys Phe Glu Glu
210                 215                 220

Lys Leu Arg Ala Ala Glu Asp Glu Leu Asn Ile Glu Ala Lys Asp Arg
225                 230                 235                 240

Ile Pro Val Ser Tyr Lys Arg Thr Gly Phe Phe Gly Asn Ala Leu Tyr
                245                 250                 255

Ser Val Gly Met Thr Ala Val Gly Leu Ala Ile Leu Trp Tyr Val Phe
                260                 265                 270

Arg Leu Ala Gly Met Thr Gly Arg Glu Gly Gly Phe Ser Ala Phe Asn
                275                 280                 285

Gln Leu Lys Met Ala Arg Phe Thr Ile Val Asp Gly Lys Met Gly Lys
290                 295                 300

Gly Val Ser Phe Lys Asp Val Ala Gly Met His Glu Ala Lys Leu Glu
305                 310                 315                 320

Val Arg Glu Phe Val Asp Tyr Leu Lys Ser Pro Glu Arg Phe Leu Gln
                325                 330                 335

Leu Gly Ala Lys Val Pro Lys Gly Ala Leu Leu Leu Gly Pro Pro Gly
                340                 345                 350

Cys Gly Lys Thr Leu Leu Ala Lys Ala Val Ala Thr Glu Ala Gln Val
                355                 360                 365

Pro Phe Leu Ala Met Ala Gly Pro Glu Phe Val Glu Val Ile Gly Gly
370                 375                 380

Leu Gly Ala Ala Arg Val Arg Ser Leu Phe Lys Glu Ala Arg Ala Arg
385                 390                 395                 400

Ala Pro Cys Ile Val Tyr Ile Asp Glu Ile Asp Ala Val Gly Lys Lys
                405                 410                 415

Arg Ser Thr Thr Met Ser Gly Phe Ser Asn Thr Glu Glu Glu Gln Thr
                420                 425                 430

Leu Asn Gln Leu Leu Val Glu Met Asp Gly Met Gly Thr Thr Asp His
                435                 440                 445

Val Ile Val Leu Ala Ser Thr Asn Arg Ala Asp Ile Leu Asp Gly Ala
450                 455                 460
```

Leu Met Arg Pro Gly Arg Leu Asp Arg His Val Phe Ile Asp Leu Pro
465                 470                 475                 480

Thr Leu Gln Glu Arg Arg Glu Ile Phe Glu Gln His Leu Lys Ser Leu
        485                 490                 495

Lys Leu Thr Gln Ser Ser Thr Phe Tyr Ser Gln Arg Leu Ala Glu Leu
            500                 505                 510

Thr Pro Gly Phe Ser Gly Ala Asp Ile Ala Asn Ile Cys Asn Glu Ala
                515                 520                 525

Ala Leu His Ala Ala Arg Glu Gly His Thr Ser Val His Thr Leu Asn
            530                 535                 540

Phe Glu Tyr Ala Val Glu Arg Val Leu Ala Gly Thr Ala Lys Lys Ser
545                 550                 555                 560

Lys Ile Leu Ser Lys Glu Glu Gln Lys Val Val Ala Phe His Glu Ser
                565                 570                 575

Gly His Ala Leu Val Gly Trp Met Leu Glu His Thr Glu Ala Val Met
            580                 585                 590

Lys Val Ser Ile Thr Pro Arg Thr Asn Ala Ala Leu Gly Phe Ala Gln
                595                 600                 605

Met Leu Pro Arg Asp Gln His Leu Phe Thr Lys Glu Gln Leu Phe Glu
610                 615                 620

Arg Met Cys Met Ala Leu Gly Gly Arg Ala Ser Glu Ala Leu Ser Phe
625                 630                 635                 640

Asn Glu Val Thr Ser Gly Ala Gln Asp Leu Arg Lys Val Thr Arg
                645                 650                 655

Ile Ala Tyr Ser Met Val Lys Gln Phe Gly Met Ala Pro Gly Ile Gly
                660                 665                 670

Pro Ile Ser Phe Pro Glu Ala Gln Glu Gly Leu Met Gly Ile Gly Arg
                675                 680                 685

Arg Pro Phe Ser Gln Gly Leu Gln Gln Met Met Asp His Glu Ala Arg
            690                 695                 700

Leu Leu Val Ala Lys Ala Tyr Arg His Thr Glu Lys Val Leu Gln Asp
705                 710                 715                 720

Asn Leu Asp Lys Leu Gln Ala Leu Ala Asn Ala Leu Leu Glu Lys Glu
                725                 730                 735

Val Ile Asn Tyr Glu Asp Ile Glu Ala Leu Ile Gly Pro Pro His
                740                 745                 750

Gly Pro Lys Lys Met Ile Ala Pro Gln Arg Trp Ile Asp Ala Gln Arg
            755                 760                 765

Glu Lys Gln Asp Leu Gly Glu Glu Thr Glu Thr Gln Gln Pro
770                 775                 780

Pro Leu Gly Gly Glu Glu Pro Thr Trp Pro Lys
785                 790                 795

<210> SEQ ID NO 25
<211> LENGTH: 373
<212> TYPE: DNA
<213> ORGANISM: Artificial Sequence
<220> FEATURE:
<223> OTHER INFORMATION: Description of Artificial Sequence:synthetic
      CD13 aminopeptidase GH1-72-PCR-G3F1

<400> SEQUENCE: 25
aggccaggcc tagggcgggg ttggcatgag cgggcagcgc gctgggaggt gctcaggcag    60
cctgggtcat caggaactag actggctcac aggcagagaa aacgtgggct ggagactttg   120
tccttgaggg gaggacactg gtgcctcggg ctccaggaat ggaggccctg caccagccgc   180

-continued

```
tgggatggac acatgtgggc accttgcatg ggggccgggt gacttcaagg gctggggact    240
atttgctgtt ttctgtgaac cactggagca ccacctcctt gttctccttc acccacttat    300
gttgctttcg tcttctccag gggcttgctc cagggcccgg gtgccttagc cgaagcctgt    360
ttcctcgttt cct                                                       373
```

<210> SEQ ID NO 26
<211> LENGTH: 967
<212> TYPE: PRT
<213> ORGANISM: Homo sapiens
<220> FEATURE:
<223> OTHER INFORMATION: aminopeptidase N, microsomal aminopeptidase, myeloid plasma membrane glycoprotein CD13 (GP150)

<400> SEQUENCE: 26

```
Met Ala Lys Gly Phe Tyr Ile Ser Lys Ser Leu Gly Ile Leu Gly Ile
 1               5                  10                  15

Leu Leu Gly Val Ala Ala Val Cys Thr Ile Ile Ala Leu Ser Val Val
             20                  25                  30

Tyr Ser Gln Glu Lys Asn Lys Asn Ala Asn Ser Ser Pro Val Ala Ser
         35                  40                  45

Thr Thr Pro Ser Ala Ser Ala Thr Thr Asn Pro Ala Ser Ala Thr Thr
     50                  55                  60

Leu Asp Gln Ser Lys Ala Trp Asn Arg Tyr Arg Leu Pro Asn Thr Leu
 65                  70                  75                  80

Lys Pro Asp Ser Tyr Gln Val Thr Leu Arg Pro Tyr Leu Thr Pro Asn
                 85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320
```

```
Thr Gly Pro Ile Leu Asn Phe Phe Ala Gly His Tyr Asp Thr Pro Tyr
            325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
            355                 360                 365

Phe Asp Pro Leu Ser Ser Ser Ser Asn Lys Glu Arg Val Val Thr
            370                 375             380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                    405                 410                 415

Val Glu Tyr Leu Gly Ala Asp Tyr Ala Glu Pro Thr Trp Asn Leu Lys
                420                 425                 430

Asp Leu Met Val Leu Asn Asp Val Tyr Arg Val Met Ala Val Asp Ala
            435                 440                 445

Leu Ala Ser Ser His Pro Leu Ser Thr Pro Ala Ser Glu Ile Asn Thr
450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                    485                 490                 495

Lys Gln Gly Leu Ala Ser Tyr Leu His Thr Phe Ala Tyr Gln Asn Thr
                500                 505                 510

Ile Tyr Leu Asn Leu Trp Asp His Leu Gln Ala Val Asn Asn Arg
            515                 520                 525

Ser Ile Gln Leu Pro Thr Thr Glu Arg Asp Ile Met Asn Arg Trp Thr
530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
                580                 585                 590

Asp Gly Arg Gln Gln Asp Tyr Trp Leu Met Asp Val Arg Ala Gln
            595                 600                 605

Asn Asp Leu Phe Ser Thr Ser Gly Asn Glu Trp Val Leu Leu Asn Leu
            610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                    645                 650                 655

Asn Arg Ala Gln Ile Ile Asn Asp Ala Phe Asn Leu Ala Ser Ala His
                660                 665                 670

Lys Val Pro Val Thr Leu Ala Leu Asn Asn Thr Leu Phe Leu Ile Glu
            675                 680                 685

Glu Arg Gln Tyr Met Pro Trp Glu Ala Ala Leu Ser Ser Leu Ser Tyr
    690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
                    725                 730                 735

Thr Asn Asn Trp Arg Glu Ile Pro Glu Asn Leu Met Asp Gln Tyr Ser
                740                 745                 750
```

```
Glu Val Asn Ala Ile Ser Thr Ala Cys Ser Asn Gly Val Pro Glu Cys
            755                 760                 765

Glu Glu Met Val Ser Gly Leu Phe Lys Gln Trp Met Glu Asn Pro Asn
        770                 775                 780

Asn Asn Pro Ile His Pro Asn Leu Arg Ser Thr Val Tyr Cys Asn Ala
785                 790                 795                 800

Ile Ala Gln Gly Gly Glu Glu Trp Asp Phe Ala Trp Gln Phe
                805                 810                 815

Arg Asn Ala Thr Leu Val Asn Glu Ala Asp Lys Leu Arg Ala Ala Leu
                820                 825                 830

Ala Cys Ser Lys Glu Leu Trp Ile Leu Asn Arg Tyr Leu Ser Tyr Thr
            835                 840                 845

Leu Asn Pro Asp Leu Ile Arg Lys Gln Asp Ala Thr Ser Thr Ile Ile
        850                 855                 860

Ser Ile Thr Asn Asn Val Ile Gly Gln Gly Leu Val Trp Asp Phe Val
865                 870                 875                 880

Gln Ser Asn Trp Lys Lys Pro Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
        915                 920                 925

Gly Phe Gly Ser Gly Thr Arg Ala Leu Glu Gln Ala Leu Glu Lys Thr
930                 935                 940

Lys Ala Asn Ile Lys Trp Val Lys Glu Asn Lys Glu Val Val Leu Gln
945                 950                 955                 960

Trp Phe Thr Glu Asn Ser Lys
                965

<210> SEQ ID NO 27
<211> LENGTH: 3494
<212> TYPE: DNA
<213> ORGANISM: Homo sapiens
<220> FEATURE:
<223> OTHER INFORMATION: alanyl (membrane) aminopeptidase,
      aminopeptidase M, microsomal aminopeptidase, CD13, p150 (ANPEP)
      cDNA

<400> SEQUENCE: 27 taattttgc ccagtctgcc tgttgtgggg ctcctcccct ttggggatat aagcccggcc      60
tggggctgct ccgttctctg cctggcctga ggctccctga gccgcctccc caccatcacc     120
atggccaagg gcttctatat ttccaagtcc ctgggcatcc tggggatcct cctgggcgtg    180
gcagccgtgt gcacaatcat cgcactgtca gtggtgtact cccaggagaa gaacaagaac    240
gccaacagct ccccgtggc ctccaccacc ccgtccgcct cagccaccac caaccccgcc    300
tcggccacca ccttggacca aagtaaagcg tggaatcgtt accgcctccc caacacgctg    360
aaacccgatt cctaccaggt gacgctgaga ccgtacctca cccccaatga caggggcctg    420
tacgttttta agggctccag caccgtccgt ttcacctgca aggaggccac tgacgtcatc    480
atcatccaca gcaagaagct caactacacc ctcagccagg gcacagggt ggtcctgcgt    540 ggtgtgggag ctcccagcc ccccgacatt gacaagactg agctggtgga gcccaccgag    600
tacctggtgg tgcacctcaa gggctccctg gtgaaggaca ccagtatga tggacagc      660 gagttcgagg gggagttggc agatgacctg gcgggcttct accgcagcga gtacatggag    720
ggcaatgtca gaaggtggt ggccactaca cagatgcagg ctgcagatgc ccggaagtcc    780
```

```
ttcccatgct tcgatgagcc ggccatgaag gccgagttca acatcacgct tatccacccc      840
aaggacctga cagccctgtc caacatgctt cccaaaggtc ccagcacccc acttccagaa      900
gaccccaact ggaatgtcac tgagttccac accacgccca agatgtccac gtacttgctg      960
gccttcattg tcagtgagtt cgactacgtg gagaagcagg catccaatgg tgtcttgatc     1020
cggatctggg cccggcccag tgccattgcg gcgggccacg gcgattatgc cctgaacgtg     1080
acgggcccca tccttaactt ctttgctggt cattatgaca cccctacccc actcccaaaa     1140
tcagaccaga ttggcctgcc agacttcaac gccggcgcca tggagaactg ggactggtg      1200
acctaccggg agaactccct gctgttcgac cccctgtcct cctccagcag caacaaggag     1260
cgggtggtca ctgtgattgc tcatgagctg gcccaccagt ggttcgggaa cctggtgacc     1320
atagagtggt ggaatgacct gtggctgaac gagggcttcg cctcctacgt ggagtacctg     1380
ggtgctgact atgcggagcc cacctggaac ttgaaagacc tcatggtgct gaatgatgtg     1440
taccgcgtga tggcagtgga tgcactggcc tcctcccacc cgctgtccac acccgcctcg     1500
gagatcaaca cgccggccca gatcagtgag ctgtttgacg ccatctccta cagcaagggc     1560
gcctcagtcc tcaggatgct ctccagcttc ctgtccgagg acgtattcaa gcagggcctg     1620
gcgtcctacc tccacacctt tgcctaccag aacaccatct acctgaacct gtgggaccac     1680
ctgcaggagg ctgtgaacaa ccggtccatc caactcccca ccaccgtgcg ggacatcatg     1740
aaccgctgga ccctgcagat gggcttcccg gtcatcacgg tggataccag cacggggacc     1800
cttttcccagg agcacttcct ccttgacccc gattccaatg ttacccgccc ctcagaattc     1860
aactacgtgt ggattgtgcc catcacatcc atcagagatg cagacagca  gcaggactac     1920
tggctgatag atgtaagagc ccagaacgat ctcttcagca catcaggcaa tgagtgggtc     1980
ctgctgaacc tcaatgtgac gggctattac cgggtgaact acgacgaaga gaactggagg     2040
aagattcaga ctcagctgca gagagaccac tcggccatcc ctgtcatcaa tcgggcacag     2100
atcattaatg acgccttcaa cctggccagt gcccataagg tccctgtcac tctggcgctg     2160
aacaacaccc tcttcctgat tgaagagaga cagtacatgc cctgggaggc cgccctgagc     2220
agcctgagct acttcaagct catgtttgac cgctccgagg tctatggccc catgaagaac     2280
tacctgaaga agcaggtcac acccctcttc attcacttca gaaataatac caacaactgg     2340
agggagatcc cagaaaacct gatggaccag tacagcgagg ttaatgccat cagcaccgcc     2400
tgctccaacg gagttccaga gtgtgaggag atggtctctg ccttttcaa gcagtggatg     2460
gagaaccccca ataataaccc gatccacccc aacctgcggt ccaccgtcta ctgcaacgct     2520
atcgcccagg gcgggaggga ggagtgggac ttcgcctggg agcagttccg aaatgccaca     2580
ctggtcaatg aggctgacaa gctccgggca gccctggcct gcagcaaaga gttgtggatc     2640
ctgaacaggt acctgagcta cccctgaac ccggacttaa tccggaagca ggacgccacc     2700
tctaccatca tcagcattac caacaacgtc attgggcaag gtctggtctg ggactttgtc     2760
cagagcaact ggaagaagct tttaacgat tatggtggtg gctcgttctc cttctccaac     2820
ctcatccagg cagtgacacg acgattctcc accgagtatg agctgcagca gctggagcag     2880
ttcaagaagg acaacgagga aacaggcttc ggctcaggca cccgggccct ggagcaagcc     2940
ctggagaaga cgaaagccaa catcaagtgg gtgaaggaga caaggaggt ggtgctccag     3000
tggttcacag aaaacagcaa atagtcccca gcccttgaag tcacccggcc ccgatgcaag     3060
gtgcccacat gtgtccatcc cagcggctgg tgcagggcct ccattcctgg agcccgaggc     3120
accagtgtcc tcccctcaag gacaaagtct ccagcccacg ttctctctgc ctgtgagcca     3180
```

```
gtctagttcc tgatgaccca ggctgcctga gcacctccca gccccctgccc ctcatgccaa    3240 ccccgccccta ggcctggcat ggcacctgtc gcccagtgcc ctggggctga tctcagggaa    3300
gcccagctcc agggccagat gagcagaagc tctcgatgga caatgaacgg ccttgctggg    3360
ggccgccctg taccctcttt cacctttccc taaagaccct aaatctgagg aatcaacagg    3420
gcagcagatc tgtatatttt tttctaagag aaaatgtaaa taaggatttt ctagatgaaa    3480
aaaaaaaaaa aaaa                                                       3494
```

<210> SEQ ID NO 28
<211> LENGTH: 967
<212> TYPE: PRT
<213> ORGANISM: Homo sapiens
<220> FEATURE:
<223> OTHER INFORMATION: membrane alanine aminopeptidase precursor,
      aminopeptidase N, aminopeptidase M, microsomal
      aminopeptidase, alanyl (membrane) aminopeptidase

<400> SEQUENCE: 28

```
Met Ala Lys Gly Phe Tyr Ile Ser Lys Ser Leu Gly Ile Leu Gly Ile
 1               5                  10                  15

Leu Leu Gly Val Ala Ala Val Cys Thr Ile Ile Ala Leu Ser Val Val
             20                  25                  30

Tyr Ser Gln Glu Lys Asn Lys Asn Ala Asn Ser Ser Pro Val Ala Ser
         35                  40                  45

Thr Thr Pro Ser Ala Ser Ala Thr Thr Asn Pro Ala Ser Ala Thr Thr
     50                  55                  60

Leu Asp Gln Ser Lys Ala Trp Asn Arg Tyr Arg Leu Pro Asn Thr Leu
 65                  70                  75                  80

Lys Pro Asp Ser Tyr Gln Val Thr Leu Arg Pro Tyr Leu Thr Pro Asn
                 85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
```

```
            290                 295                 300
Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                    325                 330                 335

Pro Leu Pro Lys Ser Asp Gln Ile Gly Leu Pro Asp Phe Asn Ala Gly
                    340                 345                 350

Ala Met Glu Asn Trp Gly Leu Val Thr Tyr Arg Glu Asn Ser Leu Leu
                355                 360                 365

Phe Asp Pro Leu Ser Ser Ser Ser Asn Lys Glu Arg Val Val Thr
            370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                    405                 410                 415

Val Glu Tyr Leu Gly Ala Asp Tyr Ala Glu Pro Thr Trp Asn Leu Lys
                420                 425                 430

Asp Leu Met Val Leu Asn Asp Val Tyr Arg Val Met Ala Val Asp Ala
                435                 440                 445

Leu Ala Ser Ser His Pro Leu Ser Thr Pro Ala Ser Glu Ile Asn Thr
450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                485                 490                 495

Lys Gln Gly Leu Ala Ser Tyr Leu His Thr Phe Ala Tyr Gln Asn Thr
                500                 505                 510

Ile Tyr Leu Asn Leu Trp Asp His Leu Gln Glu Ala Val Asn Asn Arg
            515                 520                 525

Ser Ile Gln Leu Pro Thr Thr Val Arg Asp Ile Met Asn Arg Trp Thr
530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
                580                 585                 590

Asp Gly Arg Gln Gln Gln Asp Tyr Trp Leu Ile Asp Val Arg Ala Gln
                595                 600                 605

Asn Asp Leu Phe Ser Thr Ser Gly Asn Glu Trp Val Leu Leu Asn Leu
            610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                    645                 650                 655

Asn Arg Ala Gln Ile Ile Asn Asp Ala Phe Asn Leu Ala Ser Ala His
                660                 665                 670

Lys Val Pro Val Thr Leu Ala Leu Asn Asn Thr Leu Phe Leu Ile Glu
                675                 680                 685

Glu Arg Gln Tyr Met Pro Trp Glu Ala Ala Leu Ser Ser Leu Ser Tyr
            690                 695                 700

Phe Lys Leu Met Phe Asp Arg Ser Glu Val Tyr Gly Pro Met Lys Asn
705                 710                 715                 720
```

```
Tyr Leu Lys Lys Gln Val Thr Pro Leu Phe Ile His Phe Arg Asn Asn
            725                 730                 735

Thr Asn Asn Trp Arg Glu Ile Pro Glu Asn Leu Met Asp Gln Tyr Ser
        740                 745                 750

Glu Val Asn Ala Ile Ser Thr Ala Cys Ser Asn Gly Val Pro Glu Cys
    755                 760                 765

Glu Glu Met Val Ser Gly Leu Phe Lys Gln Trp Met Glu Asn Pro Asn
770                 775                 780

Asn Asn Pro Ile His Pro Asn Leu Arg Ser Thr Val Tyr Cys Asn Ala
785                 790                 795                 800

Ile Ala Gln Gly Gly Glu Glu Trp Asp Phe Ala Trp Glu Gln Phe
                805                 810                 815

Arg Asn Ala Thr Leu Val Asn Glu Ala Asp Lys Leu Arg Ala Ala Leu
                820                 825                 830

Ala Cys Ser Lys Glu Leu Trp Ile Leu Asn Arg Tyr Leu Ser Tyr Thr
            835                 840                 845

Leu Asn Pro Asp Leu Ile Arg Lys Gln Asp Ala Thr Ser Thr Ile Ile
850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
            915                 920                 925

Gly Phe Gly Ser Gly Thr Arg Ala Leu Glu Gln Ala Leu Glu Lys Thr
            930                 935                 940

Lys Ala Asn Ile Lys Trp Val Lys Glu Asn Lys Glu Val Val Leu Gln
945                 950                 955                 960

Trp Phe Thr Glu Asn Ser Lys
                965

<210> SEQ ID NO 29
<211> LENGTH: 263
<212> TYPE: DNA
<213> ORGANISM: Artificial Sequence
<220> FEATURE:
<223> OTHER INFORMATION: Description of Artificial Sequence:synthetic
      PRK-1 GH1-54-PCR-G3F1

<400> SEQUENCE: 29
tcctttcccg ccacgcacta cagcaccctg ttgcaagccc gcgccgctca cagggaccct      60
gaggtacgag tggtgggctg cagagacctc ccagagacca tcccgtggaa ccctacccc     120 tcaatggggg gacctgggac cccagacagc gccccccttc ctgagccgcc cagcccgggg    180
ccgcagtaac ccagcacagt ggttagatag ataaagcggc cgctcgacta gtctgaggtc    240
tgatactcac tgacgtgata cgt                                            263

<210> SEQ ID NO 30
<211> LENGTH: 3001
<212> TYPE: DNA
<213> ORGANISM: Homo sapiens
<220> FEATURE:
<223> OTHER INFORMATION: protein kinase C-like 1 (PRKCL1), PRK-1 cDNA

<400> SEQUENCE: 30
tgagtaaatc gatacatcat acgcgcgctc ctctggccgc ccctccctcc gacgatcggg      60
```

```
gaccctggcg ggcggcagga ggacatggcc agcgacgccg tgcagagtga gcctcgcagc    120
tggtccctgc tagagcagct gggcctggcc ggggcagacc tggcggcccc cggggtacag    180
cagcagctgg agctggagcg ggagcggctg cggcgggaaa tccgcaagga gctgaagctg    240
aaggagggtg ctgagaacct gcggcgggcc accactgacc tgggccgcag cctgggcccc    300
gtagagctgc tgctgcgggg ctcctcgcgc cgcctcgacc tgctgcacca gcagctgcag    360
gagctgcacg cccacgtggt gcttccgac ccggcggcca cccacgatgg ccccagtcc      420 cctggtgcgg gtggcccac ctgctcggcc accaacctga gccgcgtggc gggcctggag    480
aagcagttgg ccattgagct gaaggtgaag caggggcgg agaacatgat ccagacctac     540
agcaatggca gcaccaagga ccggaagctg ctgctgacag cccagcagat gttgcaggac    600
agtaagacca agattgacat catccgcatg caactccgcc gggcgctgca ggccgaccag    660
ctggagaacc aggcagcccc ggatgacacc aagggagtc ctgacctggg ggctgtggag     720
ctgcgcatcg aagagctgcg gcaccacttc cgagtggagc acgcggtggc cgagggtgcc    780
aagaacgtac tgcgcctgct cagcgctgcc aaggccccgg accgcaaggc agtcagcgag    840
gcccaggaga aattgacaga atccaaccag aagctggggc tgctgcggga ggctctggag    900
cggagacttg gggagctgcc cgccgaccac cccaaggggc ggctgctgcg agaagagctc    960
gctgcggcct cctccgctgc cttcagcacc cgcctggccg ggccctttcc cgccacgcac   1020
tacagcaccc tgtgcaagcc cgcgccgctc acagggaccc tggaggtacg agtggtgggc   1080
tgcagagacc tcccagagac catcccgtgg aaccctaccc cctcaatggg gggacctggg   1140
accccagaca gccgcccccc cttcctgagc cgcccagccc ggggccttta cagccgaagc   1200
ggaagcctca gtgccggag cagcctcaaa gcagaagccg agaacaccag tgaagtcagc     1260
actgtgctta agctggataa cacagtggtg gggcagacgt cttggaagcc atgtggcccc    1320
aatgcctggg accagagctt cactctggag ctggaagggg cacggaaact ggagttggct    1380
gtgttctggc gggaccagcg gggcctgtgt gccctcaaat tcctgaagtt ggaggatttc    1440
ttggacaatg agaggcatga ggtgcagctg gacatggaac cccagggctg cctggtggct    1500
gaggtcacct tccgcaaccc tgtcattgag aggattcctc ggctccgacg gcagaagaaa   1560
attttctcca gcagcaagg gaaggcgttc agcgtgctaggcagatgaa catcgatgtc       1620 gccacgtggg tgcggctgct ccggaggctc atccccaatg ccacgggcac aggcaccttt    1680
agccctgggg cttctccagg atccgaggcc cggaccacgg gtgacatatc ggtgagaag    1740 ctgaacctcg gcactgactc ggacagctca cctcagaaga gctcgcggga tcctccttcc    1800
agcccatcga gcctgagctc ccccatccag gaatccactg ctcccgagct gccttcggag    1860
acccaggaga ccccaggccc cgccctgtgc agccctctga ggaagtcacc tctgacccttc  1920 gaagattcca gttcctggc ggtgctgggc cggggtcatt ttgggaaggt gctcctctcc     1980
gaattccggc ccagtgggga gctgttcgcc atcaaggctc tgaagaaagg ggacattgtg    2040
gcccgagacg aggtggagag cctgatgtgt gagaagcgga tattggcggc agtgaccagt    2100
gcgggacacc ccttcctggt gaacctcttc ggctgtttcc agacaccgga gcacgtgtgc    2160
ttcgtgatgg agtactcggc cggtgggac ctgatgctgc acatccacag cgacgtgttc    2220
tctgagcccc gtgccatctt ttattccgcc tgcgtggtgc tgggcctaca gtttcttcac    2280
gaacacaaga tcgtctacag ggacctgaag ttggacaatt gctcctgga caccgagggc    2340 tacgtcaaga tcgcagactt tggcctctgc aaggagggga tgggctatgg ggaccggacc    2400
agcacattct gtgggacccc ggagttcctg gccctgagg tgctgacgga cacgtcgtac    2460
```

```
acgcgagctg tggactggtg gggactgggt gtgctgctct acgagatgct ggttggcgag      2520
tccccattcc caggggatga tgaggaggag gtcttcgaca gcatcgtcaa cgacgaggtt      2580
cgctaccccc gcttcctgtc ggccgaagcc atcggcatca tgagaaggct gcttcggagg      2640
aacccagagc ggaggctggg atctagcgag agagatgcag aagatgtgaa gaaacagccc      2700
ttcttcagga ctctgggctg ggaagccctg ttggcccggc gcctgccacc gcccttttgtg     2760 cccacgctgt ccggccgcac cgacgtcagc aacttcgacg aggagttcac cggggaggcc      2820
cccacactga gcccgccccg cgacgcgcgg cccctcacag ccgcggagca ggcagccttc      2880
ctggacttcg acttcgtggc cggggggctgc tagccccctc ccctgcccct gcccctgccc     2940
ctgcccgaga gctcttagtt tttaaaaagg cctttgggat ttgccggaaa aaaaaaaaa      3000 a                                                                      3001
```

<210> SEQ ID NO 31
<211> LENGTH: 942
<212> TYPE: PRT
<213> ORGANISM: Homo sapiens
<220> FEATURE:
<223> OTHER INFORMATION: protein kinase C-like 1 (PRKCL1), serine-
      threonine kinase N, PRK-1

<400> SEQUENCE: 31

```
Met Ala Ser Asp Ala Val Gln Ser Glu Pro Arg Ser Trp Ser Leu Leu
  1               5                  10                  15

Glu Gln Leu Gly Leu Ala Gly Ala Asp Leu Ala Ala Pro Gly Val Gln
             20                  25                  30

Gln Gln Leu Glu Leu Glu Arg Glu Arg Leu Arg Arg Glu Ile Arg Lys
         35                  40                  45

Glu Leu Lys Leu Lys Glu Gly Ala Glu Asn Leu Arg Arg Ala Thr Thr
 50                  55                  60

Asp Leu Gly Arg Ser Leu Gly Pro Val Glu Leu Leu Leu Arg Gly Ser
 65                  70                  75                  80

Ser Arg Arg Leu Asp Leu Leu His Gln Gln Leu Gln Glu Leu His Ala
                 85                  90                  95

His Val Val Leu Pro Asp Pro Ala Ala Thr His Asp Gly Pro Gln Ser
            100                 105                 110

Pro Gly Ala Gly Gly Pro Thr Cys Ser Ala Thr Asn Leu Ser Arg Val
        115                 120                 125

Ala Gly Leu Glu Lys Gln Leu Ala Ile Glu Leu Lys Val Lys Gln Gly
    130                 135                 140

Ala Glu Asn Met Ile Gln Thr Tyr Ser Asn Gly Ser Thr Lys Asp Arg
145                 150                 155                 160

Lys Leu Leu Leu Thr Ala Gln Gln Met Leu Gln Asp Ser Lys Thr Lys
                165                 170                 175

Ile Asp Ile Ile Arg Met Gln Leu Arg Arg Ala Leu Gln Ala Asp Gln
            180                 185                 190

Leu Glu Asn Gln Ala Ala Pro Asp Asp Thr Gln Gly Ser Pro Asp Leu
        195                 200                 205

Gly Ala Val Glu Leu Arg Ile Glu Glu Leu Arg His His Phe Arg Val
    210                 215                 220

Glu His Ala Val Ala Glu Gly Ala Lys Asn Val Leu Arg Leu Leu Ser
225                 230                 235                 240

Ala Ala Lys Ala Pro Asp Arg Lys Ala Val Ser Glu Ala Gln Glu Lys
                245                 250                 255
```

-continued

```
Leu Thr Glu Ser Asn Gln Lys Leu Gly Leu Arg Glu Ala Leu Glu
            260                 265                 270

Arg Arg Leu Gly Glu Leu Pro Ala Asp His Pro Lys Gly Arg Leu Leu
        275                 280                 285

Arg Glu Glu Leu Ala Ala Ala Ser Ser Ala Ala Phe Ser Thr Arg Leu
    290                 295                 300

Ala Gly Pro Phe Pro Ala Thr His Tyr Ser Thr Leu Cys Lys Pro Ala
305                 310                 315                 320

Pro Leu Thr Gly Thr Leu Glu Val Arg Val Val Gly Cys Arg Asp Leu
                325                 330                 335

Pro Glu Thr Ile Pro Trp Asn Pro Thr Pro Ser Met Gly Gly Pro Gly
            340                 345                 350

Thr Pro Asp Ser Arg Pro Pro Phe Leu Ser Arg Pro Ala Arg Gly Leu
        355                 360                 365

Tyr Ser Arg Ser Gly Ser Leu Ser Gly Arg Ser Ser Leu Lys Ala Glu
    370                 375                 380

Ala Glu Asn Thr Ser Glu Val Ser Thr Val Leu Lys Leu Asp Asn Thr
385                 390                 395                 400

Val Val Gly Gln Thr Ser Trp Lys Pro Cys Gly Pro Asn Ala Trp Asp
                405                 410                 415

Gln Ser Phe Thr Leu Glu Leu Glu Arg Ala Arg Glu Leu Glu Leu Ala
            420                 425                 430

Val Phe Trp Arg Asp Gln Arg Gly Leu Cys Ala Leu Lys Phe Leu Lys
        435                 440                 445

Leu Glu Asp Phe Leu Asp Asn Glu Arg His Glu Val Gln Leu Asp Met
    450                 455                 460

Glu Pro Gln Gly Cys Leu Val Ala Glu Val Thr Phe Arg Asn Pro Val
465                 470                 475                 480

Ile Glu Arg Ile Pro Arg Leu Arg Arg Gln Lys Lys Ile Phe Ser Lys
                485                 490                 495

Gln Gln Gly Lys Ala Phe Gln Arg Ala Arg Gln Met Asn Ile Asp Val
            500                 505                 510

Ala Thr Trp Val Arg Leu Leu Arg Arg Leu Ile Pro Asn Ala Thr Gly
        515                 520                 525

Thr Gly Thr Phe Ser Pro Gly Ala Ser Pro Gly Ser Glu Ala Arg Thr
    530                 535                 540

Thr Gly Asp Ile Ser Val Glu Lys Leu Asn Leu Gly Thr Asp Ser Asp
545                 550                 555                 560

Ser Ser Pro Gln Lys Ser Ser Arg Asp Pro Ser Ser Pro Ser Ser
                565                 570                 575

Leu Ser Pro Ile Gln Glu Ser Thr Ala Pro Glu Leu Pro Ser Glu
            580                 585                 590

Thr Gln Glu Thr Pro Gly Pro Ala Leu Cys Ser Pro Leu Arg Lys Ser
        595                 600                 605

Pro Leu Thr Leu Glu Asp Phe Lys Phe Leu Ala Val Leu Gly Arg Gly
    610                 615                 620

His Phe Gly Lys Val Leu Leu Ser Glu Phe Arg Pro Ser Gly Glu Leu
625                 630                 635                 640

Phe Ala Ile Lys Ala Leu Lys Lys Gly Asp Ile Val Ala Arg Asp Glu
                645                 650                 655

Val Glu Ser Leu Met Cys Glu Lys Arg Ile Leu Ala Ala Val Thr Ser
            660                 665                 670

Ala Gly His Pro Phe Leu Val Asn Leu Phe Gly Cys Phe Gln Thr Pro
        675                 680                 685
```

Glu His Val Cys Phe Val Met Glu Tyr Ser Ala Gly Gly Asp Leu Met
690                 695                 700

Leu His Ile His Ser Asp Val Phe Ser Glu Pro Arg Ala Ile Phe Tyr
705                 710                 715                 720

Ser Ala Cys Val Val Leu Gly Leu Gln Phe Leu His Glu His Lys Ile
                725                 730                 735

Val Tyr Arg Asp Leu Lys Leu Asp Asn Leu Leu Leu Asp Thr Glu Gly
            740                 745                 750

Tyr Val Lys Ile Ala Asp Phe Gly Leu Cys Lys Glu Gly Met Gly Tyr
            755                 760                 765

Gly Asp Arg Thr Ser Thr Phe Cys Gly Thr Pro Glu Phe Leu Ala Pro
770                 775                 780

Glu Val Leu Thr Asp Thr Ser Tyr Thr Arg Ala Val Asp Trp Trp Gly
785                 790                 795                 800

Leu Gly Val Leu Leu Tyr Glu Met Leu Val Gly Glu Ser Pro Phe Pro
                805                 810                 815

Gly Asp Asp Glu Glu Glu Val Phe Asp Ser Ile Val Asn Asp Glu Val
            820                 825                 830

Arg Tyr Pro Arg Phe Leu Ser Ala Glu Ala Ile Gly Ile Met Arg Arg
            835                 840                 845

Leu Leu Arg Arg Asn Pro Glu Arg Arg Leu Gly Ser Ser Glu Arg Asp
850                 855                 860

Ala Glu Asp Val Lys Lys Gln Pro Phe Phe Arg Thr Leu Gly Trp Glu
865                 870                 875                 880

Ala Leu Leu Ala Arg Arg Leu Pro Pro Pro Phe Val Pro Thr Leu Ser
                885                 890                 895

Gly Arg Thr Asp Val Ser Asn Phe Asp Glu Glu Phe Thr Gly Glu Ala
            900                 905                 910

Pro Thr Leu Ser Pro Pro Arg Asp Ala Arg Pro Leu Thr Ala Ala Glu
            915                 920                 925

Gln Ala Ala Phe Leu Asp Phe Asp Phe Val Ala Gly Gly Cys
930                 935                 940

<210> SEQ ID NO 32
<211> LENGTH: 454
<212> TYPE: DNA
<213> ORGANISM: Artificial Sequence
<220> FEATURE:
<223> OTHER INFORMATION: Description of Artificial Sequence:synthetic
      Zip kinase GH1-68-PCR-G3F1

<400> SEQUENCE: 32
gctgggtttc atttcgagta ttcgcgggcc tgctctcagc taggtttagc ccgttcgtga    60
ccctccacgt gcactcgtgg tcactgtggc accgtgaggg ttgggaccca ccgaggcgca   120
aggcggccga atgcgcctgt tcagcccgga gaggtttgcg ggtagttgcc ggacattcgg   180
cggggtgctg cctgttgctg ccattatgcc caggaggagg tcgtgggacg gggagggtgg   240
gatggacggc ggacaggcag tccccacgct gcttggtggc gccggcttgg tggggtcttc   300
cactgtgtgc ccttctcgcc gagggcggtc ccccgcgtg tggggtgccc tgctgcggac    360
tcctccgcac gcgagaaacc agcacagtgg ttagagtaga taaagcgggc gagtcgacta   420
gatctgaggt ctgatactca ctgactgttc gtaa                              454

<210> SEQ ID NO 33
<211> LENGTH: 2105
<212> TYPE: DNA

<213> ORGANISM: Homo sapiens
<220> FEATURE:
<223> OTHER INFORMATION: death-associated protein kinase 3 (DAPK3) cDNA

<400> SEQUENCE: 33

| | | | | | |
|---|---|---|---|---|---|
| gttgccatta | ggggactcct | gaggtcctat | ctccaggctg | cggtgactgc | actttccctg | 60 |
| gagtggaagc | tgctggaagg | cggaccggcc | gccatgtcca | cgttcaggca | ggaggacgtg | 120 |
| gaggaccatt | atgagatggg | ggaggagctg | ggcagcggcc | agtttgcgat | cgtgcggaag | 180 |
| tgccggcaga | agggcacggg | caaggagtac | gcagccaagt | tcatcaagaa | gcgccgcctg | 240 |
| tcatccagcc | ggcgtggggt | gagccggag | gagatcgagc | gggaggtgaa | catcctgcgg | 300 |
| gagatccggc | accccaacat | catcaccctg | cacgacatct | tcgagaacaa | gacggacgtg | 360 |
| gtcctcatcc | tggagctggt | ctctggcggg | gagctctttg | acttcctggc | ggagaaagag | 420 |
| tcgctgacgg | aggacgaggc | cacccagttc | ctcaagcaga | tcctggacgg | cgttcactac | 480 |
| ctgcactcta | gcgcatcgc | acactttgac | ctgaagccgg | aaaacatcat | gctgctggac | 540 |
| aagaacgtgc | ccaacccacg | aatcaagctc | atcgacttcg | gcatcgcgca | caagatcgag | 600 |
| gcggggaacg | agttcaagaa | catcttcggc | accccgagt | ttgtggcccc | agagattgtg | 660 |
| aactatgagc | cgctgggcct | ggaggcggac | atgtggagca | tcggtgtcat | cacctatatc | 720 |
| ctcctgagcg | gtgcatcccc | gttcctgggc | gagaccaagc | aggagacgct | caccaacatc | 780 |
| tcagccgtga | actacgactt | cgacgaggag | tacttcagca | acaccagcga | gctggccaag | 840 |
| gacttcattc | gccggctgct | cgtcaaagat | cccaagcgga | gaatgaccat | tgcccagagc | 900 |
| ctggaacatt | cctggattaa | ggcgatccgg | cggcggaacg | tgcgtggtga | ggacagcggc | 960 |
| cgcaagcccg | agcggcggcg | cctgaagacc | acgcgtctga | aggagtacac | catcaagtcg | 1020 |
| cactccagct | tgccgcccaa | caacagctac | gccgacttcg | agcgcttctc | caaggtgctg | 1080 |
| gaggaggcgg | cggccgccga | ggagggcctg | cgcgagctgc | agcgcagccg | gcggctctgc | 1140 |
| cacgaggacg | tggaggcgct | ggccgccatc | tacgaggaga | aggaggcctg | gtaccgcgag | 1200 |
| gagagcgaca | gcctgggcca | ggacctgcgg | aggctacggc | aggagctgct | caagaccgag | 1260 |
| gcgctcaagc | ggcaggcgca | ggaggaggcc | aagggcgcgc | tgctggggac | cagcggcctc | 1320 |
| aagcgccgct | tcagccgcct | ggagaaccgc | tacgaggcgc | tggccaagca | agtagcctcc | 1380 |
| gagatgcgct | tcgtgcagga | cctcgtgcgc | gccctggagc | aggagaagct | gcagggcgtg | 1440 |
| gagtgcgggc | tgcgctaggc | gcagtggggt | gggccaggcc | ccaggacagc | cggagctcgg | 1500 |
| cctgcggtgg | gggcgcttcc | tgtggacgct | gcgcctccca | tcgcccgggt | gcctgtcctt | 1560 |
| gcccagcgcc | accaggctgg | aggcggagtg | ggaggagctg | gagccaggcc | cgtaagttcg | 1620 |
| caggcagggg | tgggtgtggg | acgggctgc | ttctctacac | agcctctacg | ctggccttca | 1680 |
| ccttcaccc | tgcatcgtcg | gtgaccctgg | gaccctccag | gcagcgtggc | ctgtggcacc | 1740 |
| gtgagggttg | ggacccaccg | aggcgcagag | gcggcccgaa | tgcagccctg | gttcaggccc | 1800 |
| ggaggagggt | ttgcgggtag | ttgcacggac | aattcggcgg | ggtgctgcct | gttgctgcca | 1860 |
| ttagcccagg | aggaggtcgt | gggacgggga | gggtgggatg | gacggcggac | aggcagtccc | 1920 |
| cacgctgctg | ggtggcgccg | ggcttggtgg | ggtcttccac | tgtgtgccct | tctcgccgag | 1980 |
| gccggtcccc | cgggtgtggg | gtgccctgct | gcggactcct | ccgcgagccc | catcgtcgcg | 2040 |
| cctgtggacg | cctaggcaag | agcggccctc | tgcagccaag | agaaataaaa | tactggcttc | 2100 |
| cagat | | | | | 2105 |

<210> SEQ ID NO 34

```
<211> LENGTH: 454
<212> TYPE: PRT
<213> ORGANISM: Homo sapiens
<220> FEATURE:
<223> OTHER INFORMATION: death-associated protein kinase 3 (DAPK3)

<400> SEQUENCE: 34
```

| | | | | | | | | | | | | | | |
|---|---|---|---|---|---|---|---|---|---|---|---|---|---|---|
| Met | Ser | Thr | Phe | Arg | Gln | Glu | Asp | Val | Glu | Asp | His | Tyr | Glu | Met | Gly |
| 1 | | | | 5 | | | | | 10 | | | | | 15 | |

Glu Glu Leu Gly Ser Gly Gln Phe Ala Ile Val Arg Lys Cys Arg Gln
             20                  25                  30

Lys Gly Thr Gly Lys Glu Tyr Ala Ala Lys Phe Ile Lys Lys Arg Arg
         35                  40                  45

Leu Ser Ser Ser Arg Arg Gly Val Ser Arg Glu Glu Ile Glu Arg Glu
 50                  55                  60

Val Asn Ile Leu Arg Glu Ile Arg His Pro Asn Ile Ile Thr Leu His
 65                  70                  75                  80

Asp Ile Phe Glu Asn Lys Thr Asp Val Val Leu Ile Leu Glu Leu Val
                 85                  90                  95

Ser Gly Gly Glu Leu Phe Asp Phe Leu Ala Glu Lys Glu Ser Leu Thr
            100                 105                 110

Glu Asp Glu Ala Thr Gln Phe Leu Lys Gln Ile Leu Asp Gly Val His
        115                 120                 125

Tyr Leu His Ser Lys Arg Ile Ala His Phe Asp Leu Lys Pro Glu Asn
130                 135                 140

Ile Met Leu Leu Asp Lys Asn Val Pro Asn Pro Arg Ile Lys Leu Ile
145                 150                 155                 160

Asp Phe Gly Ile Ala His Lys Ile Glu Ala Gly Asn Glu Phe Lys Asn
                165                 170                 175

Ile Phe Gly Thr Pro Glu Phe Val Ala Pro Glu Ile Val Asn Tyr Glu
            180                 185                 190

Pro Leu Gly Leu Glu Ala Asp Met Trp Ser Ile Gly Val Ile Thr Tyr
        195                 200                 205

Ile Leu Leu Ser Gly Ala Ser Pro Phe Leu Gly Glu Thr Lys Gln Glu
210                 215                 220

Thr Leu Thr Asn Ile Ser Ala Val Asn Tyr Asp Phe Asp Glu Glu Tyr
225                 230                 235                 240

Phe Ser Asn Thr Ser Glu Leu Ala Lys Asp Phe Ile Arg Arg Leu Leu
                245                 250                 255

Val Lys Asp Pro Lys Arg Arg Met Thr Ile Ala Gln Ser Leu Glu His
            260                 265                 270

Ser Trp Ile Lys Ala Ile Arg Arg Asn Val Arg Gly Glu Asp Ser
        275                 280                 285

Gly Arg Lys Pro Glu Arg Arg Arg Leu Lys Thr Thr Arg Leu Lys Glu
290                 295                 300

Tyr Thr Ile Lys Ser His Ser Ser Leu Pro Pro Asn Asn Ser Tyr Ala
305                 310                 315                 320

Asp Phe Glu Arg Phe Ser Lys Val Leu Glu Glu Ala Ala Ala Glu
                325                 330                 335

Glu Gly Leu Arg Glu Leu Gln Arg Ser Arg Arg Leu Cys His Glu Asp
            340                 345                 350

Val Glu Ala Leu Ala Ala Ile Tyr Glu Glu Lys Glu Ala Trp Tyr Arg
        355                 360                 365

Glu Glu Ser Asp Ser Leu Gly Gln Asp Leu Arg Arg Leu Arg Gln Glu
370                 375                 380

```
Leu Leu Lys Thr Glu Ala Leu Arg Gln Ala Gln Glu Glu Ala Lys
385                 390                 395                 400

Gly Ala Leu Leu Gly Thr Ser Gly Leu Lys Arg Arg Phe Ser Arg Leu
            405                 410                 415

Glu Asn Arg Tyr Glu Ala Leu Ala Lys Gln Val Ala Ser Glu Met Arg
        420                 425                 430

Phe Val Gln Asp Leu Val Arg Ala Leu Glu Gln Glu Lys Leu Gln Gly
        435                 440                 445

Val Glu Cys Gly Leu Arg
    450

<210> SEQ ID NO 35
<211> LENGTH: 2105
<212> TYPE: DNA
<213> ORGANISM: Homo sapiens
<220> FEATURE:
<223> OTHER INFORMATION: ZIP-kinase cDNA

<400> SEQUENCE: 35
gttgccatta ggggactcct gaggtcctat ctccaggctg cggtgactgc actttccctg     60
gagtggaagc tgctggaagg cggaccggcc gccatgtcca cgttcaggca ggaggacgtg    120
gaggaccatt atgagatggg ggaggagctg ggcagcggcc agtttgcgat cgtgcggaag    180
tgccggcaga agggcacggg caaggagtac gcagccaagt tcatcaagaa cgccgcctg    240 tcatccagcc ggcgtggggt gagccggagg agatcgagc gggaggtgaa catcctgcgg    300
gagatccggc accccaacat catcaccctg acgacatct tcgagaacaa gacggacgtg    360
gtcctcatcc tggagctggt ctctggcggg gagctctttg acttcctggc ggagaaagag    420
tcgctgacgg aggacgaggc cacccagttc tcaagcaga tcctggacgg cgttcactac    480
ctgcactcta agcgcatcgc acactttgac ctgaagccgg aaaacatcat gctgctggac    540
aagaacgtgc ccaacccacg aatcaagctc atcgacttcg gcatcgcgca agatcgag    600 gcggggaacg agttcaagaa catcttcggc accccggagt tgtggccccc agagattgtg    660
aactatgagc gctgggcct ggaggcggac atgtggagca tcgtgtcat cacctatatc    720 ctcctgagcg gtgcatcccc gttcctgggc gagaccaagc aggagacgct caccaacatc    780
tcagccgtga actacgactt cgacgaggag tacttcagca cacccagcga gctggccaag    840
gacttcattc gccggctgct cgtcaaagat cccaagcgga gaatgaccat tgcccagagc    900
ctggaacatt cctggattaa ggcgatccgg cggcggaacg tgcgtggtga ggacagcggc    960
cgcaagcccg agcggcggcg cctgaagacc acgcgtctga aggagtacac catcaagtcg   1020
cactccagct tgccgcccaa caacagctac gccgacttcg agcgcttctc caaggtgctg   1080
gaggaggcgg cggccgccga ggagggcctg cgcgagctgc agcgcagccg gcggctctgc   1140
cacgaggacg tggaggcgct ggccgccatc tacgaggaga aggaggcctg gtaccgcgag   1200
gagagcgaca gcctgggcca ggacctgcgg aggctacggc aggagctgct caagaccgag   1260
gcgctcaagc ggcaggcgca ggaggaggcc aagggcgcgc tgctggggac cagcggcctc   1320
aagcgccgct tcagccgcct ggagaaccgc tacgaggcgc tggccaagca agtagcctcc   1380
gagatgcgct tcgtgcagga cctcgtgcgc gccctggagc aggagaagct gcagggcgtg   1440
gagtgcgggc tgcgctaggc gcagtggggt gggccaggcc ccaggacagc cggagctcgg   1500
cctgcggtgg gggcgcttcc tgtggacgct gcgcctccca tcgcccgggt gcctgtcctt   1560
gcccagcgcc accaggctgg aggcggagtg ggaggagctg gagccaggcc gtaagttcg   1620 caggcagggg tgggtgtggg acggggctgc ttctctacac agcctctacg ctggccttca   1680
```

-continued

```
ccttcacccc tgcatcgtcg gtgaccctgg gaccctccag gcagcgtggc ctgtggcacc      1740
gtgagggttg ggacccaccg aggcgcagag gcggcccgaa tgcagccctg gttcaggccc      1800
ggaggagggt ttgcgggtag ttgcacggac aattcggcgg ggtgctgcct gttgctgcca      1860
ttagcccagg aggaggtcgt gggacgggga gggtgggatg gacggcggac aggcagtccc      1920
cacgctgctg ggtggcgccg ggcttggtgg ggtcttccac tgtgtgccct tctcgccgag      1980
gccggtcccc cgggtgtggg gtgccctgct gcggactcct ccgcgagccc catcgtcgcg      2040
cctgtggacg cctaggcaag agcggccctc tgcagccaag agaaataaaa tactggcttc      2100
cagat                                                                  2105
```

<210> SEQ ID NO 36
<211> LENGTH: 454
<212> TYPE: PRT
<213> ORGANISM: Homo sapiens
<220> FEATURE:
<223> OTHER INFORMATION: ZIP-kinase

<400> SEQUENCE: 36

```
Met Ser Thr Phe Arg Gln Glu Asp Val Glu Asp His Tyr Glu Met Gly
 1               5                  10                  15

Glu Glu Leu Gly Ser Gly Gln Phe Ala Ile Val Arg Lys Cys Arg Gln
             20                  25                  30

Lys Gly Thr Gly Lys Glu Tyr Ala Ala Lys Phe Ile Lys Lys Arg Arg
         35                  40                  45

Leu Ser Ser Ser Arg Arg Gly Val Ser Arg Glu Ile Glu Arg Glu
     50                  55                  60

Val Asn Ile Leu Arg Glu Ile Arg His Pro Asn Ile Ile Thr Leu His
 65                  70                  75                  80

Asp Ile Phe Glu Asn Lys Thr Asp Val Val Leu Ile Leu Glu Leu Val
                 85                  90                  95

Ser Gly Gly Glu Leu Phe Asp Phe Leu Ala Glu Lys Glu Ser Leu Thr
            100                 105                 110

Glu Asp Glu Ala Thr Gln Phe Leu Lys Gln Ile Leu Asp Gly Val His
        115                 120                 125

Tyr Leu His Ser Lys Arg Ile Ala His Phe Asp Leu Lys Pro Glu Asn
    130                 135                 140

Ile Met Leu Leu Asp Lys Asn Val Pro Asn Pro Arg Ile Lys Leu Ile
145                 150                 155                 160

Asp Phe Gly Ile Ala His Lys Ile Glu Ala Gly Asn Glu Phe Lys Asn
                165                 170                 175

Ile Phe Gly Thr Pro Glu Phe Val Ala Pro Glu Ile Val Asn Tyr Glu
            180                 185                 190

Pro Leu Gly Leu Glu Ala Asp Met Trp Ser Ile Gly Val Ile Thr Tyr
        195                 200                 205

Ile Leu Leu Ser Gly Ala Ser Pro Phe Leu Gly Glu Thr Lys Gln Glu
    210                 215                 220

Thr Leu Thr Asn Ile Ser Ala Val Asn Tyr Asp Phe Asp Glu Glu Tyr
225                 230                 235                 240

Phe Ser Asn Thr Ser Glu Leu Ala Lys Asp Phe Ile Arg Arg Leu Leu
                245                 250                 255

Val Lys Asp Pro Lys Arg Arg Met Thr Ile Ala Gln Ser Leu Glu His
            260                 265                 270

Ser Trp Ile Lys Ala Ile Arg Arg Arg Asn Val Arg Gly Glu Asp Ser
        275                 280                 285
```

```
Gly Arg Lys Pro Glu Arg Arg Leu Lys Thr Thr Arg Leu Lys Glu
    290                 295                 300

Tyr Thr Ile Lys Ser His Ser Ser Leu Pro Pro Asn Asn Ser Tyr Ala
305                 310                 315                 320

Asp Phe Glu Arg Phe Ser Lys Val Leu Glu Glu Ala Ala Ala Ala Glu
                325                 330                 335

Glu Gly Leu Arg Glu Leu Gln Arg Ser Arg Arg Leu Cys His Glu Asp
            340                 345                 350

Val Glu Ala Leu Ala Ala Ile Tyr Glu Glu Lys Glu Ala Trp Tyr Arg
        355                 360                 365

Glu Glu Ser Asp Ser Leu Gly Gln Asp Leu Arg Arg Leu Arg Gln Glu
    370                 375                 380

Leu Leu Lys Thr Glu Ala Leu Lys Arg Gln Ala Gln Glu Glu Ala Lys
385                 390                 395                 400

Gly Ala Leu Leu Gly Thr Ser Gly Leu Lys Arg Arg Phe Ser Arg Leu
                405                 410                 415

Glu Asn Arg Tyr Glu Ala Leu Ala Lys Gln Val Ala Ser Glu Met Arg
            420                 425                 430

Phe Val Gln Asp Leu Val Arg Ala Leu Glu Gln Glu Lys Leu Gln Gly
        435                 440                 445

Val Glu Cys Gly Leu Arg
    450

<210> SEQ ID NO 37
<211> LENGTH: 2055
<212> TYPE: DNA
<213> ORGANISM: Homo sapiens
<220> FEATURE:
<223> OTHER INFORMATION: ZIP kinase cDNA

<400> SEQUENCE: 37
gcactttccc tggagtggaa gctgctggaa ggcggaccgg ccgccatgtc cacgttcagg      60
caggaggacg tggaggacca ttatgagatg ggggaggagc tgggcagcgg ccagtttgcg     120
atcgtgcgga agtgccggca agggcacg ggcaaggagt acgcagccaa gttcatcaag      180
aagcgccgcc tgtcatccag ccggcgtggg gtgagccggg aggagatcga gcgggaggtg     240
aacatcctgc gggagatccg gcaccccaac atcatcaccc tgcacgacat cttcgagaac     300
aagacggacg tggtcctcat cctggagctg gtctctggcg ggagctcttt gacttcctg      360 gcggagaagg agtcgctgac ggaggacgag gccacccagt ccctcaagca gatcctggac     420
ggcgttcact acctgcactc taagcgcatc gcacactttg acctgaagcc ggaaaacatc     480
atgctgctgg acaagaacgt gcccaaccca cgaatcaagc tcatcgactt cggcatcgcg     540
cacaagatcg aggcggggaa cgagttcaag aacatcttcg gcaccccgga gtttgtggcc     600
ccagagattg tgaactatga gccgctgggc ctggaggcgg acatgtggag catcggtgtc     660
atcacctata tcctcctgag cggtgcatcc ccgttcctgg gcgagaccaa gcaggagacg     720
ctcaccaaca tctcagccgt gaactacgac ttcgacgagg agtacttcag caacaccagc     780
gagctggcca aggacttcat tcgccggctg ctcgtcaaag atcccaagcg agaatgacc      840 attgcccaga gcctggaaca ttcctggatt aaggcgatcc ggcggcggaa cgtgcgtggt     900
gaggacagcg gccgcaagcc cgagcggcgg cgcctgaaga ccacgcgtct gaaggagtac     960
accatcaagt cgcactccag cttgccgccc aacaacagct acgccgactt cgagcgcttc    1020
tccaaggtgc tggaggaggc ggcggccgcc gaggagggcc tgcgcgagct gcagcgcagc    1080
```

-continued

```
cggcggctct gccacgagga cgtggaggcg ctggccgcca tctacgagga gaaggaggcc    1140
tggtaccgcg aggagagcga cagcctgggc caggacctgc ggaggctacg gcaggagctg    1200
ctcaagaccg aggcgctcaa gcggcaggcg caggaggagg ccaagggcgc gctgctgggg    1260
accagcggcc tcaagcgccg cttcagccgc ctggagaacc gctacgaggc gctggccaag    1320
caagtagcct ccgagatgcg cttcgtgcag gacctcgtgc gcgccctgga gcaggagaag    1380
ctgcagggcg tggagtgcgg gctgcgctag gcgcagtggg gtgggccagg ccccaggaca    1440
gccggagctc ggcctgcggt ggggggcgtt cctgtggacg ctgcgcctcc catcgcccgg    1500
gtgcctgtcc ttgcccagcg ccaccaggct ggaggcggag tggaggagc tggagccagg     1560 cccgtaagtt cgcaggcagg ggtgggtgtg ggacggggct gcttctctac acatcctcca    1620
cgctggcctt caccttcacc cctgcatcgt cggtgaccct gggacccctcc aggcagcgtg    1680 gcctgtggca ccgtgagggt tgggacccac cgaggcgcag aggcggcccg aatgcagccc    1740
tggttcaggc ccggaggagg gtttgcgggt agttgcacgg acaattcggc ggggtgctgc    1800
ctgttgctgc cattagccca ggaggaggtc gtgggacggg gagggtggga tggacggcgg    1860
acaggcagtc cccacgctgc tgggtggcgc cgggcttggt ggggtcttcc actgtgtgcc    1920
cttctcgccg aggccggtcc cccgggtgtg gggtgccctg ctgcggactc ctccgcgagc    1980
cccatcgtcg cgcctgtgga cgcctaggca agagcggccc tctgcagcca agagaaataa    2040
aatactggct tccag                                                     2055
```

<210> SEQ ID NO 38
<211> LENGTH: 454
<212> TYPE: PRT
<213> ORGANISM: Homo sapiens
<220> FEATURE:
<223> OTHER INFORMATION: ZIP kinase

<400> SEQUENCE: 38

```
Met Ser Thr Phe Arg Gln Glu Asp Val Glu Asp His Tyr Glu Met Gly
  1               5                  10                  15

Glu Glu Leu Gly Ser Gly Gln Phe Ala Ile Val Arg Lys Cys Arg Gln
             20                  25                  30

Lys Gly Thr Gly Lys Glu Tyr Ala Ala Lys Phe Ile Lys Lys Arg Arg
         35                  40                  45

Leu Ser Ser Ser Arg Arg Gly Val Ser Arg Glu Glu Ile Glu Arg Glu
     50                  55                  60

Val Asn Ile Leu Arg Glu Ile Arg His Pro Asn Ile Ile Thr Leu His
 65                  70                  75                  80

Asp Ile Phe Glu Asn Lys Thr Asp Val Val Leu Ile Leu Glu Leu Val
                 85                  90                  95

Ser Gly Gly Glu Leu Phe Asp Phe Leu Ala Glu Lys Glu Ser Leu Thr
            100                 105                 110

Glu Asp Glu Ala Thr Gln Phe Leu Lys Gln Ile Leu Asp Gly Val His
        115                 120                 125

Tyr Leu His Ser Lys Arg Ile Ala His Phe Asp Leu Lys Pro Glu Asn
    130                 135                 140

Ile Met Leu Leu Asp Lys Asn Val Pro Asn Pro Arg Ile Lys Leu Ile
145                 150                 155                 160

Asp Phe Gly Ile Ala His Lys Ile Glu Ala Gly Asn Glu Phe Lys Asn
                165                 170                 175

Ile Phe Gly Thr Pro Glu Phe Val Ala Pro Glu Ile Val Asn Tyr Glu
            180                 185                 190
```

```
Pro Leu Gly Leu Glu Ala Asp Met Trp Ser Ile Gly Val Ile Thr Tyr
        195                 200                 205
Ile Leu Leu Ser Gly Ala Ser Pro Phe Leu Gly Glu Thr Lys Gln Glu
        210                 215                 220
Thr Leu Thr Asn Ile Ser Ala Val Asn Tyr Asp Phe Asp Glu Tyr
225                 230                 235                 240
Phe Ser Asn Thr Ser Glu Leu Ala Lys Asp Phe Ile Arg Arg Leu Leu
                245                 250                 255
Val Lys Asp Pro Lys Arg Arg Met Thr Ile Ala Gln Ser Leu Glu His
                260                 265                 270
Ser Trp Ile Lys Ala Ile Arg Arg Asn Val Arg Gly Glu Asp Ser
        275                 280                 285
Gly Arg Lys Pro Glu Arg Arg Leu Lys Thr Thr Arg Leu Lys Glu
        290                 295                 300
Tyr Thr Ile Lys Ser His Ser Ser Leu Pro Pro Asn Asn Ser Tyr Ala
305                 310                 315                 320
Asp Phe Glu Arg Phe Ser Lys Val Leu Glu Glu Ala Ala Ala Glu
                325                 330                 335
Glu Gly Leu Arg Glu Leu Gln Arg Ser Arg Arg Leu Cys His Glu Asp
        340                 345                 350
Val Glu Ala Leu Ala Ala Ile Tyr Glu Glu Lys Glu Ala Trp Tyr Arg
        355                 360                 365
Glu Glu Ser Asp Ser Leu Gly Gln Asp Leu Arg Arg Leu Arg Gln Glu
        370                 375                 380
Leu Leu Lys Thr Glu Ala Leu Lys Arg Gln Ala Gln Glu Glu Ala Lys
385                 390                 395                 400
Gly Ala Leu Leu Gly Thr Ser Gly Leu Lys Arg Arg Phe Ser Arg Leu
                405                 410                 415
Glu Asn Arg Tyr Glu Ala Leu Ala Lys Gln Val Ala Ser Glu Met Arg
                420                 425                 430
Phe Val Gln Asp Leu Val Arg Ala Leu Glu Gln Glu Lys Leu Gln Gly
        435                 440                 445
Val Glu Cys Gly Leu Arg
        450

<210> SEQ ID NO 39
<211> LENGTH: 196
<212> TYPE: DNA
<213> ORGANISM: Artificial Sequence
<220> FEATURE:
<223> OTHER INFORMATION: Description of Artificial Sequence:synthetic
      Gas6 GH1-50-PCR-G3F1

<400> SEQUENCE: 39
gcgcaggaat ctggtcatca aggtcaacag ggatgctgtc atgaaaatcg cggtggccgg        60
ggacttgttc caaccggagc gaggactgta tcatctgaac cttaccgtgg gaggtattcc       120
cttccatgag aaggactacg tgcagctata aaacctcgtc tggatgctgc actgaagagc       180
gcgcagaaac caacac                                                       196

<210> SEQ ID NO 40
<211> LENGTH: 2461
<212> TYPE: DNA
<213> ORGANISM: Homo sapiens
<220> FEATURE:
<223> OTHER INFORMATION: growth arrest-specific 6 (GAS6) cDNA

<400> SEQUENCE: 40
```

-continued

```
ccgcagccgc cgccgccgcc gccgccgcga tgtgaccttc agggccgcca ggacgggatg      60
accggagcct ccgccccgcg gcgcccgctc gcctcggcct cccgggcgct ctgaccgcgc     120
gtccccggcc cgccatggcc ccttcgctct cgcccgggcc cgccgccctg cgccgcgcgc     180
cgcagctgct gctgctgctg ctggccgcgg agtgcgcgct tgccgcgctg ttgccggcgc     240
gcgaggccac gcagttcctg cggcccaggc agcgccgcgc ctttcaggtc ttcgaggagg     300
ccaagcaggg ccacctggag agggagtgcg tggaggagct gtgcagccgc gaggaggcgc     360
gggaggtgtt cgagaacgac cccgagacgg attattttta cccaagatac ttagactgca     420
tcaacaagta tgggtctccg tacaccaaaa actcaggctt cgccacctgc gtgcaaaacc     480
tgcctgacca gtgcacgccc aacccctgcg ataggaaggg acccaagcc tgccaggacc      540 tcatgggcaa cttcttctgc ctgtgtaaag ctggctgggg gggccggctc tgcgacaaag     600
atgtcaacga atgcagccag gagaacgggg gctgcctcca gatctgccac aacaagccgg     660
gtagcttcca ctgttcctgc cacagcggct tcgagctctc ctctgatggc aggacctgcc     720
aagacataga cgagtgcgca gactcggagg cctgcgggga ggcgcgctgc aagaacctgc     780
ccggctccta ctcctgcctc tgtgacgagg cttttgcgta cagctcccag agaaaggctt     840
gccgagatgt ggacgagtgt ctgcagggcc gctgtgagca ggtctgcgtg aactcccag      900 ggagctacac ctgccactgt gacgggcgtg ggggcctcaa gctgtcccag acatggaca      960 cctgtgagga catcttgccg tgcgtgccct tcagcgtggc caagagtgtg aagtccttgt    1020
acctgggccg gatgttcagt gggaccccg tgatccgact gcgcttcaag aggctgcagc     1080
ccaccaggct ggtagctgag tttgacttcc ggacctttga ccccgagggc atcctcctct    1140
ttgccggagg ccaccaggac agcacctgga tcgtgctggc cctgagagcc ggccggctgg    1200
agctgcagct gcgctacaac ggtgtcggcc gtgtcaccag cagcggcccg gtcatcaacc    1260
atggcatgtg gcagacaatc tctgttgagg agctggcgcg gaatctggtc atcaaggtca    1320 acaggggatgc tgtcatgaaa atcgcggtgg ccggggactt gttccaaccg gagcgaggac    1380
tgtatcatct gaacctgacc gtgggaggta ttcccttcca tgagaaggac ctcgtgcagc    1440
ctataaaccc tcgtctggat ggctgcatga ggagctggaa ctggctgaac ggagaagaca    1500
ccaccatcca ggaaacggtg aaagtgaaca cgaggatgca gtgcttctcg gtgacggaga    1560
gaggctcttt ctaccccggg agcggcttcg ccttctacag cctggactac atgcggaccc    1620
ctctggacgt cgggactgaa tcaacctggg aagtagaagt cgtggctcac atccgcccag    1680
ccgcagacac aggcgtgctg tttgcgctct ggggcccga cctccgtgcc gtgcctctct    1740
ctgtggcact ggtagactat cactccacga agaaactcaa gaagcagctg tggtcctgg    1800 ccgtggagca tacggccttg gccctaatgg agatcaaggt ctgcgacggc caagagcacg    1860
tggtcaccgt ctcgctgagg gacggtgagg ccaccctgga ggtggacggc accaggggcc    1920
agagcgaggt gagcgccgcg cagctgcagg agaggctggc cgtgctcgag aggcacctgc    1980
ggagccccgt gctcaccttt gctggcggcc tgccagatgt gccggtgact tcagcgccag    2040
tcaccgcgtt ctaccgcggc tgcatgacac tggaggtcaa ccggaggctg ctggacctgg    2100
acgaggcggc gtacaagcac agcgacatca cggcccactc ctgcccccc gtggagcccg    2160 ccgcagccta ggccccacg ggacgcggca ggcttctcag tctctgtccg agacagccgg    2220
gaggagcctg ggggctcctc accacgtggg gccatgctga gagctgggct ttcctctgtg    2280
accatcccgg cctgtaacat atctgtaaat agtgagatgg acttgggggcc tctgacgccg    2340 cgcactcagc cgtgggcccg ggcgcgggga ggccggcgca gcgcagagcg ggctcgaaga    2400
```

```
aaataattct ctattatttt tattaccaag cgcttctttc tgactctaaa atatggaaaa    2460
t                                                                   2461
```

<210> SEQ ID NO 41
<211> LENGTH: 678
<212> TYPE: PRT
<213> ORGANISM: Homo sapiens
<220> FEATURE:
<223> OTHER INFORMATION: growth arrest-specific 6 (GAS6), AXL
      stimulatory factor

<400> SEQUENCE: 41

```
Met Ala Pro Ser Leu Ser Pro Gly Pro Ala Ala Leu Arg Arg Ala Pro
 1               5                  10                  15

Gln Leu Leu Leu Leu Leu Ala Ala Glu Cys Ala Leu Ala Ala Leu
             20                  25                  30

Leu Pro Ala Arg Glu Ala Thr Gln Phe Leu Arg Pro Arg Gln Arg Arg
             35                  40                  45

Ala Phe Gln Val Phe Glu Glu Ala Lys Gln Gly His Leu Glu Arg Glu
     50                  55                  60

Cys Val Glu Glu Leu Cys Ser Arg Glu Glu Ala Arg Glu Val Phe Glu
 65                  70                  75                  80

Asn Asp Pro Glu Thr Asp Tyr Phe Tyr Pro Arg Tyr Leu Asp Cys Ile
                 85                  90                  95

Asn Lys Tyr Gly Ser Pro Tyr Thr Lys Asn Ser Gly Phe Ala Thr Cys
            100                 105                 110

Val Gln Asn Leu Pro Asp Gln Cys Thr Pro Asn Pro Cys Asp Arg Lys
            115                 120                 125

Gly Thr Gln Ala Cys Gln Asp Leu Met Gly Asn Phe Phe Cys Leu Cys
        130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
            195                 200                 205

Glu Ala Arg Cys Lys Asn Leu Pro Gly Ser Tyr Ser Cys Leu Cys Asp
        210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu Asp Ile Leu Pro Cys Val Pro Phe Ser Val
            275                 280                 285

Ala Lys Ser Val Lys Ser Leu Tyr Leu Gly Arg Met Phe Ser Gly Thr
        290                 295                 300

Pro Val Ile Arg Leu Arg Phe Lys Arg Leu Gln Pro Thr Arg Leu Val
305                 310                 315                 320

Ala Glu Phe Asp Phe Arg Thr Phe Asp Pro Glu Gly Ile Leu Leu Phe
                325                 330                 335

Ala Gly Gly His Gln Asp Ser Thr Trp Ile Val Leu Ala Leu Arg Ala
            340                 345                 350
```

```
Gly Arg Leu Glu Leu Gln Leu Arg Tyr Asn Gly Val Gly Arg Val Thr
            355                 360                 365
Ser Ser Gly Pro Val Ile Asn His Gly Met Trp Gln Thr Ile Ser Val
        370                 375                 380
Glu Glu Leu Ala Arg Asn Leu Val Ile Lys Val Asn Arg Asp Ala Val
385                 390                 395                 400
Met Lys Ile Ala Val Ala Gly Asp Leu Phe Gln Pro Glu Arg Gly Leu
                405                 410                 415
Tyr His Leu Asn Leu Thr Val Gly Ile Pro Phe His Glu Lys Asp
            420                 425                 430
Leu Val Gln Pro Ile Asn Pro Arg Leu Asp Gly Cys Met Arg Ser Trp
            435                 440                 445
Asn Trp Leu Asn Gly Glu Asp Thr Thr Ile Gln Glu Thr Val Lys Val
        450                 455                 460
Asn Thr Arg Met Gln Cys Phe Ser Val Thr Glu Arg Gly Ser Phe Tyr
465                 470                 475                 480
Pro Gly Ser Gly Phe Ala Phe Tyr Ser Leu Asp Tyr Met Arg Thr Pro
                485                 490                 495
Leu Asp Val Gly Thr Glu Ser Thr Trp Glu Val Glu Val Val Ala His
            500                 505                 510
Ile Arg Pro Ala Ala Asp Thr Gly Val Leu Phe Ala Leu Trp Ala Pro
            515                 520                 525
Asp Leu Arg Ala Val Pro Leu Ser Val Ala Leu Val Asp Tyr His Ser
        530                 535                 540
Thr Lys Lys Leu Lys Lys Gln Leu Val Leu Ala Val Glu His Thr
545                 550                 555                 560
Ala Leu Ala Leu Met Glu Ile Lys Val Cys Asp Gly Gln Glu His Val
                565                 570                 575
Val Thr Val Ser Leu Arg Asp Gly Glu Ala Thr Leu Glu Val Asp Gly
            580                 585                 590
Thr Arg Gly Gln Ser Glu Val Ser Ala Ala Gln Leu Gln Glu Arg Leu
            595                 600                 605
Ala Val Leu Glu Arg His Leu Arg Ser Pro Val Leu Thr Phe Ala Gly
        610                 615                 620
Gly Leu Pro Asp Val Pro Val Thr Ser Ala Pro Val Thr Ala Phe Tyr
625                 630                 635                 640
Arg Gly Cys Met Thr Leu Glu Val Asn Arg Arg Leu Leu Asp Leu Asp
                645                 650                 655
Glu Ala Ala Tyr Lys His Ser Asp Ile Thr Ala His Ser Cys Pro Pro
            660                 665                 670
Val Glu Pro Ala Ala Ala
            675

<210> SEQ ID NO 42
<211> LENGTH: 495
<212> TYPE: DNA
<213> ORGANISM: Artificial Sequence
<220> FEATURE:
<223> OTHER INFORMATION: Description of Artificial Sequence:synthetic
      SRm160 GH1-67-PCR-G3F1
<220> FEATURE:
<221> NAME/KEY: modified_base
<222> LOCATION: (1)..(495)
<223> OTHER INFORMATION: n = g, a, c or t

<400> SEQUENCE: 42
ggttctctcc tcgtcgtctt cctccccttc cccttctaag cctggccctc aggccttgcc      60
```

```
caaacctgca agccccaaga agccacccccc ttgcgagcgg aggtccgcag ccccggaagc      120
caataactcc ctcaggggac tctcggtccc tcagctactc gcctgtggag cgtcgccgtc      180
cctcgcccca gccctcacca cgggaccagc agagcagcag cagtgagcgg ggttcccgga      240
gaggccagcg tggggacagc cgctccccca gccacaagcg cagaggagac acctagccct      300
cggccatgag acaccgctcc tccaggtctc cataaattgt ctttggggga ttncaccaca      360
cccatgctct tgagccacaa ggagtgttcc ttcttcccca gcagaaccgt ggaaggtcct      420
tgttctgcgt ctccttttaa ccttngcagc ctttgattgg agggggcgtcc cctttttccc     480 tcccccttt tttag                                                        495

<210> SEQ ID NO 43
<211> LENGTH: 9027
<212> TYPE: DNA
<213> ORGANISM: Homo sapiens
<220> FEATURE:
<223> OTHER INFORMATION: serine/arginine repetitive matrix 2 (SRRM2)
      cDNA

<400> SEQUENCE: 43
gcggcccagg cggggtgcga gtggcgcagt cggagcccgt tgcggcccct gaggaagcga       60
ggaggcgtcg gcgtcggctg aggcgggcgg accggcgagg cgaggcggcg gccccaggcc      120
cgagggactc gggagctcga gcagcggcgg cggcaagacc tctcccccte ggaggcggcg      180 ggcggaggcg gcgggagcgg tggtgccccc cccgggcacg gggccatgta caacgggatc      240
gggctgccga cgccccgggg cagcggcacc aacggctacg tccagcgcaa cctgtccctg      300
gtgcggggcc gccgggggtga gcggcctgac tacaagggag aggaggaact gcggcgcctg      360
gaggctgccc tggtgaagcg gcctaatcct gacatcctgg accacgagcg caagcggcgc      420
gtcgagctgc gatgcctcga gctggaggag atgatgaaag agcagggta cgaggaacag       480 caaattcagg aaaaagtggc gaccttctga ctcatgttgc tggagaagga tgtgaacccct      540 ggggcaagg aggagacccc agggcagagg ccagcggtca cggagactca ccagttggca      600
gaattaaatg agaagaagaa tgaaagactc cgtgctgcct ttggcatcag tgattcttac      660
gtagatggca gctctttga tcctcagcgt cgtgcccgag aagctaaaca accagctcct      720
gagcctccca aaccttacag ccttgttcgg gagtctagca gttctcgctc accaacccca      780
aagcagaaga gaagaaaaa gaagaaagat agaggacgca ggtcagagag cagctctcct      840
cgacgggaga gaaagaaaag ctcaaagaag aagaagcaca ggtcagaatc tgagtccaag      900
aaacgtaagc ataggtctcc cactccaaag agcaaacgta atctaaggga caaaaagcga      960
aagcggtctc gaagtacaac accagccccc aagagccgcc gggcccaccg ttcaacttct     1020
gctgactctg cttcctcctc cgatacttcc cgcagtcggt ctcgaagtgc tgcagctaaa     1080
actcatacaa ctgccttggc tgggcgaagt ccttcccctg cttcagggcg acgcggggag     1140
ggagatgcgc ctttcagtga accaggtact accagcacac aacggcctag tagcccggag     1200
actgctacga aacagcctag cagcccttat gaagacaaag ataaagacaa gaaggagaaa     1260
tctgcaactc gacctagccc ctctccggaa aggagcagca caggcccaga accacctgct     1320
cccactccgc tccttgctga gcgacatggc ggctccccac aacccctttgc aaccacccccc    1380 ttaagccagg agccagtgaa ccccccatct gaggcctctc caactcggga ccgttcacca     1440
cctaagtctc ccgagaaact tcccccagtct tcttcctcag agagcagccc accatcccct     1500
caacctacca aagtttctcg gcatgccagc tcttccccag aaagtcctaa acctgctcca     1560
```

```
gctccagggt cccaccgaga gatttcttct tctcccacat ctaagaatcg ctcacatggc    1620
cgagcaaaac gggataaatc acattctcat accccctccc gtaggatggg gaggtcccgt    1680
agccctgcca ccgctaagag agggcgatct cggtctcgaa ccccctaccaa gagaggtcat   1740 tctcgatccc gatctcccca gtggcgtagg tccaggtctg cacagaggtg gggaagatct    1800
agaagccccc agcgacgtgg ccgctctagg tctcctcagc gaccaggctg gtctaggagc    1860
agaaataccc agaagagagg caggtctagg tcagcaaggc gagggaggtc ccactctaga    1920
tccccagcca ctaggggtag atctcgttct agaacaccag cccgccgggg caggtcccgc    1980
tctagaacac ctgccaggcg gagatcacga tccagaactc ccaccaggcg taggtctcgg    2040
tctagaacac cagcccggag gggcaggtct cggtctagaa cacctgctag gcgcagatct    2100
aggacccgat caccagtacg acgcaggtct cgtagtagat caccagccag gagaagtggc    2160
aggtcacgct ctagaacccc agctagacgt ggccgctcac gctccagaac cccagccaga    2220
cgtggccgct cacgctctag aaccccagct agacgcagtg gtcgctcacg ctccagaaca    2280
ccagccagga gagggaggtc tcggtctagg acaccaagac gaggaagatc ccgcagtaga    2340
agcttagtta gacgtggaag atctcactct agaacacctc aaagaagagg cagatctggc    2400
tcatcttcag agcggaaaaa caaatccaga acatctcaaa gaagaagcag gtccaattca    2460
agcccagaaa tgaagaaatc tcgcatttct tcaaggcgga gcaggtctct ctcttcacca    2520
cggtccaaag caaaatctcg cttgtctttg aggcgcagcc tttcagggtc ttccccatgc    2580
cctaagcaaa agtcacagac cacccccagg cgcagtcgct ctggatcctc ccaacctaaa    2640
gctaaatcta gaacgccacc cagacgcagt cgctccagtt cttctccgcc acctaaacag    2700
aaatctaaga caccatcaag acaaagtcat tccagttcat ctcctcatcc taaagtgaaa    2760
tctggaacac caccgaggca agggtccata acaagtcccc aggccaatga gcaatctgta    2820
acgccacaga gacggagctg ttttgaatca tcacctgacc ctgagttgaa atctaggacc    2880
ccttctagac atagctgctc agggtcctct cctcctagag tgaaatctag cacacctccc    2940
agacagagcc catctaggtc atcatctcca caacccaaag tgaaggcaat aatatcacca    3000
agacaaagaa gccattctgg ctcctcttct ccaagtccta gtagggtgac gtcgagaaca    3060
actccacggc gaagcagatc agtatctccc tgctccaatg tggaatccag attgttgcca    3120
agatacagtc attctgggtc ctcctcacca gataccaaag tgaaacctga acaccgcca    3180 agacaaagtc actcagggtc tatttcacca taccccaaag taaaggccca aactccaccg    3240
gggccaagtc tttctggatc aaagtcacca tgtcccaag agaagtctaa agactcacta    3300
gttcaaagtt gccctggatc cctctctctc tgtgcaggag taaaatctag cacaccacca    3360
ggcgagagct attttggtgt ctcatctctg caactgaaag gacaatctca aacttcacca    3420
gaccacagat ctgatacttc aagtccagaa gtgagacaga gtcattcaga atcaccatct    3480
ctgcagagca atctcaaac atcacctaag ggaggtcggt ccaggtcttc atctccagtc    3540
actgagctgg catccagatc tccaataaga caagatagag gtgagttctc agcgagtcct    3600
atgttgaaat ctggaatgtc tcctgagcag agcaggttcc agtctgactc ttcttcatat    3660
cctacagtgg actcgaattc tctcttgggg cagagtagat tggagactgc tgaatcaaaa    3720
gagaaaatgg ccttacccc tcaggaggat gctactgcat cacctcctag acagaaagac    3780
aaatttagtc ccttttccagt acaggatagg cctgagtctt cactggtatt caaagacaca    3840
cttagaaccc cgccaagaga aagaagtggt gctgggtcat ctccagaaac aaaagagcaa    3900
aatagtgcat tgcctacgtc aagccaagat gaagagttaa tggaggtggt agagaagtct    3960
```

```
gaagaacccg caggccaaat cctgtctcat ttgtcttcag aacttaaaga aatgtccaca   4020
agtaactttg aatcatctcc tgaagtagaa gaaaggcctg ctgtgtcttt gactcttgat   4080
cagagccagt cacaggcttc tttggaagca gtagaagtcc cttcaatggc ctcatcttgg   4140
ggtgggccac attttctcc agaacataaa gaactgtcta actccccact cagggagaac    4200
agctttggat cacctttaga atttagaaac tcaggcccac ttggtacaga atgaatact    4260 ggattttctt ctgaggttaa agaagatttg aatggaccgt ttcttaatca gctgaaaaca   4320
gatccatctc tagacatgaa agaacaatcg acaagatcct ctggacacag cagttctgag   4380
ttatccccag atgcagtgga aaaggcaggg atgtcttcaa atcagagcat ctcttcacct   4440
gtgcttgatg ctgtacccag aacaccctcg agagaaagaa gtagttctgc atcttctcct   4500
gaaatgaaag atggtttacc cagaactcca tcaaggagaa gcaggtctgg gtcttctcca   4560
ggacttagag atgggtctgg gactccctcg aggcacagcc tgtctgggtc ctctcctgga   4620
atgaaagata tacctagaac gccatttaga gggagaagcg aatgtgattc ttccccagaa   4680
ccgaaagctt tgcctcagac tcctaggccg aggagtcgtt ctccatcatc cccagagctc   4740
aacaacaagt gtcttacccc ccagagagaa agaagcgggt cagaatcatc agttgatcag   4800
aaaactgtgg ctcggactcc cctggggcag agaagtcgtt cgggatcctc tcaagaactt   4860
gatgtgaaac ccagtgcatc ccctcaggaa agaagtgagt cagactcttc tccagattct   4920
aaagccaaga cacgaacccc acttcggcag aggagtcggt ctggatcatc tccagaggtt   4980
gacagcaaat ctcgactatc ccctcggcgc agtaggtctg gttcctcccc tgaagtgaaa   5040
gataagccaa gagcagcacc cagggcacag agtggttctg attcctctcc tgaacctaaa   5100
gctccagccc ctcgggccct tcccagacga agcagatcag gttcatcaag caaaggcaga   5160
ggcccttctc ctgaaggaag cagcagtacc gagtcctctc ctgaacatcc gcccaaatcc   5220
agaactgctc gcagaggttc caggtcatca ccagagccca agaccaagtc tcgtacacca   5280
cctcgacgtc gcagctctcg atcatctccg gagctaacaa ggaaggccag actgtcccgt   5340
agaagccgct ctgcctcatc ctcaccagaa actcgctcta gaactccccc aaggcaccgg   5400
agaagtccct cagtgtcttc cccggagcca gccgaaaaat cgaggtcttc acgccgacgg   5460
cgctcagctt catctccacg cactaagaca acctcaagga gaggccgctc tccttcgcca   5520
aagcctcgtg gactccagag gtcccgttcc cgctcaagga gagagaaaac aagaacaacc   5580
cgacgtcgag ataggtctgg atcttctcag tcaacctctc ggcgaagaca gcggagccgg   5640
tcaaggtcgc gggttactcg gcggcggagg ggaggctctg ttatcactc aaggtcacct    5700 gcccggcagg aaagttcccg gacctcctct cgacgccgaa gaggccgctc tcggacaccc   5760
ccaaccagtc ggaagcgttc tcgctcacgc acatcaccag ccccgtggaa acgctctaga   5820
tctcgagcct ctccagccac tcaccggcga tccaggtcca gaaccccct gataagccga    5880 cgtaggtcca gatctcgaac ttcaccagtc agccggagac ggtcaaggtc caggacttca   5940
gtgactcgac gaagatcccg gtcaagagca tccccagtga gcagaaggcg atccagatcc   6000
agaacgccac cagtaacccg ccgtcgttca aggtctagaa cgccaacaac acgccgccgc   6060
tcccgttcta gaactccacc agtgactcgc agaaggtcca gatccaggac tccaccagta   6120
accaggaggc gatctcgaag cagaacttcg cctatcactc gcagaagatc aagatccaga   6180
acatctccgg tcacccgaag gagatctcga tctcgcacat ctccagtaac tcgaagaagg   6240
tcccgctctc gaacctcacc agtgacacgc cgccgctcta ggtccggac acctccagct    6300 attcggcgcc gctctagatc tcgaacgcca ctgttaccac gcaaacgttc tcgaagtcgc   6360
```

```
tcaccacttg ctatccgccg ccgctccaga tcccgtactc cacgaacagc tcggggtaaa   6420
cggtccttaa caagatctcc tccagccatc cgcaggcgtt ctgcatctgg aagtagttct   6480
gatcgttcac gatctgctac tcctccagca acaagaaatc attctggttc acggacacct   6540
ccagtagcac tcaacagttc cagaatgagc tgcttcagtc gtcctagcat gtccccaaca   6600
cctcttgatc gctgcagatc acctggaatg cttgaacccc ttggcagctc tagaacaccc   6660
atgtctgtcc tgcagcaagc cggcggctcc atgatggatg gtccaggtcc ccgaatacct   6720
gaccaccaga gaacatctgt gccagaaaat catgctcagt ccaggattgc acttgccctg   6780
acagctatca gtcttggcac cgctcggcct cctccgtcca tgtctgctgc tggccttgct   6840
gcaagaatgt cccaggttcc agccccggtg cctctcatga gtctcagaac cgcaccagca   6900
gccaaccttg ccagcaggat tcctgcagcc tctgcggcag ccatgaacct agccagcgcc   6960
aggacacctg ccattccaac agcagtgaac ctggctgact ctcgaacgcc agctgcagca   7020
gcggccatga acttggccag ccccagaaca gcggtggcac cttcggctgt gaacctggct   7080
gaccctcgca ctcccacagc cccagctgtg aacctagcag gggccagaac cccagctgcc   7140
ttggcagctc tgagtctcac aggctctggc acaccaccaa ctgctgcaaa ctatccctcc   7200
agctccagaa caccacaggc tccagcctct gcaaacctgg tgggtcctcg gtctgcacat   7260
gccacagctc ctgtgaatat tgccggctcc agaaccgccg cagccttggc ccccgcgagc   7320
ctcaccagtg ctaggatggc tccagcattg tctggtgcaa acctcaccag ccccagggtg   7380
cccctttctg cctacgagcg tgtcagtggc agaacctcac caccgctcct tgaccgagct   7440
aggtccagaa caccaccgtc tgccccaagc caatctagga tgacctctga acgggctccc   7500
tccccttcct ctagaatggg ccaggctcct tcacagtctc ttctccctcc agcacaggat   7560
cagccgaggt ctcctgtgcc ttctgctttt tcagaccaat cccgttgttt gattgcccag   7620 accaccctg tagcagggtc tcagtccctt tcctctgggg cagtggcaac gaccacgtcc   7680
tctgctggtg atcacaatgg catgctctct gtccctgccc ctggggtgcc ccactctgat   7740
gtgggggagc cacctgcctc tactggggcc cagcagcctt ctgcattagc cgccctgcag   7800
ccagcaaagg agcggcggag ttcctcctcg tcgtcgtcgt cctctagctc ctcctcctct   7860
tcatcatcgt cgtcgtcgtc ctcctcctcc tctggctcca gttctagtga ctcagagggc   7920
tctagccttc ctgtgcaacc tgaggtggca ctgaagaggg tccccagccc caccccagcc   7980
ccaaaggagg ctgttcgaga gggacgtcct ccggagccaa ccccagccaa acggaagagg   8040
cgctctagca gttccagttc cagctcctcc tcttcatctt cctcctcctc ctcctcctcc   8100
tcttcttcct cctcctcttc ctcttcttct tcttcctcct catcttcctc ctcctcgtcg   8160
tcttcctccc cttcccctgc taagcctggc cctcaggcct tgcccaaacc tgcaagcccc   8220
aagaagccac ccctggcga gcggaggtcc cgcagccccc ggaagccaat agactccctc   8280
agggactctc ggtccctcag ctactcgcct gtggagcgtc gccgtccctc gccccagccc   8340
tcaccacggg accagcagag cagcagcagt gagcgggtt cccggagagg ccagcgtggg   8400
gacagccgct cccccagcca caagcgcagg agggagacac ctagccctcg gcccatgaga   8460
caccgctcct ccaggtctcc ataaattgtc tttgggggat tccaccacac ccaatgctct   8520
ggagccacaa ggagtgtccc ttcttcccca gcagagccgt gggagggtcc ttgtctgctc   8580
tcctttgaac cttggcagcc cttggatgga gggctcccct tccctccct ttttttttc   8640 tttgttcctg tgaaatgtta atctccgtga gttcttcctg gttcatgtgt tctgggggt   8700 ttggggtggg agggaatgca gatgggagtt ggggagggg aggatacagt tcaggatacc   8760
```

-continued

```
ccagcctgga gtcagggcca gggaggcatg gccccacttg tatccagaag ttcccagggg   8820
tgattgtgat ggtggttggg actgtgaggtt gtataaggtg ttcttggaag gaagggcag   8880 gagttggaat tagttggtcc ctactgtccc ccatgaggtt gtgaacccct ccccccaact   8940
tttcatgttt cttaaaggca ttttggtttt ttaaaatctg tacagcaaga gcaacttttt   9000
ctgtcaaata aaaatgagaa atgcagg                                       9027
```

<210> SEQ ID NO 44
<211> LENGTH: 2752
<212> TYPE: PRT
<213> ORGANISM: Homo sapiens
<220> FEATURE:
<223> OTHER INFORMATION: splicing coactivator subunit SRm300; RNA
      binding protein; AT-rich element binding factor

<400> SEQUENCE: 44

```
Met Tyr Asn Gly Ile Gly Leu Pro Thr Pro Arg Gly Ser Gly Thr Asn
  1               5                  10                  15

Gly Tyr Val Gln Arg Asn Leu Ser Leu Val Arg Gly Arg Gly Glu
             20                  25                  30

Arg Pro Asp Tyr Lys Gly Glu Glu Leu Arg Arg Leu Glu Ala Ala
         35                  40                  45

Leu Val Lys Arg Pro Asn Pro Asp Ile Leu Asp His Glu Arg Lys Arg
 50                  55                  60

Arg Val Glu Leu Arg Cys Leu Glu Leu Glu Glu Met Met Glu Glu Gln
 65                  70                  75                  80

Gly Tyr Glu Glu Gln Gln Ile Gln Glu Lys Val Ala Thr Phe Arg Leu
                 85                  90                  95

Met Leu Leu Glu Lys Asp Val Asn Pro Gly Gly Lys Glu Glu Thr Pro
            100                 105                 110

Gly Gln Arg Pro Ala Val Thr Glu Thr His Gln Leu Ala Glu Leu Asn
        115                 120                 125

Glu Lys Lys Asn Glu Arg Leu Arg Ala Ala Phe Gly Ile Ser Asp Ser
130                 135                 140

Tyr Val Asp Gly Ser Ser Phe Asp Pro Gln Arg Arg Ala Arg Glu Ala
145                 150                 155                 160

Lys Gln Pro Ala Pro Glu Pro Pro Lys Pro Tyr Ser Leu Val Arg Glu
                165                 170                 175

Ser Ser Ser Ser Arg Ser Pro Thr Pro Lys Gln Lys Lys Lys Lys Lys
            180                 185                 190

Lys Lys Asp Arg Gly Arg Arg Ser Glu Ser Ser Pro Arg Arg Glu
        195                 200                 205

Arg Lys Lys Ser Lys Lys Lys His Arg Ser Glu Ser Glu Ser
    210                 215                 220

Lys Lys Arg Lys His Arg Ser Pro Thr Pro Lys Ser Lys Arg Lys Ser
225                 230                 235                 240

Lys Asp Lys Lys Arg Lys Arg Ser Arg Ser Thr Thr Pro Ala Pro Lys
                245                 250                 255

Ser Arg Arg Ala His Arg Ser Thr Ser Ala Asp Ser Ala Ser Ser Ser
            260                 265                 270

Asp Thr Ser Arg Ser Arg Ser Arg Ser Ala Ala Ala Lys Thr His Thr
        275                 280                 285

Thr Ala Leu Ala Gly Arg Ser Pro Ser Pro Ala Ser Gly Arg Arg Gly
    290                 295                 300

Glu Gly Asp Ala Pro Phe Ser Glu Pro Gly Thr Thr Ser Thr Gln Arg
305                 310                 315                 320
```

```
Pro Ser Ser Pro Glu Thr Ala Thr Lys Gln Pro Ser Ser Pro Tyr Glu
                325                 330                 335

Asp Lys Asp Lys Asp Lys Lys Glu Lys Ser Ala Thr Arg Pro Ser Pro
            340                 345                 350

Ser Pro Glu Arg Ser Ser Thr Gly Pro Glu Pro Ala Pro Thr Pro
        355                 360                 365

Leu Leu Ala Glu Arg His Gly Gly Ser Pro Gln Pro Leu Ala Thr Thr
        370                 375                 380

Pro Leu Ser Gln Glu Pro Val Asn Pro Pro Ser Glu Ala Ser Pro Thr
385                 390                 395                 400

Arg Asp Arg Ser Pro Pro Lys Ser Pro Glu Lys Leu Pro Gln Ser Ser
                405                 410                 415

Ser Ser Glu Ser Ser Pro Pro Ser Pro Gln Pro Thr Lys Val Ser Arg
            420                 425                 430

His Ala Ser Ser Ser Pro Glu Ser Pro Lys Pro Ala Pro Ala Pro Gly
            435                 440                 445

Ser His Arg Glu Ile Ser Ser Pro Thr Ser Lys Asn Arg Ser His
    450                 455                 460

Gly Arg Ala Lys Arg Asp Lys Ser His Ser Thr Pro Ser Arg Arg
465                 470                 475                 480

Met Gly Arg Ser Arg Ser Pro Ala Thr Ala Lys Arg Gly Arg Ser Arg
            485                 490                 495

Ser Arg Thr Pro Thr Lys Arg Gly His Ser Arg Ser Arg Ser Pro Gln
            500                 505                 510

Trp Arg Arg Ser Arg Ser Ala Gln Arg Trp Gly Arg Ser Arg Ser Pro
        515                 520                 525

Gln Arg Arg Gly Arg Ser Arg Ser Pro Gln Arg Pro Gly Trp Ser Arg
    530                 535                 540

Ser Arg Asn Thr Gln Arg Arg Gly Arg Ser Arg Ser Ala Arg Arg Gly
545                 550                 555                 560

Arg Ser His Ser Arg Ser Pro Ala Thr Arg Gly Arg Ser Arg Ser Arg
            565                 570                 575

Thr Pro Ala Arg Arg Gly Arg Ser Arg Ser Arg Thr Pro Ala Arg Arg
            580                 585                 590

Arg Ser Arg Ser Arg Thr Pro Thr Arg Arg Arg Ser Arg Ser Arg Thr
        595                 600                 605

Pro Ala Arg Arg Gly Arg Ser Arg Ser Arg Thr Pro Ala Arg Arg Arg
    610                 615                 620

Ser Arg Thr Arg Ser Pro Val Arg Arg Ser Arg Ser Arg Ser Pro
625                 630                 635                 640

Ala Arg Arg Ser Gly Arg Ser Arg Ser Thr Pro Ala Arg Arg Gly
            645                 650                 655

Arg Ser Arg Ser Arg Thr Pro Ala Arg Arg Gly Arg Ser Arg Ser Arg
            660                 665                 670

Thr Pro Ala Arg Arg Ser Gly Arg Ser Arg Ser Arg Thr Pro Ala Arg
        675                 680                 685

Arg Gly Arg Ser Arg Ser Arg Thr Pro Arg Arg Gly Arg Ser Arg Ser
    690                 695                 700

Arg Ser Leu Val Arg Arg Gly Arg Ser His Ser Arg Thr Pro Gln Arg
705                 710                 715                 720

Arg Gly Arg Ser Gly Ser Ser Glu Arg Lys Asn Lys Ser Arg Thr
            725                 730                 735

Ser Gln Arg Arg Ser Arg Ser Asn Ser Ser Pro Glu Met Lys Lys Ser
```

-continued

```
                740                 745                 750
Arg Ile Ser Ser Arg Arg Ser Arg Ser Leu Ser Ser Pro Arg Ser Lys
        755                 760                 765
Ala Lys Ser Arg Leu Ser Leu Arg Arg Ser Leu Ser Gly Ser Ser Pro
        770                 775                 780
Cys Pro Lys Gln Lys Ser Gln Thr Pro Pro Arg Arg Ser Arg Ser Gly
785                 790                 795                 800
Ser Ser Gln Pro Lys Ala Lys Ser Arg Thr Pro Pro Arg Ser Arg
        805                 810                 815
Ser Ser Ser Ser Pro Pro Pro Lys Gln Lys Ser Lys Thr Pro Ser Arg
        820                 825                 830
Gln Ser His Ser Ser Ser Pro His Pro Lys Val Lys Ser Gly Thr
        835                 840                 845
Pro Pro Arg Gln Gly Ser Ile Thr Ser Pro Gln Ala Asn Glu Gln Ser
        850                 855                 860
Val Thr Pro Gln Arg Arg Ser Cys Phe Glu Ser Ser Pro Asp Pro Glu
865                 870                 875                 880
Leu Lys Ser Arg Thr Pro Ser Arg His Ser Cys Ser Gly Ser Ser Pro
                885                 890                 895
Pro Arg Val Lys Ser Ser Thr Pro Pro Arg Gln Ser Pro Ser Arg Ser
                900                 905                 910
Ser Ser Pro Gln Pro Lys Val Lys Ala Ile Ile Ser Pro Arg Gln Arg
                915                 920                 925
Ser His Ser Gly Ser Ser Ser Pro Ser Pro Ser Arg Val Thr Ser Arg
                930                 935                 940
Thr Thr Pro Arg Arg Ser Arg Ser Val Ser Pro Cys Ser Asn Val Glu
945                 950                 955                 960
Ser Arg Leu Leu Pro Arg Tyr Ser His Ser Gly Ser Ser Ser Pro Asp
                965                 970                 975
Thr Lys Val Lys Pro Glu Thr Pro Pro Arg Gln Ser His Ser Gly Ser
                980                 985                 990
Ile Ser Pro Tyr Pro Lys Val Lys Ala Gln Thr Pro Pro Gly Pro Ser
        995                 1000                1005
Leu Ser Gly Ser Lys Ser Pro Cys Pro Gln Glu Lys Ser Lys Asp Ser
        1010                1015                1020
Leu Val Gln Ser Cys Pro Gly Ser Leu Ser Leu Cys Ala Gly Val Lys
1025                1030                1035                1040
Ser Ser Thr Pro Pro Gly Glu Ser Tyr Phe Gly Val Ser Ser Leu Gln
                1045                1050                1055
Leu Lys Gly Gln Ser Gln Thr Ser Pro Asp His Arg Ser Asp Thr Ser
                1060                1065                1070
Ser Pro Glu Val Arg Gln Ser His Ser Glu Ser Pro Ser Leu Gln Ser
        1075                1080                1085
Lys Ser Gln Thr Ser Pro Lys Gly Gly Arg Ser Arg Ser Ser Ser Pro
        1090                1095                1100
Val Thr Glu Leu Ala Ser Arg Ser Pro Ile Arg Gln Asp Arg Gly Glu
1105                1110                1115                1120
Phe Ser Ala Ser Pro Met Leu Lys Ser Gly Met Ser Pro Glu Gln Ser
                1125                1130                1135
Arg Phe Gln Ser Asp Ser Ser Tyr Pro Thr Val Asp Ser Asn Ser
                1140                1145                1150
Leu Leu Gly Gln Ser Arg Leu Glu Thr Ala Glu Ser Lys Glu Lys Met
                1155                1160                1165
```

```
Ala Leu Pro Pro Gln Glu Asp Ala Thr Ala Ser Pro Pro Arg Gln Lys
    1170                1175                1180

Asp Lys Phe Ser Pro Phe Pro Val Gln Asp Arg Pro Glu Ser Ser Leu
1185                1190                1195                1200

Val Phe Lys Asp Thr Leu Arg Thr Pro Pro Arg Glu Arg Ser Gly Ala
            1205                1210                1215

Gly Ser Ser Pro Glu Thr Lys Glu Gln Asn Ser Ala Leu Pro Thr Ser
            1220                1225                1230

Ser Gln Asp Glu Glu Leu Met Glu Val Val Glu Lys Ser Glu Glu Pro
        1235                1240                1245

Ala Gly Gln Ile Leu Ser His Leu Ser Ser Glu Leu Lys Glu Met Ser
    1250                1255                1260

Thr Ser Asn Phe Glu Ser Ser Pro Glu Val Glu Glu Arg Pro Ala Val
1265                1270                1275                1280

Ser Leu Thr Leu Asp Gln Ser Gln Ser Gln Ala Ser Leu Glu Ala Val
            1285                1290                1295

Glu Val Pro Ser Met Ala Ser Ser Trp Gly Gly Pro His Phe Ser Pro
            1300                1305                1310

Glu His Lys Glu Leu Ser Asn Ser Pro Leu Arg Glu Asn Ser Phe Gly
        1315                1320                1325

Ser Pro Leu Glu Phe Arg Asn Ser Gly Pro Leu Gly Thr Glu Met Asn
    1330                1335                1340

Thr Gly Phe Ser Ser Glu Val Lys Glu Asp Leu Asn Gly Pro Phe Leu
1345                1350                1355                1360

Asn Gln Leu Glu Thr Asp Pro Ser Leu Asp Met Lys Glu Gln Ser Thr
            1365                1370                1375

Arg Ser Ser Gly His Ser Ser Ser Glu Leu Ser Pro Asp Ala Val Glu
            1380                1385                1390

Lys Ala Gly Met Ser Ser Asn Gln Ser Ile Ser Ser Pro Val Leu Asp
        1395                1400                1405

Ala Val Pro Arg Thr Pro Ser Arg Glu Arg Ser Ser Ser Ala Ser Ser
    1410                1415                1420

Pro Glu Met Lys Asp Gly Leu Pro Arg Thr Pro Ser Arg Arg Ser Arg
1425                1430                1435                1440

Ser Gly Ser Ser Pro Gly Leu Arg Asp Gly Ser Gly Thr Pro Ser Arg
            1445                1450                1455

His Ser Leu Ser Gly Ser Ser Pro Gly Met Lys Asp Ile Pro Arg Thr
            1460                1465                1470

Pro Phe Arg Gly Arg Ser Glu Cys Asp Ser Ser Pro Glu Pro Lys Ala
        1475                1480                1485

Leu Pro Gln Thr Pro Arg Pro Arg Ser Arg Ser Pro Ser Ser Pro Glu
    1490                1495                1500

Leu Asn Asn Lys Cys Leu Thr Pro Gln Arg Glu Arg Ser Gly Ser Glu
1505                1510                1515                1520

Ser Ser Val Asp Gln Lys Thr Val Ala Arg Thr Pro Leu Gly Gln Arg
            1525                1530                1535

Ser Arg Ser Gly Ser Ser Gln Glu Leu Asp Val Lys Pro Ser Ala Ser
            1540                1545                1550

Pro Gln Glu Arg Ser Glu Ser Asp Ser Ser Pro Asp Ser Lys Ala Lys
        1555                1560                1565

Thr Arg Thr Pro Leu Arg Gln Arg Ser Arg Ser Gly Ser Ser Pro Glu
    1570                1575                1580

Val Asp Ser Lys Ser Arg Leu Ser Pro Arg Arg Ser Arg Ser Gly Ser
1585                1590                1595                1600
```

```
Ser Pro Glu Val Lys Asp Lys Pro Arg Ala Ala Pro Arg Ala Gln Ser
            1605                1610                1615

Gly Ser Asp Ser Ser Pro Glu Pro Lys Ala Pro Ala Pro Arg Ala Leu
        1620                1625                1630

Pro Arg Arg Ser Arg Ser Gly Ser Ser Lys Gly Arg Gly Pro Ser
    1635                1640                1645

Pro Glu Gly Ser Ser Ser Thr Glu Ser Ser Pro Glu His Pro Pro Lys
    1650                1655                1660

Ser Arg Thr Ala Arg Arg Gly Ser Arg Ser Pro Glu Pro Lys Thr
1665                1670                1675                1680

Lys Ser Arg Thr Pro Pro Arg Arg Ser Ser Arg Ser Ser Pro Glu
            1685                1690                1695

Leu Thr Arg Lys Ala Arg Leu Ser Arg Arg Ser Arg Ser Ala Ser Ser
                1700                1705                1710

Ser Pro Glu Thr Arg Ser Arg Thr Pro Pro Arg His Arg Arg Ser Pro
        1715                1720                1725

Ser Val Ser Ser Pro Glu Pro Ala Glu Lys Ser Arg Ser Ser Arg Arg
    1730                1735                1740

Arg Arg Ser Ala Ser Ser Pro Arg Thr Lys Thr Thr Ser Arg Arg Gly
1745                1750                1755                1760

Arg Ser Pro Ser Pro Lys Pro Arg Gly Leu Gln Arg Ser Arg Ser Arg
        1765                1770                1775

Ser Arg Arg Glu Lys Thr Arg Thr Thr Arg Arg Arg Asp Arg Ser Gly
            1780                1785                1790

Ser Ser Gln Ser Thr Ser Arg Arg Arg Gln Arg Ser Arg Ser Arg Ser
        1795                1800                1805

Arg Val Thr Arg Arg Arg Arg Gly Gly Ser Gly Tyr His Ser Arg Ser
    1810                1815                1820

Pro Ala Arg Gln Glu Ser Ser Arg Thr Ser Ser Arg Arg Arg Arg Gly
1825                1830                1835                1840

Arg Ser Arg Thr Pro Pro Thr Ser Arg Lys Arg Ser Arg Ser Arg Thr
            1845                1850                1855

Ser Pro Ala Pro Trp Lys Arg Ser Arg Ser Arg Ala Ser Pro Ala Thr
            1860                1865                1870

His Arg Arg Ser Arg Ser Arg Thr Pro Leu Ile Ser Arg Arg Arg Ser
        1875                1880                1885

Arg Ser Arg Thr Ser Pro Val Ser Arg Arg Ser Arg Ser Arg Thr
    1890                1895                1900

Ser Val Thr Arg Arg Arg Ser Arg Ser Arg Ala Ser Pro Val Ser Arg
1905                1910                1915                1920

Arg Arg Ser Arg Ser Arg Thr Pro Pro Val Thr Arg Arg Ser Arg
            1925                1930                1935

Ser Arg Thr Pro Thr Thr Arg Arg Ser Arg Ser Arg Thr Pro Pro
        1940                1945                1950

Val Thr Arg Arg Arg Ser Arg Ser Arg Thr Pro Pro Val Thr Arg Arg
            1955                1960                1965

Arg Ser Arg Ser Arg Thr Ser Pro Ile Thr Arg Arg Arg Ser Arg Ser
1970                1975                1980

Arg Thr Ser Pro Val Thr Arg Arg Ser Arg Ser Thr Ser Pro
1985                1990                1995                2000

Val Thr Arg Arg Arg Ser Arg Ser Arg Thr Ser Pro Val Thr Arg Arg
            2005                2010                2015

Arg Ser Arg Ser Arg Thr Pro Pro Ala Ile Arg Arg Arg Ser Arg Ser
```

-continued

```
            2020                2025                2030
Arg Thr Pro Leu Leu Pro Arg Lys Arg Ser Arg Ser Arg Pro Leu
        2035                2040                2045
Ala Ile Arg Arg Arg Ser Arg Ser Arg Thr Pro Arg Thr Ala Arg Gly
    2050                2055                2060
Lys Arg Ser Leu Thr Arg Ser Pro Pro Ala Ile Arg Arg Ser Ala
2065                2070                2075                2080
Ser Gly Ser Ser Ser Asp Arg Ser Arg Ser Ala Thr Pro Pro Ala Thr
                2085                2090                2095
Arg Asn His Ser Gly Ser Arg Thr Pro Pro Val Ala Leu Asn Ser Ser
            2100                2105                2110
Arg Met Ser Cys Phe Ser Arg Pro Ser Met Ser Pro Thr Pro Leu Asp
        2115                2120                2125
Arg Cys Arg Ser Pro Gly Met Leu Glu Pro Leu Gly Ser Ser Arg Thr
    2130                2135                2140
Pro Met Ser Val Leu Gln Gln Ala Gly Gly Ser Met Met Asp Gly Pro
2145                2150                2155                2160
Gly Pro Arg Ile Pro Asp His Gln Arg Thr Ser Val Pro Glu Asn His
                2165                2170                2175
Ala Gln Ser Arg Ile Ala Leu Ala Leu Thr Ala Ile Ser Leu Gly Thr
            2180                2185                2190
Ala Arg Pro Pro Pro Ser Met Ser Ala Ala Gly Leu Ala Ala Arg Met
        2195                2200                2205
Ser Gln Val Pro Ala Pro Val Pro Leu Met Ser Leu Arg Thr Ala Pro
    2210                2215                2220
Ala Ala Asn Leu Ala Ser Arg Ile Pro Ala Ala Ser Ala Ala Ala Met
2225                2230                2235                2240
Asn Leu Ala Ser Ala Arg Thr Pro Ala Ile Pro Thr Ala Val Asn Leu
                2245                2250                2255
Ala Asp Ser Arg Thr Pro Ala Ala Ala Ala Met Asn Leu Ala Ser
            2260                2265                2270
Pro Arg Thr Ala Val Ala Pro Ser Ala Val Asn Leu Ala Asp Pro Arg
        2275                2280                2285
Thr Pro Thr Ala Pro Ala Val Asn Leu Ala Gly Ala Arg Thr Pro Ala
    2290                2295                2300
Ala Leu Ala Ala Leu Ser Leu Thr Gly Ser Gly Thr Pro Pro Thr Ala
2305                2310                2315                2320
Ala Asn Tyr Pro Ser Ser Ser Arg Thr Pro Gln Ala Pro Ala Ser Ala
                2325                2330                2335
Asn Leu Val Gly Pro Arg Ser Ala His Ala Thr Ala Pro Val Asn Ile
            2340                2345                2350
Ala Gly Ser Arg Thr Ala Ala Ala Leu Ala Pro Ala Ser Leu Thr Ser
        2355                2360                2365
Ala Arg Met Ala Pro Ala Leu Ser Gly Ala Asn Leu Thr Ser Pro Arg
    2370                2375                2380
Val Pro Leu Ser Ala Tyr Glu Arg Val Ser Gly Arg Thr Ser Pro Pro
2385                2390                2395                2400
Leu Leu Asp Arg Ala Arg Ser Arg Thr Pro Pro Ser Ala Pro Ser Gln
                2405                2410                2415
Ser Arg Met Thr Ser Glu Arg Ala Pro Ser Pro Ser Ser Arg Met Gly
            2420                2425                2430
Gln Ala Pro Ser Gln Ser Leu Leu Pro Pro Ala Gln Asp Gln Pro Arg
        2435                2440                2445
```

-continued

Ser Pro Val Pro Ser Ala Phe Ser Asp Gln Ser Arg Cys Leu Ile Ala
      2450                2455                2460

Gln Thr Thr Pro Val Ala Gly Ser Gln Ser Leu Ser Ser Gly Ala Val
2465                2470                2475                2480

Ala Thr Thr Thr Ser Ser Ala Gly Asp His Asn Gly Met Leu Ser Val
            2485                2490                2495

Pro Ala Pro Gly Val Pro His Ser Asp Val Gly Glu Pro Pro Ala Ser
        2500                2505                2510

Thr Gly Ala Gln Gln Pro Ser Ala Leu Ala Ala Leu Gln Pro Ala Lys
    2515                2520                2525

Glu Arg Arg Ser Ser Ser Ser Ser Ser Ser Ser Ser Ser Ser Ser Ser
2530                2535                2540

Ser Ser Ser Ser Ser Ser Ser Ser Ser Ser Ser Gly Ser Ser Ser
2545                2550                2555                2560

Ser Asp Ser Glu Gly Ser Ser Leu Pro Val Gln Pro Glu Val Ala Leu
            2565                2570                2575

Lys Arg Val Pro Ser Pro Thr Pro Ala Pro Lys Glu Ala Val Arg Glu
        2580                2585                2590

Gly Arg Pro Pro Glu Pro Thr Pro Ala Lys Arg Lys Arg Arg Ser Ser
    2595                2600                2605

Ser Ser Ser Ser Ser Ser Ser Ser Ser Ser Ser Ser Ser Ser Ser
2610                2615                2620

Ser Ser Ser Ser Ser Ser Ser Ser Ser Ser Ser Ser Ser Ser Ser Ser
2625                2630                2635                2640

Ser Ser Ser Ser Ser Ser Ser Pro Ser Pro Ala Lys Pro Gly Pro
        2645                2650                2655

Gln Ala Leu Pro Lys Pro Ala Ser Pro Lys Lys Pro Pro Gly Glu
            2660                2665                2670

Arg Arg Ser Arg Ser Pro Arg Lys Pro Ile Asp Ser Leu Arg Asp Ser
        2675                2680                2685

Arg Ser Leu Ser Tyr Ser Pro Val Glu Arg Arg Pro Ser Pro Gln
        2690                2695                2700

Pro Ser Pro Arg Asp Gln Gln Ser Ser Ser Glu Arg Gly Ser Arg
2705                2710                2715                2720

Arg Gly Gln Arg Gly Asp Ser Arg Ser Pro Ser His Lys Arg Arg
        2725                2730                2735

Glu Thr Pro Ser Pro Arg Pro Met Arg His Arg Ser Ser Arg Ser Pro
            2740                2745                2750

<210> SEQ ID NO 45
<211> LENGTH: 7789
<212> TYPE: DNA
<213> ORGANISM: Homo sapiens
<220> FEATURE:
<223> OTHER INFORMATION: splicing coactivator subunit SRm300 cDNA

<400> SEQUENCE: 45
gcagcgcggc caggcgggg tgcgagtggc gcagtcggag cccgttgcgg cccctgagga    60
agcgaggagg cgtcggcgtc ggctgaggcg ggcggaccgg cgaggcgagg cggcggcccc   120
aggcccgggg actcgggagc tcgagcagcg gcggcggcaa gacctctccc cctcggaggc   180
ggcgggcgga ggcggcggga gcggtggtgc ccccccgggg cacggggcca tgtacaacgg   240
gatcgggctg ccgacgcccc ggggcagcgg caccaacggc tacgtccagc gcaacctgtc   300
cctggtgcgg ggccgccggg gtgagcggcc tgactacaag ggagaggagg aactgcggcg   360
cctggaggct gccctggtga agcggcctaa tcctgacatc ctggaccacg agcgcaagcg   420

```
gcgcgtcgag ctgcgatgcc tcgagctgga ggagatgatg gaagagcaag ggtacgagga   480
acagcaaatt caggaaaaag tggcgacctt tcgactcatg ttgctggaga aggatgtgaa   540
ccctgggggc aaggaggaga ccccagggca gaggccagcg gtcacggaga ctcaccagtt   600
ggcagaatta aatgagaaga agaatgaaag actccgtgct gcctttggca tcagtgattc   660
ttacgtagat ggcagctctt ttgatcctca gcgtcgtgcc cgagaagcta aacaaccagc   720
tcctgagcct cccaaacctt acagccttgt tcgggagtct aacaattctc gctcacaacc   780
ccaaagcaga agaagaagaa aaagaagaaa gatagaggac gcaggtcaga gagcagctct   840
cctcgacggg agagaaagaa aagctcaaag aagaagaagc acaggtcaga atctgagtcc   900
aagaaacgta agcataggtc tcccactcca aagagcaaac gtaaatctaa ggacaaaaag   960
cgaaagcggt ctcgaagtac aacaccagcc cccaagagcc gccgggccca ccgttcaact  1020
tctgctgact ctgcttcctc ctccgatact cccgcagtc ggtctcgaag tgctgcagct  1080
aaaactcata caactgcctt ggctgggcga agtccttccc ctgcttcagg gcgacgcggg  1140
gagggagatg cgcctttcag tgaaccaagt actaccaagc acacaacggg ctagtagccc  1200
ggagactgct acgaaacagc ctagcagccc ttatgaagac aaagataaag acaagaagga  1260
gaaatctgca actcgaccta gcccctctcc ggaaaggagc agcacaggcc cagaaccacc  1320
tgctcccact ccgctccttg ctgagcgaca tggcggctcc ccacaacccc ttgcaaccac  1380
ccccttaagc caggagccag tgaaccccc atctgaggcc tctccaactc gggaccgttc  1440
accacctaag tctcccgaga aacttcccca gtcttcttcc tcagagagca gcccaccatc  1500
ccctcaacct accaaagttt ctcggcatgc cagctcttcc ccagaaagtc ctaaacctgc  1560
tccagctcca gggtcccacc gagagatttc ttcttctccc catctaaga atcgctcaca  1620 tggccgagca aaacgggata aatcacattc tcatacccc tcccgtagga tggggaggtc  1680
ccgtagccct gccaccgcta agagagggcg atctcggtct cgaaccccta ccaagagagg  1740
tcattctcga tcccgatctc cccagtggcg taggtccagg tctgcacaga ggtggggaag  1800
atctagaagc ccccagcgac gtggccgctc taggtctcct cagcgaccag gctggtctag  1860
gagcagaaat acccagagaa gaggcaggtc taggtcagca aggcgaggga ggtcccactc  1920
tagatcccca gccactaggg gtagatctcg ttctagaaca ccagcccgcc ggggcaggtc  1980
ccgctctaga cacctgcca ggcggagatc acgatccaga actcccacca ggcgtaggtc  2040
tcggtctaga acaccagccc ggaggggcag gtctcggtct agaacacctg ctaggcgcag  2100
atctaggacc cgatcaccag tacgacgcag gtctcgtagt agatcaccag ccaggagaag  2160
tggcaggtca cgctctagaa ccccagctag acgtggccgc tcacgctcca gaaccccagc  2220
cagacgtggc cgctcacgct ctagaacccc agctagacgc agtggtcgct cacgctccag  2280
aacaccagcc aggagaggga ggtctcggtc taggacacca agacgaggaa gatcccgcag  2340
tagaagctta gttagacgtg aagatctca ctctagaaca cctcaaagaa gaggcagatc  2400
tggctcatct tcagagcgga aaaacaaatc cagaacatct caaagaagaa gcaggtccaa  2460
ttcaagccca gaaatgaaga aatctcgcat ttcttcaagg cggagcaggt ctctctcttc  2520
accacggtcc aaagcaaaat ctcgcttgtc tttgaggcgc agcctttcag ggtcttcccc  2580
atgccctaag caaaagtcac agacaccacc caggcgcagt cgctctggat cctcccaacc  2640
taaagctaaa tctagaacgc cacccagacg cagtcgctcc agttcttctc cgccacctaa  2700
acagaaatct aagacaccat caagacaaag tcattccagt tcatctcctc atcctaaagt  2760
gaaatctgga acaccaccga ggcaagggtc cataacaagt ccccaggcca atgagcaatc  2820
```

```
tgtaacgcca cagagacgga gctgttttga atcatcacct gaccctgagt tgaaatctag   2880
gaccccttct agacatagct gctcagggtc ctctcctcct agagtgaaat ctagcacacc   2940
tcccagacag agcccatcta ggtcatcatc tccacaaccc aaagtgaagg caataatatc   3000
accaagacaa agaagccatt ctggctcctc ttctccaagt cctagtaggg tgacgtcgag   3060
aacaactcca cggcgaagca gatcagtatc tccctgctcc aatgtggaat ccagattgtt   3120
gccaagatac agtcattctg ggtcctcctc accagatacc aaagtgaaac ctgaaacacc   3180
gccaagacaa agtcactcag ggtctatttc accatacccc aaagtaaagg cccaaactcc   3240
accggggcca agtctttctg gatcaaagtc accatgtccc aagagaagt ctaaagactc    3300 actagttcaa agttgccctg gatccctctc tctctgtgca ggagtaaaat ctagcacacc   3360
accaggcgag agctattttg gtgtctcatc tctgcaactg aaaggacaat ctcaaacttc   3420
accagaccac agatctgata cttcaagtcc agaagtgaga cagagtcatt cagaatcacc   3480
atctctgcag agcaaatctc aaacatcacc taagggaggt cggtccaggt cttcatctcc   3540
agtcactgag ctggcatcca gatctccaat aagacaagat agaggtgagt tctcagcgag   3600
tcctatgttg aaatctggaa tgtctcctga gcagagcagg ttccagtctg actcttcttc   3660
atatcctaca gtggactcga attctctctt ggggcagagt agattggaga ctgctgaatc   3720
aaaagagaaa atggccttac cccctcagga ggatgctact gcatcacctc ctagacagaa   3780
agacaaattt agtcccttc cagtacagga taggcctgag tcttcactgg tattcaaaga    3840
cacacttaga accccgccaa gggaaagaag tggtgctggg tcatctccag aaacaaaaga   3900
gcaaaatagt gcattgccta cgtcaagcca agatgaagag ttaatggagg tggtagagaa   3960
gtctgaagaa cccgcaggcc aaatcctgtc tcatttgtct tcagaactta agaaatgtc    4020 cacaagtaac tttgaatcat ctcctgaagt agaagaaagg cctgctgtgt ctttgactct   4080
tgatcagagc cagtcacagg cttctttgga agcagtagaa gtcccttcaa tggcctcatc   4140
ttggggtggg ccacattttt ctccagaaca taaagaactg tctaactccc cactcaggga   4200
gaacagcttt ggatcacctt tagaatttag aaactcaggc ccacttggta cagaaatgaa   4260 tactggatt tcttctgagg ttaaagaaga tttgaatgga ccgtttctta atcagctgga    4320
aacagatcca tctctagaca tgaaagaaca atcgacaaga tcctctggac acagcagttc   4380
tgagttatcc ccagatgcag tggaaaaggc agggatgtct tcaaatcaga gcatctcttc   4440
acctgtgctt gatgctgtac ccagaacacc ctcgagagaa agaagtagtt ctgcatcttc   4500
tcctgaaatg aaagatggtt tacccagaac tccatcaagg agaagcaggt ctgggtcttc   4560
tccaggactt agagatgggt ctgggactcc ctcgaggcac agcctgtctg ggtcctctcc   4620
tggaatgaaa gatataccta gaacgccatc tagagggaga agcgaatgtg attcttcccc   4680
agaaccgaaa gctttgcctc agactcctag gccgaggagt cgttctccat catcccccaga  4740 gctcaacaac aagtgtctta ccccccagag agaaagaagc gggtcagaat catcagttga   4800
tcagaaaact gtggctcgga ctcccctggg gcagagaagt cgttcgggat cctctcaaga   4860
acttgatgtg aaacccagtg catcccctca ggaaagaagt gagtcagact cttctccaga   4920
ttctaaagcc aagacacgaa ccccacttcg gcagaggagt cggtctggat catctccaga   4980
ggttgacagc aaatctcgac tatcccctcg gcgcagtagg tctggttcct cccctgaagt   5040
gaaagataag ccaagagcag cacccagggc acagagtggt tctgattcct ctcctgaacc   5100
taaagctcca gcccctcggg cccttcccag acgaagcaga tcaggttcat caagcaaagg   5160
cagaggccct tctcctgaag gaagcagcag taccgagtcc tctcctgaac atccgcccaa   5220
```

```
atccagaact gctcgcagag gttccaggtc atcaccagag cccaagacca agtctcgtac   5280
accacctcga cgtcgcagct ctcgatcatc tccggagcta acaaggaagg ccagactgtc   5340
ccgtagaagc cgctctgcct catcctcacc agaaactcgc tctagaactc ccccaaggca   5400
ccggagaagt ccctcagtgt cttccccgga gccagccgaa aaatcgaggt cttcacgccg   5460
acggcgctca gcttcatctc cacgcactaa gacaacctca aggagaggcc gctctccttc   5520
gccaaagcct cgtggactcc agaggtcccg ttcccgctca aggagagaga aaacaagaac   5580
aacccgacgt cgagataggt ctggatcctc tcagtcaacc tctcggcgaa gacagcggag   5640
ccggtcaagg tcgcgggtta ctcggcggcg aggggaggc tctggttatc actcaaggtc    5700
acctgcccgg caggaaagtt cccggacctc ctctcgacgc cgaagaggcc gctctcggac   5760 accccccaacc agtcggaagc gttctcgctc acgcacatca ccagcccgt ggaaacgctc    5820 tagatctcga gcctctccag ccactcaccg gcgatccagg tccagaaccc ccctgataag   5880
ccgacgtagg tccagatctc gaacttcacc agtcagccgg agacggtcaa ggtccaggac   5940
ttcagtgact cgacgaagat cccggtcaag agcatcccca gtgagcagaa ggcgatccag   6000
atccagaacg ccaccagtaa cccgccgtcg ttcaaggtct agaacgccaa caacacgccg   6060
ccgctcccgt tctagaactc caccagtgac tcgcagaagg tccagatcca ggactccacc   6120
agtaaccagg aggcgatctc gaagcagaac ttcgcctatc actcgcagaa gatcaagatc   6180
cagaacatct ccggtcaccc gaaggagatc tcgatctcgc acatctccag taactcgaag   6240
aaggtcccgc tctcgaacct caccagtgac acgccgccgc tctaggtccc ggacacctcc   6300
agcacaggat cagccgaggt ctcctgtgcc ttctgctttt tcagaccaat cccgttgttt   6360
gattgcccag accacccctg tagcagggtc tcagtcccct tcctctgggg cagtggcaac   6420
gaccacgtcc tctgctggtg atcacaatgg catgctctct gtccctgccc ctggggtgcc   6480
ccactctgat gtgggggagc cacctgcctc tactggggcc cagcagcctt ctgcattagc   6540
cgccctgcag ccagcaaagg agcggcggag ttcctcctcg tcgtcgtcgt cctctagctc   6600
ctcctcttct tcatcatcgt cgtcgtcgtc ctcctcctcc tctggctcca gttctagtga   6660
ctcagagggc tctagcttcc tgtgcaacct gagtggcact gaagaggtcc ccagccccac   6720
cccagcccca aggaggctg ttcgagaggg acgtcctccg gagccaaccc cagccaaacg     6780
gaagaggcgc tctagcagtt ccagttccag ctcctcctct tcatcttcct cctcctcctc   6840
ctcctcctct tcttcctcct cctcttcctc ttcttcttct tcctcctcat cttcctcctc   6900
ctcgtcgtct tccttcccct tcccctgcaa agcctggccc tcaggccttg cccaaacctg   6960
caagccccaa gaagccaccc cctggcgagc ggaggtcccg cagcccccgg aagccaatag   7020
actccctcag ggactctcgg tccctcagct actcgcctgt ggagcgtcgc cgtccctcgc   7080
cccagccctc accacgggac cagcagagca gcagcagtga gcggggttcc cggagaggcc   7140
agcgtgggga cagccgctcc cccagccaca agcgcaggag ggagacacct agccctcggc   7200
ccatgagaca ccgctcctcc aggtctccat aaattgtctt tgggggattc caccacaccc   7260
aatgctctgg agccacaagg agtgtccctt cttccccagc agagccgtgg gagggtcctt   7320
gtctgctctc ctttgaacct tggcagccct tggatggagg gctcccttc cctcccttt      7380 tttttttctt tgttcctgtg aaatgttaat ctccgtgagt tcttcctggt tcatgtttc    7440 tgggggttt ggggttggaa ggaattcaaa tgggaattgg gggaagggaa gatacagttc    7500
aggatacccc agcctggaat tagggccagg gaagcatggc cccacttgta tccagaagtt   7560
acccaggggt gattgtgatg gtggttggga ctggaggttg tataaggtgt tcttgaaagg   7620
```

```
gagttggaat tagttggtcc ctactgtccc ccatgaggtt gtgaacccct ccccccaact    7680
tttcatgttt cttaaaggca ttttggtttt ttaaaatctg tacagcaaga gcaacttttt    7740
ctgtcaaata aaatgagaa atgcaggaaa aaaaaaaaaa aaaaaaaa                  7789
```

<210> SEQ ID NO 46
<211> LENGTH: 2296
<212> TYPE: PRT
<213> ORGANISM: Homo sapiens
<220> FEATURE:
<223> OTHER INFORMATION: splicing coactivator subunit SRm300

<400> SEQUENCE: 46

```
Met Tyr Asn Gly Ile Gly Leu Pro Thr Pro Arg Gly Ser Gly Thr Asn
  1               5                  10                  15

Gly Tyr Val Gln Arg Asn Leu Ser Leu Val Arg Gly Arg Arg Gly Glu
                 20                  25                  30

Arg Pro Asp Tyr Lys Gly Glu Glu Leu Arg Arg Leu Glu Ala Ala
             35                  40                  45

Leu Val Lys Arg Pro Asn Pro Asp Ile Leu Asp His Glu Arg Lys Arg
 50                  55                  60

Arg Val Glu Leu Arg Cys Leu Glu Leu Glu Glu Met Met Glu Glu Gln
 65                  70                  75                  80

Gly Tyr Glu Glu Gln Gln Ile Gln Glu Lys Val Ala Thr Phe Arg Leu
                 85                  90                  95

Met Leu Leu Glu Lys Asp Val Asn Pro Gly Gly Lys Glu Glu Thr Pro
            100                 105                 110

Gly Gln Arg Pro Ala Val Thr Glu Thr His Gln Leu Ala Glu Leu Asn
            115                 120                 125

Glu Lys Lys Asn Glu Arg Leu Arg Ala Ala Phe Gly Ile Ser Asp Ser
130                 135                 140

Tyr Val Asp Gly Ser Ser Phe Asp Pro Gln Arg Arg Ala Arg Glu Ala
145                 150                 155                 160

Lys Gln Pro Ala Pro Glu Pro Pro Lys Pro Tyr Ser Leu Val Arg Glu
                165                 170                 175

Ser Asn Asn Ser Arg Ser Gln Pro Gln Ser Arg Arg Arg Lys Arg
            180                 185                 190

Arg Lys Ile Glu Asp Ala Gly Gln Arg Ala Ala Leu Leu Asp Gly Arg
            195                 200                 205

Glu Arg Lys Ala Gln Arg Arg Ser Thr Gly Gln Asn Leu Ser Pro
        210                 215                 220

Arg Asn Val Ser Ile Gly Leu Pro Leu Gln Arg Ala Asn Val Asn Leu
225                 230                 235                 240

Arg Thr Lys Ser Glu Ser Gly Leu Glu Val Gln His Gln Pro Pro Arg
                245                 250                 255

Ala Ala Gly Pro Thr Val Gln Leu Leu Thr Leu Leu Pro Pro Pro
            260                 265                 270

Ile Leu Pro Ala Val Gly Leu Glu Val Leu Gln Leu Lys Leu Ile Gln
            275                 280                 285

Leu Pro Trp Leu Gly Glu Val Leu Pro Leu Gln Gly Asp Ala Gly
        290                 295                 300

Arg Glu Met Arg Leu Ser Val Asn Gln Val Leu Pro Ser Thr Gln Arg
305                 310                 315                 320

Ala Ser Ser Pro Glu Thr Ala Thr Lys Gln Pro Ser Ser Pro Tyr Glu
                325                 330                 335
```

Asp Lys Asp Lys Asp Lys Lys Glu Lys Ser Ala Thr Arg Pro Ser Pro
            340                 345                 350

Ser Pro Glu Arg Ser Ser Thr Gly Pro Glu Pro Ala Pro Thr Pro
    355                 360                 365

Leu Leu Ala Glu Arg His Gly Gly Ser Pro Gln Pro Leu Ala Thr Thr
370                 375                 380

Pro Leu Ser Gln Glu Pro Val Asn Pro Pro Ser Glu Ala Ser Pro Thr
385                 390                 395                 400

Arg Asp Arg Ser Pro Pro Lys Ser Pro Glu Lys Leu Pro Gln Ser Ser
                405                 410                 415

Ser Ser Glu Ser Ser Pro Pro Ser Pro Gln Pro Thr Lys Val Ser Arg
            420                 425                 430

His Ala Ser Ser Ser Pro Glu Ser Pro Lys Pro Ala Pro Ala Pro Gly
        435                 440                 445

Ser His Arg Glu Ile Ser Ser Pro Thr Ser Lys Asn Arg Ser His
    450                 455                 460

Gly Arg Ala Lys Arg Asp Lys Ser His Ser His Thr Pro Ser Arg Arg
465                 470                 475                 480

Met Gly Arg Ser Arg Ser Pro Ala Thr Ala Lys Arg Gly Arg Ser Arg
                485                 490                 495

Ser Arg Thr Pro Thr Lys Arg Gly His Ser Arg Ser Arg Ser Pro Gln
            500                 505                 510

Trp Arg Arg Ser Arg Ser Ala Gln Arg Trp Gly Arg Ser Arg Ser Pro
        515                 520                 525

Gln Arg Arg Gly Arg Ser Arg Ser Pro Gln Arg Pro Gly Trp Ser Arg
    530                 535                 540

Ser Arg Asn Thr Gln Arg Arg Gly Arg Ser Arg Ser Ala Arg Arg Gly
545                 550                 555                 560

Arg Ser His Ser Arg Ser Pro Ala Thr Arg Gly Arg Ser Arg Ser Arg
                565                 570                 575

Thr Pro Ala Arg Arg Gly Arg Ser Arg Ser Arg Thr Pro Ala Arg Arg
            580                 585                 590

Arg Ser Arg Ser Arg Thr Pro Thr Arg Arg Arg Ser Arg Ser Arg Thr
        595                 600                 605

Pro Ala Arg Arg Gly Arg Ser Arg Ser Arg Thr Pro Ala Arg Arg
    610                 615                 620

Ser Arg Thr Arg Ser Pro Val Arg Arg Ser Arg Ser Arg Ser Pro
625                 630                 635                 640

Ala Arg Arg Ser Gly Arg Ser Arg Ser Thr Pro Ala Arg Arg Gly
                645                 650                 655

Arg Ser Arg Ser Arg Thr Pro Ala Arg Arg Gly Arg Ser Arg Ser Arg
            660                 665                 670

Thr Pro Ala Arg Arg Ser Gly Arg Ser Arg Ser Arg Thr Pro Ala Arg
        675                 680                 685

Arg Gly Arg Ser Arg Ser Arg Thr Pro Arg Arg Gly Arg Ser Arg Ser
    690                 695                 700

Arg Ser Leu Val Arg Arg Gly Ser His Ser Arg Thr Pro Gln Arg
705                 710                 715                 720

Arg Gly Arg Ser Gly Ser Ser Ser Glu Arg Lys Asn Lys Ser Arg Thr
                725                 730                 735

Ser Gln Arg Arg Ser Arg Ser Asn Ser Ser Pro Glu Met Lys Lys Ser
            740                 745                 750

Arg Ile Ser Ser Arg Arg Ser Arg Ser Leu Ser Ser Pro Arg Ser Lys
        755                 760                 765

```
Ala Lys Ser Arg Leu Ser Leu Arg Arg Ser Leu Ser Gly Ser Ser Pro
    770                 775                 780

Cys Pro Lys Gln Lys Ser Gln Thr Pro Pro Arg Arg Ser Arg Ser Gly
785                 790                 795                 800

Ser Ser Gln Pro Lys Ala Lys Ser Arg Thr Pro Pro Arg Arg Ser Arg
                805                 810                 815

Ser Ser Ser Ser Pro Pro Pro Lys Gln Lys Ser Lys Thr Pro Ser Arg
                820                 825                 830

Gln Ser His Ser Ser Ser Ser Pro His Pro Lys Val Lys Ser Gly Thr
                835                 840                 845

Pro Pro Arg Gln Gly Ser Ile Thr Ser Pro Gln Ala Asn Glu Gln Ser
    850                 855                 860

Val Thr Pro Gln Arg Arg Ser Cys Phe Glu Ser Ser Pro Asp Pro Glu
865                 870                 875                 880

Leu Lys Ser Arg Thr Pro Ser Arg His Ser Cys Ser Gly Ser Ser Pro
                885                 890                 895

Pro Arg Val Lys Ser Ser Thr Pro Pro Arg Gln Ser Pro Ser Arg Ser
                900                 905                 910

Ser Ser Pro Gln Pro Lys Val Lys Ala Ile Ile Ser Pro Arg Gln Arg
                915                 920                 925

Ser His Ser Gly Ser Ser Ser Pro Ser Pro Ser Arg Val Thr Ser Arg
    930                 935                 940

Thr Thr Pro Arg Arg Ser Arg Ser Val Ser Pro Cys Ser Asn Val Glu
945                 950                 955                 960

Ser Arg Leu Leu Pro Arg Tyr Ser His Ser Gly Ser Ser Ser Pro Asp
                965                 970                 975

Thr Lys Val Lys Pro Glu Thr Pro Arg Gln Ser His Ser Gly Ser
                980                 985                 990

Ile Ser Pro Tyr Pro Lys Val Lys Ala Gln Thr Pro Pro Gly Pro Ser
                995                 1000                1005

Leu Ser Gly Ser Lys Ser Pro Cys Pro Gln Glu Lys Ser Lys Asp Ser
    1010                1015                1020

Leu Val Gln Ser Cys Pro Gly Ser Leu Ser Leu Cys Ala Gly Val Lys
1025                1030                1035                1040

Ser Ser Thr Pro Pro Gly Glu Ser Tyr Phe Gly Val Ser Ser Leu Gln
                1045                1050                1055

Leu Lys Gly Gln Ser Gln Thr Ser Pro Asp His Arg Ser Asp Thr Ser
        1060                1065                1070

Ser Pro Glu Val Arg Gln Ser His Ser Glu Ser Pro Ser Leu Gln Ser
    1075                1080                1085

Lys Ser Gln Thr Ser Pro Lys Gly Gly Arg Ser Arg Ser Ser Ser Pro
    1090                1095                1100

Val Thr Glu Leu Ala Ser Arg Ser Pro Ile Arg Gln Asp Arg Gly Glu
1105                1110                1115                1120

Phe Ser Ala Ser Pro Met Leu Lys Ser Gly Met Ser Pro Glu Gln Ser
                1125                1130                1135

Arg Phe Gln Ser Asp Ser Ser Ser Tyr Pro Thr Val Asp Ser Asn Ser
                1140                1145                1150

Leu Leu Gly Gln Ser Arg Leu Glu Thr Ala Glu Ser Lys Glu Lys Met
    1155                1160                1165

Ala Leu Pro Pro Gln Glu Asp Ala Thr Ala Ser Pro Pro Arg Gln Lys
    1170                1175                1180

Asp Lys Phe Ser Pro Phe Pro Val Gln Asp Arg Pro Glu Ser Ser Leu
```

```
                1185               1190              1195               1200

Val Phe Lys Asp Thr Leu Arg Thr Pro Pro Arg Glu Arg Ser Gly Ala
                1205               1210              1215

Gly Ser Ser Pro Glu Thr Lys Glu Gln Asn Ser Ala Leu Pro Thr Ser
                1220               1225              1230

Ser Gln Asp Glu Glu Leu Met Glu Val Val Glu Lys Ser Glu Glu Pro
                1235               1240              1245

Ala Gly Gln Ile Leu Ser His Leu Ser Ser Glu Leu Lys Glu Met Ser
                1250               1255              1260

Thr Ser Asn Phe Glu Ser Ser Pro Glu Val Glu Glu Arg Pro Ala Val
                1265               1270              1275              1280

Ser Leu Thr Leu Asp Gln Ser Gln Ser Gln Ala Ser Leu Glu Ala Val
                1285               1290              1295

Glu Val Pro Ser Met Ala Ser Ser Trp Gly Gly Pro His Phe Ser Pro
                1300               1305              1310

Glu His Lys Glu Leu Ser Asn Ser Pro Leu Arg Glu Asn Ser Phe Gly
                1315               1320              1325

Ser Pro Leu Glu Phe Arg Asn Ser Gly Pro Leu Gly Thr Glu Met Asn
                1330               1335              1340

Thr Gly Phe Ser Ser Glu Val Lys Glu Asp Leu Asn Gly Pro Phe Leu
1345                1350               1355              1360

Asn Gln Leu Glu Thr Asp Pro Ser Leu Asp Met Lys Glu Gln Ser Thr
                1365               1370              1375

Arg Ser Ser Gly His Ser Ser Ser Glu Leu Ser Pro Asp Ala Val Glu
                1380               1385              1390

Lys Ala Gly Met Ser Ser Asn Gln Ser Ile Ser Ser Pro Val Leu Asp
                1395               1400              1405

Ala Val Pro Arg Thr Pro Ser Arg Glu Arg Ser Ser Ser Ala Ser Ser
                1410               1415              1420

Pro Glu Met Lys Asp Gly Leu Pro Arg Thr Pro Ser Arg Arg Ser Arg
1425                1430               1435              1440

Ser Gly Ser Ser Pro Gly Leu Arg Asp Gly Ser Gly Thr Pro Ser Arg
                1445               1450              1455

His Ser Leu Ser Gly Ser Ser Pro Gly Met Lys Asp Ile Pro Arg Thr
                1460               1465              1470

Pro Ser Arg Gly Arg Ser Glu Cys Asp Ser Ser Pro Glu Pro Lys Ala
                1475               1480              1485

Leu Pro Gln Thr Pro Arg Pro Arg Ser Arg Ser Pro Ser Ser Pro Glu
                1490               1495              1500

Leu Asn Asn Lys Cys Leu Thr Pro Gln Arg Glu Arg Ser Gly Ser Glu
1505                1510               1515              1520

Ser Ser Val Asp Gln Lys Thr Val Ala Arg Thr Pro Leu Gly Gln Arg
                1525               1530              1535

Ser Arg Ser Gly Ser Ser Gln Glu Leu Asp Val Lys Pro Ser Ala Ser
                1540               1545              1550

Pro Gln Glu Arg Ser Glu Ser Asp Ser Ser Pro Asp Ser Lys Ala Lys
                1555               1560              1565

Thr Arg Thr Pro Leu Arg Gln Arg Ser Arg Ser Gly Ser Ser Pro Glu
                1570               1575              1580

Val Asp Ser Lys Ser Arg Leu Ser Pro Arg Arg Ser Arg Ser Gly Ser
1585                1590               1595              1600

Ser Pro Glu Val Lys Asp Lys Pro Arg Ala Ala Pro Arg Ala Gln Ser
                1605               1610              1615
```

-continued

Gly Ser Asp Ser Ser Pro Glu Pro Lys Ala Pro Ala Pro Arg Ala Leu
             1620                1625                1630

Pro Arg Arg Ser Arg Ser Gly Ser Ser Lys Gly Arg Gly Pro Ser
    1635                1640                1645

Pro Glu Gly Ser Ser Ser Thr Glu Ser Ser Pro Glu His Pro Pro Lys
    1650                1655                1660

Ser Arg Thr Ala Arg Arg Gly Ser Arg Ser Pro Glu Pro Lys Thr
1665                1670                1675                1680

Lys Ser Arg Thr Pro Arg Arg Ser Ser Arg Ser Pro Glu
                1685                1690                1695

Leu Thr Arg Lys Ala Arg Leu Ser Arg Arg Ser Arg Ser Ala Ser Ser
                1700                1705                1710

Ser Pro Glu Thr Arg Ser Arg Thr Pro Pro Arg His Arg Arg Ser Pro
    1715                1720                1725

Ser Val Ser Ser Pro Glu Pro Ala Glu Lys Ser Arg Ser Ser Arg Arg
    1730                1735                1740

Arg Arg Ser Ala Ser Ser Pro Arg Thr Lys Thr Thr Ser Arg Arg Gly
1745                1750                1755                1760

Arg Ser Pro Ser Pro Lys Pro Arg Gly Leu Gln Arg Ser Arg Ser Arg
                1765                1770                1775

Ser Arg Arg Glu Lys Thr Arg Thr Thr Arg Arg Asp Arg Ser Gly
                1780                1785                1790

Ser Ser Gln Ser Thr Ser Arg Arg Arg Gln Arg Ser Arg Ser Arg Ser
                1795                1800                1805

Arg Val Thr Arg Arg Arg Gly Gly Ser Gly Tyr His Ser Arg Ser
    1810                1815                1820

Pro Ala Arg Gln Glu Ser Ser Arg Thr Ser Ser Arg Arg Arg Arg Gly
1825                1830                1835                1840

Arg Ser Arg Thr Pro Pro Thr Ser Arg Lys Arg Ser Arg Ser Arg Thr
                1845                1850                1855

Ser Pro Ala Pro Trp Lys Arg Ser Arg Ser Arg Ala Ser Pro Ala Thr
                1860                1865                1870

His Arg Arg Ser Arg Ser Arg Thr Pro Leu Ile Ser Arg Arg Ser
    1875                1880                1885

Arg Ser Arg Thr Ser Pro Val Ser Arg Arg Ser Arg Ser Arg Thr
    1890                1895                1900

Ser Val Thr Arg Arg Arg Ser Arg Ser Arg Ala Ser Pro Val Ser Arg
1905                1910                1915                1920

Arg Arg Ser Arg Ser Arg Thr Pro Pro Val Thr Arg Arg Arg Ser Arg
                1925                1930                1935

Ser Arg Thr Pro Thr Thr Arg Arg Arg Ser Arg Ser Arg Thr Pro Pro
                1940                1945                1950

Val Thr Arg Arg Arg Ser Arg Ser Arg Thr Pro Pro Val Thr Arg Arg
                1955                1960                1965

Arg Ser Arg Ser Arg Thr Ser Pro Ile Thr Arg Arg Arg Ser Arg Ser
    1970                1975                1980

Arg Thr Ser Pro Val Thr Arg Arg Ser Arg Ser Arg Thr Ser Pro
1985                1990                1995                2000

Val Thr Arg Arg Arg Ser Arg Ser Arg Thr Pro Val Thr Arg Arg
                2005                2010                2015

Arg Ser Arg Ser Arg Thr Pro Pro Ala Gln Asp Gln Pro Arg Ser Pro
                2020                2025                2030

Val Pro Ser Ala Phe Ser Asp Gln Ser Arg Cys Leu Ile Ala Gln Thr
                2035                2040                2045

-continued

| | | | | | | | | | | | | |
|---|---|---|---|---|---|---|---|---|---|---|---|---|
|Thr|Pro|Val|Ala|Gly|Ser|Gln|Ser|Leu|Ser|Ser|Gly|Ala|Val|Ala|Thr|
| |2050| | | |2055| | | |2060| | | | | | |

Thr Thr Ser Ser Ala Gly Asp His Asn Gly Met Leu Ser Val Pro Ala
2065          2070          2075          2080

Pro Gly Val Pro His Ser Asp Val Gly Glu Pro Pro Ala Ser Thr Gly
          2085          2090          2095

Ala Gln Gln Pro Ser Ala Leu Ala Ala Leu Gln Pro Ala Lys Glu Arg
       2100          2105          2110

Arg Ser Ser Ser Ser Ser Ser Ser Ser Ser Ser Ser Ser
       2115          2120          2125

Ser Ser Ser Ser Ser Ser Ser Ser Ser Gly Ser Ser Ser Ser Asp
       2130          2135          2140

Ser Glu Gly Ser Ser Phe Leu Cys Asn Leu Ser Gly Thr Glu Glu Val
2145          2150          2155          2160

Pro Ser Pro Thr Pro Ala Pro Lys Glu Ala Val Arg Glu Gly Arg Pro
          2165          2170          2175

Pro Glu Pro Thr Pro Ala Lys Arg Lys Arg Arg Ser Ser Ser Ser
       2180          2185          2190

Ser Ser Ser Ser Ser Ser Ser Ser Ser Ser Ser Ser Ser
       2195          2200          2205

Ser Ser Ser Ser Ser Ser Ser Ser Ser Ser Ser Ser Ser
       2210          2215          2220

Ser Ser Ser Ser Phe Pro Phe Pro Cys Lys Ala Trp Pro Ser Gly Leu
2225          2230          2235          2240

Ala Gln Thr Cys Lys Pro Gln Glu Ala Thr Pro Trp Arg Ala Glu Val
          2245          2250          2255

Pro Gln Pro Pro Glu Ala Asn Arg Leu Pro Gln Gly Leu Ser Val Pro
          2260          2265          2270

Gln Leu Leu Ala Cys Gly Ala Ser Pro Ser Leu Ala Pro Ala Leu Thr
       2275          2280          2285

Thr Gly Pro Ala Glu Gln Gln Gln
    2290          2295

<210> SEQ ID NO 47
<211> LENGTH: 194
<212> TYPE: DNA
<213> ORGANISM: Artificial Sequence
<220> FEATURE:
<223> OTHER INFORMATION: Description of Artificial Sequence:synthetic
      non-muscle myosin heavy chain GH1-90-PCR-G3F1

<400> SEQUENCE: 47
gctccctaaa gaacaagctc aggcgcgggg acctgccgtt tgtcgtgccc cgccgaatgg      60
cccggaaagg cgccggggat ggctccgacg aagaggtaga tggcaaagcg gatgggctg     120 aggccaaacc tgccgaataa gcctcttctc ctgcagcctg agatggatgg acagacagac     180
accacagcct cccc                                                       194

<210> SEQ ID NO 48
<211> LENGTH: 7274
<212> TYPE: DNA
<213> ORGANISM: Homo sapiens
<220> FEATURE:
<223> OTHER INFORMATION: myosin, heavy polypeptide 9, non-muscle (MYH9)
      cDNA

<400> SEQUENCE: 48
atggcacagc aagctgccga taagtatctc tatgtggata aaaacttcat caacaatccg      60

```
ctggcccagg ccgactgggc tgccaagaag ctggtatggg tgccttccga caagagtggc      120
tttgagccag ccagcctcaa ggaggaggtg ggcgaagagg ccatcgtgga gctggtggag      180
aatgggaaga aggtgaaggt gaacaaggat gacatccaga agatgaaccc gcccaagttc      240
tccaaggtgg aggacatggc agagctcacg tgcctcaacg aagcctcggt gctgcacaac      300
ctcaaggagc gttactactc agggctcatc tacacctatt caggcctgtt ctgtgtggtc      360
atcaatcctt acaagaacct gcccatctac tctgaagaga ttgtggaaat gtacaagggc      420
aagaagaggc acgagatgcc ccctcacatc tatgccatca cagacaccgc ctacaggagt      480
atgatgcaag accgagaaga tcaatccatc ttgtgcactg gtgaatctgg agctggcaag      540
acggagaaca ccaagaaggt catccagtat ctggcgtacg tggcgtcctc gcacaagagc      600
aagaaggacc agggcgagct ggagcggcag ctgctgcagg ccaaccccat cctggaggcc      660
ttcgggaacg ccaagaccgt gaagaatgac aactcctccc gcttcggcaa attcattcgc      720
atcaactttg atgtcaatgg ctacattgtt ggagccaaca ttgagactta tcttttggag      780
aaatctcgtg ctatccgcca agccaaggaa gaacggacct ccacatctt ctattatctc      840 ctgtctgggg ctggagagca cctgaagacc gatctcctgt ggagccgta caacaaatac      900 cgcttcctgt ccaatggaca cgtcaccatc cccgggcagc aggacaagga catgttccag      960
gagaccatgg aggccatgag gattatgggc atcccagaag aggagcaaat gggcctgctg     1020
cgggtcatct caggggttct tcagctcggc aacatcgtct tcaagaagga gcggaacact     1080
gaccaggcgt ccatgcccga caacacagct gcccaaaagg tgtcccatct cttgggtatc     1140
aatgtgaccg atttcaccag aggaatcctc accccgcgca tcaaggtggg acgggattac     1200
gtccagaagg cgcagactaa agagcaggct gactttgcca tcgaggcctt ggccaaggcg     1260
acctatgagc ggatgttccg ctggctggtg ctgcgcatca acaaggctct ggacaagacc     1320
aagaggcagg cgcctccctt catcgggatc ctggacattg ccggcttcga gatctttgat     1380
ctgaactcgt ttgagcagct gtgcatcaat tacaccaatg agaagctgca gcagctcttc     1440
aaccacacca tgttcatcct ggagcaggag gagtaccagc gcgagggcat cgagtggaac     1500
ttcatcgact ttggcctcga cctgcagccc tgcatcgacc tcattgagaa gccagcaggc     1560
cccccgggca ttctggccct gctggacgag gagtgctggt tccccaaagc caccgacaag     1620
agcttcgtgg agaaggtgat gcaggagcag ggcacccacc ccaagttcca gaagcccaag     1680
cagctgaagg acaaagctga tttctgcatt atccactatg ccggcaaggt ggattacaaa     1740
gctgacgagt ggctgatgaa gaacatggat cccctgaatg acaacatcgc cacactgctc     1800
caccagtcct ctgacaagtt tgtctcggag ctgtggaagg atgtggaccg catcatcggc     1860
ctggaccagg tggccggcat gtcggagacc gcactgcccg ggccttcaa gacgcggaag     1920 ggcatgttcc gcactgtggg gcagctttac aaggagcagc tggccaagct gatggctacg     1980
ctgaggaaca cgaaccccaa ctttgtccgc tgcatcatcc ccaaccacga agaaggcc     2040 ggcaagctgg accgcatct cgtgctggac cagctgcgct gcaacggtgt tctcgagggc     2100
atccgtatct gccgccaggg cttccccaac agggtggtct tccaggagtt tcggcagaga     2160
tatgagatcc tgactccaaa ctccattccc aagggtttca tggacgggaa gcaggcgtgc     2220
gtgctcatga taaaagccct ggagctcgac agcaatctgt accgcattgg ccagagcaaa     2280
gtcttcttcc gtgccggtgt gctggcccac ctggaggagg agcgagacct gaagatcacc     2340
gacgtcatca taggggttcca ggcctgctgc aggggctacc tggccaggaa gcatttgcc     2400 aagcggcagc agcagcttac cgccatgaag gtcctccagc ggaactgcgc tgcctacctg     2460
```

```
aagctgcgga actggcagtg gtggcggctc ttcaccaagg tcaagccgct gctgcaggtg    2520
agccggcagg aggaggagat gatggccaag gaggaggagc tggtgaaggt cagagagaag    2580
cagctggctg cggagaacag gctcacggag atggagacgc tgcagtctca gctcatggca    2640
gagaaattgc agctgcagga gcagctccag gcagaaaccg agctgtgtgc cgaggctgag    2700
gagctccggg cccgcctgac cgccaagaag caggaattag aagagatctg ccatgaccta    2760
gaggccaggg tggaggagga ggaggagcgc tgccagcacc tgcaggcgga gaagaagaag    2820
atgcagcaga acatccagga gcttgaggag cagctggagg aggaggagag cgcccggcag    2880
aagctgcagc tggagaaggt gaccaccgag gcgaagctga aaaagctgga ggaggagcag    2940
atcatcctgg aggaccagaa ctgcaagctg gccaaggaaa agaaactgct ggaagacaga    3000
atagctgagt tcaccaccaa cctcacagaa gaggaggaga atctaagag cctcgccaag    3060 ctcaagaaca agcatgaggc aatgatcact gacttggaag agcgcctccg cagggaggag    3120
aagcagcgac aggagctgga gaagacccgc cggaagctgg agggagactc cacagacctc    3180
agcgaccaga tcgccgagct ccaggcccag atcgcggagc tcaagatgca gctggccaag    3240
aaagaggagg agctccaggc cgccctggcc agagtggaag aggaagctgc ccagaagaac    3300
atggccctca agaagatccg ggagctggaa tctcagatct ctgaactcca ggaagacctg    3360
gagtctgagc gtgcttccag gaataaagct gagaagcaga acgggacct tggggaagag    3420 ctagaggctc tgaaaacaga gttggaggac acgctggatt ccacagctgc ccagcaggag    3480
ctcaggtcaa aacgtgagca ggaggtgaac atcctgaaga gaccctgga ggaggaggcc    3540 aagacccacg aggcccagat ccaggagatg aggcagaagc actcacaggc cgtggaggag    3600
ctggcggagc agctggagca gacgaagcgg gtgaaagcaa acctcgagaa ggcaaagcag    3660
actctggaga acgagcgggg ggagctggcc aacgaggtga aggtgctgct gcagggcaaa    3720
ggggactcgg agcacaagcg caagaaagtg gaggcgcagc tgcaggagct gcaggtcaag    3780
ttcaacgagg gagagcgcgt gcgcacagag ctggccgaca aggtcaccaa gctgcaggtg    3840
gagctggaca acgtgaccgg gcttctcagc cagtccgaca gcaagtccag caagctcacc    3900
aaggacttct ccgcgctgga gtcccagctg caggacactc aggagctgct gcaggaggag    3960
aaccggcaga agctgagcct gagcaccaag ctcaagcagg tggaggacga aagaattcc    4020 ttccgggagc agctggagga ggaggaggag gccaagcaca acctggagaa gcagatcgcc    4080
accctccatg cccaggtggc cgacatgaaa aagaagatgg aggacagtgt ggggtgcctg    4140
gaaactgctg aggaggtgaa gaggaagctc cagaaggacc tggagggcct gagccagcgg    4200
cacgaggaga aggtggccgc ctacgacaag ctggagaaga ccaagacgcg gctgcagcag    4260
gagctggacg acctgctggt ggacctggac caccagcgcc agagcgcgtg caacctggag    4320
aagaagcaga agaagtttga ccagctcctg cgcgaggaga gaccatctc tgccaagtat    4380 gcagaggagc gcgaccgggc tgaggcgag gcccgagaga aggagaccaa ggctctgtcg    4440
ctggcccggg ccctgaggga agccatggag cagaaggcgg agctgagcg gctcaacaag    4500 cagttccgca cggagatgga ggaccttatg agctccaagg atgatgtggg caagagtgtc    4560
cacgagctgg agaagtccaa gcgggcccta agcagcagg tggaggagat gaagacgcag    4620
ctggaagagc tggaggacga gctgcaggcc accgaagatg ccaagctgcg gttggaggtc    4680
aacctgcagg ccatgaaggc ccagttcgag cgggacctgc agggccggga cgagcagagc    4740
gaggagaaga gaagcagct ggtcagacag gtgcgggaga tggaggcaga gctggaggac    4800
gagaggaagc agcgctcgat ggcagtggcc gcccggaaga agctggagat ggacctgaag    4860
```

```
gacctggagg cgcacatcga ctcggccaac aagaaccggg acgaagccat caaacagctg    4920
cggaagctgc aggcccagat gaaggactgc atgcgcgagc tggatgacac ccgcgcctct    4980
cgtgaggaga tcctggccca ggccaaagag aacgagaaga agctgaagag catggaggcc    5040
gagatgatcc agttgcagga ggaactggca gccgcggagc gtgccaagcg ccaggcccag    5100
caggagcggg atgagctggc tgacgagatc gccaacagca gcggcaaagg agccctggcg    5160
ttagaggaga agcggcgtct ggaggcccgc atcgcccagc tggaggagga gctggaggag    5220
gagcagggca acacggagct gatcaacgac cggctgaaga aggccaacct gcagatcgac    5280
cagatcaaca ccgacctgaa cctggagcgc agccacgccc agaagaacga gaatgctcgg    5340
cagcagctgg aacgccagaa caaggagctt aaggtcaagc tgcaggagat ggagggcact    5400
gtcaagtcca agtacaaggc ctccatcacc gccctcgagg ccaagattgc acagctggag    5460
gagcagctgg acaacgagac caaggagcgc caggcagcct gcaaacaggt gcgtcggacc    5520
gagaagaagc tgaaggatgt gctgctgcag gtggatgacg agcggaggaa cgccgagcag    5580
tacaaggacc aggccgacaa ggcatctacc cgcctgaagc agctcaagcg gcagctggag    5640
gaggccgaag aggaggccca gcgggccaac gcctcccgcc ggaaactgca gcgcgagctg    5700
gaggacgcca ctgagacggc cgatgccatg aaccgcgaag tcagctccct aaagaacaag    5760
ctcaggcgcg gggacctgcc gtttgtcgtg ccccgccgaa tggcccggaa aggcgccggg    5820
gatggctccg acgaagaggt agatggcaaa gcggatgggg ctgaggccaa acctgccgaa    5880
taagcctctt ctcctgcagc ctgagatgga tggacagaca gacaccacag cctcccttc    5940 ccagaccccg cagcacgcct ctccccacct tcttgggact gctgtgaaca tgcctcctcc    6000
tgccctccgc cccgtccccc catcccgttt ccctccaggt gttgttgagg catttggct    6060 tcctctgctg catccccttc cagctccctc ccctgctcag aatctgatac caaagagaca    6120
gggcccgggc ccaggcagag agcgaccagc aggctcctca gccctctctt gccaaaaagc    6180
acaagatgtt gaggcgagca gggcaggccc ccggggaggg gccagagttt tctatgaatc    6240 tattttttctt cagactgagg ccttttggta gtcggagccc ccgcagtcgt cagcctccct    6300
gacgtctgcc accagcgccc ccactcctcc tcctttcttt gctgtttgca atcacacgtg    6360
gtgacctcac acacctctgc cccttgggcc tcccactccc atggctctgg gcggtccaga    6420
aggagcaggc cctgggcctc cacctctgtg cagggcacag aaggctgggg tgggggagg    6480 agtggattcc tccccacccct gtcccaggca gcgccactgt ccgctgtctc cctcctgatt    6540
ctaaaatgtc tcaagtgcaa tgcccctcc cctcctttac cgaggacagc ctgcctctgc    6600
cacagcaagg ctgtcggggt caagctggaa aggccagcag ccttccagtg gcttctccca    6660
acactcttgg ggaccaaata tatttaatgg ttaagggact tgtcccaagt ctgacagcca    6720
gagcgttaga ggggccagcg gccctcccag gcgatcttgt gtctactcta ggactgggcc    6780
cgagggtggt ttacctgcac cgttgactca gtatagttta aaaatctgcc acctgcacag    6840 gtattttga aagcaaaata aggttttctt ttttcccctt tcttgtaata atgataaaa    6900 ttccgagtct ttctcactgc ctttgtttag aagagagtag ctcgtcctca ctggtctaca    6960
ctggttgccg aatttacttg tattcctaac tgttttgtat atgctgcatt gagacttacg    7020
gcaagaaggc attttttttt tttaaaggaa acaaactctc aaatcatgaa gtgatataaa    7080
agctgcatat gcctacaaag ctctgaattc aggtcccagt tgctgtcaca aaggagtgag    7140
tgaaactccc accctacccc cttttttata taataaaagt gccttagcat gtgttgcagc    7200
tgtcaccact acagtaagct ggtttacaga tgttttccac tgagcatcac aataaagaga    7260
```
accatgtgct acga 7274

<210> SEQ ID NO 49
<211> LENGTH: 1960
<212> TYPE: PRT
<213> ORGANISM: Homo sapiens
<220> FEATURE:
<223> OTHER INFORMATION: myosin, heavy polypeptide 9, non-muscle (MYH9)

<400> SEQUENCE: 49

```
Met Ala Gln Gln Ala Ala Asp Lys Tyr Leu Tyr Val Asp Lys Asn Phe
  1               5                  10                  15

Ile Asn Asn Pro Leu Ala Gln Ala Asp Trp Ala Ala Lys Lys Leu Val
             20                  25                  30

Trp Val Pro Ser Asp Lys Ser Gly Phe Glu Pro Ala Ser Leu Lys Glu
         35                  40                  45

Glu Val Gly Glu Glu Ala Ile Val Glu Leu Val Glu Asn Gly Lys Lys
     50                  55                  60

Val Lys Val Asn Lys Asp Asp Ile Gln Lys Met Asn Pro Pro Lys Phe
 65                  70                  75                  80

Ser Lys Val Glu Asp Met Ala Glu Leu Thr Cys Leu Asn Glu Ala Ser
                 85                  90                  95

Val Leu His Asn Leu Lys Glu Arg Tyr Tyr Ser Gly Leu Ile Tyr Thr
            100                 105                 110

Tyr Ser Gly Leu Phe Cys Val Val Ile Asn Pro Tyr Lys Asn Leu Pro
        115                 120                 125

Ile Tyr Ser Glu Glu Ile Val Glu Met Tyr Lys Gly Lys Lys Arg His
    130                 135                 140

Glu Met Pro Pro His Ile Tyr Ala Ile Thr Asp Thr Ala Tyr Arg Ser
145                 150                 155                 160

Met Met Gln Asp Arg Glu Asp Gln Ser Ile Leu Cys Thr Gly Glu Ser
                165                 170                 175

Gly Ala Gly Lys Thr Glu Asn Thr Lys Lys Val Ile Gln Tyr Leu Ala
            180                 185                 190

Tyr Val Ala Ser Ser His Lys Ser Lys Lys Asp Gln Gly Glu Leu Glu
        195                 200                 205

Arg Gln Leu Leu Gln Ala Asn Pro Ile Leu Glu Ala Phe Gly Asn Ala
    210                 215                 220

Lys Thr Val Lys Asn Asp Asn Ser Ser Arg Phe Gly Lys Phe Ile Arg
225                 230                 235                 240

Ile Asn Phe Asp Val Asn Gly Tyr Ile Val Gly Ala Asn Ile Glu Thr
                245                 250                 255

Tyr Leu Leu Glu Lys Ser Arg Ala Ile Arg Gln Ala Lys Glu Glu Arg
            260                 265                 270

Thr Phe His Ile Phe Tyr Tyr Leu Leu Ser Gly Ala Gly Glu His Leu
        275                 280                 285

Lys Thr Asp Leu Leu Leu Glu Pro Tyr Asn Lys Tyr Arg Phe Leu Ser
    290                 295                 300

Asn Gly His Val Thr Ile Pro Gly Gln Gln Asp Lys Asp Met Phe Gln
305                 310                 315                 320

Glu Thr Met Glu Ala Met Arg Ile Met Gly Ile Pro Glu Glu Glu Gln
                325                 330                 335

Met Gly Leu Leu Arg Val Ile Ser Gly Val Leu Gln Leu Gly Asn Ile
            340                 345                 350

Val Phe Lys Lys Glu Arg Asn Thr Asp Gln Ala Ser Met Pro Asp Asn
```

-continued

```
                355                 360                 365
Thr Ala Ala Gln Lys Val Ser His Leu Leu Gly Ile Asn Val Thr Asp
    370                 375                 380
Phe Thr Arg Gly Ile Leu Thr Pro Arg Ile Lys Val Gly Arg Asp Tyr
385                 390                 395                 400
Val Gln Lys Ala Gln Thr Lys Glu Gln Ala Asp Phe Ala Ile Glu Ala
                405                 410                 415
Leu Ala Lys Ala Thr Tyr Glu Arg Met Phe Arg Trp Leu Val Leu Arg
                420                 425                 430
Ile Asn Lys Ala Leu Asp Lys Thr Lys Arg Gln Gly Ala Ser Phe Ile
                435                 440                 445
Gly Ile Leu Asp Ile Ala Gly Phe Glu Ile Phe Asp Leu Asn Ser Phe
    450                 455                 460
Glu Gln Leu Cys Ile Asn Tyr Thr Asn Glu Lys Leu Gln Gln Leu Phe
465                 470                 475                 480
Asn His Thr Met Phe Ile Leu Glu Gln Glu Glu Tyr Gln Arg Glu Gly
                485                 490                 495
Ile Glu Trp Asn Phe Ile Asp Phe Gly Leu Asp Leu Gln Pro Cys Ile
                500                 505                 510
Asp Leu Ile Glu Lys Pro Ala Gly Pro Pro Gly Ile Leu Ala Leu Leu
    515                 520                 525
Asp Glu Glu Cys Trp Phe Pro Lys Ala Thr Asp Lys Ser Phe Val Glu
    530                 535                 540
Lys Val Met Gln Glu Gln Gly Thr His Pro Lys Phe Gln Lys Pro Lys
545                 550                 555                 560
Gln Leu Lys Asp Lys Ala Asp Phe Cys Ile Ile His Tyr Ala Gly Lys
                565                 570                 575
Val Asp Tyr Lys Ala Asp Glu Trp Leu Met Lys Asn Met Asp Pro Leu
                580                 585                 590
Asn Asp Asn Ile Ala Thr Leu Leu His Gln Ser Ser Asp Lys Phe Val
                595                 600                 605
Ser Glu Leu Trp Lys Asp Val Asp Arg Ile Ile Gly Leu Asp Gln Val
    610                 615                 620
Ala Gly Met Ser Glu Thr Ala Leu Pro Gly Ala Phe Lys Thr Arg Lys
625                 630                 635                 640
Gly Met Phe Arg Thr Val Gly Gln Leu Tyr Lys Glu Gln Leu Ala Lys
                645                 650                 655
Leu Met Ala Thr Leu Arg Asn Thr Asn Pro Asn Phe Val Arg Cys Ile
                660                 665                 670
Ile Pro Asn His Glu Lys Lys Ala Gly Lys Leu Asp Pro His Leu Val
                675                 680                 685
Leu Asp Gln Leu Arg Cys Asn Gly Val Leu Glu Gly Ile Arg Ile Cys
    690                 695                 700
Arg Gln Gly Phe Pro Asn Arg Val Val Phe Gln Glu Phe Arg Gln Arg
705                 710                 715                 720
Tyr Glu Ile Leu Thr Pro Asn Ser Ile Pro Lys Gly Phe Met Asp Gly
                725                 730                 735
Lys Gln Ala Cys Val Leu Met Ile Lys Ala Leu Glu Leu Asp Ser Asn
                740                 745                 750
Leu Tyr Arg Ile Gly Gln Ser Lys Val Phe Phe Arg Ala Gly Val Leu
                755                 760                 765
Ala His Leu Glu Glu Glu Arg Asp Leu Lys Ile Thr Asp Val Ile Ile
    770                 775                 780
```

```
Gly Phe Gln Ala Cys Cys Arg Gly Tyr Leu Ala Arg Lys Ala Phe Ala
785                 790                 795                 800

Lys Arg Gln Gln Gln Leu Thr Ala Met Lys Val Leu Gln Arg Asn Cys
        805                 810                 815

Ala Ala Tyr Leu Lys Leu Arg Asn Trp Gln Trp Trp Arg Leu Phe Thr
            820                 825                 830

Lys Val Lys Pro Leu Leu Gln Val Ser Arg Gln Glu Glu Met Met
        835                 840                 845

Ala Lys Glu Glu Glu Leu Val Lys Val Arg Glu Lys Gln Leu Ala Ala
850                 855                 860

Glu Asn Arg Leu Thr Glu Met Glu Thr Leu Gln Ser Gln Leu Met Ala
865                 870                 875                 880

Glu Lys Leu Gln Leu Gln Glu Gln Leu Gln Ala Glu Thr Glu Leu Cys
        885                 890                 895

Ala Glu Ala Glu Glu Leu Arg Ala Arg Leu Thr Ala Lys Lys Gln Glu
            900                 905                 910

Leu Glu Glu Ile Cys His Asp Leu Glu Ala Arg Val Glu Glu Glu Glu
        915                 920                 925

Glu Arg Cys Gln His Leu Gln Ala Glu Lys Lys Met Gln Gln Asn
930                 935                 940

Ile Gln Glu Leu Glu Glu Gln Leu Glu Glu Glu Ser Ala Arg Gln
945                 950                 955                 960

Lys Leu Gln Leu Glu Lys Val Thr Thr Glu Ala Lys Leu Lys Lys Leu
            965                 970                 975

Glu Glu Glu Gln Ile Ile Leu Glu Asp Gln Asn Cys Lys Leu Ala Lys
        980                 985                 990

Glu Lys Lys Leu Leu Glu Asp Arg Ile Ala Glu Phe Thr Thr Asn Leu
        995                 1000                1005

Thr Glu Glu Glu Glu Lys Ser Lys Ser Leu Ala Lys Leu Lys Asn Lys
    1010                1015                1020

His Glu Ala Met Ile Thr Asp Leu Glu Glu Arg Leu Arg Arg Glu Glu
1025                1030                1035                1040

Lys Gln Arg Gln Glu Leu Glu Lys Thr Arg Arg Lys Leu Glu Gly Asp
            1045                1050                1055

Ser Thr Asp Leu Ser Asp Gln Ile Ala Glu Leu Gln Ala Gln Ile Ala
            1060                1065                1070

Glu Leu Lys Met Gln Leu Ala Lys Lys Glu Glu Glu Leu Gln Ala Ala
        1075                1080                1085

Leu Ala Arg Val Glu Glu Glu Ala Ala Gln Lys Asn Met Ala Leu Lys
    1090                1095                1100

Lys Ile Arg Glu Leu Glu Ser Gln Ile Ser Glu Leu Gln Glu Asp Leu
1105                1110                1115                1120

Glu Ser Glu Arg Ala Ser Arg Asn Lys Ala Glu Lys Gln Lys Arg Asp
            1125                1130                1135

Leu Gly Glu Glu Leu Glu Ala Leu Lys Thr Glu Leu Glu Asp Thr Leu
            1140                1145                1150

Asp Ser Thr Ala Ala Gln Gln Glu Leu Arg Ser Lys Arg Glu Gln Glu
            1155                1160                1165

Val Asn Ile Leu Lys Lys Thr Leu Glu Glu Glu Ala Lys Thr His Glu
    1170                1175                1180

Ala Gln Ile Gln Glu Met Arg Gln Lys His Ser Gln Ala Val Glu Glu
1185                1190                1195                1200

Leu Ala Glu Gln Leu Glu Gln Thr Lys Arg Val Lys Ala Asn Leu Glu
            1205                1210                1215
```

Lys Ala Lys Gln Thr Leu Glu Asn Glu Arg Gly Glu Leu Ala Asn Glu
        1220                1225                1230

Val Lys Val Leu Leu Gln Gly Lys Gly Asp Ser Glu His Lys Arg Lys
        1235                1240                1245

Lys Val Glu Ala Gln Leu Gln Glu Leu Gln Val Lys Phe Asn Glu Gly
    1250                1255                1260

Glu Arg Val Arg Thr Glu Leu Ala Asp Lys Val Thr Lys Leu Gln Val
1265                1270                1275                1280

Glu Leu Asp Asn Val Thr Gly Leu Leu Ser Gln Ser Asp Ser Lys Ser
            1285                1290                1295

Ser Lys Leu Thr Lys Asp Phe Ser Ala Leu Glu Ser Gln Leu Gln Asp
        1300                1305                1310

Thr Gln Glu Leu Leu Gln Glu Glu Asn Arg Gln Lys Leu Ser Leu Ser
        1315                1320                1325

Thr Lys Leu Lys Gln Val Glu Asp Glu Lys Asn Ser Phe Arg Glu Gln
        1330                1335                1340

Leu Glu Glu Glu Glu Glu Ala Lys His Asn Leu Glu Lys Gln Ile Ala
1345                1350                1355                1360

Thr Leu His Ala Gln Val Ala Asp Met Lys Lys Lys Met Glu Asp Ser
            1365                1370                1375

Val Gly Cys Leu Glu Thr Ala Glu Glu Val Lys Arg Lys Leu Gln Lys
        1380                1385                1390

Asp Leu Glu Gly Leu Ser Gln Arg His Glu Glu Lys Val Ala Ala Tyr
        1395                1400                1405

Asp Lys Leu Glu Lys Thr Lys Thr Arg Leu Gln Gln Glu Leu Asp Asp
    1410                1415                1420

Leu Leu Val Asp Leu Asp His Gln Arg Gln Ser Ala Cys Asn Leu Glu
1425                1430                1435                1440

Lys Lys Gln Lys Lys Phe Asp Gln Leu Leu Ala Glu Glu Lys Thr Ile
            1445                1450                1455

Ser Ala Lys Tyr Ala Glu Glu Arg Asp Arg Ala Glu Ala Glu Ala Arg
        1460                1465                1470

Glu Lys Glu Thr Lys Ala Leu Ser Leu Ala Arg Ala Leu Glu Glu Ala
        1475                1480                1485

Met Glu Gln Lys Ala Glu Leu Glu Arg Leu Asn Lys Gln Phe Arg Thr
        1490                1495                1500

Glu Met Glu Asp Leu Met Ser Ser Lys Asp Asp Val Gly Lys Ser Val
1505                1510                1515                1520

His Glu Leu Glu Lys Ser Lys Arg Ala Leu Glu Gln Gln Val Glu Glu
            1525                1530                1535

Met Lys Thr Gln Leu Glu Glu Leu Glu Asp Glu Leu Gln Ala Thr Glu
        1540                1545                1550

Asp Ala Lys Leu Arg Leu Glu Val Asn Leu Gln Ala Met Lys Ala Gln
        1555                1560                1565

Phe Glu Arg Asp Leu Gln Gly Arg Asp Glu Gln Ser Glu Glu Lys Lys
    1570                1575                1580

Lys Gln Leu Val Arg Gln Val Arg Glu Met Glu Ala Glu Leu Glu Asp
1585                1590                1595                1600

Glu Arg Lys Gln Arg Ser Met Ala Val Ala Ala Arg Lys Lys Leu Glu
            1605                1610                1615

Met Asp Leu Lys Asp Leu Glu Ala His Ile Asp Ser Ala Asn Lys Asn
        1620                1625                1630

Arg Asp Glu Ala Ile Lys Gln Leu Arg Lys Leu Gln Ala Gln Met Lys

-continued

Asp Cys Met Arg Glu Leu Asp Asp Thr Arg Ala Ser Arg Glu Glu Ile
1650                1655                1660

Leu Ala Gln Ala Lys Glu Asn Glu Lys Lys Leu Lys Ser Met Glu Ala
1665                1670                1675                1680

Glu Met Ile Gln Leu Gln Glu Glu Leu Ala Ala Ala Glu Arg Ala Lys
            1685                1690                1695

Arg Gln Ala Gln Gln Glu Arg Asp Glu Leu Ala Asp Glu Ile Ala Asn
                1700                1705                1710

Ser Ser Gly Lys Gly Ala Leu Ala Leu Glu Glu Lys Arg Arg Leu Glu
        1715                1720                1725

Ala Arg Ile Ala Gln Leu Glu Glu Glu Leu Glu Glu Glu Gln Gly Asn
    1730                1735                1740

Thr Glu Leu Ile Asn Asp Arg Leu Lys Lys Ala Asn Leu Gln Ile Asp
1745                1750                1755                1760

Gln Ile Asn Thr Asp Leu Asn Leu Glu Arg Ser His Ala Gln Lys Asn
            1765                1770                1775

Glu Asn Ala Arg Gln Gln Leu Glu Arg Gln Asn Lys Glu Leu Lys Val
            1780                1785                1790

Lys Leu Gln Glu Met Glu Gly Thr Val Lys Ser Lys Tyr Lys Ala Ser
        1795                1800                1805

Ile Thr Ala Leu Glu Ala Lys Ile Ala Gln Leu Glu Glu Gln Leu Asp
    1810                1815                1820

Asn Glu Thr Lys Glu Arg Gln Ala Ala Cys Lys Gln Val Arg Arg Thr
1825                1830                1835                1840

Glu Lys Lys Leu Lys Asp Val Leu Leu Gln Val Asp Asp Glu Arg Arg
            1845                1850                1855

Asn Ala Glu Gln Tyr Lys Asp Gln Ala Asp Lys Ala Ser Thr Arg Leu
            1860                1865                1870

Lys Gln Leu Lys Arg Gln Leu Glu Glu Ala Glu Glu Ala Gln Arg
        1875                1880                1885

Ala Asn Ala Ser Arg Arg Lys Leu Gln Arg Glu Leu Glu Asp Ala Thr
    1890                1895                1900

Glu Thr Ala Asp Ala Met Asn Arg Glu Val Ser Ser Leu Lys Asn Lys
1905                1910                1915                1920

Leu Arg Arg Gly Asp Leu Pro Phe Val Val Pro Arg Arg Met Ala Arg
            1925                1930                1935

Lys Gly Ala Gly Asp Gly Ser Asp Glu Glu Val Asp Gly Lys Ala Asp
            1940                1945                1950

Gly Ala Glu Ala Lys Pro Ala Glu
        1955                1960

<210> SEQ ID NO 50
<211> LENGTH: 287
<212> TYPE: DNA
<213> ORGANISM: Artificial Sequence
<220> FEATURE:
<223> OTHER INFORMATION: Description of Artificial Sequence:synthetic
      calmodulin 2 GH1-84-PCR-G3F1

<400> SEQUENCE: 50
gctgtctgta aatacctggt gctaacatcc catgccgctc cctcctcacg atgcacccac      60
cgccctgagg gcccgtccta ggaatggatg tggggatggt cgctttgtaa tgtgctggtt     120 ctctttttt ttcttccccc tctttggccc ttaagacttt cattttgttc agaaccatgc     180
tgggctagct aaagggtggg gagagggaag atgggcccca ccacgctctc aagagaacgc     240

```
acctgcaata aaacagtctt gtcggccagc tgcccagggg acggcag         287
```

<210> SEQ ID NO 51
<211> LENGTH: 2190
<212> TYPE: DNA
<213> ORGANISM: Homo sapiens
<220> FEATURE:
<223> OTHER INFORMATION: calmodulin 2 (phosphorylase kinase, delta),
      clone MGC:1447 cDNA

<400> SEQUENCE: 51

```
ggcacgaggg cgcggcggag ctggaactgc tgcagctgct gccgccgccg gaggaacctt    60
gatccccgtg ctccggacac cccgggcctc gccatggctg accagctgac tgaggagcag   120
attgcagagt tcaaggaggc cttctccctc tttgacaagg atggagatgg cactatcacc   180
accaaggagt tggggacagt gatgagatcc ctgggacaga cccccactga agcagagctg   240
caggatatga tcaatgaggt ggatgcagat gggaacggga ccattgactt cccggagttc   300
ctgaccatga tggccagaaa gatgaaggac acagacagtg aggaggagat ccgagaggcg   360
ttccgtgtct ttgacaagga tgggaatggc tacatcagcg ccgcagagct gcgtcacgta   420
atgacgaacc tgggggagaa gctgaccgat gaggaggtgg atgagatgat cagggaggct   480
gacatcgatg gagatggcca ggtcaattat gaagagtttg tacagatgat gactgcaaag   540
tgaaggcccc ccgggcagct ggcgatgccc gttctcttga tctctctctt ctcgcgcgcg   600
cactctctct tcaacactcc cctgcgtacc ccggttctag caaacaccaa ttgattgact   660
gagaatctga taaagcaaca aaagatttgt cccaagctgc atgattgctc tttctccttc   720
ttccctgagt ctctctccat gcccctcatc tcttcctttt gccctcgcct cttccatcca   780
tgtcttccaa ggcctgatgc attcataagt tgaagccctc cccagatccc cttggggagc   840
ctctgccctc ctccagcccg gatggctctc ctccattttg gtttgtttcc tcttgtttgt   900
catcttattt tgggtgctgg ggtggctgcc agccctgtcc cggacctgc tgggagggac    960
aagaggccct cccccaggca gaagagcatg ccctttgccg ttgcatgcaa ccagccctgt  1020
gattccacgt gcagatccca gcagcctgtt ggggcagggg tgccaagaga ggcattccag  1080
aaggactgag ggggcgttga ggaattgtgg cgttgactgg atgtggccca ggaggggtc   1140
gagggggcca actcacagaa ggggactgac agtgggcaac actcacatcc cactggctgc  1200
tgttctgaaa ccatctgatt ggctttctga ggtttggctg ggtggggact gctcatttgg  1260
ccactctgca gattggactt gcccgcgttc ctgaagcgct ctcgagctgt tctgtaaata  1320
cctggtgcta acatcccatg ccgctccctc ctcacgatgc acccaccgcc ctgagggccc  1380
gtcctaggaa tggatgtggg gatggtcgct ttgtaatgtg ctggttctct ttttttttct  1440
ttcccctcta tggcccttaa gactttcatt ttgttcagaa ccatgctggg ctagctaaag  1500
ggtggggaga gggaagatgg gccccaccac gctctcaaga gaacgcacct gcaataaaac  1560
agtcttgtcg gccagctgcc caggggacgg cagctacagc agcctctgcg tcctggtccg  1620
ccagcacctc ccgcttctcc gtggtgactt ggcgccgctt cctcacatct gtgctccgtg  1680
ccctcttccc tgcctcttcc ctcgcccacc tgcctgcccc catactcccc cagcggagag  1740
catgatccgt gccttgcttc tgactttcg cctctgggac aagtaagtca atgtgggcag   1800
ttcagtcgtc tgggtttttt cccctttttct gttcatttca tctggctccc cccaccacct  1860
ccccacccca cccccaccc cctgcttccc ctcactgccc aggtcgatca agtggctttt   1920
cctgggacct gcccagcttt gagaatctct tctcatccac cctctggcac ccagcctctg  1980
```

```
agggaaggag ggatggggca tagtgggaga cccagccaag agctgagggt aaggtcaggt    2040
aggcgtgagg ctgtggacat tttcggaatg ttttggtttt gttttttta aaccgggcaa    2100 tattgtgttc agttcaagct gtgaagaaaa atatatatca atgttttcca ataaaataca    2160
gtgactacct gaaaaaaaaa aaaaaaaaaa                                      2190

<210> SEQ ID NO 52
<211> LENGTH: 149
<212> TYPE: PRT
<213> ORGANISM: Homo sapiens
<220> FEATURE:
<223> OTHER INFORMATION: calmodulin 2 (phosphorylase kinase, delta)

<400> SEQUENCE: 52

Met Ala Asp Gln Leu Thr Glu Glu Gln Ile Ala Glu Phe Lys Glu Ala
 1               5                  10                  15

Phe Ser Leu Phe Asp Lys Asp Gly Asp Gly Thr Ile Thr Thr Lys Glu
                20                  25                  30

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
        50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu
        115                 120                 125

Ala Asp Ile Asp Gly Asp Gly Gln Val Asn Tyr Glu Glu Phe Val Gln
    130                 135                 140

Met Met Thr Ala Lys
145

<210> SEQ ID NO 53
<211> LENGTH: 296
<212> TYPE: DNA
<213> ORGANISM: Artificial Sequence
<220> FEATURE:
<223> OTHER INFORMATION: Description of Artificial Sequence:synthetic
      novel symporter GH1-178-PCR-G3F1

<400> SEQUENCE: 53
ctgggttctt gcgagacttg gctggagatc acgatgatgc cctcactgtc ctcagtgaaa     60
ctcaaaactc catcacagag ccatctccaa tgctcaagta gcggcccttc cctgccaggc    120
ccggccgggc gacccgagtg ggcgatcgcg gagcaggtcg gggccagagg ccgcctccct    180
tccggaggct ctcacctgcc acagccaccg ctgcaccgca ggaacccagc acagtggtta    240
gattgataag cggccgctcg actagtctga ggtctgatac tcactgactg tcgtat         296

<210> SEQ ID NO 54
<211> LENGTH: 527
<212> TYPE: DNA
<213> ORGANISM: Artificial Sequence
<220> FEATURE:
<223> OTHER INFORMATION: Description of Artificial Sequence:synthetic
      novel semaphorin GH1-204-PCR-G3F1

<400> SEQUENCE: 54
```

```
aaaaaatcta cttctaagct tgttcttatt gttggcagaa ttcaggtcct tgtggctgta      60
ggaccgaggc cccagcttcc tgctgatgtc cgctggagac tgctgtcagc tcccagaggc     120 caccccatt  cctggacacg tggcccctcc atctcaaacc tgcagtgggt gttaaaccct     180
tctcatgctt ctcatctcta cttcaggaat acagatagtg tctggtggct tgacgtgatt     240
ttaatgaatt tggactccat gtggatttgg tcgtctccct attccgagct gcgggcaggg     300
agaggggcct cgcgccgccc tcagcagccg gcggcggccg aggtagacga gcggggacgg     360
aaggacagac cgacgtcgcc agctggaatc atgtgagggc caaccgggga aggtggagca     420
gatgagcaca cacaggagcc gtctcctcac cgccgcccct ctcagcatgg aacagaggcg     480
ccctggcccc gggccctgga ggtggacagc cgctctgtgg tcctgct                   527
```

<210> SEQ ID NO 55
<211> LENGTH: 482
<212> TYPE: DNA
<213> ORGANISM: Artificial Sequence
<220> FEATURE:
<223> OTHER INFORMATION: Description of Artificial Sequence:synthetic
      novel Zn finger helicase GH1-31-PCR-G3F1

<400> SEQUENCE: 55

```
gaaggagaag atggtataaa ctggtccatc agtgacaaag acattgaggc ccagatagct      60
aataaccgaa cacctggaag atggacccag cgggtactat tcagcacaaa aaacatttct     120
gtgaaattgt gacaaacgtg gtcatttatc aaaaaactgc cccttaccac gaaaagttcg     180
tcgctgcttc ctgtgctcca ggagaggaca tctcctgtat tcctgttcag ccccccttttg    240 cgaatactgt cctgtgccta atgtttgacc actcatgtct tttcagacat tcctggataa     300
acagtgtgac cgatgtcata ttgctaggca ctatacagat tcttgccaga atcttgagg     360 cagttatcac cttacgacaa acttgaccac cccaaagccg aaaacctttc cgcaaaaacc     420
cgcacagtgg tttgattgat taaggcggcg ctcgactagt ctgaggtctg atactcactg     480
ac                                                                    482
```

<210> SEQ ID NO 56
<211> LENGTH: 253
<212> TYPE: DNA
<213> ORGANISM: Artificial Sequence
<220> FEATURE:
<223> OTHER INFORMATION: Description of Artificial Sequence:synthetic
      novel sugar transporter GH1-175-PCR-G3F1

<400> SEQUENCE: 56

```
accgagccag agaatgtcac caatggcaca gtgggcggca cagcagagcc ggggcacgag      60
gaggtgagct ggatgaacgg ctggctcagc tgccaggccc aggacgagat gctaaatttg     120
gccttcactg tgggctcctt tctgctcagt gccatcaccc tgcccctggg tatcgtcatg     180
gacaagtatg gcccgaggaa gctcaggctg ctgggcagcg cctgcttcgc ggtttcctgc     240
ttgctgattg cgt                                                        253
```

<210> SEQ ID NO 57
<211> LENGTH: 7554
<212> TYPE: DNA
<213> ORGANISM: Homo sapiens
<220> FEATURE:
<223> OTHER INFORMATION: plexin-A2

<400> SEQUENCE: 57

```
gctgccggga ggagcggcat ccgcgccaga ctggagcggg agggcggcgg agggcagttg      60
```

-continued

```
ctgggaattt ttcagccgag agggcgagcg atccggagag agaccccgag agcttgggag    120
cggtagggcg tgcgagcgcc gcagccagcg gagcaaacct cgaaatagat ctggaaagcc    180
aggctcccgg aggaaatggg actgtgaacg aaccggagag caagaaggga aggaagcgcc    240
gggattgctg atgtcagagg agcccggaaa gtcgcgctgg aaaaatctga agacagccgg    300
ggctctgctt cttcctcagg agagacaccg ccggccgccc ccacacgccc cctcggcgcc    360
tccgggtgcc ccctgagagc cggcgacagc gcccagccgg gctgctgcgg ggcgacggag    420
gactgagggg cgcgcggagc ggagaccgag gagcgacttc aggaatacag ataagtgtct    480
ggtggcttga cgtggatttt aatgaatttg gactccatgt ggatttggtc gtctccctga    540
ttccgagctg cgggcaggga gagggcctc gcgccgccct cagcagccgg cggcggccga    600
ggtagaccga gcggggacgg aaggacagac cgacgtcgcc gagctggaat catgtgaggg    660
ccaaccgggg aaggtggagc agatgagcac acacaggagc cgtctcctca ccgccgcccc    720
tctcagcatg gaacagaggc ggccctggcc ccggggccctg gaggtggaca gccgctctgt    780
ggtcctgctc tcagtggtct gggtgctgct ggccccccca gcagccggca tgcctcagtt    840
cagcaccttc cactctgaga atcgtgactg gaccttcaac cacttgaccg tccaccaagg    900
gacgggggcc gtctatgtgg gggccatcaa ccgggtctat aagctgacag gcaacctgac    960
catccaggtg gctcataaga cagggccaga agaggacaac aagtcttgtt acccgccccct   1020
catcgtgcag ccctgcagcg aagtgctcac cctcaccaac aatgtcaaca gctgctcat    1080
cattgactac tctgagaacc gcctgctggc ctgtgggagc ctctaccagg ggtctgcaa    1140
gctgctgcgg ctggatgacc tcttcatcct ggtggagcca tcccacaaga aggagcacta   1200
cctgtccagt gtcaacaaga cgggcaccat gtacggggtg attgtgcgct ctgagggtga   1260
ggatggcaag ctcttcatcg gcacggctgt ggatgggaag caggattact tcccgaccct   1320
gtccagccgg aagctgcccc gagaccctga gtcctcagcc atgctcgact atgagctaca   1380
cagcgatttt gtctcctctc tcatcaagat cccttcagac accctggccc tggtctccca   1440
cttttgacatc ttctacatct acggcttgc tagtgggggc tttgtctact ttctcactgt   1500
ccagcccgag acccctgagg gtgtggccat caactccgct ggagacctct tctacacctc   1560
acgcatcgtg cggctctgca aggatgaccc caagttccac tcatacgtgt ccctgccctt   1620
cggctgcacc cgggccgggg tggaataccg cctcctgcag gctgcttacc tggccaagcc   1680
tgggggactca ctggcccagg ccttcaatat caccagccag gacgatgtac tctttgccat   1740
cttctccaaa gggcagaagc agtatcacca cccgcccgat gactctgccc tgtgtgcctt   1800
ccctatccgg gccatcaact tgcagatcaa ggagcgcctg cagtcctgct accagggcga   1860
gggcaacctg gagctcaact ggctgctggg aaggacgtc cagtgcacca aggcgcctgt   1920
ccccatcgat gataacttct gtggactgga catcaaccag cccctgggag gctcaactcc   1980
agtggagggc ctgaccctgt acaccaccag cagggaccgc atgacctctg tggcctccta   2040
cgtttacaac ggctacagcg tggttttgt ggggactaag agtggcaagc tgaaaaagat   2100
tcgggccgac ggtcccccc atggtgggt ccagtacgag atggtctctg tgctcaagga    2160
cggaagcccc atcctccggg acatggcctt ctccattgat cagcgctacc tgtacgtcat   2220
gtctgagaga caggtcacca gggtcccgt ggagtcatgt gagcagtata cgacttgtgg   2280
ggagtgcctg agctctgggg accctcactg tggctggtgt gccctgcaca acatgtgctc   2340
ccgcagggac aaatgccaac aggcctggga acctaatcga tttgctgcca gcatcagcca   2400
gtgtgtgagc cttgcagtgc atcccagcag catctcagta tctgagcaca gccggttgct   2460
```

```
tagcctggta gtgagtgatg ctcctgatct atctgcgggt atcgcctgtg cctttgggaa    2520
cctgacagag gtggagggc aggtgtccgg gagccaggtc atctgcatct cacctgggcc    2580
caaggatgtc cctgtcatcc cgctggatca agactggttt gggctggagc tacagctgag    2640
gtccaaggag acagggaaga tatttgtcag caccgagttc aagttttaca actgcagtgc    2700
ccaccaactg tgcctgtcct gtgtcaacag cgccttccgc tgccattggt gcaagtaccg    2760
caacctctgc actcatgacc ccaccacctg ctccttccag gagggccgga tcaatatttc    2820
agaggactgt ccccagctgg tgcccacaga ggagatcttg attccagtcg gggaggtaaa    2880
gccaatcacc cttaaggcgc gaaatctgcc ccagccgcag tccggccagc gaggctatga    2940
gtgtgtcctc aacatacaag gagccatcca ccgggtcccc gctctgcgct caacagctc    3000 cagcgttcag tgtcagaaca gctcgtacca gtatgatggc atggacatca gcaatctggc    3060
cgtggatttc gctgtggtgt ggaacggcaa tttcatcatt gacaaccctc aggacctgaa    3120
agtccatctc tacaagtgtg cagcccagcg ggagagctgc ggcctctgcc tcaaggccga    3180
ccggaagttt gagtgtggct ggtgcagcgg cgagcgcagg tgcaccctcc accagcactg    3240
taccagcccc tccagcccct ggctcgactg gtccagccac aatgtcaagt gctccaaccc    3300
tcaaatcacc gagattttga cggtgtctgg accgccggaa ggagggacgc gagtgaccat    3360
ccatggcgtg aacctgggtc tggacttctc cgagatcgcc caccatgtgc aggtggctgg    3420
ggtgccctgc acgcccctcc caggggaata catcatcgct gagcagattg tctgtgagat    3480
gggccatgcc ctcgtgggaa ccacctccgg gccagtacgc ctgtgtattg gcagtgtaa    3540 gccagagttc atgacgaagt cccatcagca gtacaccttc gtgaaccctt ctgtgctgtc    3600
actcaaccca atccgaggtc ccgagtcagg aggcactatg gtgaccatta ccggccatta    3660
ccttggggct gggagcagcg tggcagtcta cctgggcaac cagacctgcg agttctacgg    3720
gaggtcaatg agtgagatcg tgtgtgtctc accccatca tccaatggcc ttggcccggt    3780 ccctgttct gtgagtgtcg accgagccca tgtggatagc aacctgcagt ttgagtacat    3840
agatgaccct cgggtccagc gcatcgagc agagtggagc attgccagtg gccacacacc    3900
cctgaccatc acaggcttca acctggatgt cattcaggag ccaaggatcc gagtcaaatt    3960
caatggcaaa gaatctgtca atgtgtgtaa agttgtgaac acaaccaccc tcacctgcct    4020
ggcaccctct ctgaccacgg actaccgccc tggcctggac actgtggaac gcccagatga    4080
gtttggattt gtctttaaca atgtccaatc cttgctaatt tacaacgaca ccaagtttat    4140
ctactacccc aacccgacct ttgaactgct tagccctact ggagtcttgg atcaaaagcc    4200
aggatcgccc atcattctga agggcaaaaa cctctgccct cctgcctctg aggggccaa    4260 actcaactac actgtgctca tcggagagac cccttgtgct gtcaccgtat ctgagaccca    4320
gcttctctgc gagcctccca acctcaccgg gcagcacaag gtcatggttc acgtgggcgg    4380
gatggtgttc tcgcctggct cggtgagtgt catctcagac agcttgctga ccctgccagc    4440
catcgtcagc atcgcggccg gcggcagcct cctcctcatc atcgtcatca tcgtcctcat    4500
tgcctacaag cgcaagtctc gagaaaatga cctcactctc aagcggctgc aaatgcagat    4560
ggacaatctg gagtcccgtg tggccttgga gtgcaaggaa gcttttgctg agctccagac    4620
ggatatcaat gagttgacca gtgacctgga ccgctcagga atcccttacc tggactatcg    4680
tacctacgct atgcgagtcc tgttcccggg catcgaggac caccccgtcc tgcgggagct    4740
ggaggtacaa ggaaacgggc agcagcacgt ggagaaggcc ctgaagctct ttgcccagct    4800
catcaacaac aaggtgttcc tgctgacctt catccgcacc ctggagctgc agcgcagttt    4860
```

-continued

```
ctccatgcgc gaccggggca acgtggcttc gctcatcatg accggcctgc agggccgcct    4920
ggaatatgcc actgatgtcc tcaagcagct gctctctgac ctcatcgata agaacctgga    4980
gaacaagaac caccccaagc tgctactccg aggacagag tctgtggctg aaaagatgct     5040
gaccaattgg ttcgccttcc tcctgcacaa gttcctaaag gagtgcgcag ggagccact     5100
cttcatgcta tactgtgcca tcaagcagca gatggagaag ggcccattg atgccatcac     5160
gggcgaggcc cgctactccc tgagcgagga caagctcatc cggcagcaga tcgagtacaa    5220
gaccctgatc ctgaactgcg tcaaccctga caacgagaac agtccagaga tcccagtgaa    5280
ggtgttaaac tgtgacacca tcacacaggt caaggagaag attcttgatg ccgtgtataa    5340
gaatgtgccc tattcccagc ggccgagggc agtggacatg gacttggagt ggcgccaagg    5400
ccggatcgcc cggtcgtgc tgcaagatga ggacatcacc accaagattg agggtgactg     5460
gaagcggctc aacacactga tgcattatca ggtgtcagac aggtcggtgg tggctctggt    5520
ccccaaacag acctcctcct acaacatccc tgcctctgcc agcatctccc ggacgtccat    5580
cagcagatac ggtgactcct ccttcaggta tacgggcagc cccgacagcc tgcggtcccg    5640
ggccccgatg atcaccccag acctggaaag tggggtcaag gtgtggcatc tggtgaagaa    5700
ccatgaccac ggtgaccaga aggagggtga ccggggcagc aagatggtgt ccgagatcta    5760
cctgaccccgg ctactggcca ccaagggcac cctgcagaag tttgtggacg acttgtttga    5820
gaccttgttc agcactgtgc accggggcag cgctctcccc ctggccatca agtacatgtt    5880
tgatttccta gatgagcagg cagacaggca cagcatccat gacacagatg tgcggcacac    5940
ctggaaaagc aactgcctcc ctctgcgctt ctgggtgaac gtgattaaga accccccagtt    6000
cgtgttttgac atccacaagg gcagcatcac ggacgcctgc ctctctgtgg tggcccagac    6060
cttcatggac tcttgttcaa cgtcagagca ccggctgggc aaggactccc cctccaacaa    6120
gctgctctat gccaaggaca tccccagcta caagagctgg gtggagagat actacgcaga    6180
catcgccaag ctcccagcca tcagtgacca ggacatgaat gcctacctcg ccgagcagtc    6240
ccgcctgcac gccgtggagt tcaacatgct gagtgccctc aatgagatct actcctatgt    6300
cagcaagtat agtgaggagc tcatcggggc cctagagcag gatgagcagg cacggcggca    6360
gcggctggct tataaggtgg agcagctcat taatgccatg tccattgaga gctgagagga    6420
ggagcctcgc attcctggga agagggacct gtccaagctg tcacactggg agtctcagat    6480
ggaaggacaa gtgatgggga tcaggcccca gagcttgctg tcccctgaga ccccatcctg    6540
gggagagggg aggactcctc tccctacgcc agccaagttt cgtcatagcc agttccagct    6600
gggagagaca gtgggcgtcg tccatcctca gtgagaacac cagagaaccc ggggccggga    6660
gaaggtggtt cttcaagccg agaggcacga gctgggaca gttctgcctc tgtgactgct     6720
gctttgcatg aaaactcatt tgatgtatat tggggaaata atgagaactt tatttaattt    6780
ttttaagaaa aagggaaaaa aacagaaata aacaaaaag ccgccctgtt aatcccgtcc     6840
aacttttgtt taattctgat ttctgtctcc cttccatctt ttctcccatt cctccttctt    6900
tatataatgc ctatttccaa atgccagaga aagcagagat gctgagagac attggagaga    6960
aaatgactgt ctcctttttcc ttgaaattaa aaaaaaaaa aaaaagagaa agaggagaag    7020
aagaatgatg agcacaagta tgcaccaaac acttcgcaaa aacagaggcc agtaaaacct    7080
ggaattatcc cggcagccag aggagtatgg aacttccaga actttgcaca aattgcaaag    7140
ccatcaagag ctcaccctgg ctgactggaa actgagcttt atctaccaca cacctgtata    7200
ttctcatctt ttgagaggag atgtgtacct agatagtacc aatgcttttt gctactgttt    7260
```

```
tttgttttgt tttatttaat cctaaacctc aacaaatgag gagctggtct ttgatatgtt    7320
tcctttcaat ttccctaaag ttactatgag aagtggggtg aggtgggcct ctcccagacc    7380
agacacctgg cagccctgcc tcatatcaat ccctgtcata aaccaggcac cctggggaaa    7440
cggcctggag gtgtgtgggc caggcctcca cgaggttcca tttgaaagtt gatttggaga    7500
cataggtgtt tgactttgga gttcactcca atcatccagt ggtccctggc aatt          7554
```

<210> SEQ ID NO 58
<211> LENGTH: 1895
<212> TYPE: PRT
<213> ORGANISM: Homo sapiens
<220> FEATURE:
<223> OTHER INFORMATION: plexin-A2

<400> SEQUENCE: 58

Met Glu Gln Arg Arg Pro Trp Pro Arg Ala Leu Glu Val Asp Ser Arg
 1               5                  10                  15

Ser Val Val Leu Leu Ser Val Val Trp Val Leu Leu Ala Pro Pro Ala
            20                  25                  30

Ala Gly Met Pro Gln Phe Ser Thr Phe His Ser Glu Asn Arg Asp Trp
        35                  40                  45

Thr Phe Asn His Leu Thr Val His Gln Gly Thr Gly Ala Val Tyr Val
    50                  55                  60

Gly Ala Ile Asn Arg Val Tyr Lys Leu Thr Gly Asn Leu Thr Ile Gln
65                  70                  75                  80

Val Ala His Lys Thr Gly Pro Glu Glu Asp Asn Lys Ser Cys Tyr Pro
                85                  90                  95

Pro Leu Ile Val Gln Pro Cys Ser Glu Val Leu Thr Leu Thr Asn Asn
            100                 105                 110

Val Asn Lys Leu Leu Ile Ile Asp Tyr Ser Glu Asn Arg Leu Leu Ala
        115                 120                 125

Cys Gly Ser Leu Tyr Gln Gly Val Cys Lys Leu Arg Leu Asp Asp
    130                 135                 140

Leu Phe Ile Leu Val Glu Pro Ser His Lys Lys Glu His Tyr Leu Ser
145                 150                 155                 160

Ser Val Asn Lys Thr Gly Thr Met Tyr Gly Val Ile Val Arg Ser Glu
                165                 170                 175

Gly Glu Asp Gly Lys Leu Phe Ile Gly Thr Ala Val Asp Gly Lys Gln
            180                 185                 190

Asp Tyr Phe Pro Thr Leu Ser Ser Arg Lys Leu Pro Arg Asp Pro Glu
        195                 200                 205

Ser Ser Ala Met Leu Asp Tyr Glu Leu His Ser Asp Phe Val Ser Ser
    210                 215                 220

Leu Ile Lys Ile Pro Ser Asp Thr Leu Ala Leu Val Ser His Phe Asp
225                 230                 235                 240

Ile Phe Tyr Ile Tyr Gly Phe Ala Ser Gly Gly Phe Tyr Phe Leu
                245                 250                 255

Thr Val Gln Pro Glu Thr Pro Glu Gly Val Ala Ile Asn Ser Ala Gly
            260                 265                 270

Asp Leu Phe Tyr Thr Ser Arg Ile Val Arg Leu Cys Lys Asp Asp Pro
        275                 280                 285

Lys Phe His Ser Tyr Val Ser Leu Pro Phe Gly Cys Thr Arg Ala Gly
    290                 295                 300

Val Glu Tyr Arg Leu Leu Gln Ala Ala Tyr Leu Ala Lys Pro Gly Asp
305                 310                 315                 320

```
Ser Leu Ala Gln Ala Phe Asn Ile Thr Ser Gln Asp Val Leu Phe
                325                 330                 335

Ala Ile Phe Ser Lys Gly Gln Lys Gln Tyr His His Pro Asp Asp
            340                 345                 350

Ser Ala Leu Cys Ala Phe Pro Ile Arg Ala Ile Asn Leu Gln Ile Lys
            355                 360                 365

Glu Arg Leu Gln Ser Cys Tyr Gln Gly Glu Gly Asn Leu Glu Leu Asn
        370                 375                 380

Trp Leu Leu Gly Lys Asp Val Gln Cys Thr Lys Ala Pro Val Pro Ile
385                 390                 395                 400

Asp Asp Asn Phe Cys Gly Leu Asp Ile Asn Gln Pro Leu Gly Gly Ser
                405                 410                 415

Thr Pro Val Glu Gly Leu Thr Leu Tyr Thr Thr Ser Arg Asp Arg Met
            420                 425                 430

Thr Ser Val Ala Ser Tyr Val Tyr Asn Gly Tyr Ser Val Val Phe Val
            435                 440                 445

Gly Thr Lys Ser Gly Lys Leu Lys Lys Ile Arg Ala Asp Gly Pro Pro
    450                 455                 460

His Gly Val Gln Tyr Glu Met Val Ser Val Leu Lys Asp Gly Ser
465                 470                 475                 480

Pro Ile Leu Arg Asp Met Ala Phe Ser Ile Asp Gln Arg Tyr Leu Tyr
                485                 490                 495

Val Met Ser Glu Arg Gln Val Thr Arg Val Pro Val Glu Ser Cys Glu
            500                 505                 510

Gln Tyr Thr Thr Cys Gly Glu Cys Leu Ser Ser Gly Asp Pro His Cys
        515                 520                 525

Gly Trp Cys Ala Leu His Asn Met Cys Ser Arg Arg Asp Lys Cys Gln
    530                 535                 540

Gln Ala Trp Glu Pro Asn Arg Phe Ala Ala Ser Ile Ser Gln Cys Val
545                 550                 555                 560

Ser Leu Ala Val His Pro Ser Ser Ile Ser Val Ser Glu His Ser Arg
                565                 570                 575

Leu Leu Ser Leu Val Val Ser Asp Ala Pro Asp Leu Ser Ala Gly Ile
            580                 585                 590

Ala Cys Ala Phe Gly Asn Leu Thr Glu Val Glu Gly Gln Val Ser Gly
        595                 600                 605

Ser Gln Val Ile Cys Ile Ser Pro Gly Pro Lys Asp Val Pro Val Ile
    610                 615                 620

Pro Leu Asp Gln Asp Trp Phe Gly Leu Glu Leu Gln Leu Arg Ser Lys
625                 630                 635                 640

Glu Thr Gly Lys Ile Phe Val Ser Thr Glu Phe Lys Phe Tyr Asn Cys
                645                 650                 655

Ser Ala His Gln Leu Cys Leu Ser Cys Val Asn Ser Ala Phe Arg Cys
            660                 665                 670

His Trp Cys Lys Tyr Arg Asn Leu Cys Thr His Asp Pro Thr Thr Cys
        675                 680                 685

Ser Phe Gln Glu Gly Arg Ile Asn Ile Ser Glu Asp Cys Pro Gln Leu
    690                 695                 700

Val Pro Thr Glu Glu Ile Leu Ile Pro Val Gly Glu Val Lys Pro Ile
705                 710                 715                 720

Thr Leu Lys Ala Arg Asn Leu Pro Gln Pro Gln Ser Gly Gln Arg Gly
                725                 730                 735

Tyr Glu Cys Val Leu Asn Ile Gln Gly Ala Ile His Arg Val Pro Ala
            740                 745                 750
```

```
Leu Arg Phe Asn Ser Ser Val Gln Cys Gln Asn Ser Ser Tyr Gln
        755                 760                 765

Tyr Asp Gly Met Asp Ile Ser Asn Leu Ala Val Asp Phe Ala Val Val
    770                 775                 780

Trp Asn Gly Asn Phe Ile Ile Asp Asn Pro Gln Asp Leu Lys Val His
785                 790                 795                 800

Leu Tyr Lys Cys Ala Ala Gln Arg Glu Ser Cys Gly Leu Cys Leu Lys
                805                 810                 815

Ala Asp Arg Lys Phe Glu Cys Gly Trp Cys Ser Gly Glu Arg Arg Cys
            820                 825                 830

Thr Leu His Gln His Cys Thr Ser Pro Ser Ser Pro Trp Leu Asp Trp
        835                 840                 845

Ser Ser His Asn Val Lys Cys Ser Asn Pro Gln Ile Thr Glu Ile Leu
    850                 855                 860

Thr Val Ser Gly Pro Pro Glu Gly Gly Thr Arg Val Thr Ile His Gly
865                 870                 875                 880

Val Asn Leu Gly Leu Asp Phe Ser Glu Ile Ala His His Val Gln Val
                885                 890                 895

Ala Gly Val Pro Cys Thr Pro Leu Pro Gly Glu Tyr Ile Ile Ala Glu
            900                 905                 910

Gln Ile Val Cys Glu Met Gly His Ala Leu Val Gly Thr Thr Ser Gly
        915                 920                 925

Pro Val Arg Leu Cys Ile Gly Glu Cys Lys Pro Glu Phe Met Thr Lys
    930                 935                 940

Ser His Gln Gln Tyr Thr Phe Val Asn Pro Ser Val Leu Ser Leu Asn
945                 950                 955                 960

Pro Ile Arg Gly Pro Glu Ser Gly Gly Thr Met Val Thr Ile Thr Gly
                965                 970                 975

His Tyr Leu Gly Ala Gly Ser Ser Val Ala Val Tyr Leu Gly Asn Gln
            980                 985                 990

Thr Cys Glu Phe Tyr Gly Arg Ser Met Ser Glu Ile Val Cys Val Ser
        995                 1000                1005

Pro Pro Ser Ser Asn Gly Leu Gly Pro Val Pro Val Ser Val Ser Val
    1010                1015                1020

Asp Arg Ala His Val Asp Ser Asn Leu Gln Phe Glu Tyr Ile Asp Asp
1025                1030                1035                1040

Pro Arg Val Gln Arg Ile Glu Pro Glu Trp Ser Ile Ala Ser Gly His
                1045                1050                1055

Thr Pro Leu Thr Ile Thr Gly Phe Asn Leu Asp Val Ile Gln Glu Pro
            1060                1065                1070

Arg Ile Arg Val Lys Phe Asn Gly Lys Glu Ser Val Asn Val Cys Lys
        1075                1080                1085

Val Val Asn Thr Thr Thr Leu Thr Cys Leu Ala Pro Ser Leu Thr Thr
    1090                1095                1100

Asp Tyr Arg Pro Gly Leu Asp Thr Val Glu Arg Pro Asp Glu Phe Gly
1105                1110                1115                1120

Phe Val Phe Asn Asn Val Gln Ser Leu Leu Ile Tyr Asn Asp Thr Lys
                1125                1130                1135

Phe Ile Tyr Tyr Pro Asn Pro Thr Phe Glu Leu Leu Ser Pro Thr Gly
            1140                1145                1150

Val Leu Asp Gln Lys Pro Gly Ser Pro Ile Ile Leu Lys Gly Lys Asn
        1155                1160                1165

Leu Cys Pro Pro Ala Ser Gly Gly Ala Lys Leu Asn Tyr Thr Val Leu
```

-continued

```
                1170                1175                1180
Ile Gly Glu Thr Pro Cys Ala Val Thr Val Ser Glu Thr Gln Leu Leu
    1185                1190                1195                1200

Cys Glu Pro Pro Asn Leu Thr Gly Gln His Lys Val Met Val His Val
                1205                1210                1215

Gly Gly Met Val Phe Ser Pro Gly Ser Val Ser Val Ile Ser Asp Ser
                1220                1225                1230

Leu Leu Thr Leu Pro Ala Ile Val Ser Ile Ala Ala Gly Gly Ser Leu
                1235                1240                1245

Leu Leu Ile Ile Val Ile Ile Val Leu Ile Ala Tyr Lys Arg Lys Ser
                1250                1255                1260

Arg Glu Asn Asp Leu Thr Leu Lys Arg Leu Gln Met Gln Met Asp Asn
1265                1270                1275                1280

Leu Glu Ser Arg Val Ala Leu Glu Cys Lys Glu Ala Phe Ala Glu Leu
                1285                1290                1295

Gln Thr Asp Ile Asn Glu Leu Thr Ser Asp Leu Asp Arg Ser Gly Ile
                1300                1305                1310

Pro Tyr Leu Asp Tyr Arg Thr Tyr Ala Met Arg Val Leu Phe Pro Gly
                1315                1320                1325

Ile Glu Asp His Pro Val Leu Arg Glu Leu Glu Val Gln Gly Asn Gly
                1330                1335                1340

Gln Gln His Val Glu Lys Ala Leu Lys Leu Phe Ala Gln Leu Ile Asn
1345                1350                1355                1360

Asn Lys Val Phe Leu Leu Thr Phe Ile Arg Thr Leu Glu Leu Gln Arg
                1365                1370                1375

Ser Phe Ser Met Arg Asp Arg Gly Asn Val Ala Ser Leu Ile Met Thr
                1380                1385                1390

Gly Leu Gln Gly Arg Leu Glu Tyr Ala Thr Asp Val Leu Lys Gln Leu
                1395                1400                1405

Leu Ser Asp Leu Ile Asp Lys Asn Leu Glu Asn Lys Asn His Pro Lys
                1410                1415                1420

Leu Leu Leu Arg Arg Thr Glu Ser Val Ala Glu Lys Met Leu Thr Asn
1425                1430                1435                1440

Trp Phe Ala Phe Leu Leu His Lys Phe Leu Lys Glu Cys Ala Gly Glu
                1445                1450                1455

Pro Leu Phe Met Leu Tyr Cys Ala Ile Lys Gln Gln Met Glu Lys Gly
                1460                1465                1470

Pro Ile Asp Ala Ile Thr Gly Glu Ala Arg Tyr Ser Leu Ser Glu Asp
                1475                1480                1485

Lys Leu Ile Arg Gln Gln Ile Glu Tyr Lys Thr Leu Ile Leu Asn Cys
                1490                1495                1500

Val Asn Pro Asp Asn Glu Asn Ser Pro Glu Ile Pro Val Lys Val Leu
1505                1510                1515                1520

Asn Cys Asp Thr Ile Thr Gln Val Lys Glu Lys Ile Leu Asp Ala Val
                1525                1530                1535

Tyr Lys Asn Val Pro Tyr Ser Gln Arg Pro Arg Ala Val Asp Met Asp
                1540                1545                1550

Leu Glu Trp Arg Gln Gly Arg Ile Ala Arg Val Val Leu Gln Asp Glu
                1555                1560                1565

Asp Ile Thr Thr Lys Ile Glu Gly Asp Trp Lys Arg Leu Asn Thr Leu
                1570                1575                1580

Met His Tyr Gln Val Ser Asp Arg Ser Val Val Ala Leu Val Pro Lys
1585                1590                1595                1600
```

```
Gln Thr Ser Ser Tyr Asn Ile Pro Ala Ser Ala Ser Ile Ser Arg Thr
            1605                1610                1615

Ser Ile Ser Arg Tyr Gly Asp Ser Ser Phe Arg Tyr Thr Gly Ser Pro
        1620                1625                1630

Asp Ser Leu Arg Ser Arg Ala Pro Met Ile Thr Pro Asp Leu Glu Ser
    1635                1640                1645

Gly Val Lys Val Trp His Leu Val Lys Asn His Asp His Gly Asp Gln
1650                1655                1660

Lys Glu Gly Asp Arg Gly Ser Lys Met Val Ser Glu Ile Tyr Leu Thr
1665                1670                1675                1680

Arg Leu Leu Ala Thr Lys Gly Thr Leu Gln Lys Phe Val Asp Asp Leu
            1685                1690                1695

Phe Glu Thr Leu Phe Ser Thr Val His Arg Gly Ser Ala Leu Pro Leu
        1700                1705                1710

Ala Ile Lys Tyr Met Phe Asp Phe Leu Asp Glu Gln Ala Asp Arg His
    1715                1720                1725

Ser Ile His Asp Thr Asp Val Arg His Thr Trp Lys Ser Asn Cys Leu
1730                1735                1740

Pro Leu Arg Phe Trp Val Asn Val Ile Lys Asn Pro Gln Phe Val Phe
1745                1750                1755                1760

Asp Ile His Lys Gly Ser Ile Thr Asp Ala Cys Leu Ser Val Val Ala
            1765                1770                1775

Gln Thr Phe Met Asp Ser Cys Ser Thr Ser Glu His Arg Leu Gly Lys
        1780                1785                1790

Asp Ser Pro Ser Asn Lys Leu Leu Tyr Ala Lys Asp Ile Pro Ser Tyr
    1795                1800                1805

Lys Ser Trp Val Glu Arg Tyr Tyr Ala Asp Ile Ala Lys Leu Pro Ala
1810                1815                1820

Ile Ser Asp Gln Asp Met Asn Ala Tyr Leu Ala Glu Gln Ser Arg Leu
1825                1830                1835                1840

His Ala Val Glu Phe Asn Met Leu Ser Ala Leu Asn Glu Ile Tyr Ser
            1845                1850                1855

Tyr Val Ser Lys Tyr Ser Glu Glu Leu Ile Gly Ala Leu Glu Gln Asp
        1860                1865                1870

Glu Gln Ala Arg Arg Gln Arg Leu Ala Tyr Lys Val Glu Gln Leu Ile
    1875                1880                1885

Asn Ala Met Ser Ile Glu Ser
   1890                1895

<210> SEQ ID NO 59
<211> LENGTH: 1831
<212> TYPE: DNA
<213> ORGANISM: Homo sapiens
<220> FEATURE:
<223> OTHER INFORMATION: deoxycytidylate deaminase

<400> SEQUENCE: 59
atgagtgaag tttcctgcaa gaaacgggac gactatttgg aatggccaga gtatttatg     60 gctgtggcct tcttatcagc acagagaagc aaagatccaa attcccaggt cggcgcctgc    120
atcgtgaatt cagaaaacaa gattgtcggg attgggtaca atgggatgcc aaatgggtgc    180
agtgatgacg tgttgccttg gagaaggaca gcagagaata agctgacac caaatacccg     240 tacgtgtgcc atgcggagct gaatgccatc atgaacaaaa attcgaccga tgtgaaggc     300 tgtagtatgt atgtcgcctt gttcccttgt aatgaatgcg ctaagctcat catccaggca    360
ggtataaaag aagtgatttt cacgtctgat aaataccatg atagtgacga ggcaactgct    420
```

```
gcgaggctcc tgtttaatat ggccggggtg acattccgga aattcatacc gaagtgcagc    480
aagattgtca ttgactttga ttcaattaac agcagaccgt gtcaaaagct tcagtgagtt    540
acatctcatt caatctccag aagatttgga ttatcgtctt ctaagaggtt gctaatgcct    600
ttcatcttga agttacacat aacttcttac tagccagtat ggcaaaagta ggcatctaaa    660
gaatataaag cctcaaatct tccttactgt ctctcttgtc acatggaatc tacatgtgtt    720
tgaactattg ctttaggatt taaaataggg gagcctgtgg tggcctggtg cacagggcta    780
gaacgagagt gcctccccctt cttgtgtcct ggctggctgg gatgctggtg gctcttcaga    840
ggagcatcag ctgtctgtca tctgctgcga tccggcagcc tctcttcact gctacatgtg    900
ctggaaggac aaataaataa ttgtggttgt gttcttaatg gggacgagca gacacactga    960
tctgaacatc tggcccaagt gaagcatggc atatagtgcc cttggaagaa aattaggcct   1020
caaatgacag tagcattgaa gtgtttgctg cagagttgag ggaaaccccc agccacccctc   1080
ccggaatccg atagggtgc gcacatctgt cctgacagac gaggagtgta actgaaccag   1140
gaatatttcc tccattcctg ctctcccact gcacacaggg tggtggcaca ttatccctct   1200
gggggtggg gacgcctgtt gttttggctc aatttgggtt tgttggtcac atggagctct   1260
tccatttcgt ttagctgaat aatgagttgt tcctagagga gacagcctgt ctctccttgt   1320
tgcccccaaa gcccatgccc tgccgtggtg gcagctgggg ctgtggatgg gaggggtccc   1380
caacatggat gtgttgcccc tcctccgcat gccaacgcag ttcatgtaca aggcccctct   1440
gcaactggag agaaaattaa ttcctatccc gtgagtggat tgtgagaaat tccacccacg   1500
tggagacagc ttactgcagc actgttggtg ttcggagctc ttctgtgccc tggctccatg   1560
ctttcaccta cacaagcatc accttcctaa tcaccgcggg gcggggagcg tgtggctgtg   1620
cccccttctct ttaatctcat ttaatttttta ttaaacatgc tcagtacctg tgttgagaaa   1680
aggctttctt tatcctaaag attattacct ttttaaagtg ctcttatatt ttcatgagtt   1740
tttattttgt ctctgagatt ttgtattcca cattctaggg tattctgtaa tttggctcct   1800
taccaatatt attaaaatct tattaaaatc t                                     1831
```

<210> SEQ ID NO 60
<211> LENGTH: 178
<212> TYPE: PRT
<213> ORGANISM: Homo sapiens
<220> FEATURE:
<223> OTHER INFORMATION: deoxycytidylate deaminase

<400> SEQUENCE: 60

Met Ser Glu Val Ser Cys Lys Lys Arg Asp Asp Tyr Leu Glu Trp Pro
1               5                   10                  15

Glu Tyr Phe Met Ala Val Ala Phe Leu Ser Ala Gln Arg Ser Lys Asp
            20                  25                  30

Pro Asn Ser Gln Val Gly Ala Cys Ile Val Asn Ser Glu Asn Lys Ile
        35                  40                  45

Val Gly Ile Gly Tyr Asn Gly Met Pro Asn Gly Cys Ser Asp Asp Val
    50                  55                  60

Leu Pro Trp Arg Arg Thr Ala Glu Asn Lys Leu Asp Thr Lys Tyr Pro
65                  70                  75                  80

Tyr Val Cys His Ala Glu Leu Asn Ala Ile Met Asn Lys Asn Ser Thr
                85                  90                  95

Asp Val Lys Gly Cys Ser Met Tyr Val Ala Leu Phe Pro Cys Asn Glu
            100                 105                 110

```
Cys Ala Lys Leu Ile Ile Gln Ala Gly Ile Lys Glu Val Ile Phe Thr
        115                 120                 125

Ser Asp Lys Tyr His Asp Ser Asp Glu Ala Thr Ala Ala Arg Leu Leu
    130                 135                 140

Phe Asn Met Ala Gly Val Thr Phe Arg Lys Phe Ile Pro Lys Cys Ser
145                 150                 155                 160

Lys Ile Val Ile Asp Phe Asp Ser Ile Asn Ser Arg Pro Ser Gln Lys
                165                 170                 175

Leu Gln
```

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence:synthetic
      Axl 2

<400> SEQUENCE: 61
gacatcctct ttctcctgcg aagcccatga ag                                  32

<210> SEQ ID NO 62
<211> LENGTH: 32
<212> TYPE: DNA
<213> ORGANISM: Artificial Sequence
<220> FEATURE:
<223> OTHER INFORMATION: Description of Artificial Sequence:synthetic
      Axl 2

<400> SEQUENCE: 62
cttgatgggc ttcgcaggag aaagaggatg tc                                  32

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence:synthetic
      Axl-2

<400> SEQUENCE: 63
aagacatcct ctttctcctg c                                              21

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence:synthetic
      Axl 2

<400> SEQUENCE: 64
gacatcctct ttctcctgcg aagcccat                                       28

<210> SEQ ID NO 65
<211> LENGTH: 32
<212> TYPE: DNA
<213> ORGANISM: Artificial Sequence
<220> FEATURE:
<223> OTHER INFORMATION: Description of Artificial Sequence:synthetic
      Axl4

<400> SEQUENCE: 65
gaagatttgg agaacacact gaaggcctga ag                                  32

<210> SEQ ID NO 66
<211> LENGTH: 32
<212> TYPE: DNA
<213> ORGANISM: Artificial Sequence
<220> FEATURE:
<223> OTHER INFORMATION: Description of Artificial Sequence:synthetic
      Axl4

<400> SEQUENCE: 66
cttgaggcct tcagtgtgtt ctccaaatct tc                                    32

<210> SEQ ID NO 67
<211> LENGTH: 32
<212> TYPE: DNA
<213> ORGANISM: Artificial Sequence
<220> FEATURE:
<223> OTHER INFORMATION: Description of Artificial Sequence:synthetic
      Axl4.2

<400> SEQUENCE: 67
gatttggaga acacactgaa ggccttgcga ag                                    32

<210> SEQ ID NO 68
<211> LENGTH: 32
<212> TYPE: DNA
<213> ORGANISM: Artificial Sequence
<220> FEATURE:
<223> OTHER INFORMATION: Description of Artificial Sequence:synthetic
      Axl4.2

<400> SEQUENCE: 68
cttggcaagg ccttcagtgt gttctccaaa tc                                    32

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence:synthetic
      Axl-4

<400> SEQUENCE: 69
aagatttgga gaacacactg a                                                21

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence:synthetic
      Axl4

<400> SEQUENCE: 70
gaagatttgg agaacacact gaaggcct                                         28

<210> SEQ ID NO 71
<211> LENGTH: 28
<212> TYPE: DNA
<213> ORGANISM: Artificial Sequence
<220> FEATURE:
<223> OTHER INFORMATION: Description of Artificial Sequence:synthetic
      Axl4.2

<400> SEQUENCE: 71
gagaacacac tgaaggcctt gcctcctg                                         28

```
<210> SEQ ID NO 72
<211> LENGTH: 200
<212> TYPE: PRT
<213> ORGANISM: Artificial Sequence
<220> FEATURE:
<223> OTHER INFORMATION: Description of Artificial Sequence:synthetic
      poly Gly flexible linker
<220> FEATURE:
<221> NAME/KEY: MOD_RES
<222> LOCATION: (6)..(200)
<223> OTHER INFORMATION: Gly residues from position 6 to 200 may be
      present or absent

<400> SEQUENCE: 72

Gly Gly Gly Gly Gly Gly Gly Gly Gly Gly Gly Gly Gly Gly Gly Gly
  1               5                  10                  15

Gly Gly Gly Gly Gly Gly Gly Gly Gly Gly Gly Gly Gly Gly Gly Gly
             20                  25                  30

Gly Gly Gly Gly Gly Gly Gly Gly Gly Gly Gly Gly Gly Gly Gly Gly
         35                  40                  45

Gly Gly Gly Gly Gly Gly Gly Gly Gly Gly Gly Gly Gly Gly Gly Gly
     50                  55                  60

Gly Gly Gly Gly Gly Gly Gly Gly Gly Gly Gly Gly Gly Gly Gly Gly
 65                  70                  75                  80

Gly Gly Gly Gly Gly Gly Gly Gly Gly Gly Gly Gly Gly Gly Gly Gly
                 85                  90                  95

Gly Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly Gly
145                 150                 155                 160

Gly Gly Gly Gly Gly Gly Gly Gly Gly Gly Gly Gly Gly Gly Gly Gly
                165                 170                 175

Gly Gly Gly Gly Gly Gly Gly Gly Gly Gly Gly Gly Gly Gly Gly Gly
            180                 185                 190

Gly Gly Gly Gly Gly Gly Gly Gly
        195                 200
```